(12) United States Patent
Okubo et al.

(10) Patent No.: US 8,044,068 B2
(45) Date of Patent: Oct. 25, 2011

(54) AMINOPYRROLIDINE COMPOUND

(75) Inventors: Taketoshi Okubo, Asaka (JP); Toshihito Kumagai, Toshima-ku (JP); Takaaki Ishii, Toshima-ku (JP); Toshio Nakamura, Toshima-ku (JP); Kumi Abe, Toshima-ku (JP); Yuri Amada, Toshima-ku (JP); Tomoko Ishizaka, Toshima-ku (JP); Xiang-Min Sun, Toshima-ku (JP); Yoshinori Sekiguchi, Toshima-ku (JP); Shigetada Sasako, Funabashi (JP); Takanori Shimizu, Funabashi (JP); Takayuki Nagatsuka, Funabashi (JP)

(73) Assignees: Taisho Pharmaceutical Co., Ltd, Tokyo (JP); Nissan Chemical Industries, Ltd., Tokyo (JP)

( * ) Notice: Subject to any disclaimer, the term of this patent is extended or adjusted under 35 U.S.C. 154(b) by 384 days.

(21) Appl. No.: 12/296,082

(22) PCT Filed: Mar. 30, 2007

(86) PCT No.: PCT/JP2007/057054
§ 371 (c)(1),
(2), (4) Date: Oct. 3, 2008

(87) PCT Pub. No.: WO2007/114323
PCT Pub. Date: Oct. 11, 2007

(65) Prior Publication Data
US 2009/0291940 A1    Nov. 26, 2009

(30) Foreign Application Priority Data
Apr. 4, 2006 (JP) ................... 2006-102744

(51) Int. Cl.
*A61K 31/47* (2006.01)
*C07D 453/04* (2006.01)
(52) U.S. Cl. ...................... 514/314; 546/135
(58) Field of Classification Search .............. 514/314; 546/135
See application file for complete search history.

(56) References Cited

U.S. PATENT DOCUMENTS

| 7,759,336 B2 * | 7/2010 | Habashita et al. ....... 514/212.01 |
| 2007/0191364 A1 | 8/2007 | Braun et al. |
| 2010/0261701 A1 * | 10/2010 | Kaneko et al. ........... 514/210.18 |

FOREIGN PATENT DOCUMENTS

| JP | 2005-523237 A | | 8/2005 |
| WO | 03/028641 A2 | | 4/2003 |
| WO | WO2004052862 | * | 6/2004 |
| WO | 2005/047251 A1 | | 5/2005 |
| WO | 2006/021656 A2 | | 3/2006 |

OTHER PUBLICATIONS

Caprathe et al., 2005, CAS: 142:430293.*

* cited by examiner

Primary Examiner — Rei-tsang Shiao
(74) Attorney, Agent, or Firm — Sughrue Mion, PLLC

(57) ABSTRACT

Disclosed is an aminopyrrolidine compound represented by the formula [I] or a pharmaceutically acceptable salt thereof. The compound or the salt is useful as a prophylactic/therapeutic agent for mode disorder such as depression, anxiety disorder, anorexia, cachexia, pain and drug dependence, whose action relies on the $MC_4$ receptor antagonistic effect.

23 Claims, No Drawings

AMINOPYRROLIDINE COMPOUND

CROSS REFERENCE TO RELATED APPLICATION

This application is a National Stage of International Application No. PCT/JP2007/057054 filed Mar. 30, 2007, claiming priority based on Japanese Patent Application No. 2006-102744, filed Apr. 4, 2006, the contents of all of which are incorporated herein by reference in their entirety.

TECHNICAL FIELD

The present invention relates to a novel aminopyrrolidine compound having an antagonistic action on the $MC_4$ receptor.

BACKGROUND ART

It has been reported that melanocortins (α, β, γ-MSH, ACTH) are biosynthesized in the brain by processing pro-opiomelanocortin (POMC), a precursor thereof and involved in various physiological functions. Melanocortins express their physiological functions by binding to their specific receptors. Currently, the melanocortin receptors (MC receptors) are classified into five subtypes, $MC_1$ to $MC_5$. Of these receptors, the $MC_4$ receptor is expressed specifically in the brain and extensively distributed in the brain.

Reports have suggested an association between the $MC_4$ receptor and appetite and obesity. It has been reported that animal experiments using peptide agonists and antagonists selective to the $MC_4$ and $MC_3$ receptors show a potent inhibitory action on appetite in fasting mice and various obesity model animals (refer to Non-Patent Document 1).

Furthermore, marked increases in body weight and increases in blood insulin and glucose levels were observed in $MC_4$ receptor knockout mice, suggesting that the $MC_4$ receptor has an inhibitory action on eating behavior and obesity.

Meanwhile, in the brain, the $MC_4$ receptor is widely distributed in the limbic system such as the hippocampus and the amygdala as well as raphe nuclei, the nuclei of origin of serotonin neurons, in addition to the hypothalamus, which is closely related to eating behavior. Furthermore, animal experiments have shown that ACTH and α-MSH act on regulation of body temperature, blood pressure, the neuroendocrine system, learning, memory, and arousal. Furthermore, it has been reported that they cause anxiety-like symptoms and activation of the hypothalamus-pituitary gland-adrenal gland system.

Recent reports have shown that $MC_4$ receptor antagonists exhibit anxiolytic-like and antidepressant-like effects (refer to Non-Patent Document 2). Furthermore, since it has been suggested that HS014, an $MC_4$ receptor antagonist, has efficacy in the stress-induced anorexia animal model (refer to Non-Patent Document 3), and the $MC_4$ receptor is associated with functions regulating eating behavior and body weight, it is thought that $MC_4$ receptor antagonists are effective for the treatment of cachexia in patients with cancer or AIDS or eating disorders such as stress-induced anorexia.

Furthermore, there have also been reports suggesting an association of the $MC_4$ receptor with drug dependence (refer to Non-Patent Document 4) and pain (refer to Non-Patent Document 5).

The above findings are summed up that $MC_4$ receptor antagonists are expected to be used as anxiolytic agents and antidepressants as well as therapeutic agents for eating disorders such as cachexia and anorexia or prophylactic or therapeutic agents for pain, drug dependence, and the like.

As $MC_4$ receptor antagonists, piperazine derivatives have been reported (refer to Patent Documents 1 and 2).

Meanwhile, aminopyrrolidine derivatives have been reported in Patent Documents 3 and 4. However, aminopyrrolidine compounds encompassed in the technical scope of the present invention have not been reported, and relations between these compounds and the $MC_4$ receptor have not been reported.

[Patent Document 1] WO02/00259
[Patent Document 2] WO03/053927
[Patent Document 3] WO03/028641
[Patent Document 4] WO02/068409
[Non-Patent Document 1] Nature, 385, 165, 1997
[Non-Patent Document 2] J. Pharmacol. Exp. Ther., 04(2), 818, 2003
[Non-Patent Document 3] Eur. J. Pharmacol., 369, 11, 1999
[Non-Patent Document 4] Eur. J. Neurosci., 21(8), 2233, 2005
[Non-Patent Document 5] Anesth. Analg., 93, 1572, 2001

DISCLOSURE OF THE INVENTION

An object of the present invention is to provide a novel aminopyrrolidine compound or a salt thereof which is useful as a prophylactic or therapeutic agent for mood disorders such as depression, anxiety, anorexia, cachexia, pain, drug dependence, and the like based on an antagonistic action on the $MC_4$ receptor.

The present inventors made intensive studies on novel aminopyrrolidine compounds having an antagonistic action on the $MC_4$ receptor. As a result, the inventors found that a compound represented by the following formula (I) is an excellent $MC_4$ antagonist, and accomplished the present invention.

Hereafter, the present invention will be described.

The present invention provides the following.

(1) An aminopyrrolidine compound, a tautomer, a stereoisomer, a prodrug, or a pharmaceutically acceptable salt of the compound, or a solvate thereof represented by the formula [I]:

[Formula 1]

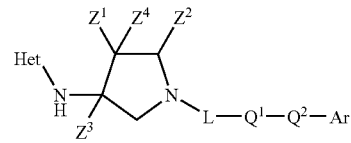

wherein

Het represents an aromatic heterocyclic group represented by the following formula [II], [III], or [IV]:

[Formula 2]

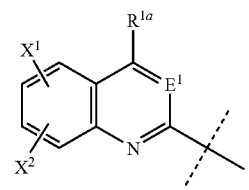

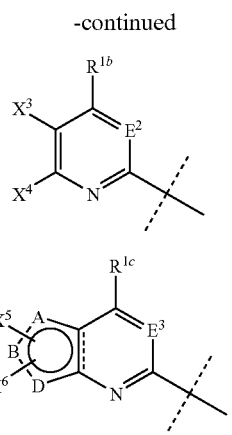

[III]

[IV]

wherein $E^1$, $E^2$, and $E^3$ represent a nitrogen atom or a group represented by formula $CR^1$ (wherein, $R^1$ represents a hydrogen atom or a $C_{1-6}$alkyl group), in the formula [IV], —A—B—D— represents —S—C=C—, =C—S—C=, —C=C—S—, —SO$_2$—C=C—, =C—SO$_2$—C=, —C=C—SO$_2$—, —O—C=C—, =C—O—C=, or —C=C—O—, $R^{1a}$, $R^{1b}$, and $R^{1c}$ represent a group selected from the group consisting of a hydroxy group, a $C_{1-6}$alkyl group, a $C_{3-8}$cycloalkyl group, a $C_{1-6}$alkoxy group, a hydroxy$C_{2-6}$alkoxy group, a $C_{3-8}$cycloalkoxy group, a halogen atom, a trifluoromethyl group, a phenyl group, a $C_{1-9}$heteroaryl group, a di($C_{1-6}$alkyl)aminocarbonyl group, and a group represented by —NR$^2$R$^3$ (wherein, $R^2$ and $R^3$ may be the same or different and represent a hydrogen atom, a $C_{1-6}$alkyl group (the $C_{1-6}$alkyl group is unsubstituted or substituted with one or two substituents selected from the group consisting of a hydroxy group, a carboxy group, a carbamoyl group, a cyano group, a $C_{1-6}$alkoxy group, a $C_{3-8}$cycloalkyl group, a morpholino group, a phenyl group, a $C_{1-9}$heteroaryl group, a phenoxy group, a di($C_{1-6}$alkyl)aminocarbonyl group, a $C_{1-6}$alkoxycarbonyl group, a 1-($C_{1-6}$alkylsulfonyl)piperidin-4-yl group, and a 1-($C_{1-6}$acyl)piperidin-4-yl group), a $C_{3-8}$cycloalkyl group, a pyrrolidin-3-yl group, a piperidin-3-yl group, or a piperidin-4-yl group (wherein the pyrrolidin-3-yl group, the piperidin-3-yl group, and the piperidin-4-yl group are unsubstituted or substituted with a $C_{1-6}$alkyl group, a $C_{1-6}$alkylsulfonyl group, or a $C_{1-6}$acyl group), or $R^2$ and $R^3$, together with an adjacent nitrogen atom, form a cyclic amino group represented by the formula [V]:

[Formula 3]

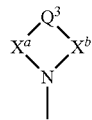

[V]

wherein $Q^3$ represents —O—, —NR$^4$—, —CHR$^5$—, —NR$^6$CO—, —CHR$^7$CHR$^8$—, —CR$^9$=CR$^{10}$—, —S—, —SO—, —SO$_2$—, or a single bond, $X^a$ and $X^b$ may be the same or different and represent a straight $C_{1-3}$alkylene group (wherein the alkylene group is unsubstituted or substituted with one to three substituents selected from the group consisting of a $C_{1-6}$alkyl group, a cyano group, a carboxy group, a carbamoyl group, a ($C_{1-6}$alkyl)aminocarbonyl group, a di($C_{1-6}$alkyl)aminocarbonyl group, a morpholinocarbonyl group, a pyrrolidin-1-ylcarbonyl group, a piperidin-1-ylcarbonyl group, a trifluoromethyl group, an amino$C_{1-6}$alkyl group, a di($C_{1-6}$alkyl)amino$C_{1-6}$alkyl group, a $C_{1-6}$alkoxycarbonyl group, a $C_{1-6}$alkoxy$C_{1-6}$alkyl group, a $C_{1-6}$alkylsulfonyl group, a $C_{1-6}$alkylsulfonylamino$C_{1-6}$alkyl group, a phenyl group, a phenylcarbonyl group (wherein the phenyl group and the phenylcarbonyl group are unsubstituted or substituted with one to three substituents selected from the substituent group A defined below), and a $C_{1-9}$heteroarylcarbonyl group), $R^4$ represents a hydrogen atom, a $C_{1-6}$alkyl group, a $C_{3-8}$cycloalkyl group, a phenyl group, a $C_{1-9}$heteroaryl group, a $C_{1-6}$acyl group, a $C_{3-8}$cycloalkylcarbonyl group, a $C_{1-6}$alkoxycarbonyl group, a morpholinocarbonyl group, a $C_{1-6}$alkylsulfonyl group, a trifluoromethylsulfonyl group, a hydroxy$C_{1-6}$alkyl group, a carbamoyl group, a ($C_{1-6}$alkyl)aminocarbonyl group, a di($C_{1-6}$alkyl)aminocarbonyl group, a $C_{1-9}$heteroarylcarbonyl group, a pyrrolidylcarbonyl group, or a $C_{1-6}$alkoxy$C_{2-6}$alkyl group, $R^5$ represents a hydrogen atom, a hydroxy group, a $C_{1-6}$alkoxy group, an amino group, a ($C_{1-6}$alkyl)amino group, a di($C_{1-6}$alkyl)amino group, a $C_{1-6}$acylamino group, a $C_{1-6}$alkylsulfonylamino group, a pyrrolidin-1-yl group, a piperidin-1-yl group, a morpholino group, a $C_{1-9}$heteroaryl group, a phenylamino group, or a phenoxy group (wherein the phenylamino group and the phenoxy group are unsubstituted or substituted with one to three substituents selected from the substituent group A defined below), $R^6$ represents a hydrogen atom or a $C_{1-6}$alkyl group, $R^7$ and $R^8$ may be the same or different and represent a group selected from the group consisting of a hydrogen atom, a $C_{1-6}$alkyl group, and a $C_{1-6}$alkoxy group, $R^9$ represents a phenyl group or a $C_{1-9}$heteroaryl group (wherein the phenyl group and the $C_{1-9}$heteroaryl group are unsubstituted or substituted with one to three substituents selected from the substituent group A defined below), $R^{10}$ represents a hydrogen atom, or $R^{10}$ forms a benzene ring together with $R^9$ and the carbon atoms to which they bond), $X^1$, $X^2$, $X^3$, $X^4$, $X^5$, and $X^6$ may be the same or different and represent a group selected from the group consisting of a hydrogen atom, a $C_{1-6}$alkyl group, a $C_{1-6}$alkoxy group, a halogen atom, a phenyl group, a trifluoromethyl group, a hydroxy group, a $C_{3-8}$cycloalkyl group, a $C_{3-8}$cycloalkoxy group, a ($C_{1-6}$alkyl)amino group, a di($C_{1-6}$alkyl)amino group, a hydroxyl$C_{1-6}$alkyl group, a $C_{1-6}$alkoxy$C_{1-6}$alkyl group, and a methoxy group substituted with one to three fluorine atoms, or $X^3$ and $X^4$ form —(CH$_2$)$_3$— or —(CH$_2$)$_4$— together, or $X^5$ and $X^6$ form —CH=CH—CH=CH— together when they are substituted on the adjacent carbon atoms, L represents a group represented by —CO— or —CS—, Ar represents a phenyl group, a naphthyl group, or a $C_{1-9}$heteroaryl group (wherein the phenyl group, the naphthyl group, and the $C_{1-9}$heteroaryl group are unsubstituted or substituted with one to five substituents selected from the substituent group B defined below or one substituent selected from the substituent group C defined below), $Z^1$, $Z^2$, $Z^3$, and $Z^4$ may be the same or different and represent a group selected from the group consisting of a hydrogen atom, a hydroxy group, a $C_{1-6}$alkyl group, a $C_{1-6}$alkoxy group, a halogen atom, a $C_{1-6}$alkoxycarbonyl group, and a di($C_{1-6}$alkyl)aminocarbonyl group, or $Z^4$ forms $C_{3-8}$cycloalkane together with $Z^1$, $Q^1$ represents a single bond or —(CH$_2$)$_n$— (wherein, n is an integer of 1 to 10), $Q^2$ represents —$(CR^{11}R^{12})$—, —CO—, —$NR^{13}$—, —O—, —S—, —$CR^{14}$=$CR^{15}$—, —$OCH_2$—, —$SCH_2$—, or —$(CR^{16}R^{17})O$—, $R^{11}$ and $R^{12}$ may be the same or different and represent a group selected from the group consisting of a hydrogen atom, a $C_{1-6}$alkyl group, a $C_{3-8}$cycloalkyl group, a hydroxy group, a hydroxy$C_{1-6}$alkyl group, a $C_{1-6}$acyloxy group, a $C_{1-6}$alkoxy group, a $C_{1-6}$acylamino group, a phenyl group, a benzyl group, a phenyloxy group, a naphthyloxy group, and a phenylthio group, or $R^{11}$ and $R^{12}$ form $C_{3-8}$cycloalkane together, $R^{13}$ represents a hydrogen atom or a $C_{1-6}$alkyl group, $R^{14}$ and $R^{15}$ may be the same or different and represent a hydrogen atom or a $C_{1-6}$alkyl group, $R^{16}$ and $R^{17}$ may be the same or different and represent a hydrogen atom or a $C_{1-6}$alkyl group, the substituent group A includes a halogen atom, a $C_{1-6}$alkyl group, a $C_{1-6}$alkoxy group, a $C_{1-6}$alkylthio group, a trifluoromethyl group, a $C_{1-6}$alkylsulfonyl group, a methoxy group substituted with one to three fluorine atoms, a methylthio group substituted with one to three fluorine atoms, a methylsulfonyl group substituted with one to three fluorine atoms, and a nitro group, the substituent group B includes a halogen atom, a $C_{1-6}$alkyl group, a hydroxy group, a $C_{1-6}$alkoxy group, a $C_{1-6}$alkylthio group, a $C_{1-6}$alkylsulfonyl group, a trifluoromethyl group, a methoxy group substituted with one to three fluorine atoms, a methylthio group substituted with one to three fluorine atoms, a methylsulfonyl group substituted with one to three fluorine atoms, a nitro group, a phenoxy group, a benzyloxy group, a ($C_{1-6}$acyl)oxy group, an amino group, a carboxy group, a $C_{3-8}$cycloalkyl group, a $C_{3-8}$cycloalkoxy group, a ($C_{1-6}$alkyl)amino group, a di($C_{1-6}$alkyl)amino group, a hydroxy$C_{1-6}$alkyl group, a $C_{1-6}$alkoxycarbonyl group, a carbamoyl group, a sulfamoyl group, a cyano group, a methylenedioxyphenyl group, a $C_{1-9}$heteroaryl group, a phenyl group, a phenylamino group, a phenylaminocarbonyl group, a phenylcarbonyl group, a $C_{1-9}$heteroarylcarbonyl group, and a phenyl$C_{1-6}$alkyl group (wherein the phenyl group, the phenylamino group, the phenylaminocarbonyl group, the phenylcarbonyl group, the $C_{1-9}$heteroarylcarbonyl group, and the phenyl$C_{1-6}$alkyl group are unsubstituted or substituted with one to three substituents selected from the substituent group A), and the substituent group C includes a methylenedioxy group, an ethylenedioxy group, a trimethylenedioxy group, and an ethyleneoxy group.

(2) The aminopyrrolidine compound, a tautomer, a stereoisomer, a prodrug, or a pharmaceutically acceptable salt of the compound, or a solvate thereof according to the above (1), wherein Het represents an aromatic heterocyclic group represented by the following formula [VI]:

[Formula 4]

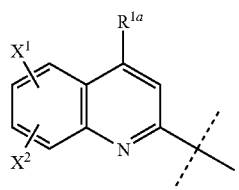

wherein $R^{1a}$, $X^1$, and $X^2$ have the same meanings as defined in the above (1), L represents —CO—, and Ar and $Q^2$ have the same meanings as defined in the above (1) (provided that when $R^{1a}$ is a hydroxy group, a $C_{1-6}$alkyl group, a $C_{1-6}$alkoxy group, a halogen atom, a trifluoromethyl group, or a group represented by —$NR^2R^3$ (wherein, $R^2$ and $R^3$ may be the same or different and represent a hydrogen atom or a $C_{1-6}$alkyl group), (i) Ar represents a phenyl group, a naphthyl group, or a $C_{1-9}$heteroaryl group (wherein the phenyl group, the naphthyl group, and the $C_{1-9}$heteroaryl group are substituted with one substituent selected from the group consisting of a hydroxy group, a $C_{1-6}$alkylthio group, a $C_{1-6}$alkylsulfonyl group, a methoxy group substituted with one to three fluorine atoms, a methylthio group substituted with one to three fluorine atoms, a methylsulfonyl group substituted with one to three fluorine atoms, a nitro group, a phenoxy group, a benzyloxy group, an amino group, a carboxy group, a $C_{3-8}$cycloalkoxy group, a ($C_{1-6}$alkyl)amino group, a di($C_{1-6}$alkyl)amino group, a hydroxy$C_{1-6}$alkyl group, a $C_{1-6}$alkoxycarbonyl group, a carbamoyl group, a sulfamoyl group, a cyano group, a phenyl group (wherein the phenyl group is unsubstituted or substituted with one to three substituents selected from the substituent group A (wherein the substituent group A has the same meaning as defined in the above (1))), a methylenedioxyphenyl group, and a pyridyl group, or are further substituted with one or two substituents selected from the group consisting of a halogen atom, a trifluoromethyl group, a $C_{1-6}$alkyl group, and a $C_{1-6}$alkoxy group), and/or (ii) $Q^2$ represents —$(CR^{11}R^{12})$— (wherein, $R^{11}$ and $R^{12}$ form a $C_{3-8}$cycloalkane together)).

(3) The aminopyrrolidine compound, a tautomer, a stereoisomer, a prodrug, or a pharmaceutically acceptable salt of the compound, or a solvate thereof according to the above (1) or (2), wherein Het represents an aromatic heterocyclic group represented by the following formula [VI]:

[Formula 5]

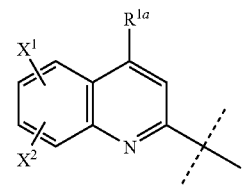

wherein $R^{1a}$ represents a $C_{1-6}$alkyl group, a $C_{1-6}$alkoxy group, or a group represented by the formula —$NR^2R^3$ (wherein, $R^2$ and $R^3$ may be the same or different and represent a hydrogen atom or a $C_{1-6}$alkyl group), and $X^1$ and $X^2$ have the same meanings as defined in the above (1), L represents —CO—, and Ar represents a phenyl group (wherein the phenyl group is substituted with one substituent selected from the group consisting of a hydroxy group, a $C_{1-6}$alkylthio group, a $C_{1-6}$alkylsulfonyl group, a methoxy group substituted with one to three fluorine atoms, a methylthio group substituted with one to three fluorine atoms, a methylsulfonyl group substituted with one to three fluorine atoms, a nitro group, a phenoxy group, a benzyloxy group, an amino group, a carboxy group, a $C_{3-8}$cycloalkoxy group, a ($C_{1-6}$alkyl)amino group, a di($C_{1-6}$alkyl) amino group, a hydroxy$C_{1-6}$alkyl group, a $C_{1-6}$alkoxycarbonyl group, a carbamoyl group, a sulfamoyl group, a cyano group, a phenyl group (wherein the phenyl group is unsubstituted or substituted with one to three substituents selected from the substituent group A (wherein the substituent group A has the same meaning as defined in the above (1))), a methylenedioxyphenyl group, and a pyridyl group, or is further substituted with one to two substituents selected from the group consisting of a halogen atom, a trifluoromethyl group, a $C_{1-6}$alkyl group, and a $C_{1-6}$alkoxy group).

(4) The aminopyrrolidine compound, a tautomer, a stereoisomer, a prodrug, or a pharmaceutically acceptable salt of the compound, or a solvate thereof according to the above (1) or (2), wherein Het represents an aromatic heterocyclic group represented by the following formula [VI]:

[Formula 6]

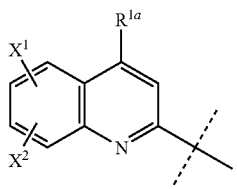

[VI]

wherein $R^{1a}$ represents a $C_{1-6}$alkyl group, a $C_{1-6}$alkoxy group, or a group represented by formula —$NR^2R^3$ (wherein, $R^2$ and $R^3$ may be the same or different and represent a hydrogen atom or a $C_{1-6}$alkyl group), and $X^1$ and $X^2$ have the same meanings as defined in the above (1), L represents —CO—, $Q^1$ represents a single bond, and $Q^2$ represents —($CR^{11}R^{12}$)— (wherein, $R^{11}$ and $R^{12}$ form $C_{3-8}$cycloalkane together).

(5) The aminopyrrolidine compound, a tautomer, a stereoisomer, a prodrug, or a pharmaceutically acceptable salt of the compound, or a solvate thereof according to the above (2), (3), or (4), wherein $R^{1a}$ represents a $C_{1-6}$alkyl group or a $C_{1-6}$alkoxy group.

(6) The aminopyrrolidine compound, a tautomer, a stereoisomer, a prodrug, or a pharmaceutically acceptable salt of the compound, or a solvate thereof according to the above (1) or (2), wherein Het represents an aromatic heterocyclic group represented by the following formula [VI]:

[Formula 7]

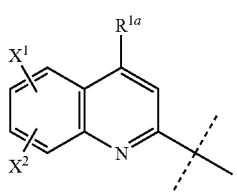

[VI]

wherein $R^{1a}$ represents a group represented by the formula —$NR^2R^3$ (wherein, $R^2$ and $R^3$, together with the nitrogen atom to which they bond, represents a cyclic amino group represented by the formula [V]:

[Formula 8]

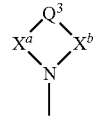

[V]

wherein $X^a$, $X^b$, and $Q^3$ have the same meanings as defined in the above (1)), and $X^1$ and $X^2$ have the same meanings as defined in the above (1), and L represents —CO—.

(7) The aminopyrrolidine compound, a tautomer, a stereoisomer, a prodrug, or a pharmaceutically acceptable salt of the compound, or a solvate thereof according to any one of the above (2) to (6), wherein $Z^1$ represent a hydrogen atom, a hydroxy group, a halogen atom, or a $C_{1-6}$alkoxy group, and $Z^2$, $Z^3$, and $Z^4$ represent a hydrogen atom.

(8) The aminopyrrolidine compound, a tautomer, a stereoisomer, a prodrug, or a pharmaceutically acceptable salt of the compound, or a solvate thereof according to any one of the above (2), (3), (5), (6), and (7), wherein $Q^1$ represents a single bond, and $Q^2$ represents —($CR^{11}R^{12}$)— (wherein, $R^{11}$ and $R^{12}$ both represent a hydrogen atom, or one of them is a methyl group and the other is a hydrogen atom, or $R^{11}$ and $R^{12}$ form cyclopropane together).

(9) The aminopyrrolidine compound, a tautomer, a stereoisomer, a prodrug, or a pharmaceutically acceptable salt of the compound, or a solvate thereof according to the above (1), wherein Het represents an aromatic heterocyclic group represented by the following formula [VI]:

[Formula 9]

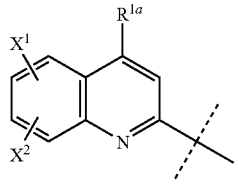

[VI]

wherein $R^{1a}$ has the same meaning as defined in the above (1), $X^1$ represents a hydroxy group, a $C_{1-6}$alkyl group, or a $C_{1-6}$alkoxy group, and $X^2$ represents a halogen atom, and L represents —CO—.

(10) The aminopyrrolidine compound, a tautomer, a stereoisomer, a prodrug, or a pharmaceutically acceptable salt of the compound, or a solvate thereof according to any one of the above (2) to (8), wherein $X^1$ represents a hydrogen atom, a hydroxy group, a $C_{1-6}$alkyl group, or a $C_{1-6}$alkoxy group, and $X^2$ represents a hydrogen atom or a halogen atom.

(11) The aminopyrrolidine compound, a tautomer, a stereoisomer, a prodrug, or a pharmaceutically acceptable salt of the compound, or a solvate thereof according to the above (1), wherein Het represents an aromatic heterocyclic group represented by the following formula [VII]:

[Formula 10]

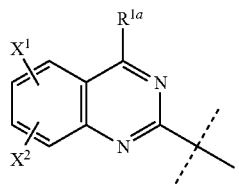

[VII]

wherein $R^{1a}$, $X^1$ and $X^2$ have the same meanings as defined in the above (1), L represents —CO—, and Ar, $Z^1$, and $Q^2$ have the same meanings as defined in the above (1) (provided that when $R^{1a}$ is a hydroxy group, a $C_{1-6}$alkyl group, a $C_{1-6}$alkoxy group, a halogen atom, a trifluoromethyl group, or a group represented by —$NR^2R^3$ (wherein, $R^2$ and $R^3$ may be the same or different and represent a hydrogen atom or a $C_{1-6}$alkyl group, or $R^2$ and $R^3$ form a morpholino group, a 4-acetylpiperazino group, or a 4-phenylpiperazino group together), (i) Ar represents a phenyl group, a naphthyl group, or a $C_{1-9}$heteroaryl group (the phenyl group, the naphthyl group, and the $C_{1-9}$heteroaryl group are substituted with one substituent selected from the group consisting of a hydroxy group, a $C_{1-6}$alkylthio group, a $C_{1-6}$alkylsulfonyl group, a methoxy group substituted with one to three fluorine atoms, a methylthio group substituted with one to three fluorine atoms, a methylsulfonyl group substituted with one to three fluorine atoms, a nitro group, a phenoxy group, a benzyloxy group, an amino group, a carboxy group, a $C_{3-8}$cycloalkoxy group, a ($C_{1-6}$alkyl)amino group, a di($C_{1-6}$alkyl)amino group, a hydroxy$C_{1-6}$alkyl group, a $C_{1-6}$alkoxycarbonyl group, a carbamoyl group, a sulfamoyl group, a cyano group, a phenyl group (wherein the phenyl group is unsubstituted or substituted with one to three substituents selected from the substituent group A (wherein the substituent group A has the same meaning as defined in the above (1))), a methylenedioxyphenyl group, and a pyridyl group, or are further substituted with one or two substituents selected from the group consisting of a halogen atom, a trifluoromethyl group, a $C_{1-6}$alkyl group, and a $C_{1-6}$alkoxy group), and $X^1$ represents a group selected from the group consisting of a $C_{1-6}$alkyl group, a $C_{1-6}$alkoxy group, a halogen atom, a phenyl group, a trifluoromethyl group, a hydroxy group, a $C_{3-8}$cycloalkyl group, a $C_{3-8}$cycloalkoxy group, a ($C_{1-6}$alkyl)amino group, a di($C_{1-6}$alkyl)amino group, a hydroxy$C_{1-6}$alkyl group, and a methoxy group substituted with one to three fluorine atoms, (ii) $Q^2$ represents —($CR^{11}R^{12}$)— (wherein, $R^{11}$ and $R^{12}$ form $C_{3-8}$cycloalkane together), and $X^1$ represents a group selected from the group consisting of a $C_{1-6}$alkyl group, a $C_{1-6}$alkoxy group, a halogen atom, a phenyl group, a trifluoromethyl group, a hydroxy group, a $C_{3-8}$cycloalkyl group, a $C_{3-8}$cycloalkoxy group, a ($C_{1-6}$alkyl)amino group, a di($C_{1-6}$alkyl)amino group, a hydroxy$C_{1-6}$alkyl group, and a methoxy group substituted with one to three fluorine atoms, (iii) Ar represents a phenyl group, a naphthyl group, or a $C_{1-9}$heteroaryl group (wherein the phenyl group, the naphthyl group, and the $C_{1-9}$heteroaryl group are substituted with one substituent selected from the group consisting of a hydroxy group, a $C_{1-6}$alkylthio group, a $C_{1-6}$alkylsulfonyl group, a methoxy group substituted with one to three fluorine atoms, a methylthio group substituted with one to three fluorine atoms, a methylsulfonyl group substituted with one to three fluorine atoms, a nitro group, a phenoxy group, a benzyloxy group, an amino group, a carboxy group, a $C_{3-8}$cycloalkoxy group, a ($C_{1-6}$alkyl)amino group, a di($C_{1-6}$alkyl)amino group, a hydroxy$C_{1-6}$alkyl group, a $C_{1-6}$alkoxycarbonyl group, a carbamoyl group, a sulfamoyl group, a cyano group, a phenyl group (wherein the phenyl group is unsubstituted or substituted with one to three substituents selected from the substituent group A (wherein the substituent group A has the same meaning as defined in the above (1))), a methylenedioxyphenyl group, and a pyridyl group, or are further substituted with one or two substituents selected from the group consisting of a halogen atom, a trifluoromethyl group, a $C_{1-6}$alkyl group, and a $C_{1-6}$alkoxy group), and $Z^1$ represents a group selected from the group consisting of a hydroxy group, a $C_{1-6}$alkoxy group, and a halogen atom, or (iv) $Q^2$ represents a group represented by —($CR^{11}R^{12}$)— (wherein, $R^{11}$ and $R^{12}$ form $C_{3-8}$cycloalkane together), and $Z^1$ represents a group selected from the group consisting of a hydroxy group, a $C_{1-6}$alkoxy group, and a halogen atom).

(12) The aminopyrrolidine compound, a tautomer, a stereoisomer, a prodrug, or a pharmaceutically acceptable salt of the compound, or a solvate thereof according to the above (1) or (11), wherein Het represents an aromatic heterocyclic group represented by the following formula [VII]:

[Formula 11]

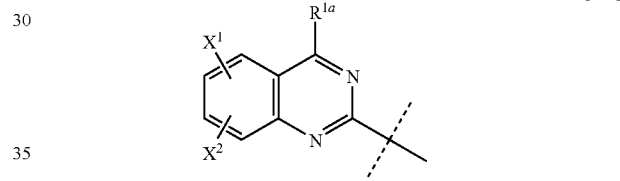

[VII]

wherein $R^{1a}$ represents a $C_{1-6}$alkyl group, a $C_{1-6}$alkoxy group, or a group represented by formula —$NR^2R^3$ (wherein, $R^2$ and $R^3$ may be the same or different and represent a hydrogen atom or a $C_{1-6}$alkyl group, or $R^2$ and $R^3$ form a morpholino group, a 4-acetylpiperazino group, or a 4-phenylpiperazino group together), $X^1$ represents a group selected from the group consisting of a $C_{1-6}$alkyl group, a $C_{1-6}$alkoxy group, a halogen atom, a phenyl group, a trifluoromethyl group, a hydroxy group, a $C_{3-8}$cycloalkyl group, a $C_{3-8}$cycloalkoxy group, a ($C_{1-6}$alkyl)amino group, a di($C_{1-6}$alkyl)amino group, a hydroxy$C_{1-6}$alkyl group, and a methoxy group substituted with one to three fluorine atoms, and $X^2$ has the same meanings as defined in the above (1), L represents —CO—, and Ar represents a phenyl group, a naphthyl group, or a $C_{1-9}$heteroaryl group (wherein the phenyl group, the naphthyl group, and the $C_{1-9}$heteroaryl group are substituted with one substituent selected from the group consisting of a hydroxy group, a $C_{1-6}$alkylthio group, a $C_{1-6}$alkylsulfonyl group, a methoxy group substituted with one to three fluorine atoms, a methylthio group substituted with one to three fluorine atoms, a methylsulfonyl group substituted with one to three fluorine atoms, a nitro group, a phenoxy group, a benzyloxy group, an amino group, a carboxy group, a $C_{3-8}$cycloalkoxy group, a ($C_{1-6}$alkyl)amino group, a di($C_{1-6}$alkyl)amino group, a hydroxy$C_{1-6}$alkyl group, a $C_{1-6}$alkoxycarbonyl group, a carbamoyl group, a sulfamoyl group, a cyano group, a phenyl group (wherein the phenyl group is unsubstituted or substituted with one to three substituents selected from the substituent group A (wherein the substituent group A has the same meaning as defined in the above (1))), a methylenedioxyphenyl group, and a pyridyl group, or are further substituted with one or two substituents selected from the group consisting of a halogen atom, a trifluoromethyl group, a $C_{1-6}$alkyl group, and a $C_{1-6}$alkoxy group).

(13) The aminopyrrolidine compound, a tautomer, a stereoisomer, a prodrug, or a pharmaceutically acceptable salt of the compound, or a solvate thereof according to the above (1) or (11), wherein Het represents an aromatic heterocyclic group represented by the following formula [VII]:

[Formula 12]

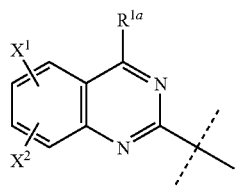

wherein $R^{1a}$ represents a $C_{1-6}$alkyl group, a $C_{1-6}$alkoxy group, or a group represented by —$NR^2R^3$ (wherein, $R^2$ and $R^3$ may be the same or different and represent a hydrogen atom or a $C_{1-6}$alkyl group, or $R^2$ and $R^3$ form a morpholino group, a 4-acetylpiperazino group, or a 4-phenylpiperazino group together), and $X^1$ and $X^2$ have the same meanings as defined in the above (1), $Z^1$ represents a group selected from the group consisting of a hydrogen atom, a hydroxy group, a $C_{1-6}$alkoxy group, and a halogen atom, L represents —CO—, and Ar represents a phenyl group, a naphthyl group, or a $C_{1-9}$heteroaryl group (wherein the phenyl group, the naphthyl group, and the $C_{1-9}$heteroaryl group are substituted with one substituent selected from the group consisting of a hydroxy group, a $C_{1-6}$alkylthio group, a $C_{1-6}$alkylsulfonyl group, a methoxy group substituted with one to three fluorine atoms, a methylthio group substituted with one to three fluorine atoms, a methylsulfonyl group substituted with one to three fluorine atoms, a nitro group, a phenoxy group, a benzyloxy group, an amino group, a carboxy group, a $C_{3-8}$cycloalkoxy group, a ($C_{1-6}$alkyl)amino group, a di($C_{1-6}$alkyl)amino group, a hydroxy$C_{1-6}$alkyl group, a $C_{1-6}$alkoxycarbonyl group, a carbamoyl group, a sulfamoyl group, a cyano group, a phenyl group (wherein the phenyl group is unsubstituted or substituted with one to three substituents selected from the substituent group A (wherein the substituent group A has the same meaning as defined in the above (1))), a methylenedioxyphenyl group, and a pyridyl group, or are further substituted with one or two substituents selected from the group consisting of a halogen atom, a trifluoromethyl group, a $C_{1-6}$alkyl group, and a $C_{1-6}$alkoxy group).

(14) The aminopyrrolidine compound, a tautomer, a stereoisomer, a prodrug, or a pharmaceutically acceptable salt of the compound, or a solvate thereof according to the above (1) or (11), wherein Het represents an aromatic heterocyclic group represented by the following formula [VII]:

[Formula 13]

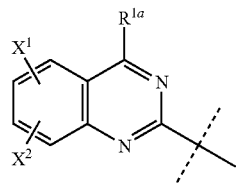

wherein $R^{1a}$ represents a $C_{1-6}$alkyl group, a $C_{1-6}$alkoxy group, or a group represented by formula —$NR^2R^3$ (wherein, $R^2$ and $R^3$ may be the same or different and represent a hydrogen atom or a $C_{1-6}$alkyl group, or $R^2$ and $R^3$ form a morpholino group, a 4-acetylpiperazino group, or a 4-phenylpiperazino group together), and $X^1$ represents a group selected from the group consisting of a $C_{1-6}$alkyl group, a $C_{1-6}$alkoxy group, a halogen atom, a phenyl group, a trifluoromethyl group, a hydroxy group, a $C_{3-8}$cycloalkyl group, a $C_{3-8}$cycloalkoxy group, a ($C_{1-6}$alkyl)amino group, a di($C_{1-6}$alkyl)amino group, a hydroxy$C_{1-6}$alkyl group, and a methoxy group substituted with one to three fluorine atoms), L represents —CO—, and $Q^2$ represents —($CR^{11}R^{12}$)— (wherein, $R^{11}$ and $R^{12}$ form $C_{3-8}$cycloalkane together).

(15) The aminopyrrolidine compound, a tautomer, a stereoisomer, a prodrug, or a pharmaceutically acceptable salt of the compound, or a solvate thereof according to the above (1) or (11), wherein Het represents an aromatic heterocyclic group represented by the following formula [VII]:

[Formula 14]

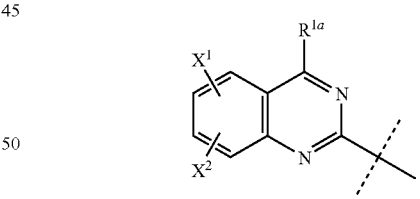

wherein $R^{1a}$ represents a $C_{1-6}$alkyl group, a $C_{1-6}$alkoxy group, or a group represented by the formula —$NR^2R^3$ (wherein, $R^2$ and $R^3$ may be the same or different and represent a hydrogen atom or a $C_{1-6}$alkyl group, or $R^2$ and $R^3$ form a morpholino group, a 4-acetylpiperazino group, or a 4-phenylpiperazino group together), and $X^1$ and $X^2$ have the same meanings as defined in the above (1), $Z^1$ represents a group selected from the group consisting of a hydrogen atom, a hydroxy group, a $C_{1-6}$alkoxy group, and a halogen atom, L represents —CO—, and $Q^2$ represents —($CR^{11}R^{12}$)— (wherein, $R^{11}$ and $R^{12}$ form a $C_{3-8}$cycloalkane together).

(16) The aminopyrrolidine compound, a tautomer, a stereoisomer, a prodrug, or a pharmaceutically acceptable salt of the compound, or a solvate thereof according to the above (1) or (11), wherein Het represents an aromatic heterocyclic group represented by the following formula [VII]:

[Formula 15]

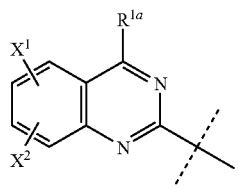

[VII]

wherein $R^{1a}$ represents a group represented by formula —$NR^2R^3$ (wherein, $R^2$ represents a pyrrolidin-3-yl group, a piperidin-3-yl group, or a piperidin-4-yl group (wherein the pyrrolidin-3-yl group, the piperidin-3-yl group, and the piperidin-4-yl group are unsubstituted or substituted with a $C_{1-6}$alkyl group, a $C_{1-6}$alkylsulfonyl group, or a $C_{1-6}$acyl group)), and $X^1$ and $X^2$ have the same meanings as defined in the above (1), and L represents —CO—.

(17) The aminopyrrolidine compound, a tautomer, a stereoisomer, a prodrug, or a pharmaceutically acceptable salt of the compound, or a solvate thereof according to the above (1) or (11), wherein Het represents an aromatic heterocyclic group represented by the following formula [VII]:

[Formula 16]

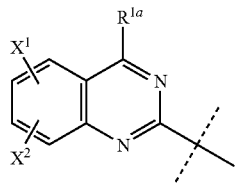

[VII]

wherein $R^{1a}$ represents a group represented by formula —$NR^2R^3$ (wherein, $R^2$ and $R^3$, together with the nitrogen atom to which they bond, represent a cyclic amino group represented by the formula [V]:

[Formula 17]

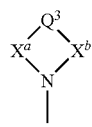

[V]

wherein $X^a$, $X^b$, and $Q^3$ have the same meanings as defined in the above (1)), and $X^1$ and $X^2$ have the same meanings as defined in the above (1), $Z^1$ has the same meaning as defined in the above (1) (provided that when the cyclic amino group represented by the formula (V) represents a morpholino group, a 4-acetylpiperazino group, or a 4-phenylpiperazino group, (i) $X^1$ represents a group selected from the group consisting of a $C_{1-6}$alkyl group, a $C_{1-6}$alkoxy group, a halogen atom, a phenyl group, a trifluoromethyl group, a hydroxy group, a $C_{3-8}$cycloalkyl group, a $C_{3-8}$cycloalkoxy group, a ($C_{1-6}$alkyl)amino group, a di($C_{1-6}$alkyl)amino group, a hydroxy$C_{1-6}$alkyl group, and a methoxy group substituted with one to three fluorine atoms, and/or (ii) $Z^1$ represents a group selected from the group consisting of a hydrogen atom, a hydroxy group, a $C_{1-6}$alkoxy group, or a halogen atom), and L represents —CO—.

(18) The aminopyrrolidine compound, a tautomer, a stereoisomer, a prodrug, or a pharmaceutically acceptable salt of the compound, or a solvate thereof according to any one of the above (11) to (17), wherein $Z^1$ represents a hydrogen atom, a hydroxy group, a halogen atom, or a $C_{1-6}$alkoxy group, and $Z^2$, $Z^3$, and $Z^4$ represent a hydrogen atom.

(19) The aminopyrrolidine compound, a tautomer, a stereoisomer, a prodrug, or a pharmaceutically acceptable salt of the compound, or a solvate thereof according to any one of the above (11), (12), (13), (16), and (17), wherein $Q^1$ represents a single bond, and $Q^2$ represents —($CR^{11}R^{12}$)— (wherein, $R^{11}$ and $R^{12}$ both represent a hydrogen atom or one of them is a methyl group and the other is a hydrogen atom, or $R^{11}$ and $R^{12}$ form cyclopropane together).

(20) The aminopyrrolidine compound, a tautomer, a stereoisomer, a prodrug, or a pharmaceutically acceptable salt of the compound, or a solvate thereof according to the above (14) or (15), wherein $Q^1$ represents a single bond.

(21) The aminopyrrolidine compound, a tautomer, a stereoisomer, a prodrug, or a pharmaceutically acceptable salt of the compound, or a solvate thereof according to any one of the above (11) to (17), wherein $X^1$ represents a hydrogen atom, a hydroxy group, a $C_{1-6}$alkyl group, a $C_{1-6}$alkoxy group, or a halogen atom, and $X^2$ represents a hydrogen atom or a halogen atom.

(22) The aminopyrrolidine compound, a tautomer, a stereoisomer, a prodrug, or a pharmaceutically acceptable salt of the compound, or a solvate thereof according to the above (1), wherein Het represents an aromatic heterocyclic group represented by the following formula [III]:

[Formula 18]

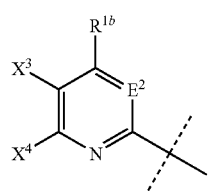

[III]

wherein $R^{1b}$, $X^3$, $X^4$, and $E^2$ have the same meanings as defined in the above (1), L represents —CO—, and Ar and $Q^2$ have the same meanings as defined in the above (1) (provided that when $R^{1b}$ represents a hydroxy group, a $C_{1-6}$alkyl group, a $C_{1-6}$alkoxy group, halogen atom, a trifluoromethyl group, or a group represented by —$NR^2R^3$ (wherein, $R^2$ and $R^3$ may be the same or different and represent a hydrogen atom or a $C_{1-6}$alkyl group), (i) Ar represents a phenyl group, a naphthyl group, or a $C_{1-9}$heteroaryl group (wherein the phenyl group, the naphthyl group, and the $C_{1-9}$heteroaryl group are substituted with one substituent selected from the group consisting of a hydroxy group, a $C_{1-6}$alkylthio group, a $C_{1-6}$alkylsulfonyl group, a methoxy group substituted with one to three fluorine atoms, a methylthio group substituted with one to three fluorine atoms, a methylsulfonyl group substituted with one to three fluorine atoms, a nitro group, a phenoxy group, a benzyloxy group, an amino group, a carboxy group, a $C_{3-8}$cycloalkoxy group, a $(C_{1-6}$alkyl)amino group, a di$(C_{1-6}$alkyl)amino group, a hydroxy$C_{1-6}$alkyl group, a $C_{1-6}$alkoxycarbonyl group, a carbamoyl group, a sulfamoyl group, a cyano group, a phenyl group (wherein the phenyl group is unsubstituted or substituted with one to three substituents selected from the substituent group A (wherein the substituent group A has the same meaning as defined in the above (1))), a methylenedioxyphenyl group, and a pyridyl group, or are further substituted with one or two substituents selected from the group consisting of a halogen atom, a trifluoromethyl group, a $C_{1-6}$alkyl group, and a $C_{1-6}$alkoxy group), and/or (ii) $Q^2$ represents —$(CR^{11}R^{12})$— (wherein, $R^{11}$ and $R^{12}$ form $C_{3-8}$cycloalkane together)).

(23) The aminopyrrolidine compound, a tautomer, a stereoisomer, a prodrug, or a pharmaceutically acceptable salt of the compound, or a solvate thereof according to the above (1) or (22), wherein Het represents an aromatic heterocyclic group represented by the following formula [III]:

[Formula 19]

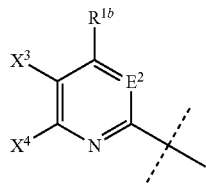

[III]

wherein $R^{1b}$ represents a $C_{1-6}$alkyl group, a $C_{1-6}$alkoxy group, or a group represented by formula —$NR^2R^3$ (wherein, $R^2$ and $R^3$ may be the same or different and represent a hydrogen atom or a $C_{1-6}$alkyl group), and $E^2$, $X^3$, and $X^4$ have the same meanings as defined in the above (1), L represents —CO—, and Ar represents a phenyl group (wherein the phenyl group is substituted with one substituent selected from the group consisting of a hydroxy group, a $C_{1-6}$alkylthio group, a $C_{1-6}$alkylsulfonyl group, a methoxy group substituted with one to three fluorine atoms, a methylthio group substituted with one to three fluorine atoms, a methylsulfonyl group substituted with one to three fluorine atoms, a nitro group, a phenoxy group, a benzyloxy group, an amino group, a carboxy group, a $C_{3-8}$cycloalkoxy group, a $(C_{1-6}$alkyl)amino group, a di$(C_{1-6}$alkyl)amino group, a hydroxy$C_{1-6}$alkyl group, a $C_{1-6}$alkoxycarbonyl group, a carbamoyl group, a sulfamoyl group, a cyano group, a phenyl group (wherein the phenyl group is unsubstituted or substituted with one to three substituents selected from the substituent group A (wherein the substituent group A has the same meaning as defined in the above (1))), a methylenedioxy phenyl group, and a pyridyl group, or is further substituted with one or two substituents selected from the group consisting of a halogen atom, a trifluoromethyl group, a $C_{1-6}$alkyl group, and a $C_{1-6}$alkoxy group).

(24) The aminopyrrolidine compound, a tautomer, a stereoisomer, a prodrug, or a pharmaceutically acceptable salt of the compound, or a solvate thereof according to the above (1) or (22), wherein Het represents an aromatic heterocyclic group represented by the following formula [III]:

[Formula 20]

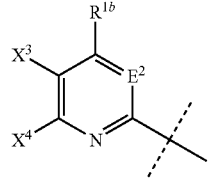

[III]

wherein $R^{1b}$ represents a $C_{1-6}$alkyl group, a $C_{1-6}$alkoxy group, or a group represented by formula —$NR^2R^3$ (wherein, $R^2$ and $R^3$ may be the same or different and represent a hydrogen atom or a $C_{1-6}$alkyl group), and $E^2$, $X^3$, and $X^4$ have the same meanings as defined in the above (1), L represents —CO—, and $Q^2$ represents —$(CR^{11}R^{12})$— (wherein, $R^{11}$ and $R^{12}$ form $C_{3-8}$cycloalkane together).

(25) The aminopyrrolidine compound, a tautomer, a stereoisomer, a prodrug, or a pharmaceutically acceptable salt of the compound, or a solvate thereof according to the above (1) or (22), wherein Het represents an aromatic heterocyclic group represented by the following formula [III]:

[Formula 21]

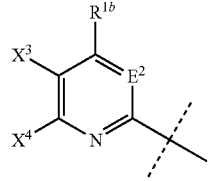

[III]

wherein $R^{1b}$ represents a group represented by formula —$NR^2R^3$ (wherein, $R^2$ and $R^3$, together with the nitrogen atom to which they bond, represent a cyclic amino group represented by the formula [V]:

[Formula 22]

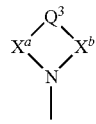

[V]

wherein $X^a$, $X^b$, and $Q^3$ have the same meanings as defined in the above (1), and $E^2$, $X^3$, and $X^4$ have the same meanings as defined in the above (1)), and L represents —CO—.

(26) The aminopyrrolidine compound, a tautomer, a stereoisomer, a prodrug, or a pharmaceutically acceptable salt of the compound, or a solvate thereof according to any one of the above (22) to (25), wherein $E^2$ represents a nitrogen atom.

(27) The aminopyrrolidine compound, a tautomer, a stereoisomer, a prodrug, or a pharmaceutically acceptable salt of the compound, or a solvate thereof according to any one of the above (22) to (25), wherein $E^2$ represents CH.

(28) The aminopyrrolidine compound, a tautomer, a stereoisomer, a prodrug, or a pharmaceutically acceptable salt of the compound, or a solvate thereof according to any one of the above (22) to (27), wherein $Z^1$ represents a hydrogen atom, a hydroxy group, a halogen atom, or a $C_{1-6}$alkoxy group, and $Z^2$, $Z^3$, and $Z^4$ represent a hydrogen atom.

(29) The aminopyrrolidine compound, a tautomer, a stereoisomer, a prodrug, or a pharmaceutically acceptable salt of the compound, or a solvate thereof according to any one of the above (22), (23), (25), (26), and (27), wherein $Q^1$ represents a single bond, and $Q^2$ represents —($CR^{11}R^{12}$)— (wherein, $R^{11}$ and $R^{12}$ both represent a hydrogen atom or one of them is a methyl group and the other is a hydrogen atom, or $R^{11}$ and $R^{12}$ form a cyclopropane together).

(30) The aminopyrrolidine compound, a tautomer, a stereoisomer, a prodrug, or a pharmaceutically acceptable salt of the compound, or a solvate thereof according to the above (24), wherein $Q^1$ represents a single bond.

(31) The aminopyrrolidine compound, a tautomer, a stereoisomer, a prodrug, or a pharmaceutically acceptable salt of the compound, or a solvate thereof according to any one of the above (22) to (27), wherein $X^3$ represents a hydrogen atom, and $X^4$ represents a methyl group.

(32) The aminopyrrolidine compound, a tautomer, a stereoisomer, a prodrug, or a pharmaceutically acceptable salt of the compound, or a solvate thereof according to the above (1), wherein Het represents an aromatic heterocyclic group represented by the following formula [IV]:

[Formula 23]

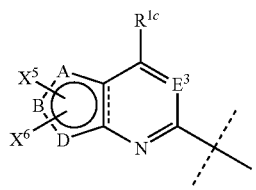

[IV]

wherein $R^{1c}$, $X^5$, $X^6$, and A—B—D have the same meanings as defined in the above (1), and $E^3$ represents a nitrogen atom or CH, and L represents —CO—.

(33) The aminopyrrolidine compound, a tautomer, a stereoisomer, a prodrug, or a pharmaceutically acceptable salt of the compound, or a solvate thereof according to the above (1) or (32), wherein Het represents an aromatic heterocyclic group represented by the following formula [VIII]:

[Formula 24]

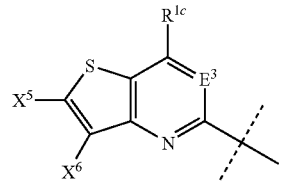

[VIII]

wherein $R^{1c}$, $X^5$, and $X^6$ have the same meanings as defined in the above (1), $E^3$ represents a nitrogen atom or CH.

(34) The aminopyrrolidine compound, a tautomer, a stereoisomer, a prodrug, or a pharmaceutically acceptable salt of the compound, or a solvate thereof according to the above (1) or (32), wherein Het represents an aromatic heterocyclic group represented by the following formula [IX]:

[Formula 25]

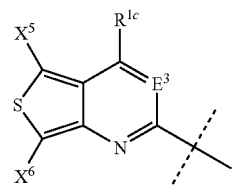

[IX]

wherein $R^{1c}$, $X^5$, and $X^6$ have the same meanings as defined in the above (1), and $E^3$ represents a nitrogen atom or CH.

(35) The aminopyrrolidine compound, a tautomer, a stereoisomer, a prodrug, or a pharmaceutically acceptable salt of the compound, or a solvate thereof according to any one of the above (32) to (34), wherein $Z^1$ represents a hydrogen atom, a hydroxy group, a halogen atom, or a $C_{1-6}$alkoxy group, and $Z^2$, $Z^3$, and $Z^4$ represent a hydrogen atom.

(36) The aminopyrrolidine compound, a tautomer, a stereoisomer, a prodrug, or a pharmaceutically acceptable salt of the compound, or a solvate thereof according to any one of the above (32) to (34), wherein $Q^1$ represents a single bond, and $Q^2$ represents —($CR^{11}R^{12}$)— (wherein, $R^{11}$ and $R^{12}$ may be the same or different and represent a hydrogen atom or a methyl group, or $R^{11}$ and $R^{12}$ form a cyclopropane together).

(37) The aminopyrrolidine compound, a tautomer, a stereoisomer, a prodrug, or a pharmaceutically acceptable salt of the compound, or a solvate thereof according to any one of the above (32) to (34), wherein $X^5$ and $X^6$ represent a hydrogen atom.

(38) An $MC_4$ receptor antagonist, containing the aminopyrrolidine compound, a tautomer, a stereoisomer, a prodrug, or a pharmaceutically acceptable salt of the compound, or a solvate thereof according to any one of the above (1) to (37) as an active ingredient.

(39) A prophylactic or therapeutic agent for depression, anxiety, anorexia, cachexia, pain, and drug dependence, containing the aminopyrrolidine compound, a tautomer, a stereoisomer, a prodrug, or a pharmaceutically acceptable salt of the compound, or a solvate thereof according to any one of the above (1) to (37) as an active ingredient.

The present invention can provide anxiolytic agents, antidepressants, therapeutic agent for eating disorder such as cachexia and anorexia which have antagonistic effects on the $MC_4$ receptor and enables prophylactic and therapeutic treatment of pain and drug dependence.

BEST MODE FOR CARRYING OUT THE INVENTION

Hereafter, the present invention will be described more specifically.

First, the terms used in the present specification will be explained.

In the present specification, "n" means normal, "i" means iso, "s" means secondary, "t" means tertiary, "c" means cyclo, "o" means ortho, "m" means metha, "p" means para, "Ph" means phenyl, "Py" means pyridyl, "Bn" means benzyl, "Me" means methyl, "Et" means ethyl, "Pr" means propyl, and "Bu" means butyl.

"$C_{1-6}$alkyl group" means straight or branched alkyl groups having 1 to 6 carbon atoms, and examples thereof include a methyl group, an ethyl group, an n-propyl group, an i-propyl group, an n-butyl group, an i-butyl group, a t-butyl group, an n-pentyl group, an i-pentyl group, and an n-hexyl group.

Examples of "$C_{3-8}$cycloalkyl group" include a c-propyl group, a c-butyl group, a c-pentyl group, a c-hexyl group, a c-heptyl group, and a c-octyl group.

"$C_{1-6}$alkoxy group" means straight or branched alkoxy groups having 1 to 6 carbon atoms, and examples thereof include a methoxy group, an ethoxy group, an n-propoxy group, an i-propoxy group, an n-butoxy group, an i-butyloxy group, an n-pentyloxy group, an i-pentyloxy group, and an n-hexyloxy group.

"Hydroxy$C_{2-6}$alkoxy group" means $C_{2-6}$alkoxy groups having a hydroxy group as a substituent, and examples thereof include a 2-hydroxyethoxy group, a 3-hydroxy-n-propoxy group, and a 2-hydroxy-n-propoxy group.

Examples of "$C_{3-8}$cycloalkoxy group" include a c-propyloxy group, a c-butyloxy group, a c-pentyloxy group, a c-hexyloxy group, a c-heptyloxy group, and a c-octyloxy group.

"Halogen atom" means a fluorine atom, a chlorine atom, a bromine atom, or an iodine atom.

"Di($C_{1-6}$alkyl)aminocarbonyl group" means aminocarbonyl groups having 2 $C_{1-6}$alkyl groups as substituents, and examples thereof include a dimethylaminocarbonyl group and a diethylaminocarbonyl group.

"($C_{1-6}$alkyl)aminocarbonyl group" means aminocarbonyl groups having 1 $C_{1-6}$alkyl group as a substituent, and examples thereof include a methylaminocarbonyl group and an ethylaminocarbonyl group.

"($C_{1-6}$alkyl)amino group" means amino groups having 1 $C_{1-6}$alkyl group as a substituent, and examples thereof include a methylamino group and an ethylamino group.

"Di($C_{1-6}$alkyl)amino group" means amino groups having 2 $C_{1-6}$alkyl groups as substituents, and examples thereof include a dimethylamino group and a diethylamino group.

"Hydroxy$C_{1-6}$alkyl group" means $C_{1-6}$alkyl groups having a hydroxy group as a substituent, and examples thereof include a hydroxymethyl group, a 2-hydroxyethyl group, and a 3-hydroxypropyl group.

"$C_{1-6}$alkylthio group" means straight or branched alkylthio groups having 1 to 6 carbon atoms, and examples thereof include a methylthio group, an ethylthio group, an n-propylthio group, an i-propylthio group, an n-butylthio group, an i-butylthio group, an n-pentylthio group, an i-pentylthio group, and an n-hexylthio group.

"$C_{1-6}$alkylsulfonyl group" means straight or branched alkylsulfonyl groups having 1 to 6 carbon atoms, and examples thereof include a methanesulfonyl group, an ethylsulfonyl group, a propane-1-sulfonyl group, a 2-methylpropane-1-sulfonyl group, a butane-1-sulfonyl group, a 2-methylpropane-1-sulfonyl group, a pentane-1-sulfonyl group, a 3-methylbutane-1-sulfonyl group, and a hexane-1-sulfonyl group.

"$C_{1-9}$heteroaryl group" means monocyclic or bicyclic heteroaryl groups having 1 to 9 carbon atoms which have 1 to 4 hetero atoms selected from the group consisting of a nitrogen atom, a sulfur atom, and an oxygen atom, and examples thereof include a thienyl group, a furyl group, a thiazolyl group, an oxazolyl group, an isooxazolyl group, an imidazolyl group, a pyrazolyl group, a triazolyl group, a tetrazolyl group, a pyridyl group, a pyrimidyl group, a pyrazinyl group, a pyridazinyl group, a benzofuranyl group, a benzothienyl group, an indolyl group, an isoindolyl group, a benzoimidazolyl group, a quinolyl group, a quinoxalinyl group, a purinyl group, and 2-oxo-2H-chromen-8-yl.

"$C_{1-9}$heteroarylcarbonyl group" means carbonyl groups having a $C_{1-9}$heteroaryl group, and examples thereof include a pyridylcarbonyl group, a pyrimidylcarbonyl group, an imidazolylcarbonyl group, and a pyrazylcarbonyl group.

"$C_{1-6}$alkoxycarbonyl group" means carbonyl groups having a $C_{1-6}$alkoxy group, and examples thereof include a methoxycarbonyl group and an ethoxycarbonyl group.

Examples of "$C_{3-8}$cycloalkane" include c-propane, c-butane, c-pentane, c-hexane, c-heptane, and c-octane.

"$C_{1-6}$acyl group" means straight or branched acyl groups having 1 to 6 carbon atoms, and examples thereof include a formyl group, an acetyl group, a propionyl group, an n-butyryl group, an i-butyryl group, an n-varelyl group, an i-varelyl group, and a pivaloyl group "Amino$C_{1-6}$alkyl group" means $C_{1-6}$alkyl groups having an amino group as a substituent, and examples thereof include an aminomethyl group, a 2-aminoethyl group, and a 3-aminopropyl group.

"Di$C_{1-6}$alkylamino$C_{1-6}$alkyl group" means $C_{1-6}$alkyl groups having a di$C_{1-6}$alkyl amino group as a substituent, and examples thereof include a dimethylaminomethyl group, a 2-(dimethylamino)ethyl group, and a 3-(dimethylamino)propyl group.

"$C_{1-6}$alkoxy$C_{1-6}$alkyl group" means $C_{1-6}$alkyl groups having a $C_{1-6}$alkoxy group as a substituent, and examples thereof include a methoxymethyl group, a 2-methoxyethyl group and 3-methoxypropyl group.

"$C_{1-6}$alkylsulfonylamino group" means amino groups having a $C_{1-6}$alkylsulfonyl group as a substituent, and examples thereof include a methanesulfonylamino group and an ethanesulfonylamino group.

"$C_{1-6}$alkylsulfonylamino$C_{1-6}$alkyl group" means $C_{1-6}$alkyl groups substituted by a $C_{1-6}$alkylsulfonylamino group, and examples thereof include a methanesulfonylaminomethyl group and a 2-(methanesulfonylamino)ethyl group.

"$C_{3-8}$cycloalkylcarbonyl group" means carbonyl groups having a $C_{3-8}$cycloalkyl group, and examples thereof include a c-propylcarbonyl group, a c-butylcarbonyl group, a c-pentylcarbonyl group, and a c-hexylcarbonyl group.

"$C_{1-6}$acylamino group" means amino groups having a $C_{1-6}$acyl group as a substituent, and examples thereof include a formyl amino group, an acetyl amino group, and a propionylamino group.

"$C_{1-6}$acyloxy group" means straight or branched acyloxy groups having 1 to 6 carbon atoms, and examples thereof include an acetoxy group, a propionyloxy group, and a butyryloxy group.

Examples of "straight $C_{1-3}$alkylene group" include a methylene group, an ethylene group, or a trimethylene group.

Examples of "phenyl$C_{1-6}$alkyl group" include a benzyl group and a 2-phenylethyl group.

Preferred embodiments of the compounds of the present invention are as follows.

Specifically, preferred $E^1$ is a nitrogen atom or CH.

Preferred $E^2$ is a nitrogen atom or CH.

Preferred $E^3$ is a nitrogen atom or CH.

Preferred $R^{1a}$, $R^{1b}$, and $R^{1c}$ are a $C_{1-6}$alkyl group or a $C_{1-6}$alkoxy group. More preferred $R^{1a}$ is a methyl group or a methoxy group.

Other preferred $R^{1a}$, $R^{1b}$, and $R^{1c}$ are a group represented by —$NR^2R^3$ (where, $R^2$ and $R^3$ may be the same or different and represent a hydrogen atom, a $C_{1-6}$alkyl group (the $C_{1-6}$alkyl group is unsubstituted or substituted with one or two substituents selected from the group consisting of a hydroxy group, a carboxy group, a carbamoyl group, a cyano group, a $C_{1-6}$alkoxy group, a $C_{3-8}$cycloalkyl group, a morpholino group, a phenyl group, a $C_{1-9}$heteroaryl group, a phenoxy group, a di($C_{1-6}$alkyl)aminocarbonyl group, a $C_{1-6}$alkoxycarbonyl group, a 1-($C_{1-6}$alkylsulfonyl)piperidin-4-yl group, and a 1-($C_{1-6}$acyl)piperidin-4-yl group), a $C_{3-8}$cycloalkyl group, a pyrrolidin-3-yl group, a piperidin-3-yl group, or a piperidin-4-yl group (the pyrrolidin-3-yl group, the piperidin-3-yl group, and the piperidin-4-yl group are unsubstituted or substituted with a $C_{1-6}$alkyl group, a $C_{1-6}$alkylsulfonyl group, or a $C_{1-6}$acyl group)). More preferred $R^{1a}$, $R^{1b}$, and $R^{1c}$ are a group represented by the —$NR^2R^3$ (where, $R^2$ and $R^3$ may be the same or different and represent a hydrogen atom, a $C_{1-6}$alkyl group (the $C_{1-6}$alkyl group is unsubstituted or substituted with one or two substituents selected from the group consisting of a hydroxy group, a cyano group, a $C_{1-6}$alkoxy group, a morpholino group, a phenyl group, a $C_{1-9}$heteroaryl group, a di($C_{1-6}$alkyl)aminocarbonyl group, a 1-($C_{1-6}$alkylsulfonyl)piperidin-4-yl group, and a 1-($C_{1-6}$acyl)piperidin-4-yl group), a pyrrolidin-3-yl group, a piperidin-3-yl group, or piperidin-4-yl group (the pyrrolidin-3-yl group, the piperidin-3-yl group, and the piperidin-4-yl group are substituted with a $C_{1-6}$alkylsulfonyl group or a $C_{1-6}$acyl group)).

Other preferred $R^{1a}$, $R^{1b}$, and $R^{1c}$ are a group represented by —$NR^2R^3$ (the $R^2$ and $R^3$, together with an adjacent nitrogen atom, form a cyclic amino group represented by the formula [V]:

[Formula 26]

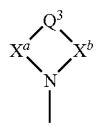

[V]

wherein $Q^3$ represents —O—, —$NR^4$—, —$CHR^5$—, —$NR^6CO$—, —$CHR^7CHR^8$—, —$CR^9$=$CR^{10}$—, —S—, —SO—, —$SO_2$—, or a single bond, $X^a$ and $X^b$ may be the same or different and represent a straight $C_{1-3}$alkylene group (the alkylene group is unsubstituted or substituted with one to three substituents selected from the group consisting of a $C_{1-6}$alkyl group, a cyano group, a carboxy group, a carbamoyl group, a ($C_{1-6}$alkyl)aminocarbonyl group, a di($C_{1-6}$alkyl)aminocarbonyl group, a morpholinocarbonyl group, a pyrrolidin-1-ylcarbonyl group, a piperidin-1-ylcarbonyl group, an amino$C_{1-6}$alkyl group, a di($C_{1-6}$alkyl)amino$C_{1-6}$alkyl group, a $C_{1-6}$alkoxycarbonyl group, a $C_{1-6}$alkoxy$C_{1-6}$alkyl group, a $C_{1-6}$alkylsulfonyl group, a $C_{1-6}$alkylsulfonylamino$C_{1-6}$alkyl group, a phenyl group, a phenylcarbonyl group (the phenyl group and the phenylcarbonyl group are unsubstituted or substituted with one to three substituents selected from the above-mentioned substituent group A), and a $C_{1-9}$heteroarylcarbonyl group), $R^4$ represents a hydrogen atom, a $C_{1-6}$alkyl group, a $C_{3-8}$cycloalkyl group, a phenyl group, a $C_{1-9}$heteroaryl group, a $C_{1-6}$acyl group, a $C_{3-8}$cycloalkylcarbonyl group, a $C_{1-6}$alkoxycarbonyl group, a morpholinocarbonyl group, a $C_{1-6}$alkylsulfonyl group, a trifluoromethylsulfonyl group, a hydroxy$C_{1-6}$alkyl group, a carbamoyl group, a ($C_{1-6}$alkyl)aminocarbonyl group, a di($C_{1-6}$alkyl)aminocarbonyl group, a $C_{1-9}$heteroarylcarbonyl group, a pyrrolidylcarbonyl group, or a $C_{1-6}$alkoxy$C_{2-6}$ alkyl group, $R^5$ represents a hydrogen atom, a hydroxy group, a $C_{1-6}$alkoxy group, an amino group, a ($C_{1-6}$alkyl)amino group, a di($C_{1-6}$alkyl)amino group, a $C_{1-6}$acylamino group, a $C_{1-6}$alkylsulfonylamino group, a pyrrolidin-1-yl group, a piperidin-1-yl group, a morpholino group, an imidazol-1-yl group, a phenylamino group, or a phenoxy group (the phenylamino group and the phenoxy group are unsubstituted or substituted with one to three substituents selected from the above-mentioned substituent group A), $R^6$ represents a hydrogen atom or a $C_{1-6}$alkyl group, $R^7$ and $R^8$ may be the same or different and represent a group selected from the group consisting of a hydrogen atom, a $C_{1-6}$alkyl group, and a $C_{1-6}$alkoxy group, $R^9$ represents a phenyl group or a $C_{3-7}$heteroaryl group (the phenyl group and the $C_{3-7}$heteroaryl group are unsubstituted or substituted with one to three substituents selected from the above-mentioned substituent group A), and $R^{10}$ represents a hydrogen atom, or $R^{10}$ forms a benzene ring with a substituted carbon together with $R^9$).

Preferred $X^1$ is a hydrogen atom, a $C_{1-6}$alkyl group, a $C_{1-6}$alkoxy group, a halogen atom, or a hydroxy group. More preferred $X^1$ is a hydrogen atom, a methyl group, a methoxy group, an ethyl group, an ethoxy group, or a hydroxy group. Preferred $X^1$ is substituted at the 6 position.

Preferred $X^2$ is a hydrogen atom or a halogen atom.

Preferred $X^3$ is a hydrogen atom.

Preferred $X^4$ is a $C_{1-6}$alkyl group. More preferred $X^4$ is a methyl group.

Preferred $X^5$ is a hydrogen atom.

Preferred $X^6$ is a hydrogen atom.

Preferred L is —CO—.

Preferred $Q^1$ is a single bond or —$(CH_2)_n$— (where, n is an integer of 1 or 2). More preferred $Q^1$ is a single bond.

Preferred $Q^2$ is a group represented by —$(CR^{11}R^{12})$— (where, $R^{11}$ and $R^{12}$ may be the same or different and represent a hydrogen atom or a $C_{1-6}$alkyl group, or $R^{11}$ and $R^{12}$ form $C_{3-8}$cycloalkane together). More preferred $Q^2$ is a methylene group or a group represented by —$(CR^{11}R^{12})$— (where, $R^{11}$ and $R^{12}$ form a cyclopropane together).

Preferred $Z^1$ is a hydrogen atom, a hydroxy group, a $C_{1-6}$alkoxy group, or a fluorine atom. More preferred $Z^1$ is a hydrogen atom, a hydroxy group, a methoxy group, or a fluorine atom.

Preferred $Z^2$ is a hydrogen atom.

Preferred $Z^3$ is a hydrogen atom.

Preferred $Z^4$ is a hydrogen atom.

Preferred Ar is a phenyl group (where, the phenyl group is substituted with one to three substituents selected from the group consisting of a halogen atom, a $C_{1-6}$alkyl group, a $C_{1-6}$alkoxy group, a $C_{1-6}$alkylthio group, a trifluoromethyl group, a trifluoromethoxy group, a trifluoromethylthio group, and a phenyl group (the phenyl group is unsubstituted or substituted with one to three substituents selected from the group consisting of a halogen atom, a $C_{1-6}$alkyl group, a $C_{1-6}$alkoxy group, a $C_{1-6}$alkylthio group, a trifluoromethyl group, a trifluoromethoxy group, and a trifluoromethylthio group)). More preferred Ar is a phenyl group (where, the phenyl group is substituted with 1 or 2 substituents selected from the group consisting of a halogen atom, a trifluoromethyl group, a trifluoromethoxy group, a trifluoromethylthio group, and a phenyl group (the phenyl group is unsubstituted or substituted with one to three substituents selected from the group consisting of a halogen atom, a $C_{1-6}$alkyl group, a $C_{1-6}$alkoxy group, a trifluoromethyl group, and a trifluoromethoxy group)). Furthermore, preferred Ar is a 4-trifluoromethoxyphenyl group, a 4-trifluoromethylphenyl group, a 4-trifluoromethylthio group, a 4-fluorophenyl group, a 4-chlorophenyl group, a 4-bromophenyl group, a 3,4-difluorophenyl group, a 3,4-dichlorophenyl group, or a biphenyl group (the biphenyl group is substituted with 1 to 2 groups selected from the group consisting of a fluorine atom, a chlorine atom, a bromine atom, a trifluoromethyl group, and a trifluoromethoxy group).

Furthermore, tautomers, stereoisomer, and optical isomers of the aminopyrrolidine compound of the present invention may exist, and these are also included in the scope of the present invention.

Furthermore, examples of pharmaceutically acceptable salts in the present invention include salts with mineral acids such as sulfuric acid, hydrochloric acid, and phosphoric acid and salts with organic acids such as acetic acid, oxalic acid, lactic acid, tartaric acid, fumaric acid, maleic acid, methanesulfonic acid, and benzenesulfonic acid.

Examples of prodrugs include derivatives of the present invention having a group or groups that can be chemically or metabolically degraded, which are compounds that form pharmacologically active compounds of the present invention by solvolysis or in vivo under a physiological condition. Methods of selecting and producing suitable prodrug derivatives are described in, for example, DESIGN OF PRODRUG (Elsevier, Amsterdam, 1985). Examples of prodrugs of the compound of the present invention having a hydroxy group include acyloxy derivatives produced by reacting the compound and a suitable acyl halide or a suitable acid anhydride. Examples of particularly preferred acyloxy groups as prodrugs include —$OCOC_2H_5$, —$OCO(t\text{-}Bu)$, —$OCOC_{15}H_{31}$, —$OCO(m\text{-}CO_2Na\text{-}Ph)$, —$OCOCH_2CH_2CO_2Na$, —$OCOCH(NH_2)CH_3$, and —$OCOCH_2N(CH_3)_2$. When a compound forming the present invention has an amino group, examples of prodrugs thereof include amide derivatives produced by reacting the compound having an amino group and a suitable acid halide or a suitable mixed acid anhydride. Examples of particularly preferred amides as prodrugs include —$NHCOCH(NH_2)CH_3$. When a compound forming the present invention has a carboxyl group, examples of prodrugs thereof include carboxylic acid esters synthesized by reacting with an aliphatic alcohol or with free alcohol hydroxy group of 1,2- or 1,3-diglyceride. Examples of particularly preferred carboxylic acid esters as prodrugs include methyl esters, and ethyl esters.

The compound represented by the formula [I] can be produced by the following general production methods. However, the methods for producing the compound of the present invention are not limited to the following methods.

In the following general production methods, $R^{1a}$, $R^{1b}$, $R^{1c}$, $R^1$, —A—B—D—, $Z^1$, $Z^2$, $Z^3$, $Z^4$, $X^1$, $X^2$, $X^3$, $X^4$, $X^5$, $X^6$, L, $Q^1$, $Q^2$, and Ar have the same meanings as defined above, $T^1$ represents a chlorine atom, a bromine atom, an iodine atom, a methanesulfonyloxy group, a trifluoromethanesulfonyloxy group, a benzenesulfonyloxy group, a methanesulfonyl group, or a toluenesulfonyloxy group, $T^2$ represents a chlorine atom, a bromine atom, or a hydroxy group, P represents common protection groups of an amino group described in PROTECTIVE GROUPS IN ORGANIC SYNTHESIS, THEODORA W. GREENE and PETER G. M. WUTS, such as a t-butoxycarbonyl group, a benzyloxycarbonyl group, and a benzyl group, $R^x$ represents a hydrogen atom or a $C_{1-6}$alkyl group, and $R^y$ represents a $C_{1-6}$alkyl group. Examples of an "inactive solvent" include alcohols such as methanol, ethanol, isopropanol, n-butanol, and ethylene glycol, ethers such as diethyl ether, tetrahydrofuran, 1,4-dioxane, and 1,2-dimethoxyethane, hydrocarbons such as toluene, benzene, and xylene, esters such as ethyl acetate and ethyl formate, ketones such as acetone and methyl ethyl ketone, halogenated carbon solvents such as chloroform and dichloromethane, amides such as N,N-dimethylformamide and N-methylpyrrolidone, acetonitrile, dimethyl sulfoxide, water, and mixed solvents thereof. Examples of a "base" include amines such as triethylamine, N,N-diisopropylethylamine, pyridine, 1,8-diazabicyclo[5.4.0]undec-7-ene, N,N-dimethylaniline, N,N-diethylaniline, and 4-dimethylaminopyridine, inorganic bases such as sodium carbonate, potassium carbonate, sodium hydrogencarbonate, potassium hydrogencarbonate, sodium hydroxide, potassium hydroxide, barium hydroxide, and sodium hydride, metal alcholates such as sodium methoxide, sodium ethoxide, and potassium t-butoxide, metal amides such as sodium amide, lithium diisopropyl amide, lithium hexamethyl disilazanide, sodium hexamethyl disilazanide, and potassium hexamethyl disilazanide, alkyllithiums such as n-butyllithium, s-butyllithium, t-butyllithium, and methyllithium, and Grignard reagents such as methylmagnesium bromide. Examples of an "acid" include inorganic acids such as hydrochloric acid, hydrobromic acid, sulfuric acid, nitric acid, phosphoric acid, and polyphosphoric acid and organic acids such as p-toluenesulfonic acid, methanesulfonic acid, trifluoroacetic acid, formic acid, and acetic acid.

[General production method 1]

[Formula 27]

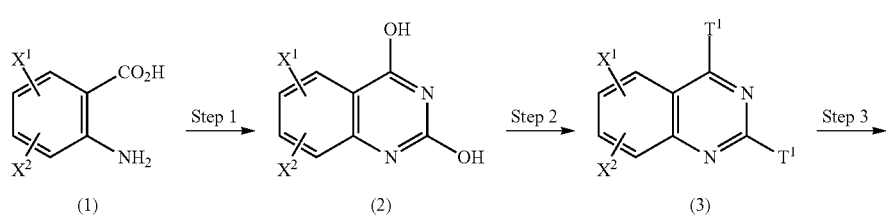

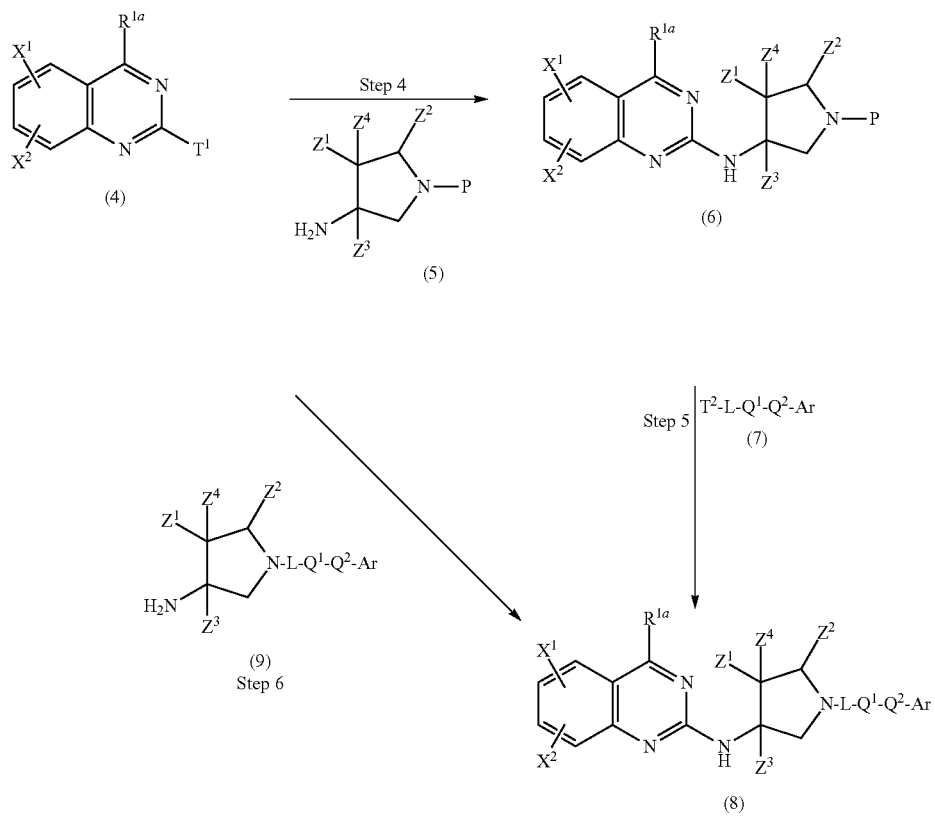

Step 1: Compound (2) can be obtained by heating a mixture of compound (1) and urea. In addition, compound (2) can also be obtained by reacting compound (1) and potassium cyanate in an inactive solvent in the presence of an acid and then treating with a base followed by treatment with an acid.

Step 2: Compound (3) can be obtained by reacting compound (2) with a halogenating agent such as phosphorus oxychloride, phosphorus oxybromide, phenylphosphoric dichloride (phenylphosphonic acid dichloride), or thionyl chloride, a sulfonylating agent such as methanesulfonylchloride, benzenesulfonylchloride, p-toluenesulfonylchloride, methanesulfonic acid anhydride, benzenesulfonic acid anhydride, p-toluenesulfonic acid anhydride, trifluoromethanesulfonic acid anhydride, or N-phenyl trifluoromethane sulfonimide in an inactive solvent or in the absence of a solvent in the presence or absence of a base.

Step 3: When $R^{1a}$ is a group represented by —$NR^2R^3$, compound (4) can be obtained by reacting a corresponding amine with compound (3) in an inactive solvent in the presence or absence of a base. When $R^{1a}$ is a $C_{1-6}$alkoxy group, a hydroxy$C_{2-6}$alkoxy group, or a $C_{3-8}$cycloalkoxy group, compound (4) can be obtained by reacting compound (3) with a corresponding alcohol, potassium alkoxide, or sodium alkoxide in an inactive solvent in the presence or absence of a base. When $R^{1a}$ is a $C_{1-6}$alkyl group or a $C_{3-8}$cycloalkyl group, compound (4) can be obtained by reacting compound (3) with a corresponding Grignard reagent, an alkyllithium reagent, or an alkyl zinc reagent in an inactive solvent in the presence of a palladium catalyst such as Pd(P$^t$Bu$_3$)$_2$ or an iron catalyst such as Fe(III) acetyl acetonate, as required.

Step 4: Compound (6) can be obtained by reacting compound (4) with compound (5) in an inactive solvent in the presence or absence of a palladium catalyst such as Pd(OAc)$_2$, Pd$_2$(dba)$_3$, or Pd(PPh$_3$)$_4$, and a ligand such as BINAP, 2-(di-t-butylphosphino)biphenyl, 9,9-dimethyl-4,5-bis(diphenylphosphino)xanthene (Xantphos), or triphenylphosphine and in the presence of a base.

Step 5: Compound (8) of the present invention can be obtained by deprotecting compound (6) by the method described in PROTECTIVE GROUPS IN ORGANIC SYNTHESIS, THEODORA W. GREENE and PETER G. M. WUTS and then (i) when $T^2$ is a chlorine atom or a bromine atom, reacting it with compound (7) in an inactive solvent in the presence or absence of a base, or (ii) when $T^2$ is a hydroxy group, amidating it with compound (7) in an inactive solvent in the presence or absence of a base. Here, "amidating" means an amidation reaction via a mixed acid anhydride using ethyl chlorocarbonate, isobutyl chlorocarbonate, or the like, or a common amidation reaction of a carboxyl group using a condensing agent such as 1-(3,3-dimethylaminopropyl)-3-ethylcarbodiimide, 1,3-dicyclohexylcarbodiimide, diphenylphosphoryl azide, diethyl cyanophosphate, or carbonyldiimidazole, and additives such as 1-hydroxy benzotriazole (HOBt) can be used as required.

Step 6: The compound (8) of the present invention can also be obtained by reacting compound (4) with compound (9) by the same method as in Step 4.

[General production method 2]

[Formula 28]

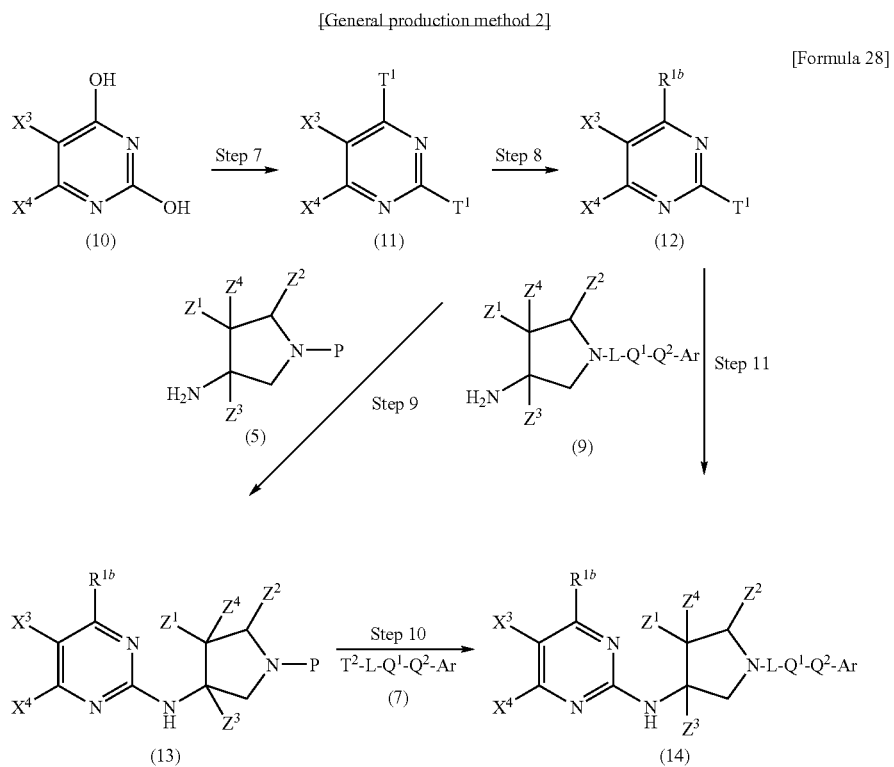

Step 7: Compound (10) can be converted to compound (11) by the same method as in Step 2 in [General production method 1].
Step 8: Compound (11) can be converted to compound (12) by the same method as in Step 3 in [General production method 1].
Step 9: Compound (12) can be converted to compound (13) by the same method as in Step 4 in [General production method 1].

Step 10: Compound (13) can be converted to compound (14) of the present invention by the same method as in Step 5 in [General production method 1].

Step 11: Compound (12) can be converted to compound (14) of the present invention by the same method as in Step 4 in [General production method 1].

[General production method 3]

[Formula 29]

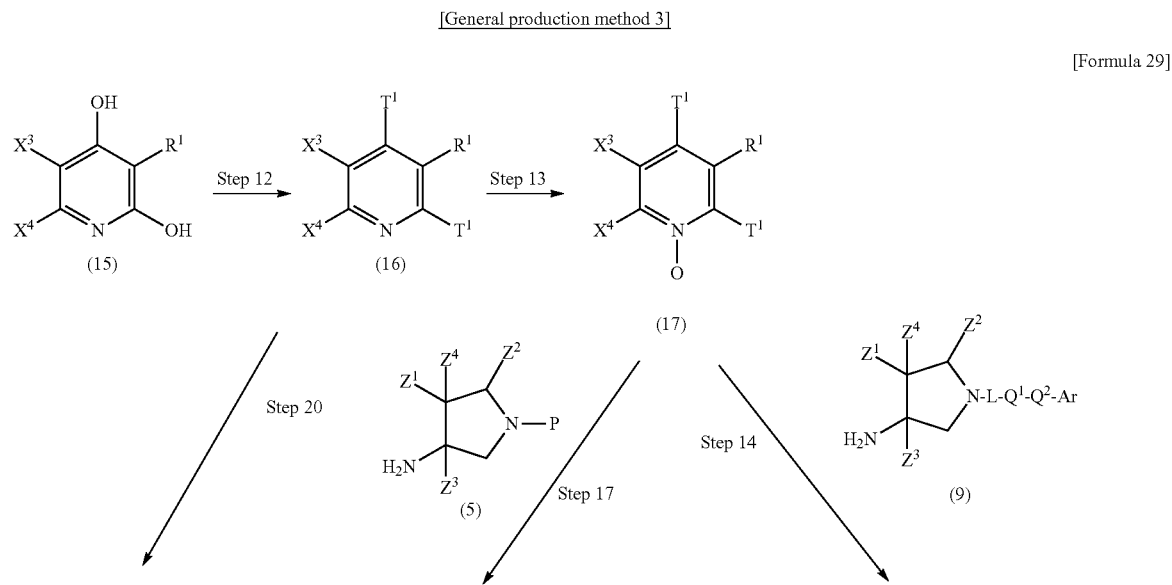

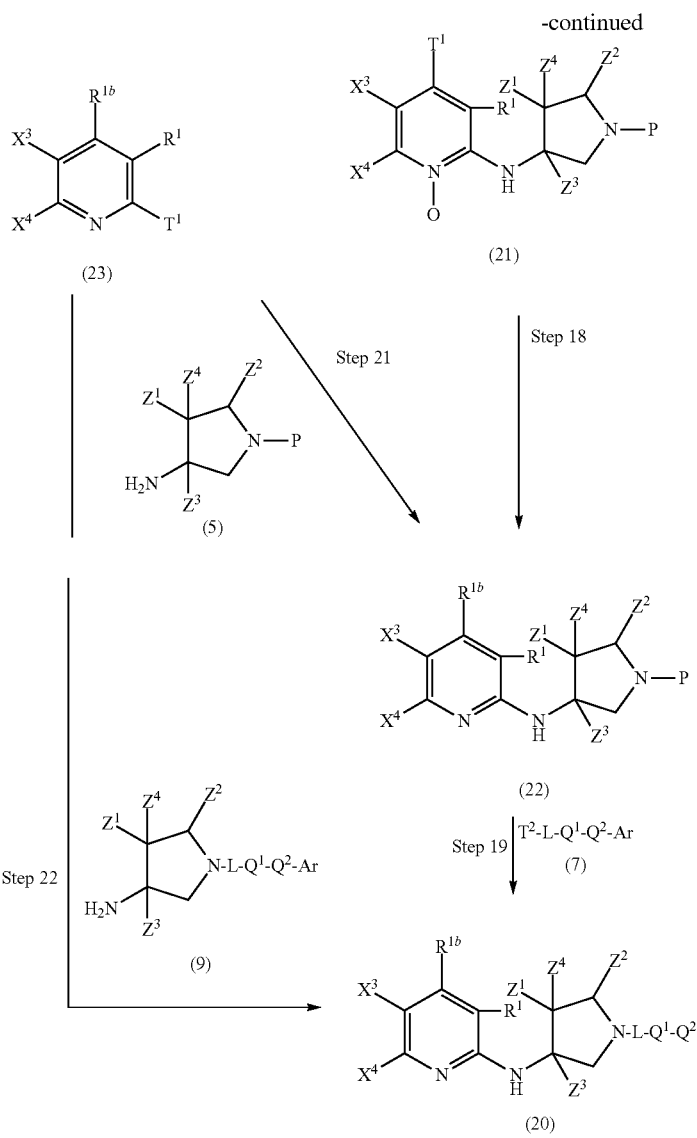

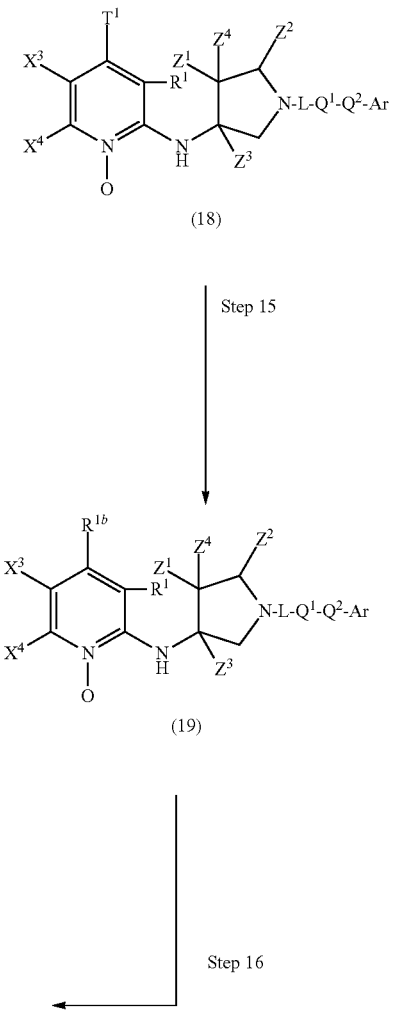

Step 12: Compound (15) can be converted to compound (16) by the same method as in Step 2 in [General production method 1].

Step 13: Compound (17) can be obtained by oxidizing compound (16) in an inactive solvent in the presence or absence of an acid or a base. Here, "oxidizing" means to carry out a reaction using oxidizing agent such as peracetic acid, trifluoroperacetic acid, m-chloroperbenzoic acid (mCPBA), a peracid such as monoperoxyphthalic acid, hydrogen peroxide, dimethyl dioxolane, methyl trifluoromethyl dioxolane, ditrifluorodioxolane, a peroxide such as t-butyl hydroperoxide, or oxone.

Step 14: Compound (17) can be converted to compound (18) by the same method as in Step 4 in [General production method 1].

Step 15: Compound (18) can be converted to compound (19) by the same method as in Step 3 in [General production method 1].

Step 16: The compound (20) of the present invention can be obtained by reducing compound (19) in an inactive solvent in the presence or absence of an acid or a base. Here, "reducing" means a reduction reaction using a metal such as iron, zinc, or titanium or hydrogenation using a catalyst such as palladium carbon, palladium black, palladium hydroxide, platinum dioxide, or Raney nickel. Furthermore, this step can be omitted by reacting compound (18) and a corresponding amine by heating them in an inactive solvent in the presence of a base such as triethylamine or N,N-diisopropylethylamine in Step 15.

Step 17: Compound (17) can be converted to compound (21) by the same method as in Step 4 in [General production method 1].

Step 18: Compound (21) can be converted to compound (22) by introducing $R^{1b}$ into compound (21) by the same method as in Step 3 in [General production method 1] and then reducing the compound by the same method as in Step 16. In addition, when $R^{1b}$ is a group represented by —$NR^2R^3$, compound (22) can also be directly obtained by reacting a corresponding amine and compound (21) heating them in an inactive solvent in the presence of a base such as triethylamine or N,N-diisopropylethylamine.

Step 19: Compound (22) can be converted to compound (20) of the present invention by the same method as in Step 5 in [General production method 1].

Step 20: Compound (16) can be converted to compound (23) by the same method as in Step 3 in [General production method 1].

Step 21: Compound (23) can be converted to compound (22) by the same method as in Step 4 in [General production method 1].

Step 22: Compound (23) can be converted to compound (20) of the present invention by the same method as in Step 4 in [General production method 1].

etoxyborohydride, and cyanotrihydrosodium borate, an aluminium reducing agent such as lithium aluminium hydride, bis(2-methoxyethoxy)aluminium hydride sodium (Red-Al), or diisobutyl aluminium hydride, or the like.

Step 24: Compound (27) can be obtained by deprotecting compound (26) by the method described in PROTECTIVE GROUPS IN ORGANIC SYNTHESIS, THEODORA W. GREENE and PETER G. M. WUTS.

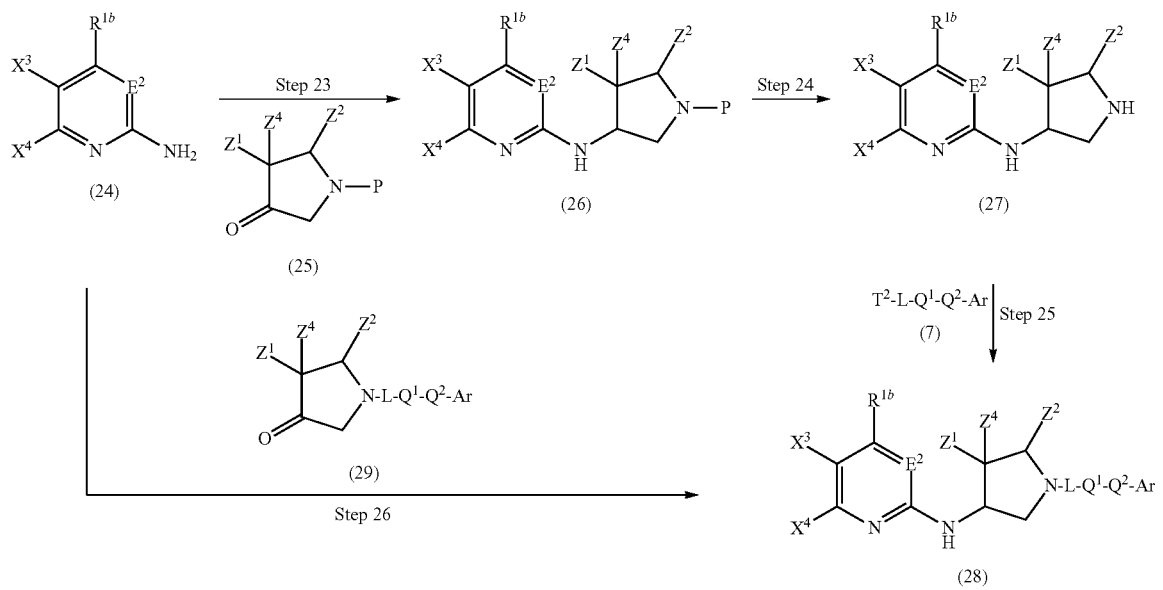

[General production method 4]

[Formula 30]

Step 23: Compound (26) can be obtained by reducing a mixture of compound (24) and compound (25) in an inactive solvent in the presence or absence of an acid. Here, "reducing" means hydrogenation using a catalyst such as palladium carbon, palladium black, palladium hydroxide, platinum dioxide, or Raney nickel or a reduction reaction under an acidic, neutral, or basic condition using a boron reducing agent such as diborane, sodium borohydride, sodium triac- Step 25: Compound (27) can be converted to the compound (28) of the present invention by the same method as the amidation reaction in Step 5 in [General production method 1].

Step 26: The compound (28) of the present invention can be obtained by reducing a mixture of compound (24) and compound (29) in the same manner as in Step 23.

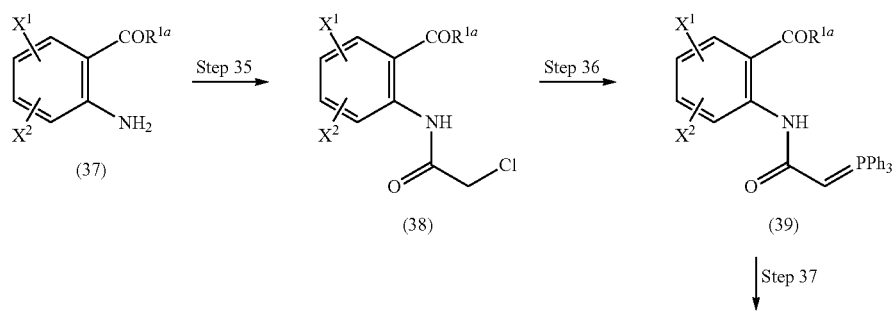

[General production method 5]

[Formula 31]

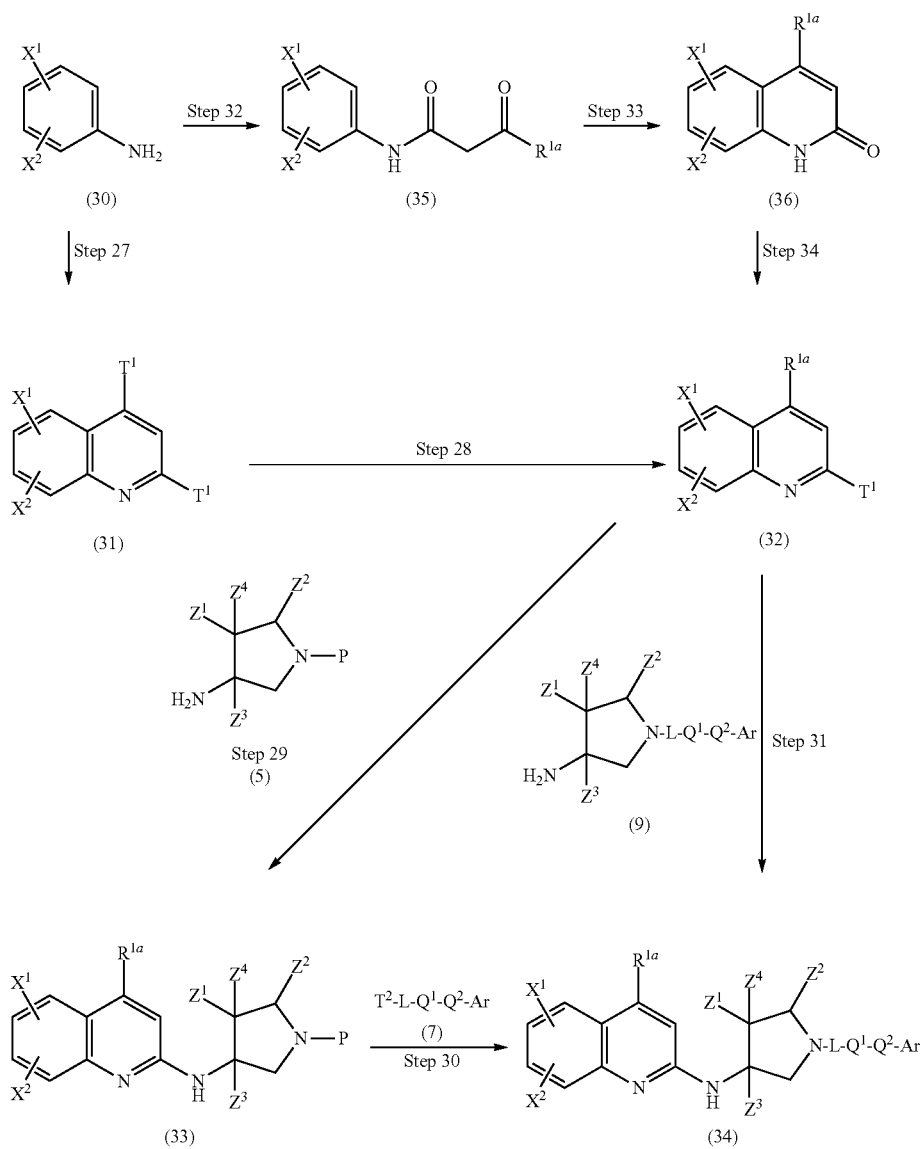

Step 27: Compound (31) can be obtained by heating a mixture of compound (30), malonic acid and a halogenating agent such as phosphorus oxychloride.

Step 28: Compound (31) can be converted to compound (32) by the same method as in Step 3 in [General production method 1].

Step 29: Compound (32) can be converted to compound (33) by the same method as in Step 4 in [General production method 1].

Step 30: Compound (33) can be converted to compound (34) of the present invention by the same method as in Step 5 in [General production method 1].

Step 31: Compound (32) can be converted to compound (34) of the present invention by the same method as in Step 4 in [General production method 1].

Step 32: When $R^{1a}$ is a $C_{1-6}$alkyl group, compound (35) can be obtained by heating a mixture of compound (30) and a corresponding acylacetate ester such as ethyl acetoacetate in an inactive solvent or in the absence of a solvent.

Step 33: Compound (36) can be obtained by heating compound (35) in an inactive solvent or in the absence of a solvent in the presence of an acid.

Step 34: Compound (36) can be converted to compound (32) by the same method as in Step 2 in [General production method 1].

Step 35: When $R^{1a}$ is a $C_{1-6}$alkoxy group, compound (38) can be obtained by reacting a mixture of a corresponding anthranilate ester compound (37) and chloroacetyl chloride in an inactive solvent in the presence or absence of a base.

Step 36: Compound (39) can be obtained by reacting compound (38) with triphenylphosphine in an inactive solvent in the presence or absence of a base and then further treating the reaction mixture with a base.

Step 37: Compound (36) can be obtained by heating compound (39) in an inactive solvent or in the absence of a solvent in the presence or absence of a base.

[General production method 6]

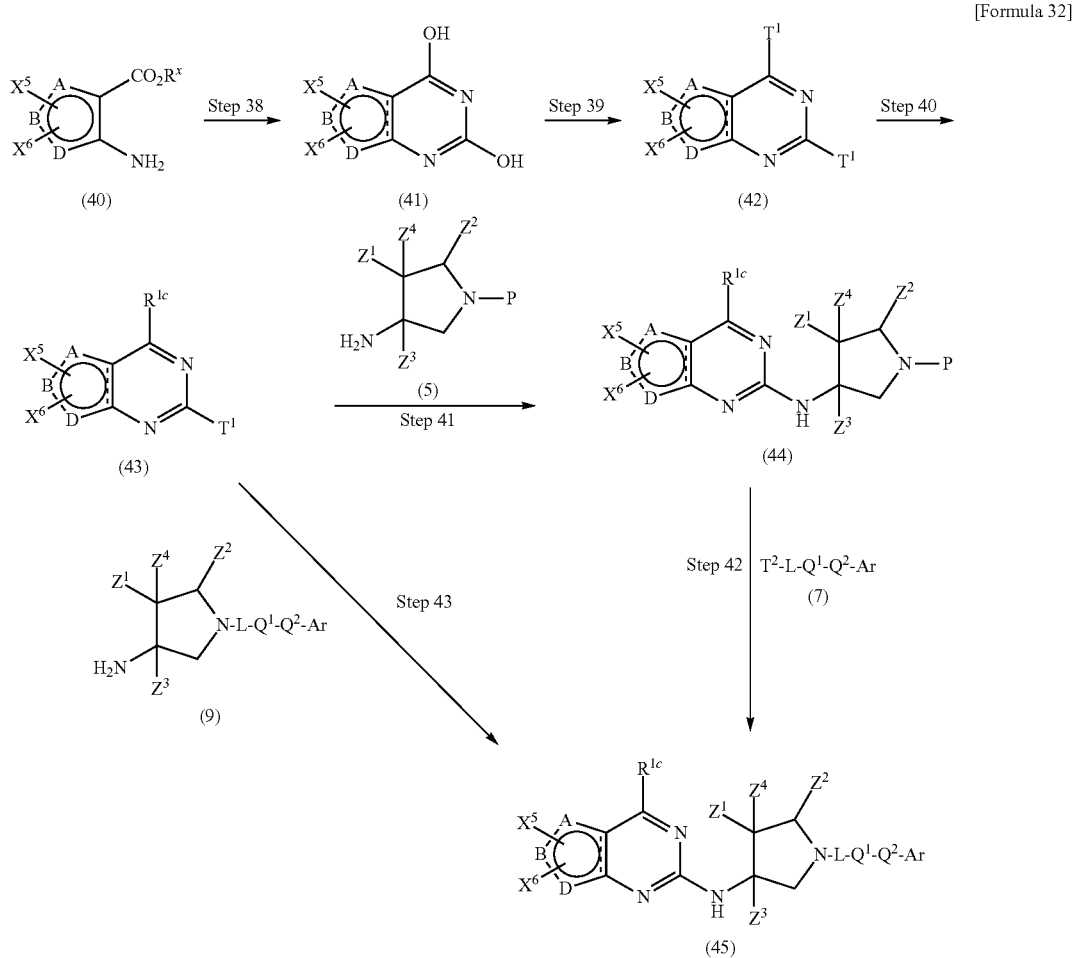

Step 38: Compound (41) can be obtained by the same method as in Step 1 in [General production method 1] using compound (40).

Step 39: Compound (41) can be converted to compound (42) by the same method as in Step 2 in [General production method 1].

Step 40: Compound (42) can be converted to compound (43) by the same method as in Step 3 in [General production method 1].

Step 41: Compound (43) can be converted to compound (44) by the same method as in Step 4 in [General production method 1].

Step 42: Compound (44) can be converted to the compound (45) of the present invention by the same method as in Step 5 in [General production method 1].

Step 43: Compound (43) can be converted to the compound (45) of the present invention by the same method as in Step 4 in [General production method 1].

[General production method 7]

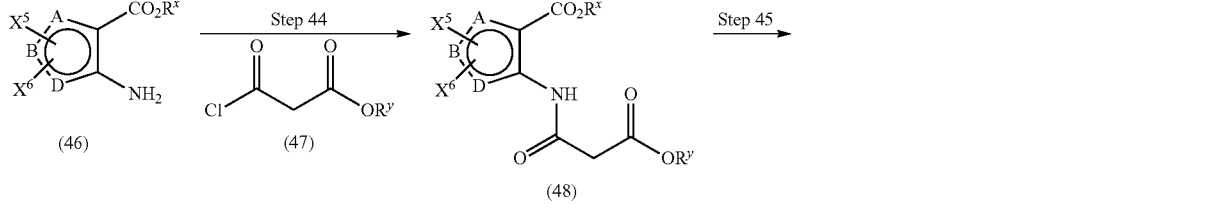

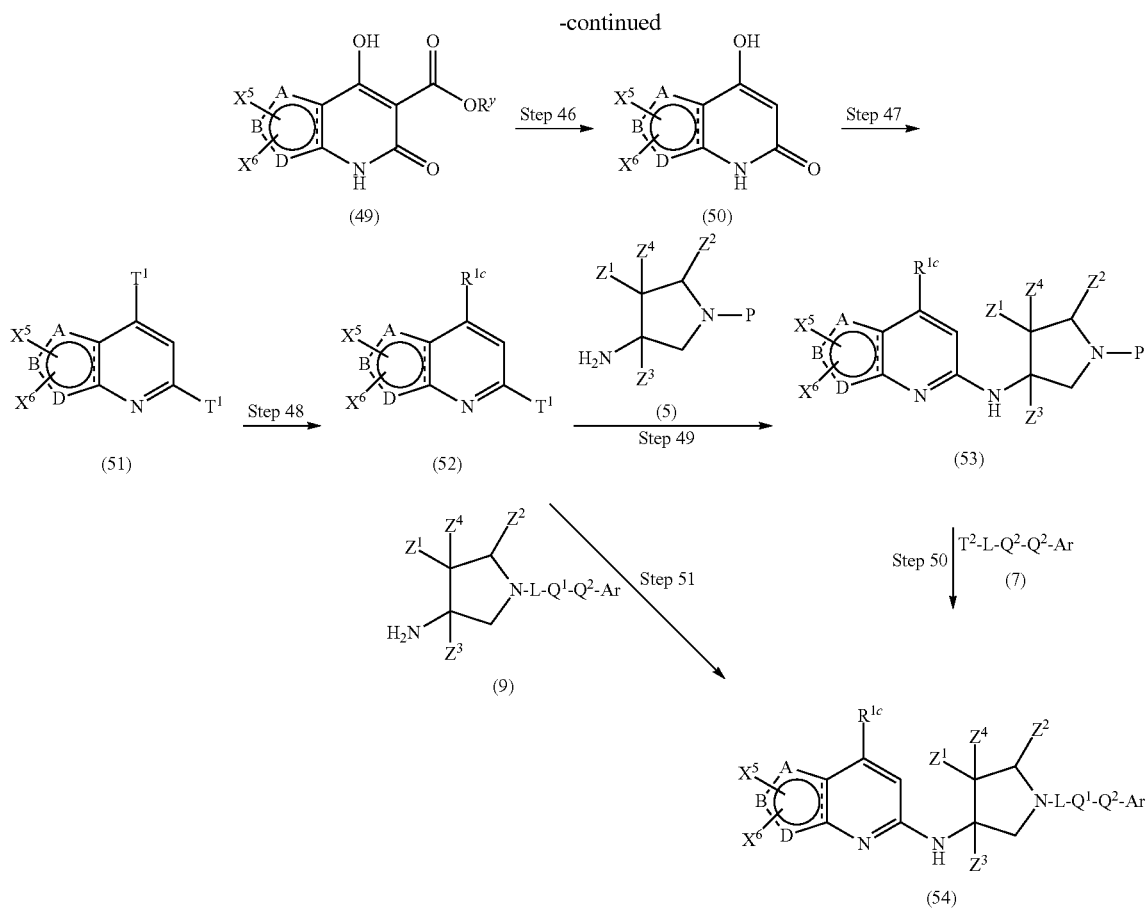

Step 44: Compound (48) can be obtained by reacting a mixture of compound (46) and compound (47) in an inactive solvent in the presence or absence of a base.
Step 45: Compound (49) can be obtained by reacting compound (48) in an inactive solvent in the presence of a base at room temperature or with heating.
Step 46: Compound (50) can be obtained by reacting compound (49) in water or an inactive solvent at room temperature or with heating in the presence of a base and then reacting in water or an inactive solvent under an acidic condition at room temperature or with heating.
Step 47: Compound (50) can be converted to compound (51) by the same method as in Step 2 in [General production method 1].
Step 48: Compound (51) can be converted to compound (52) by the same method as in Step 3 in [General production method 1].
Step 49: Compound (52) can be converted to compound (53) by the same method as in Step 4 in [General production method 1].
Step 50: Compound (53) can be converted to the compound (54) of the present invention by the same method as in Step 5 in [General production method 1].
Step 51: Compound (52) can be converted to the compound (54) of the present invention by the same method as in Step 4 in [General production method 1].
When $R^{1a}$, $R^{1b}$, and $R^{1c}$ in the compound of the present invention obtained by the methods described above include an amino group, a hydroxy group, or a carboxy group protected by the protection group described in PROTECTIVE GROUPS IN ORGANIC SYNTHESIS, THEODORA W. GREENE and PETER G. M. WUTS, these compounds can be converted to the compound of the present invention including an amino group or a hydroxy group by deprotecting them by the method described in this document.

Furthermore, the obtained compound of the present invention having a amino group or a hydroxy group can be converted to the compound of the present invention whose amino group or hydroxy group is acylated or sulfonylated by performing an acylation reaction or a sulfonylation reaction.

When $Z^2$ in the compound of the present invention synthesized by the methods described above is a $C_{1-6}$alkoxycarbonyl group, this substituent can be converted to a carboxyl group by performing a common hydrolysis reaction using an acid or a base. Furthermore, the carboxyl group obtained here can be converted to a di($C_{1-6}$alkyl)aminocarbonyl group by performing an amidation reaction similar to the method described in Step 5 in General production method 1.

When Ar is substituted with a chlorine atom, a bromine atom, or a trifluoromethanesulfonyloxy group in the compound of the present invention obtained by the methods described above, these substituents can be converted to an aryl group or a heteroaryl group in the presence of a palladium catalyst using an arylboric acid or a heteroarylboric acid.

When $X^1$, $X^2$, $X^3$, $X^4$, $X^5$, and $X^6$ obtained by the methods described above are a hydroxy group or a hydroxy$C_{1-6}$alkyl group protected by the protection group described in PROTECTIVE GROUPS IN ORGANIC SYNTHESIS, THEODORA W. GREENE and PETER G. M. WUTS, they can be converted to the compound of the present invention whose $X^1$, $X^2$, $X^3$, $X^4$, $X^5$, and $X^6$ are a hydroxy group or a hydroxy$C_{1-6}$alkyl group by performing deprotection by the method described in this document.

The compound of the present invention can be orally or parenterally administered. The dosage forms thereof include tablet, capsule, granule, powder, dust formulation, lozenge, ointment, cream, emulsion, suspension, suppository, injection etc., all of which can be produced by commonly used formulation techniques (for example, methods specified in The Japanese Pharmacopoeia 14th Edition). These dosage forms can be suitably selected depending on the patient's symptom, age, and purpose of treatment. In production of formulations in various dosage forms, conventional excipients (for example, crystalline cellulose, starch, lactose, and mannitol), binders (for example, hydroxypropyl cellulose and polyvinylpyrrolidone), lubricants (for example, magnesium stearate and talc), disintegrating agents (for example, carboxymethylcellulose calcium), and the like can be used.

The doses of the compound of the present invention for treatment of adults are 1 to 2000 mg per day, which are administered once daily or divided into several doses per day. These doses can be suitably adjusted depending on the patient's age, body weight, and symptom.

EXAMPLES

The present invention will be explained more specifically with reference to the following Examples and Test Examples. However, the scope of the present invention is not limited to these examples.

Unless otherwise specified in the Examples, the following apparatuses were used.
[$^1$H-NMR]
600 MHz: JNM-ECA600
300 MHz: Varian 300/JEOL 300
200 MHz: Varian 200
[LC/MS] waters
Abbreviations used in the Examples are described below.

| | |
|---|---|
| Pr: | n-propyl |
| Ms: | methanesulfonyl |
| Ac: | acetyl |
| Ph: | phenyl |
| Et: | ethyl |
| Boc: | t-butoxycarbonyl |
| iPr: | i-propyl |
| tBu: | t-butyl |
| Bu: | n-butyl |
| Bn: | benzyl |
| BINAP: | 2,2'-bis(diphenylphosphino)-1,1-binaphthyl |
| PVP: | poly(4-vinylpyridine) |
| PS-DCC: | carbodiimide binding to a polymer |
| DMF: | N,N-dimethylformamide |
| THF: | tetrahydrofuran |
| HOBt: | hydroxybenzotriazole |
| EDC: | 1-ethyl-3-(3-dimethylaminopropyl)carbodiimide |
| Cbz: | benzyloxycarbonyl |
| SCX: | BONDESIL-SCX (Varian) |
| dba: | bis(dibenzylideneacetone) |
| PSA: | BONDESIL-PSA (Varian) |
| Lowesson's reagent: | 2,4-bis(4-methoxyphenyl)-1,3-dithia-2,4-diphosphetane-2,4-disulfide |
| TLC: | thin layer chromatography |
| SDS: | sodium dodecyl sulfate |
| Tr: | trityl |
| Tf: | trifluoromethanesulfonyl |
| TBS: | t-butyldimethylsilyl |

Example 1

Synthesis of 1-(7-fluoro-2-((S)-1-(2-(4-trifluoromethoxyphenyl)ethanoyl)pyrrolidin-3-ylamino)quinazolin-4-yl)piperidine-4-carboxylic acid dimethylamide mono hydrochloride (Compound 1-067)

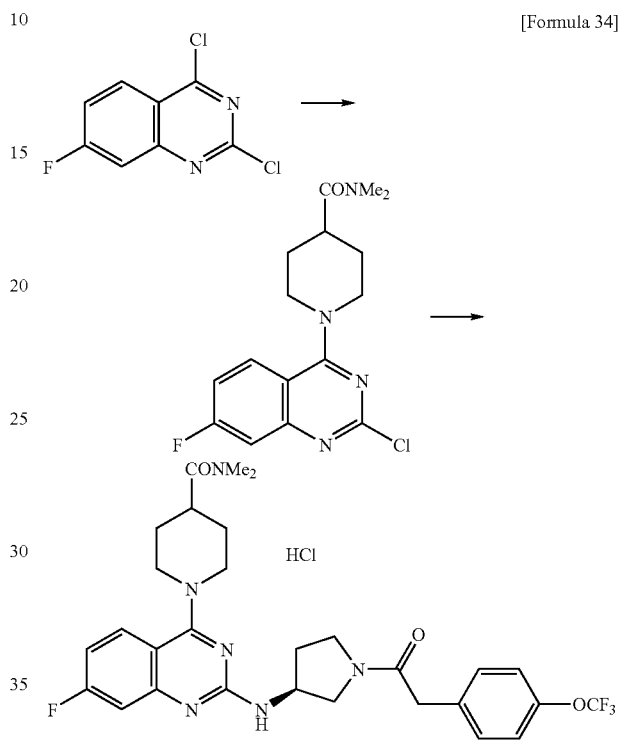

[Formula 34]

(1) A mixture of 2,4-dichloro-7-fluoroquinazoline (250 mg), piperidine-4-carboxylic acid dimethylamide (189 mg), triethylamine (0.24 mL), THF (6 mL), and DMF (4 mL) was stirred at room temperature for 13 h. The reaction mixture was diluted with a mixture of chloroform and saturated aqueous sodium hydrogencarbonate, and then the aqueous layer was extracted 3 times with chloroform. The organic layer was dried with anhydrous sodium sulfate, the desiccant was removed by filtration, the filtrate was concentrated under reduced pressure, and the residue was purified by silica gel column chromatography (hexane/ethyl acetate=7:3) to obtain colorless solid 1-(2-chloro-7-fluoroquinazolin-4-yl)piperidine-4-carboxylic acid dimethylamide (407 mg).

(2) A mixture of 1-(2-chloro-7-fluoroquinazolin-4-yl)piperidine-4-carboxylic acid dimethylamide (250 mg), 1-((S)-3-aminopyrrolidin-1-yl)-2-(4-trifluoromethoxyphenyl)ethanone mono hydrochloride (265 mg), N,N-diisopropylethylamine (0.32 mL), and n-butanol (1.2 mL) was heated at 120° C. for 57 h with stirring. The reaction mixture was diluted with a mixture of chloroform and saturated aqueous sodium hydrogencarbonate, and then the aqueous layer was extracted with chloroform. The organic layer was dried with anhydrous sodium sulfate, the desiccant was removed by filtration, the filtrate was concentrated under reduced pressure, and the residue was purified by silica gel column chromatography (NH silica gel, hexane/ethyl acetate=4:1–ethyl acetate, and silica gel, chloroform/methanol=95:5). The resulting purification product was dissolved in ethyl acetate (2.0 mL), followed by addition of a solution (0.1 mL) of 4 M HCl in ethyl acetate, and the mixture was stirred at room temperature for 3.5 h. The solvent was evaporated under reduced pressure to obtain the amorphous title compound (110 mg).

The structures and the physical property data of this compound and similarly obtained compounds are shown in Tables 1, 3, 4, 13, 15, 16, and 17.

Example 2

Synthesis of 1-((S)-3-(4-(4-methyl-[1,4]-diazepan-1-yl)quinazolin-2-ylamino)pyrrolidin-1-yl)-2-(4-trifluoromethoxyphenyl)ethanone (Compound 1-211)

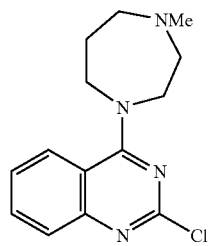

[Formula 35]

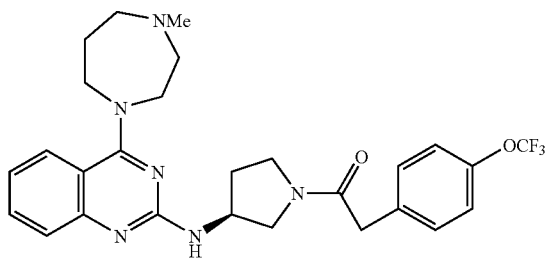

To a mixture of 2-chloro-4-(4-methyl-[1,4]-diazepan-1-yl)quinazoline (0.10 g), Pd$_2$(dba)$_3$ (0.017 g), (±)-BINAP (0.034 g), (S)-1-(3-aminopyrrolidin-1-yl)-2-(4-trifluoromethoxyphenyl)ethanone mono hydrochloride (0.13 g), and 1,4-dioxane (2 mL) was added sodium t-butoxide (0.10 g) under nitrogen atmosphere, and the mixture was stirred at 80° C. for 3 h. The reaction mixture was diluted with ethyl acetate and water, then the interlayer was removed by Celite filtration, and the organic layer was washed with saturated brine. The organic layer was dried with anhydrous magnesium sulfate, the desiccant was removed by filtration, the filtrate was concentrated under reduced pressure, and the residue was purified by silica gel column chromatography (NH silica gel, ethyl acetate–ethyl acetate/methanol=10:1) to obtain colorless amorphous 1-((S)-3-(4-(4-methyl-[1,4]-diazepan-1-yl)quinazolin-2-ylamino)pyrrolidin-1-yl)-2-(4-trifluoromethoxyphenyl)ethanone (0.12 g).

The structures and the physical property data of this compound and similarly obtained compounds are shown in Tables 1, 4, and 13.

Examples 3 and 4

Example 3

Synthesis of 2-biphenyl-2-yl-1-((S)-3-(4-[1,4]diazepan-1-ylquinazolin-2-ylamino)pyrrolidin-1-yl)ethanone dihydrochloride (Compound 1-210)

Example 4

Synthesis of 1-((S)-3-(4-(4-acetyl[1,4]diazepan-1-yl)quinazolin-2-ylamino)pyrrolidin-1-yl)-2-biphenyl-2-ylethanone mono hydrochloride (Compound 1-212)

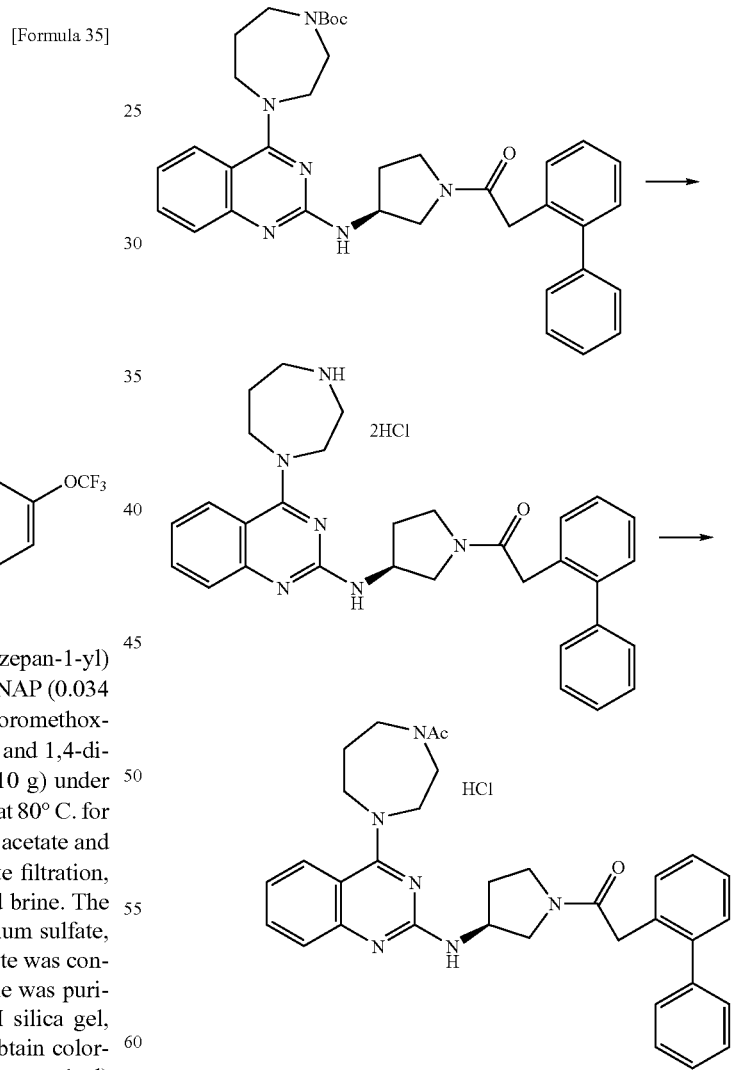

[Formula 36]

(1) t-Butyl 4-(2-((S)-1-(2-biphenyl-2-ylethanoyl)pyrrolidin-3-ylamino)quinazolin-4-yl)-[1,4]diazepane-1-carboxylate (0.53 g) synthesized in the same manner as in Example 1 was dissolved in ethyl acetate (3 mL), followed by addition of a solution (2.2 mL) of 4 M HCl in ethyl acetate, and the mixture was stirred overnight. Precipitated solids were collected by filtration and then washed with hexane to obtain 2-biphenyl-2-yl-1-((S)-3-(4-[1,4]diazepan-1-ylquinazolin-2-ylamino)pyrrolidin-1-yl)ethanone dihydrochloride (0.15 g).

(2) 2-Biphenyl-2-yl-1-((S)-3-(4-[1,4]diazepan-1-ylquinazolin-2-ylamino)pyrrolidin-1-yl)ethanone di hydrochloride (40 mg) was suspended in chloroform (3 mL), followed by addition of pyridine (12 mg) and acetic anhydride (8.5 mg), and the mixture was stirred at room temperature for 3 h. The reaction solution was concentrated under reduced pressure and purified by silica gel column chromatography (chloroform/methanol=10:1) to obtain the title compound (compound 1-210) (46 mg). The resulting purification product was dissolved in ethyl acetate (1.0 mL), followed by addition of a solution (0.015 mL) of 4 M HCl in ethyl acetate, and the mixture was stirred to obtain the title compound (compound 1-212) (12 mg).

The structures and the physical property data of this compound and similarly obtained compounds are shown in Tables 1, 4, and 16.

Example 5

Synthesis of 2-(4-chlorophenyl)-1-((S)-3-(4-piperazin-1-ylquinazolin-2-ylamino)pyrrolidin-1-yl)ethanone dihydrochloride (Compound 1-114)

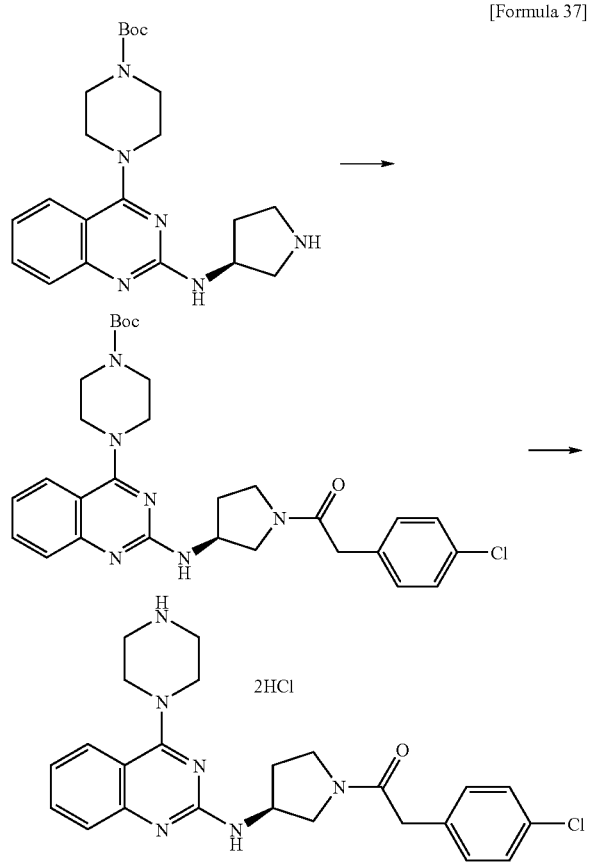

[Formula 37]

(1) To a mixture of t-butyl 4-(2-((S)-pyrrolidin-3-ylamino)quinazolin-4-yl)piperazine-1-carboxylate (0.30 g), p-chlorophenylacetic acid (0.13 g), and chloroform (5 mL) were added HOBt.H₂O (0.18 g) and EDC.HCl (0.18 g), and the mixture was stirred at room temperature for 2 days. To the reaction mixture was added saturated aqueous sodium hydrogencarbonate, and the mixture was extracted with chloroform. The organic layer was dried with anhydrous sodium sulfate, the desiccant was removed by filtration, the filtrate was concentrated under reduced pressure, and the residue was purified by silica gel column chromatography (NH silica gel, hexane/ethyl acetate=3:2) to obtain t-butyl 4-(2-((S)-1-(2-(4-chlorophenyl)ethanoyl)pyrrolidin-3-ylamino)quinazolin-4-yl)piperazine-1-carboxylate (0.29 g).

(2) To a solution of t-butyl 4-(2-((S)-1-(2-(4-chlorophenyl)ethanoyl)pyrrolidin-3-ylamino)quinazolin-4-yl)piperazine-1-carboxylate (0.28 g) in methanol (5 mL) was added a solution (1.3 mL) of 4 M HCl in ethyl acetate, and the mixture was stirred overnight. The solvent was evaporated under reduced pressure, and the residue was crystallized in diethyl ether to obtain the title compound (0.15 g).

The structures and the physical property data of this compound and similarly obtained compounds are shown in Tables 1, 4, 5, 13, and 15.

Example 6

Synthesis of 4-(7-fluoro-2-((S)-1-(2-(4'-trifluoromethoxybiphenyl-2-yl)ethanoyl)pyrrolidin-3-ylamino)quinazolin-4-yl)piperazin-2-one (Compound 1-132) and 4-(7-fluoro-2-((S)-1-(2-phenylethanoyl)pyrrolidin-3-ylamino)quinazolin-4-yl)piperazin-2-one (Compound 1-135)

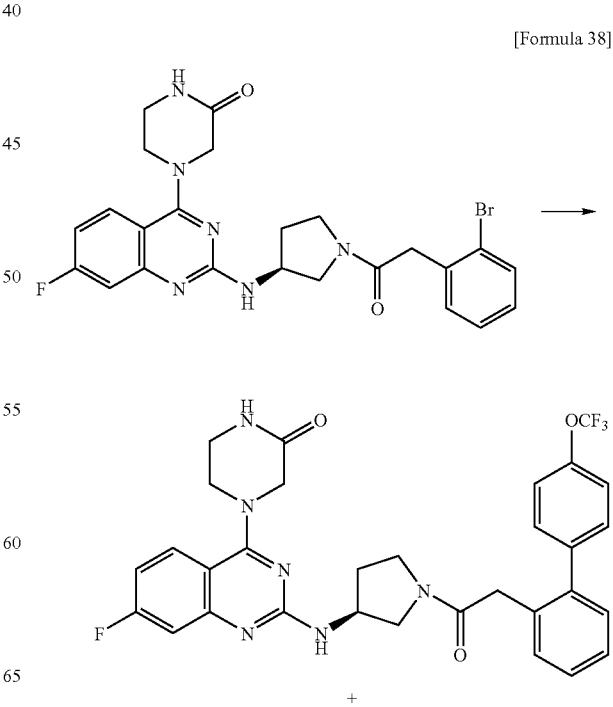

[Formula 38]

-continued

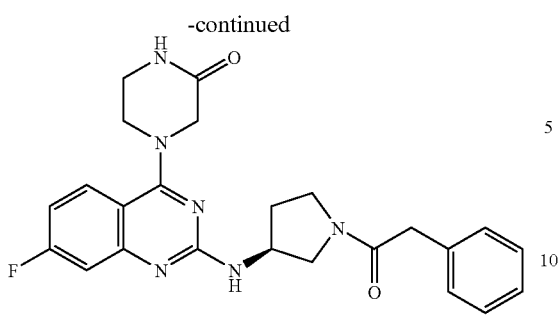

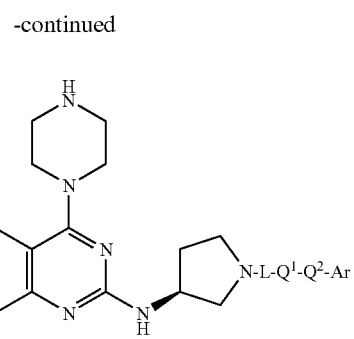

To a mixture of 4-(2-(S)-(1-(2-(2-bromophenyl)ethanoyl)pyrrolidin-3-ylamino)-7-fluoroquinazolin-4-yl)piperazin-2-one (0.27 g) synthesized in the same manner as in the method described in Example 1, 4-trifluoromethylphenylboroic acid (0.16 g), 2 M aqueous sodium carbonate solution (1.0 mL), toluene (5.0 mL), and ethanol (1.6 mL) was added Pd(PPh$_3$)$_4$ (58 mg), and the mixture was stirred at 100° C. for 6.5 h. The reaction mixture was diluted with ethyl acetate and then washed with saturated aqueous sodium hydrogencarbonate and saturated brine. The organic layer was dried with anhydrous sodium sulfate, the desiccant was removed by filtration, the filtrate was concentrated under reduced pressure, and the residue was purified by silica gel column chromatography (NH silica gel, hexane/ethyl acetate=1:1, and silica gel, chloroform/methanol=50:1-30:1) to obtain 4-(7-fluoro-2-((S)-1-(2-(4'-trifluoromethoxybiphenyl-2-yl)ethanoyl)pyrrolidin-3-ylamino)quinazolin-4-yl)piperazin-2-one (0.06 g) and 4-(7-fluoro-2-((S)-1-(2-phenylethanoyl)pyrrolidin-3-ylamino)quinazolin-4-yl)piperazin-2-one (0.07 g).

The structures and the physical property data of these compounds and similarly obtained compounds are shown in Table 1.

Example 7

Synthesis of Compounds Listed in Table 2

[Formula 39]

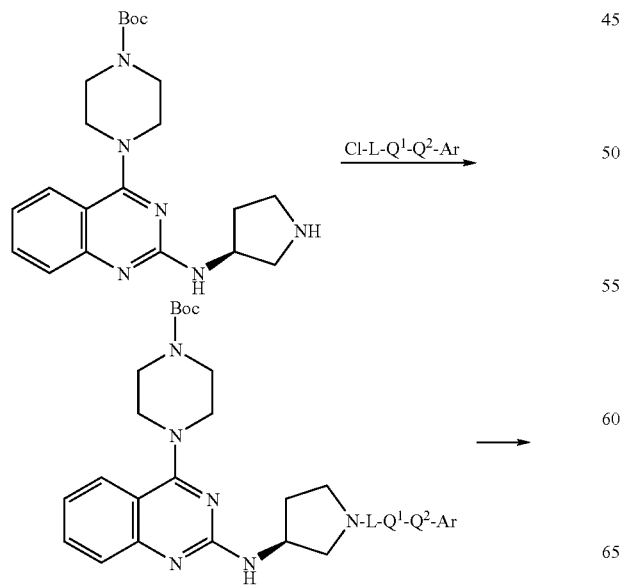

(1) To PVP (150 μL) were added chloroform (200 μL), a solution of 0.15 M t-butyl (S)-4-(2-(pyrrolidin-3-ylamino)quinazolin-4-yl)piperazine-1-carboxylate in chloroform (200 μL), and a solution of 0.3 M Cl—L—Q$^1$—Q$^2$—Ar (where, L represents —CO—) in chloroform (200 μL), and the mixture was stirred overnight. PVP was removed by filtration, PSA (300 μL) and a chloroform solution (700 μL) were added to the filtrate, and the mixture was stirred overnight. The reaction mixture was purified by silica gel column chromatography (NH silica gel, ethyl acetate).

(2) To the compound obtained in (1) was added a mixture solution (600 μL) of chloroform and trifluoromethanesulfonic acid (10:1), and the mixture was stirred overnight. To the reaction mixture were added chloroform (300 μL) and 1 M aqueous sodium hydroxide (300 μL) to separate the layers. The aqueous layer was extracted with chloroform and ethyl acetate, and the organic layer was dried with anhydrous magnesium sulfate. The residue was charged to SCX and eluted with a solution of chloroform and 2 M ammonia in methanol (=1:1), and the eluent was evaporated under reduced pressure to obtain a compound listed in Table 2.

The structures and the physical property data of this compound and similarly obtained compounds are shown in Table 2.

Example 8

Synthesis of Compounds Listed in Table 2

[Formula 40]

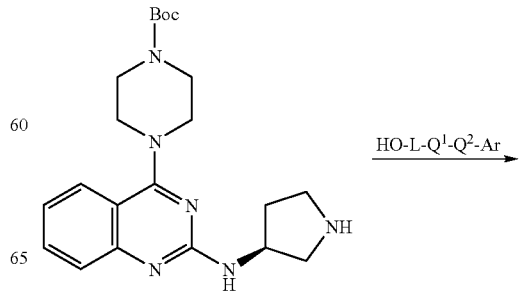

-continued

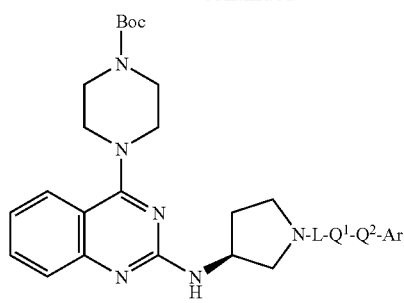

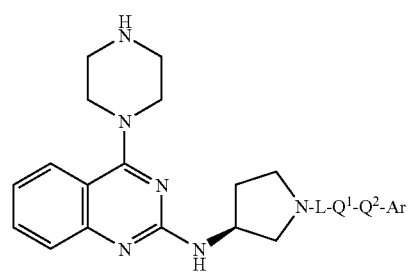

(1) To PS-DCC (150 μL) were added a solution of 1.2 M HOBt in chloroform (200 μL), a solution of 0.15 M t-butyl (S)-4-(2-(pyrrolidin-3-ylamino)quinazolin-4-yl)piperazine-1-carboxylate in chloroform (200 μL), and a solution of 0.3 M HO—L—Q$^1$—Q$^2$—Ar (where, L represents —CO—)carboxylic acid in DMF (200 μL), and the mixture was stirred overnight. PS-DCC was removed by filtration, and the solvent was evaporated under reduced pressure. The residue was purified by silica gel column chromatography (NH silica gel, ethyl acetate).

(2) A compound listed in Table 2 was obtained in the same manner as in Example 7 (2).

The structures and the physical property data of this compound and similarly obtained compounds are shown in Table 2.

Example 9

Synthesis of 1-((S)-3-(4-cyclohexylquinazolin-2-ylamino)pyrrolidin-1-yl)-2-(4-trifluoromethoxyphenyl)ethanone (Compound 1-219)

[Formula 41]

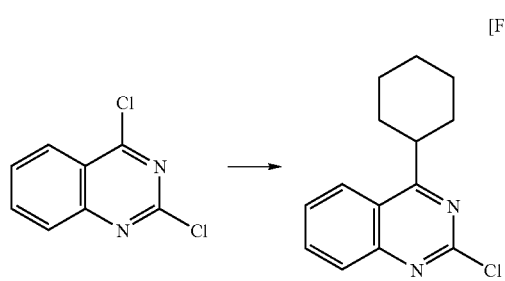

-continued

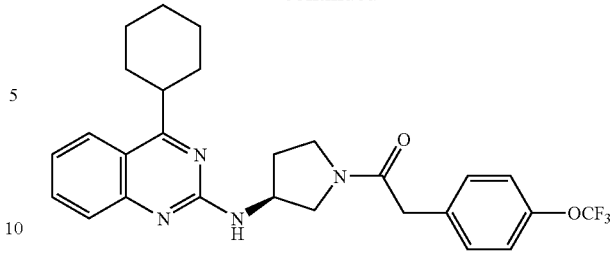

(1) To a solution of 2 M cyclohexylmagnesium bromide in diethyl ether (3.3 mL) was added a solution of 0.5 M zinc chloride in THF (14 mL) under nitrogen atmosphere, and the mixture was stirred at room temperature for 20 min. N-methylpyrrolidine (10 mL) was added, the mixture was stirred for 5 min, followed by addition of Pd(P$^t$Bu$_3$)$_2$ (0.13 g) and 2,4-dichloroquinoline (1.0 g), and the mixture was stirred at room temperature for 4 h. Water was added to the reaction mixture, and the mixture was extracted with chloroform. The organic layer was dried with anhydrous sodium sulfate, the desiccant was removed by filtration, the filtrate was concentrated under reduced pressure, and the residue was purified by silica gel column chromatography (hexane/ethyl acetate=6:1) to obtain 2-chloro-4-cyclohexylquinazoline (1.1 g).

MS: ESI$^+$ (m/z) 247 (M$^+$+1)

(2) A mixture of 2-chloro-4-cyclohexylquinazoline (0.25 g), 1-((S)-3-aminopyrrolidin-1-yl)-2-(4-trifluoromethoxyphenyl)ethanone mono hydrochloride (0.49 g), N,N-diisopropylethylamine (0.52 mL), N-methylpyrrolidone (1.0 mL), and n-butanol (1.0 mL) was stirred at 130° C. for 24 h. To the reaction mixture was added saturated aqueous sodium hydrogencarbonate, and the mixture was extracted with chloroform. The organic layer was dried with anhydrous sodium sulfate, the desiccant was removed by filtration, the filtrate was concentrated under reduced pressure, and the residue was purified by silica gel column chromatography (NH silica gel, ethyl acetate) to obtain the title compound (0.21 g).

The structures and the physical property data of this compound and similarly obtained compounds are shown in Tables 1 and 11.

Example 10

Synthesis of 1-((S)-3-(4-methylquinolin-2-ylamino)pyrrolidin-1-yl)-2-(4-trifluoromethoxyphenyl)ethanone mono hydrochloride (Compound 3-014)

[Formula 42]

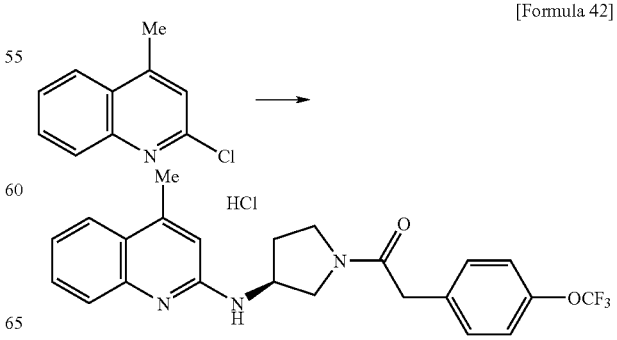

(1) A mixture of 2-chloro-4-methylquinoline (0.30 g), 1-((S)-3-aminopyrrolidin-1-yl)-2-(4-trifluoromethoxyphenyl)ethanone mono hydrochloride (0.60 g), N,N-diisopropylethylamine (0.74 mL), and n-butanol (1.5 mL) was heated at 140° C. in a sealed tube for 23 h. The reaction mixture was diluted with chloroform and saturated aqueous sodium hydrogencarbonate, and then the aqueous layer was extracted with chloroform. The organic layer was dried with anhydrous sodium sulfate, the desiccant was removed by filtration, the filtrate was concentrated under reduced pressure, and the residue was purified by silica gel column chromatography (NH silica gel, hexane/ethyl acetate=1:1) to obtain 1-((S)-3-(4-methylquinolin-2-ylamino)pyrrolidin-1-yl)-2-(4-trifluoromethoxyphenyl)ethanone (0.24 g).

(2) 1-((S)-3-(4-Methylquinolin-2-ylamino)pyrrolidin-1-yl)-2-(4-trifluoromethoxyphenyl)ethanone (0.24 g) was dissolved in ethyl acetate (2.5 mL), followed by addition of a solution (0.28 mL) of 4 M HCl in ethyl acetate, the mixture was stirred at room temperature for 2 h, concentrated under reduced pressure, and then solidified with diethyl ether to obtain the title compound (0.24 g).

The structures and the physical property data of this compound and similarly obtained compounds are shown in Table 3.

Example 11

Synthesis of 1-((S)-3-(4-dimethylamino-6-methylpyrimidin-2-ylamino)pyrrolidin-1-yl)-2-(4-trifluoromethoxyphenyl)ethanone mono hydrochloride (Compound 4-006)

[Formula 43]

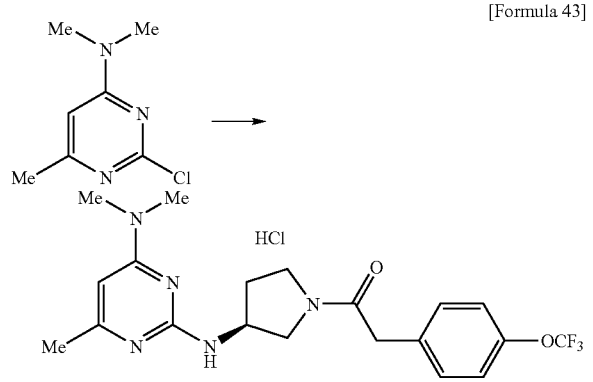

(1) A mixture of 2-chloro-4-dimethylamino-6-methylpyrimidine (0.20 g), 1-((S)-3-aminopyrrolidin-1-yl)-2-(4-trifluoromethoxyphenyl)ethanone mono hydrochloride (0.38 g), triethylamine (0.30 g), and isopropanol (2.9 mL) was heated at 160° C. in a microwave reaction apparatus for 3.5 h. The reaction mixture was concentrated under reduced pressure, and the residue was purified by silica gel column chromatography (chloroform/methanol=95:5) to obtain 1-((S)-3-(4-dimethylamino-6-methylpyrimidin-2-ylamino)pyrrolidin-1-yl)-2-(4-trifluoromethoxyphenyl)ethanone (0.43 g).

(2) 1-((S)-3-(4-Dimethylamino-6-methylpyrimidin-2-ylamino)pyrrolidin-1-yl)-2-(4-trifluoromethoxyphenyl)ethanone obtained in (1) was dissolved in ethyl acetate (2.0 mL), followed by addition of a solution (0.58 mL) of 4 M HCl in ethyl acetate, and the mixture was stirred at room temperature for 5 min. The reaction mixture was concentrated under reduced pressure, and the residue was solidified with diisopropyl ether to obtain the title compound (0.10 g).

The structures and the physical property data of this compound and similarly obtained compounds are shown in Tables 1 and 4.

Example 12

Synthesis of methyl (2S,4S)-4-(4-dimethylamino-6-methylpyrimidin-2-amino)-1-(2-(4-trifluoromethoxyphenyl)ethanoyl)pyrrolidine-2-carboxylate (Compound 13-009) and (2S,4S)-4-(4-dimethylamino-6-methylpyrimidin-2-amino)-1-(2-(4-trifluoromethoxyphenyl)ethanoyl)pyrrolidine-2-carboxylic acid dimethylamide mono hydrochloride (Compound 13-010)

[Formula 44]

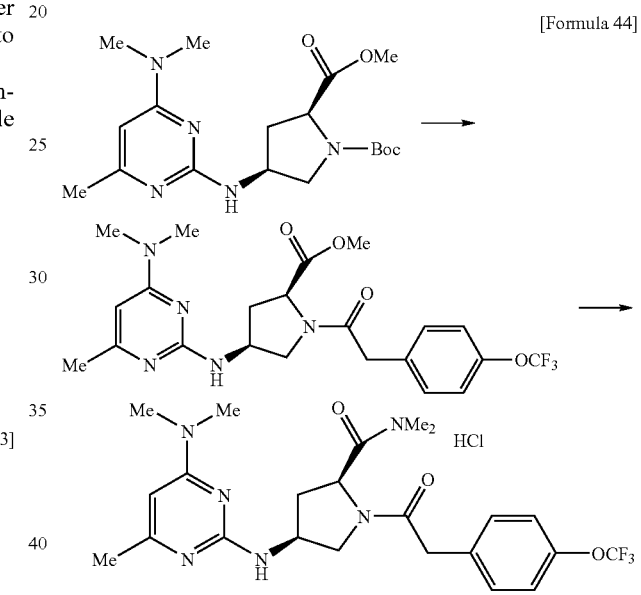

(1) 1-t-Butyl 2-methyl (2S,4S)-4-(4-Dimethylamino-6-methylpyrimidin-2-ylamino)pyrrolidine-1,2-dicarboxylate (1.2 g) synthesized in the same manner as the method described in Example 11 was dissolved in chloroform (12 mL), followed by addition of a solution (8 mL) of 4 M HCl in ethyl acetate, and the mixture was stirred for 18 h. The solvent was evaporated under reduced pressure, the residue was dissolved in chloroform (12 mL), followed by addition of 4-trifluoromethoxyphenylacetic acid (0.77 g), triethylamine (0.48 g), HOBt.H₂O (0.73 g), and EDC.HCl (0.73 g), and the mixture was stirred for 18 h. To the reaction mixture was added saturated aqueous sodium hydrogencarbonate to separate the layers, the aqueous layer was extracted with chloroform, the organic layer was dried with anhydrous magnesium sulfate, the desiccant was removed by filtration, the filtrate was concentrated under reduced pressure, and the residue was purified by silica gel column chromatography (NH silica gel, hexane/ethyl acetate=1:2) to obtain methyl (2S,4S)-4-(4-dimethylamino-6-methylpyrimidin-2-amino)-1-(2-(4-trifluoromethoxyphenyl)ethanoyl)pyrrolidine-2-carboxylate (0.86 g).

(2) Methyl (2S,4S)-4-(4-dimethylamino-6-methylpyrimidin-2-amino)-1-(2-(4-trifluoromethoxyphenyl)ethanoyl)pyrrolidine-2-carboxylate (0.20 g) was dissolved in methanol (2.0 mL), followed by addition an aqueous solution (0.5 mL) of sodium hydroxide (18 mg), and the mixture was stirred at room temperature for 2 h. The solvent was evaporated under reduced pressure, the residue was suspended in THF (2 mL), followed by addition of HOBt.H$_2$O (93 mg), EDC.HCl (93 mg), and 50% aqueous dimethyl amine (44 mg), and the mixture was stirred for 2 h. The solvent was evaporated under reduced pressure, followed by addition of chloroform and saturated aqueous sodium hydrogencarbonate to separate the layers. The organic layer was dried with anhydrous magnesium sulfate, the desiccant was removed by filtration, then the filtrate was concentrated under reduced pressure, and the residue was purified by silica gel column chromatography (NH silica gel, ethyl acetate) to obtain (2S,4S)-4-(4-dimethylamino-6-methylpyrimidin-2-ylamino)-1-(2-(4-trifluoromethoxyphenyl)ethanoyl)pyrrolidine-2-carboxylic acid dimethylamide (0.18 g).

(3) (2S,4S)-4-(4-Dimethylamino-6-methylpyrimidin-2-ylamino)-1-(2-(4-trifluoromethoxyphenyl)ethanoyl)pyrrolidine-2-carboxylic acid dimethylamide (70 mg) was dissolved in ethyl acetate (2 mL), followed by addition of a solution (0.07 mL) of 4 M HCl in ethyl acetate, and the mixture was stirred at room temperature for 2.5 h. Diethyl ether was added, and the precipitated crystals were collected by filtration to obtain the title compound (61 mg).

The structures and the physical property data of these compounds and similarly obtained compounds are shown in Table 13.

Example 13

Synthesis of 1-((S)-3-(4-dimethylamino-6-methylpyridin-2-ylamino)pyrrolidin-1-yl)-2-(4-trifluoromethoxyphenyl)ethanone (Compound 5-001)

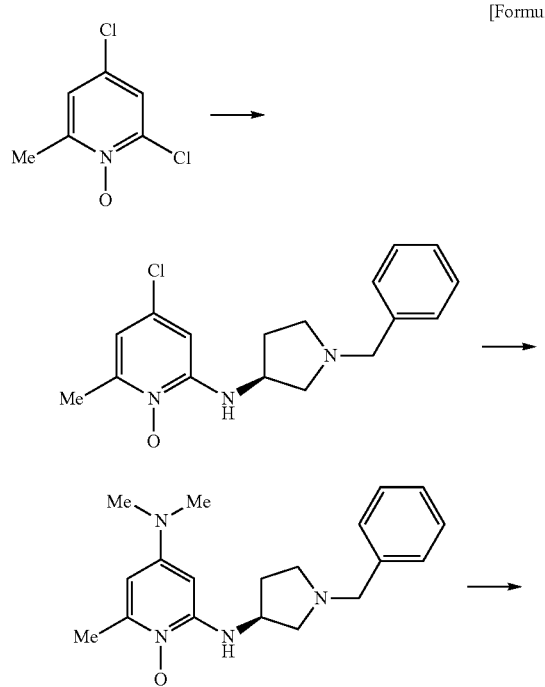

[Formula 45]

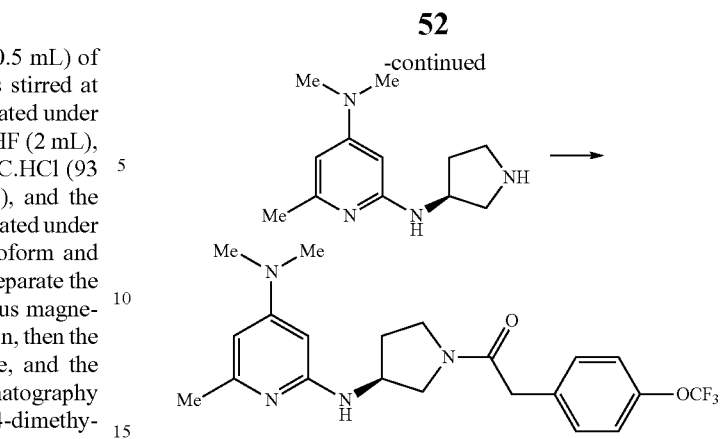

(1) A mixture of 2,4-dichloro-6-methylpyridin-1-oxide (3.0 g) synthesized in the same manner as the method described in WO9533750, (S)-1-benzyl-3-aminopyrrolidine (4.5 g), and n-butanol (9.0 mL) was heated to reflux for 10.5 h. After cooled to room temperature, the reaction mixture was diluted with a mixture solution of chloroform and saturated aqueous sodium hydrogencarbonate, and then the aqueous layer was extracted with chloroform. The organic layer was dried with anhydrous sodium sulfate, then the desiccant was removed by filtration, the filtrate was concentrated under reduced pressure, and the residue was purified by silica gel column chromatography (NH silica gel, hexane/ethyl acetate=2:1) to obtain ((S)-1-benzylpyrrolidin-3-yl)(4-chloro-6-methyl-1-oxypyridin-2-yl)amine (4.8 g).

(2) ((S)-1-Benzylpyrrolidin-3-yl)(4-chloro-6-methyl-1-oxypyridin-2-yl)amine (1.0 g), 50% aqueous dimethyl amine (1.7 mL), and n-butanol (0.5 mL) were heated at 160° C. in a microwave reaction apparatus for 1 h and 40 min. The reaction mixture was diluted with a mixture solution of chloroform and saturated aqueous sodium hydrogencarbonate, and then the aqueous layer was extracted 3 times with chloroform. The organic layer was dried with anhydrous sodium sulfate, then the desiccant was removed by filtration, the filtrate was concentrated under reduced pressure, and the residue was purified by silica gel column chromatography (chloroform/methanol=95:5) to obtain N$^2$-((S)-1-benzylpyrrolidin-3-yl)-6,N$^4$,N$^4$-trimethyl-1-oxypyridine-2,4-diamine (0.76 g).

(3) N$^2$-((S)-1-Benzylpyrrolidin-3-yl)-6,N$^4$,N$^4$-trimethyl-1-oxypyridine-2,4-diamine (0.70 g) was dissolved in methanol (7.0 mL), followed by addition of 10% Pd—C (70 mg), and the mixture was stirred at 50° C. under hydrogen atmosphere for 1 day. The catalyst was removed by Celite filtration, then the filtrate was concentrated under reduced pressure, the residue was dissolved in methanol (7.0 mL) again, followed by addition of 10% Pd—C (70 mg), and the mixture was stirred at 50° C. under hydrogen atmosphere for 1 day. The catalyst was removed by Celite filtration, and then the filtrate was concentrated under reduced pressure to obtain 6,N$^4$,N$^4$-trimethyl-N$^2$-(S)-pyrrolidin-3-yl-pyridine-2,4-diamine (0.52 g). This compound was used for the subsequent reaction without further purification.

(4) A mixture solution of 6,N$^4$,N$^4$-trimethyl-N$^2$-(S)-pyrrolidin-3-yl-pyridine-2,4-diamine (0.30 g), 4-trifluoromethoxyphenylacetic acid (0.36 g), EDC.HCl (0.31 g), HOBt.H$_2$O (0.28 g), and chloroform (9 mL) was stirred at room temperature for 34 h. After completion of the reaction, the reaction mixture was poured into saturated aqueous sodium hydrogencarbonate and extracted with chloroform. The organic layer was dried with anhydrous sodium sulfate, then the desiccant was removed by filtration, the filtrate was concentrated under reduced pressure, and the residue was purified by silica gel column chromatography (NH silica gel, chloroform/methanol=98:2-1:1) to obtain the title compound (0.22 g).

The structures and the physical property data of this compound and similarly obtained compounds are shown in Table 5.

Example 14

Synthesis of (S)-1-(3-(4,6'-dimethyl-3,4,5,6-tetrahydro-2H-[1,4']bipyridinyl-2'-ylamino)pyrrolidin-1-yl)-2-(4-trifluoromethoxyphenyl)ethanone (Compound 5-009)

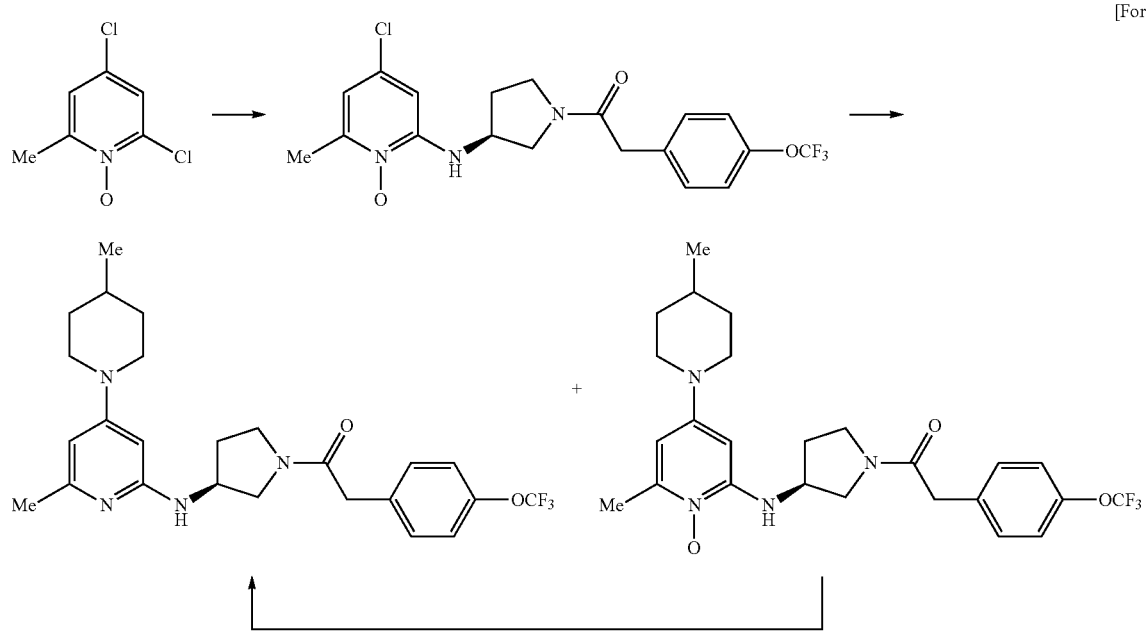

[Formula 46]

(1) In the same manner as in Example 13 (1), 1-((S)-3-(4-chloro-6-methyl-1-oxypyridin-2-ylamino)pyrrolidin-1-yl)-2-(4-trifluoromethoxyphenyl)ethanone (0.64 g) was obtained from 2,4-dichloro-6-methylpyridin-1-oxide (0.50 g) and 1-((S)-3-aminopyrrolidin-1-yl)-2-(4-trifluoromethoxyphenyl)ethanone mono hydrochloride (1.1 g).

(2) A mixture of 1-((S)-3-(4-chloro-6-methyl-1-oxypyridin-2-ylamino)pyrrolidin-1-yl)-2-(4-trifluoromethoxyphenyl)ethanone (300 mg), 4-methylpiperidine (0.30 g), N,N-diisopropylethylamine (0.40 mL), and n-butanol (0.60 mL) was heated at 110° C. for 15 h. The mixture was cooled to room temperature, then the solvent was evaporated under reduced pressure, and the residue was purified by silica gel column chromatography (NH silica gel, ethyl acetate–ethyl acetate/methanol=10:1) to obtain the title compound (40 mg) and 1-((S)-3-(4,6'-dimethyl-1'-oxy-3,4,5,6-tetrahydro-2H-[1,4']bipyridinyl-2'-ylamino)pyrrolidin-1-yl)-2-(4-trifluoromethoxyphenyl)ethanone (200 mg).

(3) 1-((S)-3-(4,6'-Dimethyl-1'-oxy-3,4,5,6-tetrahydro-2H-[1,4']bipyridinyl-2'-ylamino)pyrrolidin-1-yl)-2-(4-trifluoromethoxyphenyl)ethanone (200 mg) was dissolved in methanol (6 mL), followed by addition of 10% Pd—C (200 mg), and the mixture stirred overnight at 40° C. under hydrogen atmosphere. The catalyst was removed by Celite filtration, then the filtrate was concentrated under reduced pressure, and the residue was purified by silica gel column chromatography (NH silica gel, chloroform/methanol=10:1) to obtain the title compound (64 mg).

The structures and the physical property data of this compound and similarly obtained compounds are shown in Table 5.

Example 15

Synthesis of 1-((3R,4R)-3-hydroxy-4-(6-methyl-4-morpholin-4-ylpyridin-2-ylamino)pyrrolidin-1-yl)-2-(4-trifluoromethoxyphenyl)ethanone (Compound 14-001)

[Formula 47]

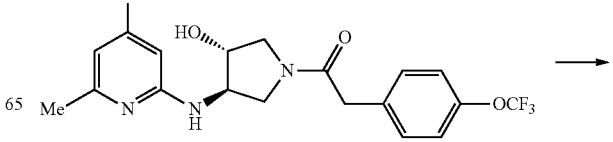

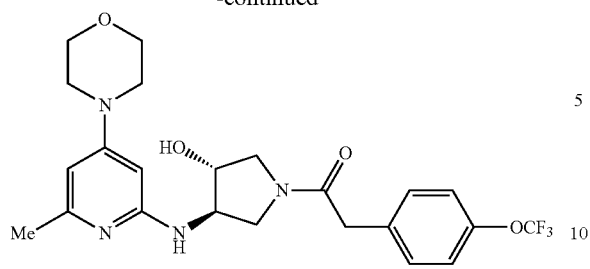

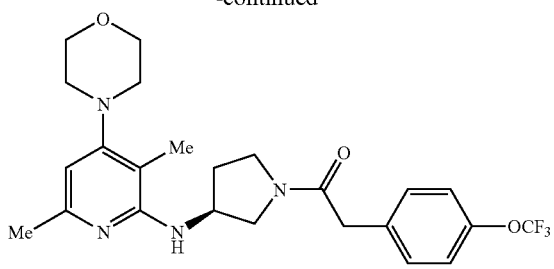

(1) A mixture of 2,4-dichloro-6-methylpyridine 1-oxide (200 mg), 1-((3R,4R)-3-amino-4-hydroxypyrrolidin-1-yl)-2-(4-trifluoromethoxyphenyl)ethanone (340 mg), and n-butanol (0.6 mL) was stirred at 130° C. for 10 h. The reaction mixture was concentrated under reduced pressure, the residue was purified by silica gel column chromatography (NH silica gel, ethyl acetate–ethyl acetate/methanol=20:1), and then the resulting solids were washed with hexane and diethyl ether to obtain 1-((3R,4R)-3-(4-chloro-6-methylpyridin-2-ylamino)-4-hydroxypyrrolidin-1-yl)-2-(4-trifluoromethoxyphenyl)ethanone (75 mg).

(2) A mixture of 1-((3R,4R)-3-(4-chloro-6-methylpyridin-2-ylamino)-4-hydroxypyrrolidin-1-yl)-2-(4-trifluoromethoxyphenyl)ethanone (68 mg), morpholine (0.02 mL), sodium t-butoxide (42 mg), Pd(OAc)$_2$ (1 mg), 2-(di-t-butylphosphino)biphenyl (3 mg), and toluene (1 mL) was heated at 100° C. for 10 h. The mixture was cooled to room temperature, then the reaction mixture was diluted with chloroform, insoluble matters were removed by Celite filtration, and then the filtrate was concentrated under reduced pressure. The residue was purified by preparative TLC (NH silica gel, ethyl acetate, and silica gel, hexane/acetone=1:1) to obtain the title compound (8 mg).

The structures and the physical property data of this compound and similarly obtained compounds are shown in Tables 5 and 14.

(1) A mixture of 3,6-dimethyl-2,4-bistrifluoromethanesulfonyloxypyridine (0.50 g), morpholine (0.12 g), N,N-diisopropylethylamine (0.34 mL), and N-methylpyrrolidone (2.0 mL) was stirred at 60° C. for 2.5 h. The reaction mixture was cooled to room temperature, followed by addition of water, and the mixture was extracted with ethyl acetate. The organic layer was dried with anhydrous sodium sulfate, the desiccant was removed by filtration, the filtrate was concentrated under reduced pressure, and the residue was purified by silica gel column chromatography (hexane/ethyl acetate=1:1) to obtain 3,6-dimethyl-4-morpholin-1-yl-2-trifluoromethanesulfonyloxypyridine (0.15 g).

(2) To a mixture of 3,6-dimethyl-4-morpholin-1-yl-2-trifluoromethanesulfonyloxypyridine (0.13 g), 1-((S)-3-aminopyrrolidin-1-yl)-2-(4-trifluoromethoxyphenyl)ethanone mono hydrochloride (0.15 g), and toluene (2.0 mL) were added Pd$_2$(dba)$_3$ (52 mg), 2-(di-t-butylphosphino)biphenyl (34 mg), and potassium phosphate (0.40 g), and the mixture was stirred at 105° C. under nitrogen atmosphere for 22 h. Water was added to the reaction mixture, the mixture was extracted with chloroform, the organic layer was dried with anhydrous sodium sulfate, then the desiccant was removed by filtration, the filtrate was concentrated under reduced pressure, and the residue was purified by silica gel column chromatography (NH silica gel, ethyl acetate, and silica gel, ethyl acetate) to obtain the title compound (30 mg).

The structures and the physical property data of this compound and similarly obtained compounds are shown in Tables 5, 14, and 15.

Example 16

Synthesis of (S)-1-(3-(3,6-dimethyl-4-morpholin-4-ylpyridin-2-ylamino)pyrrolidin-1-yl)-2-(4-trifluoromethoxyphenyl)ethanone (Compound 5-004)

Example 17

Synthesis of 1-((S)-3-(4-(1,1-dioxo-1λ$^6$-thiomorpholin-4-yl)-6-methylpyridin-2-ylamino)pyrrolidin-1-yl)-2-(4-trifluoromethoxyphenyl)ethanone (Compound 5-006)

[Formula 48]

[Formula 49]

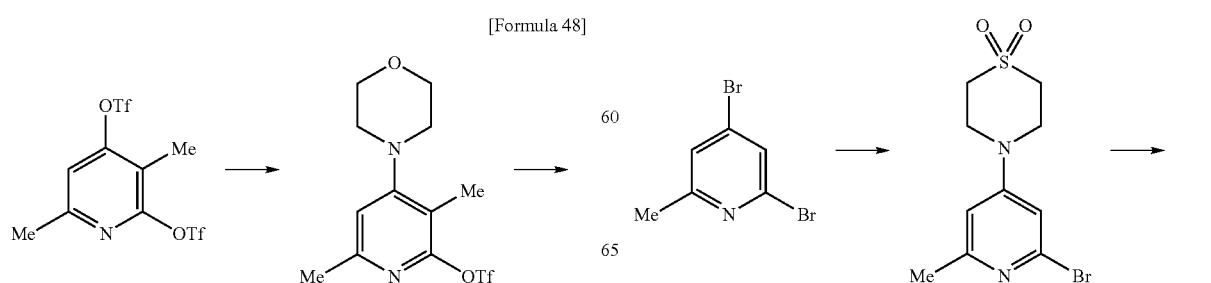

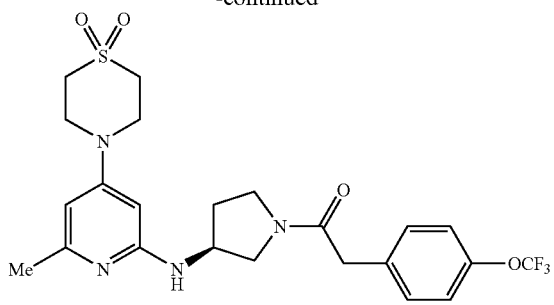

(1) A mixture of 2,4-dibromo-6-methylpyridine (0.50 g), thiomorpholine 1,1-dioxide (0.32 g), N,N-diisopropylethylamine (0.70 mL), and N-methylpyrrolidone (2.0 mL) was stirred at 135° C. for 27 h. The reaction mixture was cooled to room temperature, followed by addition of water, and the mixture was extracted with ethyl acetate. The organic layer was dried with anhydrous sodium sulfate, then the desiccant was removed by filtration, the filtrate was concentrated under reduced pressure, and the residue was purified by silica gel column chromatography (NH silica gel, hexane/ethyl acetate=1:1–ethyl acetate) to obtain 4-(2-bromo-6-methylpyridin-4-yl)thiomorpholine 1,1-oxide (0.11 g).

(2) To a mixture of 4-(2-bromo-6-methylpyridin-4-yl)thiomorpholine 1,1-oxide (0.11 g), 1-((S)-3-aminopyrrolidin-1-yl)-2-(4-trifluoromethoxyphenyl)ethanone mono hydrochloride (0.14 g), and toluene (1 mL) were added Pd(OAc)$_2$ (12 mg), 2-(di-t-butylphosphino)biphenyl (32 mg), and sodium t-butoxide (0.14 g), and the mixture was heated at 105° C. under nitrogen atmosphere for 21 h with stirring. Water was added to the reaction mixture, the mixture was extracted with chloroform, the organic layer was dried with anhydrous sodium sulfate, then the desiccant was removed by filtration, the filtrate was concentrated under reduced pressure, and the residue was purified by silica gel column chromatography (NH silica gel, ethyl acetate–ethyl acetate/methanol=9:1) to obtain the title compound (40 mg).

The structures and the physical property data of this compound and similarly obtained compounds are shown in Table 5.

Example 18

Synthesis of 1-(3-(4,6-dimethylpyridin-2-ylamino)pyrrolidin-1-yl)-2-(4-trifluoromethoxyphenyl)ethanone (Compound 5-015)

[Formula 50]

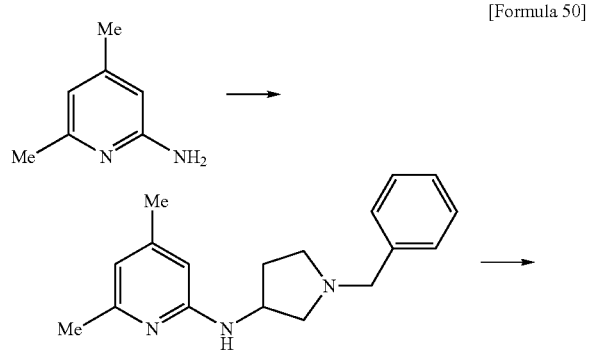

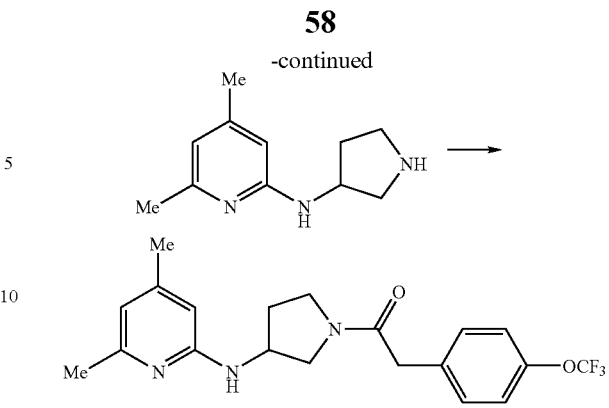

(1) A mixture of 2-amino-4,6-dimethylpyridine (2.0 g), 1-benzylpyrrolidin-3-one (2.9 g), acetic acid (2.9 mL), and chloroform (34 mL) was ice-cooled, followed by addition of sodium triacetoxyborohydride (4.9 g), and the mixture was stirred for 18 h while heating slowly to room temperature. To the reaction mixture was added 1 M aqueous sodium hydroxide to make it basic, and then the mixture was extracted with chloroform. The organic layer was dried with anhydrous magnesium sulfate, then the desiccant was removed by filtration, the filtrate was concentrated under reduced pressure, and the residue was purified by silica gel column chromatography (NH silica gel, hexane/ethyl acetate=65:35) to obtain 1-benzyl-3-(4,6-dimethylpyridin-2-ylamino)pyrrolidine (1.3 g).

(2) 1-Benzyl-3-(4,6-dimethylpyridin-2-ylamino)pyrrolidine (1.3 g) was dissolved in methanol (13 mL), followed by addition of 20% Pd(OH)$_2$/C (0.26 g), and the mixture was stirred at room temperature for 20 h under hydrogen atmosphere. The catalyst was removed by Celite filtration, then the filtrate was concentrated under reduced pressure, and the residue was purified by silica gel column chromatography (NH silica gel, chloroform/methanol=19:1) to obtain 3-(4,6-dimethylpyridin-2-ylamino)pyrrolidine (0.10 g).

(3) A mixture solution of 3-(4,6-dimethylpyridin-2-ylamino)pyrrolidine (0.73 g), 4-trifluoromethoxyphenylacetic acid (0.12 g), EDC.HCl (0.12 g), HOBt.H$_2$O (0.12 g), and chloroform (1.0 mL) was stirred at room temperature. After completion of the reaction, the reaction mixture was diluted with chloroform and washed with 1 M aqueous sodium hydroxide and brine. The organic layer was dried with anhydrous magnesium sulfate, then the desiccant was removed by filtration, the filtrate was concentrated under reduced pressure, and the residue was purified by silica gel column chromatography (chloroform/methanol=19:1) and then crystallized with hexane and diethyl ether to obtain the title compound (0.14 g).

The structures and the physical property data of this compound and similarly obtained compounds are shown in Table 5.

Example 19

Synthesis of (S)-1-(3-(6-methoxy-4-morpholinoquinolin-2-ylamino)pyrrolidin-1-yl)-2-(4-trifluoromethoxyphenyl)ethanone (Compound 3-011)

[Formula 51]

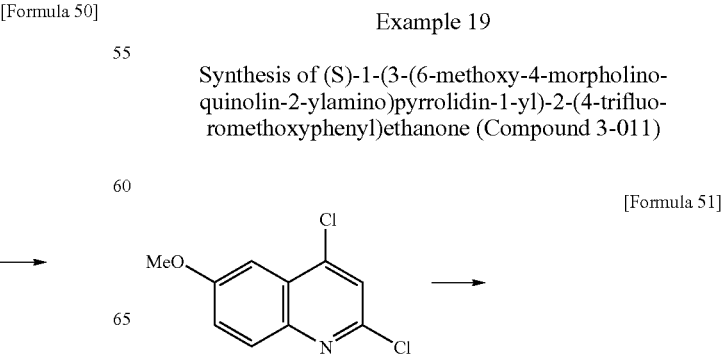

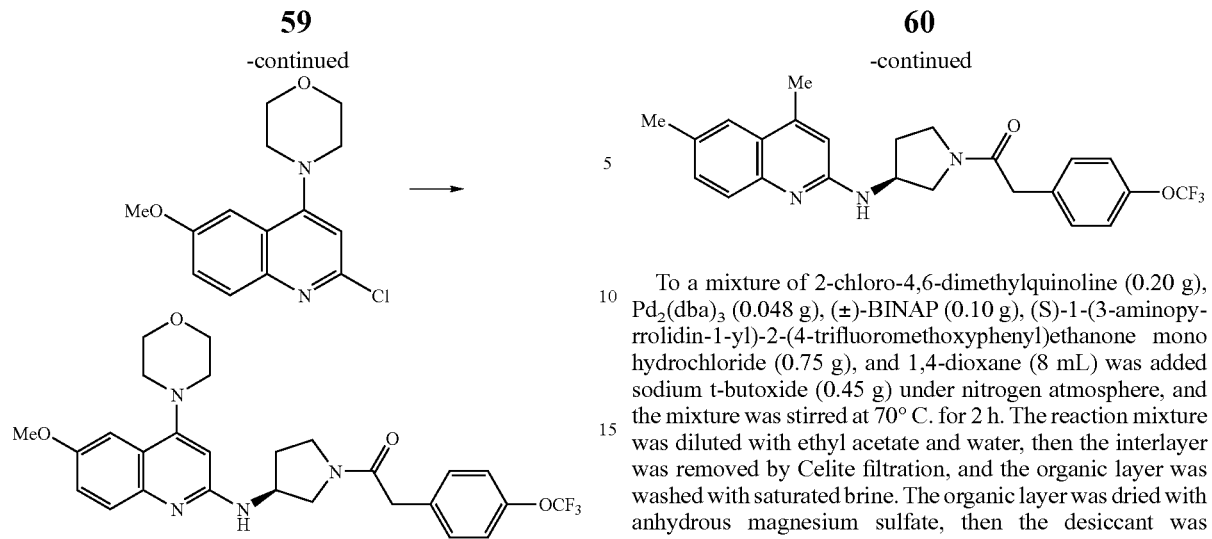

(1) A mixture of 2,4-dichloro-6-methoxyquinoline (0.228 g), morpholine (262 μL), N,N-diisopropylethylamine (348 μL), and ethylene glycol (4 mL) was heated with microwave (145° C.) for 75 min with stirring. The reaction mixture was cooled to room temperature, followed by addition of water, the mixture was extracted with chloroform and washed with saturated brine, and the organic layer was dried with anhydrous sodium sulfate. The desiccant was removed by filtration, the residue concentrated under reduced pressure was purified by silica gel column chromatography (chloroform/hexane=1/1) to obtain 2-chloro-6-methoxy-4-morpholinoquinoline (0.182 g).

(2) To a mixture of 2-chloro-6-methoxy-4-morpholinoquinoline (0.160 g), Pd$_2$(dba)$_3$ (0.026 g), (±)-BINAP (0.054 g), (S)-1-(3-aminopyrrolidin-1-yl)-2-(4-trifluoromethoxyphenyl)ethanone mono hydrochloride (0.210 g), and 1,4-dioxane (3 mL) was added sodium t-butoxide (0.111 g) under nitrogen atmosphere, and the mixture was stirred at 70° C. for 1.5 h. After cooled to room temperature, the reaction mixture was diluted with ethyl acetate and water, the interlayer was removed by Celite filtration, and the organic layer was washed with saturated brine. The organic layer was dried with anhydrous magnesium sulfate, the desiccant was removed by filtration, the filtrate was concentrated under reduced pressure, and the residue was purified by silica gel column chromatography (silica gel, chloroform/methanol, and NH silica gel, ethyl acetate/hexane) to obtain light yellow amorphous (S)-1-(3-(6-methoxy-4-morpholinoquinolin-2-ylamino)pyrrolidin-1-yl)-2-(4-trifluoromethoxyphenyl)ethanone (0.081 g).

The structures and the physical property data of this compound and similarly obtained compounds are shown in Tables 3 and 12.

Example 20

Synthesis of (S)-1-(3-(4,6-dimethylquinolin-2-ylamino)pyrrolidin-1-yl)-2-(4-trifluoromethoxyphenyl)ethanone (Compound 3-021)

[Formula 52]

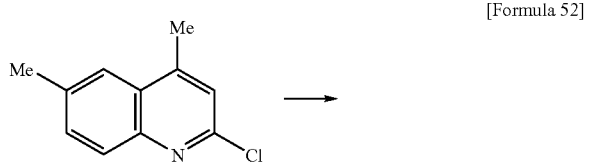

To a mixture of 2-chloro-4,6-dimethylquinoline (0.20 g), Pd$_2$(dba)$_3$ (0.048 g), (±)-BINAP (0.10 g), (S)-1-(3-aminopyrrolidin-1-yl)-2-(4-trifluoromethoxyphenyl)ethanone mono hydrochloride (0.75 g), and 1,4-dioxane (8 mL) was added sodium t-butoxide (0.45 g) under nitrogen atmosphere, and the mixture was stirred at 70° C. for 2 h. The reaction mixture was diluted with ethyl acetate and water, then the interlayer was removed by Celite filtration, and the organic layer was washed with saturated brine. The organic layer was dried with anhydrous magnesium sulfate, then the desiccant was removed by filtration, the filtrate was concentrated under reduced pressure, and the residue was purified by silica gel column chromatography (silica gel, chloroform/methanol, and NH silica gel, ethyl acetate) to obtain colorless amorphous (S)-1-(3-(4,6-dimethylquinolin-2-ylamino)pyrrolidin-1-yl)-2-(4-trifluoromethoxyphenyl)ethanone (0.30 g).

The structures and the physical property data of this compound and similarly obtained compounds are shown in Tables 3 and 12.

Example 21

Synthesis of (S)-(1-(4-chlorophenyl)cyclobutyl)-(3-(6-methoxy-4-methylquinolin-2-ylamino)pyrrolidin-1-yl)methanone (Compound 3-043)

[Formula 53]

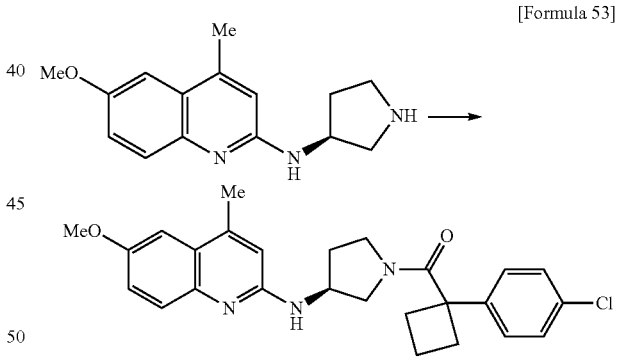

To a mixture of (S)-6-methoxy-4-methyl-N-(pyrrolidin-3-yl)quinolin-2-amine (0.50 g), 1-(4-chlorophenyl)-1-cyclobutane carboxylic acid (0.41 g), and DMF (6 mL) were added HOBt (0.39 g) and EDC.HCl (0.56 g), and the mixture was stirred at room temperature for 12 h. The reaction mixture was diluted with ethyl acetate and water, followed by addition of a saturated sodium hydrogencarbonate solution to extract the mixture. The organic layer was dried with anhydrous magnesium sulfate, then the desiccant was removed by filtration, the filtrate was concentrated under reduced pressure, and the residue was purified by silica gel column chromatography (silica gel, chloroform/methanol, and NH silica gel, ethyl acetate) to obtain colorless amorphous (S)-(1-(4-chlorophenyl)cyclobutyl)-(3-(6-methoxy-4-methylquinolin-2-ylamino)pyrrolidin-1-yl)methanone (0.67 g).

The structures and the physical property data of this compound and similarly obtained compounds are shown in Tables 3, 5, and 19.

Example 22

Synthesis of (S)-(1-(4-chlorophenyl)cyclobutyl)-(3-(6-hydroxy-4-methylquinolin-2-ylamino)pyrrolidin-1-yl)methanone (Compound 3-039)

[Formula 54]

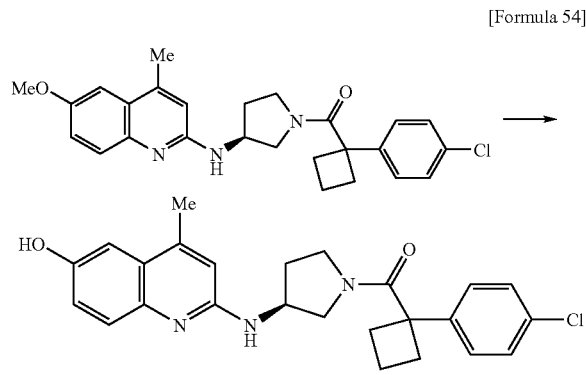

A solution of (S)-(1-(4-chlorophenyl)cyclobutyl)-(3-(6-methoxy-4-methylquinolin-2-ylamino)pyrrolidin-1-yl) methanone (0.60 g) in dichloromethane (50 mL) was cooled to −78° C., followed by addition of a solution of 1 M boron tribromide in dichloromethane (7.3 mL), and the mixture was stirred for 12 h while slowly heating to room temperature. To the reaction mixture was added a saturated sodium hydrogencarbonate solution to make it basic, and the mixture was extracted with chloroform. The aqueous layer was reextracted with a mixed solution of ethyl acetate and n-butanol, then the organic layer was combined and concentrated under reduced pressure, and the residue was purified by silica gel column chromatography (silica gel, chloroform/methanol, and NH silica gel, chloroform/methanol) and crystallized with ethyl acetate to obtain white solid (S)-(1-(4-chlorophenyl)cyclobutyl)-(3-(6-hydroxy-4-methylquinolin-2-ylamino)pyrrolidin-1-yl)methanone (0.278 g).

The structures and the physical property data of this compound and similarly obtained compounds are shown in Tables 3, 12, and 20.

Example 23

Synthesis of 1-((3R,4R)-3-(6-hydroxy-4-methylquinolin-2-ylamino)-4-methoxypyrrolidin-1-yl)-2-(4-trifluoromethoxyphenyl)ethanone (Compound 12-008)

[Formula 55]

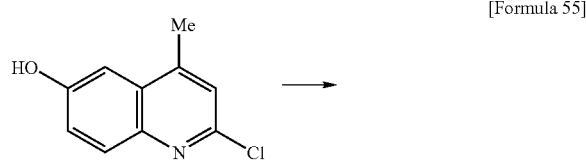

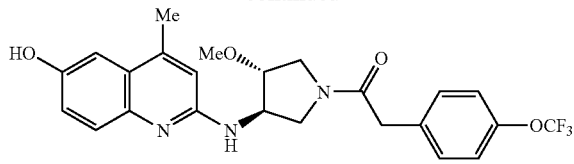

To a mixture of 2-chloro-6-hydroxy-4-methylquinoline (0.153 g), Pd$_2$(dba)$_3$ (0.036 g), (±)-BINAP (0.073 g), 1-((3R,4R)-3-amino-4-methoxypyrrolidin-1-yl)-2-(4-trifluoromethoxyphenyl)ethanone (0.25 g), and 1,4-dioxane (7 mL) was added sodium t-butoxide (0.241 g) under nitrogen atmosphere, and the mixture was stirred at 65° C. for 3 h. Pd$_2$(dba)$_3$ (0.036 g), (±)-BINAP (0.073 g), and sodium t-butoxide (0.241 g) were further added, and the mixture was stirred at 65° C. for 5 h. The reaction mixture was diluted with ethyl acetate and water, then the interlayer was removed by Celite filtration, and the organic layer washed with saturated brine. The organic layer was dried with anhydrous magnesium sulfate, the desiccant was removed by filtration, the filtrate was concentrated under reduced pressure, and the residue was purified by silica gel column chromatography (silica gel, chloroform/methanol and NH silica gel, ethyl acetate) to obtain colorless amorphous 1-((3R,4R)-3-(6-hydroxy-4-methylquinolin-2-ylamino)-4-methoxypyrrolidin-1-yl)-2-(4-trifluoromethoxyphenyl)ethanone (0.064 g).

The structures and the physical property data of this compound and similarly obtained compounds are shown in Table 12.

Example 24

Synthesis of 1-((3R,4R)-3-hydroxy-4-(4-methoxy-6-methylquinolin-2-ylamino)pyrrolidin-1-yl)-2-(4-trifluoromethoxyphenyl)ethanone (Compound 12-015)

[Formula 56]

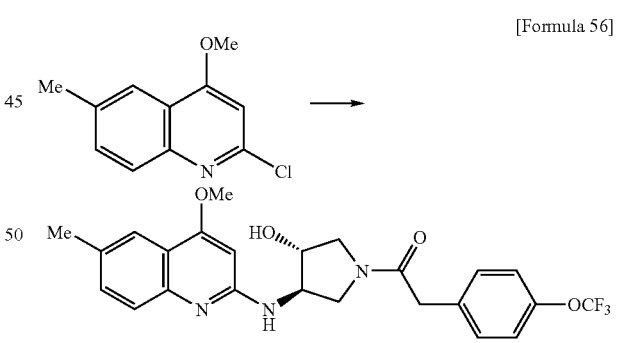

To a mixture of 2-chloro-4-methoxy-6-methylquinoline (0.12 g), Pd$_2$(dba)$_3$ (0.027 g), (±)-BINAP (0.056 g), 1-((3R,4R)-3-amino-4-hydroxypyrrolidin-1-yl)-2-(4-trifluoromethoxyphenyl)ethanone (0.22 g), and 1,4-dioxane (2 mL) was added sodium t-butoxide (0.17 g) under nitrogen atmosphere, and the mixture was stirred at 70° C. for 1 h. The reaction mixture was diluted with ethyl acetate and water, then the interlayer was removed by Celite filtration, and the organic layer was washed with saturated brine. The organic layer was dried with anhydrous magnesium sulfate, the desiccant was removed by filtration, the filtrate was concentrated under reduced pressure, and the residue was purified by silica gel column chromatography (silica gel, ethyl acetate, and NH silica gel, ethyl acetate/chloroform) to obtain white solid 1-((3R,4R)-3-hydroxy-4-(4-methoxy-6-methylquinolin-2-ylamino)pyrrolidin-1-yl)-2-(4-trifluoromethoxyphenyl)ethanone (0.16 g).

The structures and the physical property data of this compound and similarly obtained compounds are shown in Tables 3 and 12.

Examples 25 and 26

Example 25

Synthesis of (S)-1-(4-chlorophenyl)-2-(3-(6-methoxy-4-methylquinolin-2-ylamino)pyrrolidin-1-yl)ethane-1,2-dione (Compound 3-044)

Example 26

Synthesis of (S)-1-(4-chlorophenyl)-2-(3-(6-hydroxy-4-methylquinolin-2-ylamino)pyrrolidin-1-yl)ethane-1,2-dione (Compound 3-040)

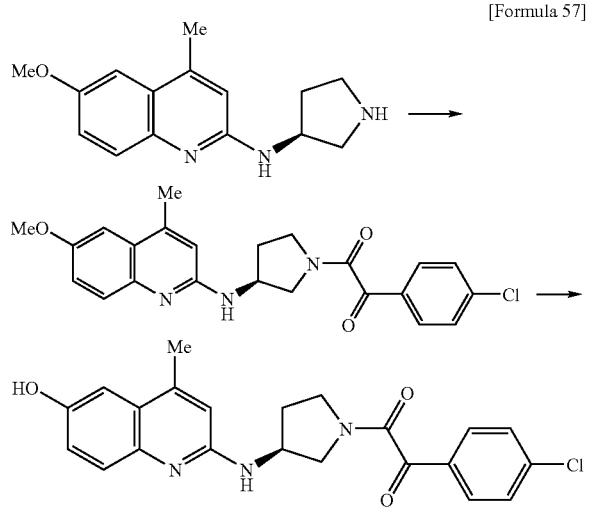

[Formula 57]

(1) To a mixture of (S)-6-methoxy-4-methyl-N-(pyrrolidin-3-yl)quinolin-2-amine (0.773 g), 2-(4-chlorophenyl)-2-oxoacetic acid (0.544 g), and DMF (10 mL) were added HOBt (0.609 g) and EDC.HCl (0.864 g), and the mixture was stirred at room temperature for 12 h. The reaction mixture was diluted with ethyl acetate and water, followed by addition of saturated sodium hydrogencarbonate solution, and the mixture was extracted with ethyl acetate.

The organic layer was dried with anhydrous magnesium sulfate, the desiccant was removed by filtration, the filtrate was concentrated under reduced pressure, and the residue was purified by silica gel column chromatography (silica gel, chloroform/methanol, and NH silica gel, ethyl acetate) to obtain light yellow amorphous (S)-1-(4-chlorophenyl)-2-(3-(6-methoxy-4-methylquinolin-2-ylamino)pyrrolidin-1-yl)ethane-1,2-dione (0.559 g).

(2) A solution of (S)-1-(4-chlorophenyl)-2-(3-(6-methoxy-4-methylquinolin-2-ylamino)pyrrolidin-1-yl)ethane-1,2-dione (0.467 g) in dichloromethane (50 mL) was cooled to −78° C., followed by addition of a solution (6.1 mL) of 1 M boron tribromide in dichloromethane, and the mixture was stirred for 3 h while heating slowly to room temperature. To the reaction mixture was added a saturated sodium hydrogencarbonate solution to make it basic, and then the mixture was extracted with chloroform. The aqueous layer was reextracted with a mixed solution of ethyl acetate and n-butanol, then the organic layer was combined, the filtrate was concentrated under reduced pressure, and the residue was purified by silica gel column chromatography (silica gel, chloroform/methanol, and NH silica gel, chloroform/methanol) to obtain light yellow amorphous (S)-1-(4-chlorophenyl)-2-(3-(6-hydroxy-4-methylquinolin-2-ylamino)pyrrolidin-1-yl)ethane-1,2-dione (0.068 g).

The structures and the physical property data of this compound and similarly obtained compounds are shown in Table 3.

Example 27

Synthesis of (S)-1-(3-(4-dimethylaminothieno[3,2-d]pyrimidin-2-ylamino)pyrrolidin-1-yl)-2-(4-trifluoromethoxyphenyl)ethanone 1 maleate (Compound 6-001)

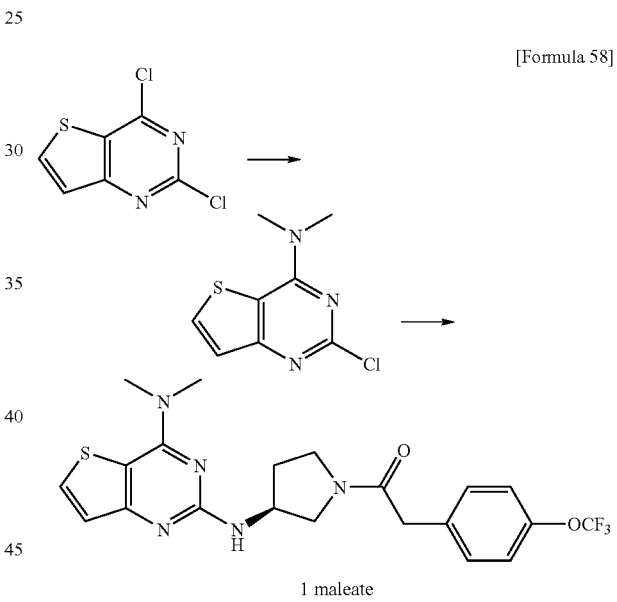

[Formula 58]

1 maleate (1) To a solution of 50% aqueous dimethyl amine (0.77 g) in ethanol (30 mL) was added 2,4-dichlorothieno[3,2-d]pyrimidine (1.00 g) with ice cooling, and the mixture was stirred for 12 h while heating to room temperature. The reaction mixture was concentrated under reduced pressure and diluted with chloroform and water, and then the aqueous layer was extracted with chloroform. The organic layer was washed with 1 M hydrochloric acid and saturated brine, then the organic layer was dried with anhydrous magnesium sulfate, then the desiccant was removed by filtration, the filtrate was concentrated under reduced pressure, and the residue was crystallized with diethyl ether to obtain 2-chloro-N,N-dimethylthieno[3,2-d]pyrimidin-4-amine (0.90 g).

(2) A mixture of 2-chloro-N,N-dimethylthieno[3,2-d]pyrimidin-4-amine (0.60 g), (S)-1-(3-aminopyrrolidin-1-yl)-2-(4-trifluoromethoxyphenyl)ethanone mono hydrochloride (2.70 g), N,N-diisopropylethylamine (1.80 g), and ethylene glycol (18 mL) was heated at 110° C. for 20 h with stirring. The reaction mixture was diluted with chloroform and water, and then the aqueous layer was extracted with chloroform. The organic layer was concentrated under reduced pressure, and the residue was purified by silica gel column chromatography (silica gel, chloroform/methanol, and NH silica gel, chloroform/methanol) and crystallized with diethyl ether to obtain white solid (S)-1-(3-(4-dimethylaminothieno[3,2-d]pyrimidin-2-ylamino)pyrrolidin-1-yl)-2-(4-trifluoromethoxyphenyl)ethanone (0.16 g).

A solution of (S)-1-(3-(4-dimethylaminothieno[3,2-d]pyrimidin-2-ylamino)pyrrolidin-1-yl)-2-(4-trifluoromethoxyphenyl)ethanone (0.11 g) and maleic acid (25 mg) in isopropyl alcohol (10 mL) was concentrated under reduced pressure and crystallized with a mixed solution of isopropyl alcohol and diethyl ether to obtain white solid (S)-1-(3-(4-dimethylaminothieno[3,2-d]pyrimidin-2-ylamino)pyrrolidin-1-yl)-2-(4-trifluoromethoxyphenyl)ethanone 1 maleate (0.10 g).

The structures and the physical property data of this compound and similarly obtained compounds are shown in Tables 6, 8, and 10.

Example 28

Synthesis of 1-((3R,4R)-3-(4-dimethylaminothieno[3,4-d]pyrimidin-2-ylamino)-4-hydroxypyrrolidin-1-yl)-2-(4-trifluoromethoxyphenyl)ethanone (Compound 8-008)

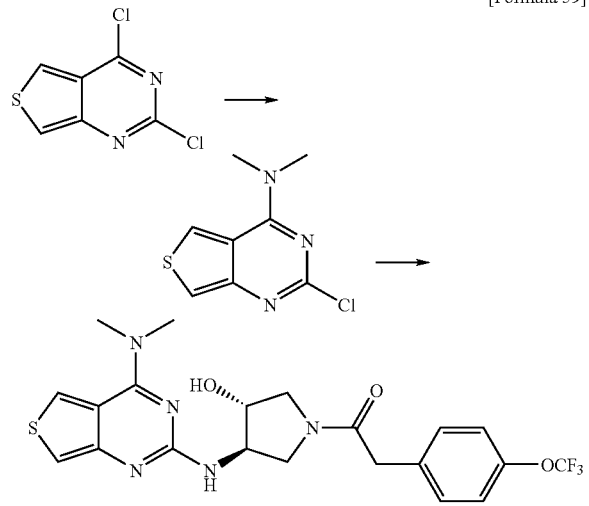

[Formula 59]

(1) To a solution of 50% aqueous dimethyl amine (0.13 g) in ethanol (5 mL) were added 2,4-dichlorothieno[3,4-d]pyrimidine (0.20 g) and triethylamine (0.10 g) at room temperature, and the mixture was stirred for 2 h. The reaction mixture was concentrated under reduced pressure and diluted with chloroform and water, and then the aqueous layer was extracted with chloroform. The organic layer was washed with 1 M hydrochloric acid and saturated brine, then the organic layer was dried with anhydrous magnesium sulfate, then the desiccant was removed by filtration, the filtrate was concentrated under reduced pressure, and the residue was crystallized with diethyl ether to obtain 2-chloro-N,N-dimethylthieno[3,4-d]pyrimidin-4-amine (0.16 g).
(2) To a mixture of 2-chloro-N,N-dimethylthieno[3,4-d]pyrimidin-4-amine (0.156 g), Pd$_2$(dba)$_3$ (0.033 g), (±)-BINAP (0.068 g), 1-((3R,4R)-3-amino-4-hydroxypyrrolidin-1-yl)-2-(4-trifluoromethoxyphenyl)ethanone (0.27 g), and 1,4-dioxane (8 mL) was added sodium t-butoxide (0.21 g) under nitrogen atmosphere, and the mixture was stirred at room temperature for 12 h. The reaction mixture was diluted with ethyl acetate and water, the interlayer was removed by Celite filtration, and the organic layer was washed with saturated brine. The organic layer was dried with anhydrous magnesium sulfate, then the desiccant was removed by filtration, the filtrate was concentrated under reduced pressure, and the residue was purified by silica gel column chromatography (silica gel, chloroform/methanol, and NH silica gel, ethyl acetate) to obtain light yellow amorphous 1-((3R,4R)-3-(4-dimethylaminothieno[3,4-d]pyrimidin-2-ylamino)-4-hydroxypyrrolidin-1-yl)-2-(4-trifluoromethoxyphenyl)ethanone (0.037 g).

The structures and the physical property data of this compound and similarly obtained compounds are shown in Table 8.

Example 29

Synthesis of 1-((3R,4R)-3-(4-dimethylamino-6-methylthieno[3,2-d]pyrimidin-2-ylamino)-4-hydroxypyrrolidin-1-yl)-2-(4-trifluoromethoxyphenyl)ethanone (Compound 6-012)

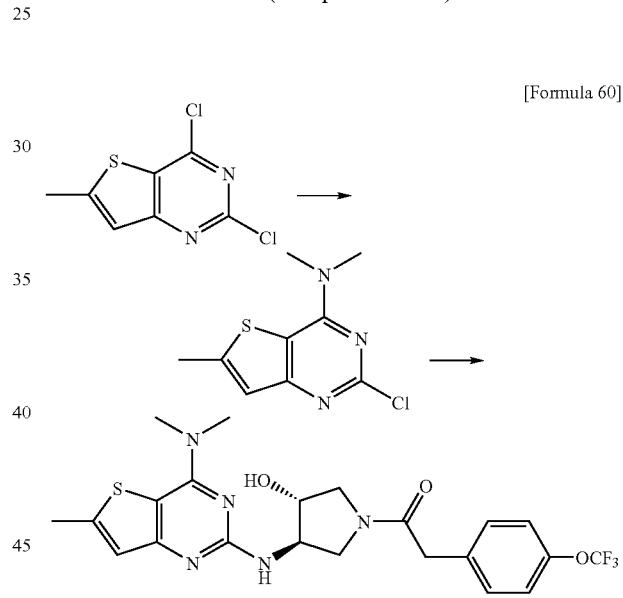

[Formula 60]

(1) To a solution of 50% aqueous dimethyl amine (0.15 g) in ethanol (5 mL) were added 2,4-dichloro-6-methylthieno[3,2-d]pyrimidine (0.25 g) and triethylamine (0.12 g) at room temperature, and the mixture was stirred for 2 h. The reaction mixture was concentrated under reduced pressure and diluted with chloroform and water, and then the aqueous layer was extracted with chloroform. The organic layer was washed with 1 M hydrochloric acid and saturated brine and then dried with anhydrous magnesium sulfate, the desiccant was removed by filtration, and the filtrate was concentrated under reduced pressure and crystallized with diethyl ether to obtain 2-chloro-N,N,6-trimethylthieno[3,2-d]pyrimidin-4-amine (0.16 g).
(2) To a mixture of 2-chloro-N,N,6-trimethylthieno[3,2-d]pyrimidin-4-amine (0.150 g), Pd$_2$(dba)$_3$ (0.033 g), (±)-BINAP (0.067 g), 1-((3R,4R)-3-amino-4-hydroxypyrrolidin-1-yl)-2-(4-trifluoromethoxyphenyl)ethanone (0.26 g), and 1,4-dioxane (8 mL) was added sodium t-butoxide (0.21 g) under nitrogen atmosphere, and the mixture was stirred at 60° C. for 5 h. The reaction mixture was diluted with ethyl acetate and water, then the interlayer was removed by Celite filtration, and the organic layer was washed with saturated brine. The organic layer was dried with anhydrous magnesium sulfate, then the desiccant was removed by filtration, the filtrate was concentrated under reduced pressure, and the residue was purified by silica gel column chromatography (silica gel, chloroform/methanol, and NH silica gel, ethyl acetate) to obtain light yellow amorphous 1-((3R,4R)-3-(4-dimethylamino-6-methylthieno[3,2-d]pyrimidin-2-ylamino)-4-hydroxypyrrolidin-1-yl)-2-(4-trifluoromethoxyphenyl)ethanone (0.097 g).

The structures and the physical property data of this compound and similarly obtained compounds are shown in Table 6.

Example 30

Synthesis of (S)-1-(3-(7-(4-methylsulfonylpiperidin-1-yl)thieno[3,2-b]pyridin-5-ylamino)pyrrolidin-1-yl)-2-(4-trifluoromethoxyphenyl)ethanone (Compound 7-002)

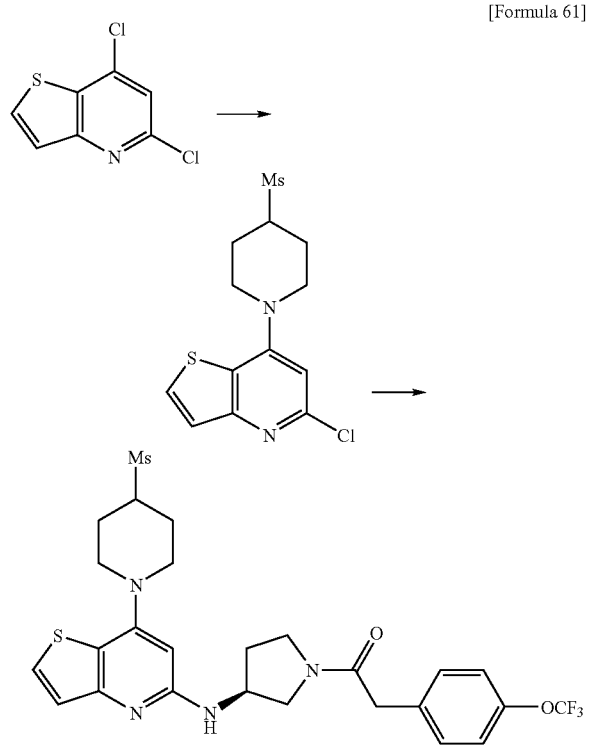

[Formula 61]

(1) A mixture of 5,7-dichlorothieno[3,2-b]pyridine (0.52 g), triethylamine (0.90 mL), 4-(methylsulfonyl)piperidine mono hydrochloride (0.62 g), and ethylene glycol (1.1 mL) was stirred at 120° C. for 6 h. Ethylene glycol (4.0 mL) and 1,4-dioxane (4.0 mL) were added, and the mixture was further stirred at room temperature for 16 h. The reaction mixture was diluted with ethyl acetate and washed with saturated brine. The organic layer was dried with anhydrous magnesium sulfate, and then silica gel was added to the organic layer. Silica gel and the desiccant were removed by filtration, the filtrate was concentrated under reduced pressure, and the resulting solids were washed with a mixture solution of ethyl acetate and diisopropyl ether. The resulting solids were purified by silica gel column chromatography (ethyl acetate/hexane=1:1-1:0) to obtain 5-chloro-7-(4-(methylsulfonyl)piperidin-1-yl)thieno[3,2-b]pyridine (0.11 g).

(2) To a mixture of 5-chloro-7-(4-(methylsulfonyl)piperidin-1-yl)thieno[3,2-b]pyridine (0.11 g), Pd$_2$(dba)$_3$ (0.016 g), (±)-BINAP (0.032 g), 1-((S)-3-aminopyrrolidin-1-yl)-2-(4-trifluoromethoxyphenyl)ethanone mono hydrochloride (0.13 g), and 1,4-dioxane (2.2 mL) was added sodium t-butoxide (0.099 g) under nitrogen atmosphere, and the mixture was stirred at room temperature for 20 h. The mixture was further stirred at 70° C. for 2 h and 30 min. The reaction mixture was diluted with ethyl acetate and water, and then the organic layer was washed with water. The organic layer was dried with anhydrous magnesium sulfate, then the desiccant was removed by filtration, the filtrate was concentrated under reduced pressure, and the residue was purified by silica gel column chromatography (NH silica gel, ethyl acetate/hexane=2:1–ethyl acetate/methanol=10:1, and silica gel, chloroform/methanol=50:1-10:1) to obtain colorless amorphous (S)-1-(3-(7-(4-methylsulfonylpiperidin-1-yl)thieno[3,2-b]pyridin-5-ylamino)pyrrolidin-1-yl)-2-(4-trifluoromethoxyphenyl)ethanone (0.074 g).

The structures and the physical property data of this compound and similarly obtained compounds are shown in Tables 7 and 9.

Example 31

Synthesis of (S)-1-(3-(4-methylthieno[3,4-b]pyridin-2-ylamino)pyrrolidin-1-yl)-2-(4-trifluoromethoxyphenyl)ethanone (Compound 9-004)

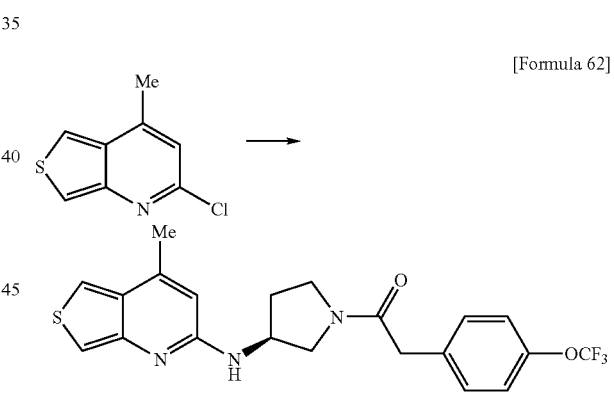

[Formula 62]

To a mixture of 2-chloro-4-methylthieno[3,4-b]pyridine (0.022 g), Pd$_2$(dba)$_3$ (0.005 g), (±)-BINAP (0.011 g), 1-((S)-3-aminopyrrolidin-1-yl)-2-(4-trifluoromethoxyphenyl)ethanone mono hydrochloride (0.046 g), and 1,4-dioxane (0.5 mL) was added sodium t-butoxide (0.045 g) under nitrogen atmosphere, and the mixture was stirred at 70° C. for 30 min. The reaction mixture was diluted with ethyl acetate and water, then the interlayer was removed by Celite filtration, and the organic layer was washed with saturated brine. The organic layer was dried with anhydrous magnesium sulfate, then the desiccant was removed by filtration, the filtrate was concentrated under reduced pressure, and the residue was purified by silica gel column chromatography (NH silica gel, ethyl acetate/methanol=20:1, and silica gel, chloroform/methanol=20:1) to obtain light yellow oily (S)-1-(3-(4-methylthieno[3,4-b]pyridin-2-ylamino)pyrrolidin-1-yl)-2-(4-trifluoromethoxyphenyl)ethanone (0.014 g).

The structures and the physical property data of this compound and similarly obtained compounds are shown in Tables 7 and 9.

Example 32

Synthesis of 1-((S)-3-(4-dimethylamino-benzo[4,5]thieno[3,2-d]pyrimidin-2-ylamino)pyrrolidin-1-yl)-2-(4-trifluoromethoxy-phenyl)ethanone (Compound 6-013)

[Formula 63]

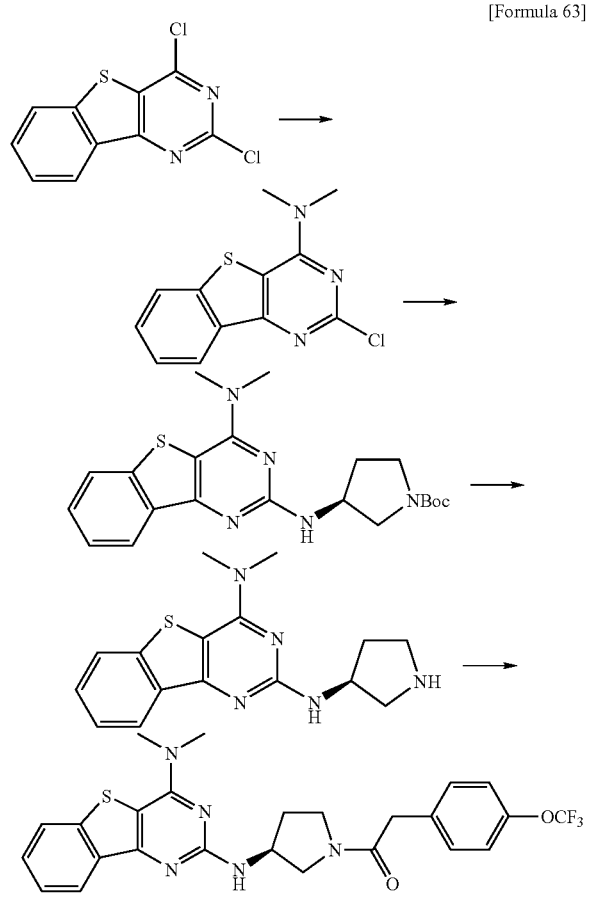

(1) A mixture of 2,4-dichlorobenzo[4,5]thieno[3,2-d]pyrimidine (1.0 g), 50% aqueous dimethyl amine (2 mL), ethanol (10 mL), and 1,4-dioxane (10 mL) was stirred at 40° C. for 1 h. Water was added to the reaction mixture, the resulting solids were collected by filtration and washed with water to obtain 2-chloro-4-dimethylamino-benzo[4,5]thieno[3,2-d]pyrimidine (0.98 g).

(2) To a mixture of 2-chloro-4-dimethylamino-benzo[4,5]thieno[3,2-d]pyrimidine (0.10 g), Pd$_2$(dba)$_3$ (0.035 g), Xantphos (0.066 g), (S)-t-butyl 3-aminopyrrolidine-1-carboxylate (0.071 mL), and 1,4-dioxane (1 mL) was added sodium t-butoxide (0.11 g) under nitrogen atmosphere, and the mixture was stirred at 60° C. for 6 h and then at room temperature for 15 h. The reaction mixture was diluted with ethyl acetate and water, then the interlayer was removed by Celite filtration, and the organic layer was washed with saturated brine. The organic layer was dried with anhydrous magnesium sulfate, then the desiccant was removed by filtration, the filtrate was concentrated under reduced pressure, and the residue was purified by silica gel column chromatography (ethyl acetate/hexane=2:1) to obtain t-butyl (S)-3-(4-dimethylamino-benzo[4,5]thieno[3,2-d]pyrimidin-2-ylamino)pyrrolidine-1-carboxylate (0.13 g).

(3) To a solution of t-butyl (S)-3-(4-dimethylamino-benzo[4,5]thieno[3,2-d]pyrimidin-2-ylamino)pyrrolidine-1-carboxylate (0.13 g) in 1,4-dioxane (1 mL) were added several drops of a solution (1 mL) of 4 M HCl in 1,4-dioxane and concentrated hydrochloric acid, and the mixture was stirred at room temperature for 3 h. To the reaction suspension was added a small amount of methanol, the mixture was stirred, followed by addition of ethyl acetate, and the solids were collected by filtration. The resulting solids were dissolved in ethyl acetate and 1 M aqueous sodium hydroxide, and the aqueous layer was extracted with ethyl acetate. The organic layer was dried with anhydrous magnesium sulfate, then the desiccant was removed by filtration, and the filtrate was concentrated under reduced pressure to obtain (S)-3-(4-dimethylamino-benzo[4,5]thieno[3,2-d]pyrimidin-2-ylamino)pyrrolidine (0.092 g).

(4) To a solution of (S)-3-(4-dimethylamino-benzo[4,5]thieno[3,2-d]pyrimidin-2-ylamino)pyrrolidine (0.091 g) in DMF (2 mL) were added 4-trifluoromethoxyphenylacetic acid (0.096 g), HOBt (0.039 g), and EDC.HCl (0.17 g), and the mixture was stirred at room temperature for 1 h. The reaction solution was diluted with ethyl acetate, and then the organic layer was washed with saturated aqueous sodium hydrogencarbonate and saturated brine and dried with anhydrous magnesium sulfate. The desiccant was removed by filtration, and the filtrate was concentrated under reduced pressure. The residue was purified by silica gel column chromatography (chloroform/methanol=40:1) to obtain white solid 1-((S)-3-(4-dimethylamino-benzo[4,5]thieno[3,2-d]pyrimidin-2-ylamino)pyrrolidin-1-yl)-2-(4-trifluoromethoxy-phenyl)ethanone (0.024 g).

The structures and the physical property data of this compound and similarly obtained compounds are shown in Tables 6, 7, and 9.

Example 33

Synthesis of 1-(3-(4-(3-aminopiperidin-1-yl)quinazolin-2-ylamino)pyrrolidin-1-yl)-2-biphenyl-2-ylethanone (Compound 16-007)

[Formula 64]

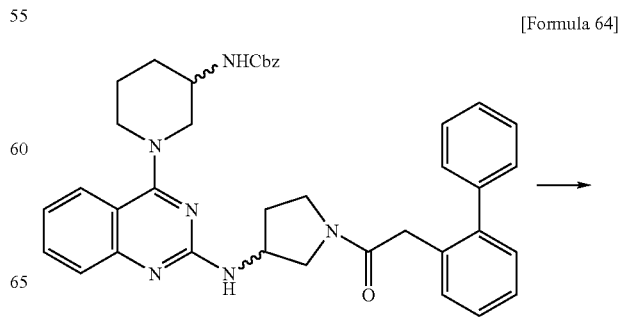

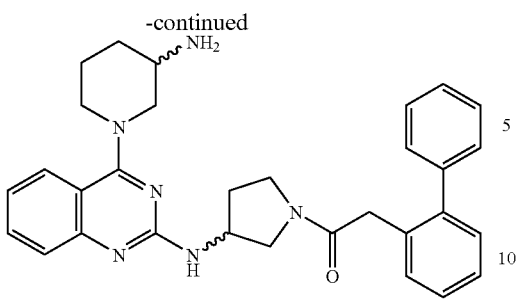

Benzyl (1-(2-(1-(2-biphenyl-2-ylacetyl)pyrrolidin-3-ylamino)quinazolin-4-yl)piperidin-3-yl)carbamate (570 mg) synthesized in the same manner as the method described in Example 1 was dissolved in methanol (6 mL), followed by addition of a solution (0.25 mL) of 4 M HCl in ethyl acetate and 10% Pd—C (100 mg), and the mixture was stirred at room temperature under hydrogen atmosphere for 3 days. The catalyst was removed by filtration, then the filtrate was concentrated, made basic with saturated aqueous sodium hydrogencarbonate, and then extracted with chloroform, and the organic layer was dried with anhydrous magnesium sulfate. The desiccant was removed by filtration, the filtrate was concentrated under reduced pressure, then the residue was purified by silica gel column chromatography (chloroform/methanol=3:1), and the resulting compound was solidified in hexane to obtain the title compound.

The structures and the physical property data of this compound and similarly obtained compounds are shown in Table 16.

Example 34

Synthesis of 2-biphenyl-2-yl-1-((S)-3-(4-piperazin-1-ylquinolin-2-ylamino)pyrrolidin-1-yl)ethanone (Compound 3-012)

[Formula 65]

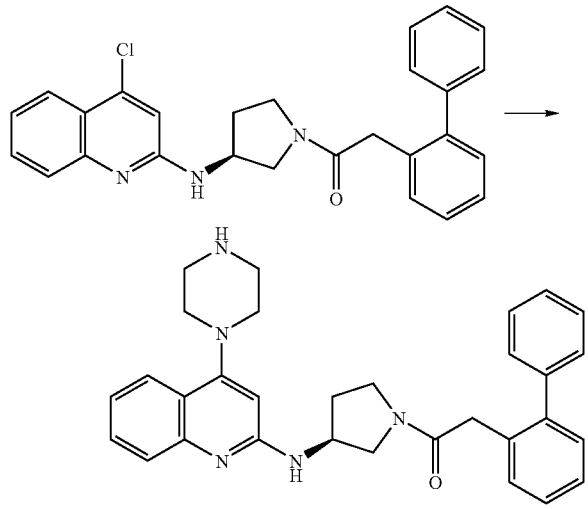

A mixture of 2-biphenyl-2-yl-1-((S)-3-(4-chloroquinolin-2-ylamino)pyrrolidin-1-yl)ethanone (0.43 g), 1-(t-butoxycarbonyl)piperazine (0.18 g), triethylamine (0.17 g), and isopropanol (1.3 mL) was heated at 180° C. in a microwave reaction apparatus for 5 h. The reaction mixture was diluted with chloroform and water, and then the aqueous layer was extracted with chloroform and dried with anhydrous magnesium sulfate. The desiccant was removed by filtration, then the filtrate was concentrated under reduced pressure, and the residue was purified by silica gel column chromatography (chloroform/a solution of 2 M ammonia in methanol=9:1) and then solidified in diethyl ether to obtain the title compound (22 mg).

The structures and the physical property data of this compound and similarly obtained compounds are shown in Table 3.

Example 35

Synthesis of 2-phenyl-1-((S)-3-(4-piperazin-1-ylquinazolin-2-ylamino)pyrrolidin-1-yl)ethanone (Compound 1-113)

[Formula 66]

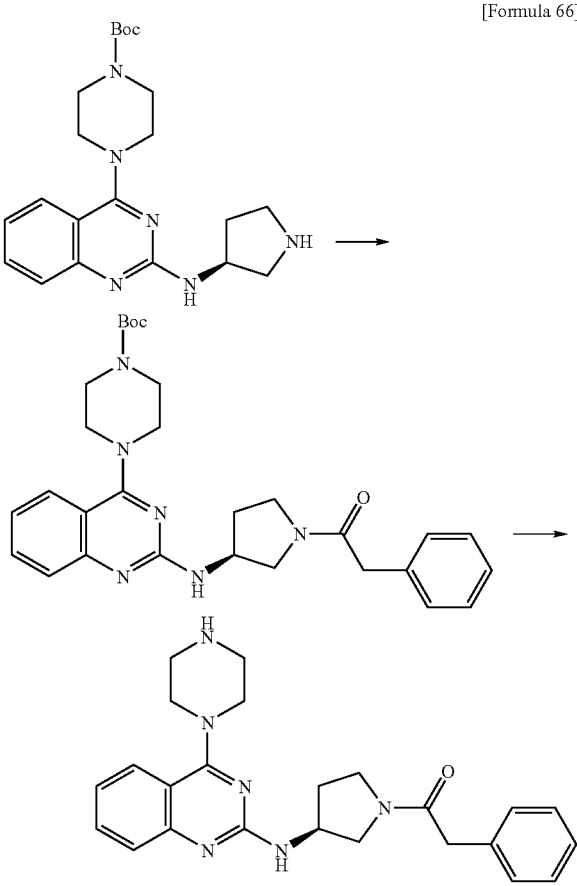

(1) To a mixture of t-butyl 4-(2-((S)-pyrrolidin-3-ylamino)quinazolin-4-yl)piperazine-1-carboxylate (0.15 g), pyridine (60 mg), and chloroform was added phenylacetic acid chloride (87 mg), and the mixture was stirred at room temperature for 16 h. To the reaction mixture was added saturated aqueous sodium hydrogencarbonate, the mixture was extracted with chloroform, and the organic layer was dried with anhydrous magnesium sulfate. The desiccant was removed by filtration, the filtrate was concentrated under reduced pressure, and then the residue was purified by silica gel column chromatography (NH silica gel, hexane/ethyl acetate=2:1–ethyl acetate) to obtain t-butyl 4-(2-((S)-1-(2-phenylethanoyl)pyrrolidin-3-ylamino)quinazolin-4-yl)piperazine-1-carboxylate (0.12 g).

(2) To t-butyl 4-(2-((S)-1-(2-phenylethanoyl)pyrrolidin-3-ylamino)quinazolin-4-yl)piperazine-1-carboxylate (0.12 g) was added a mixed solution (7.5 mL) of chloroform and trifluoroacetic acid (10:1), and the mixture was stirred overnight at room temperature. To the reaction mixture was added 1 M aqueous sodium hydroxide, the mixture was extracted with chloroform, and the organic layer was dried with anhydrous magnesium sulfate. The desiccant was removed by filtration, then the solvent was evaporated, and the residue was purified by preparative TLC to obtain title compound (69 mg).

The structures and the physical property data of this compound and similarly obtained compounds are shown in Table 1.

Example 36

Synthesis of 2-((S)-1-(2-(4-trifluoromethoxyphenyl)ethanoyl)pyrrolidin-3-ylamino)quinoline-4-carboxylic acid dimethylamide mono hydrochloride (Compound 3-036)

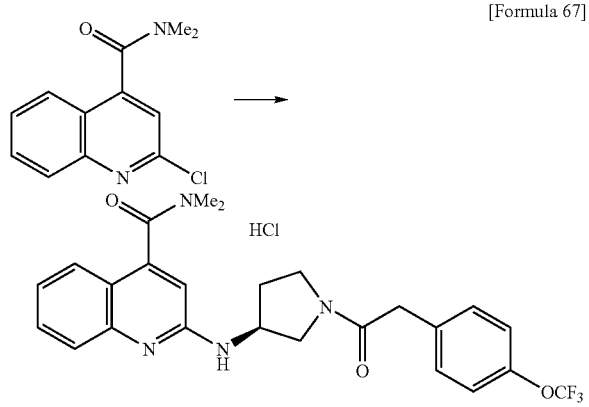

[Formula 67]

(1) A mixture of 2-chloroquinoline-4-carboxylic acid dimethylamide (0.20 g), 1-((S)-3-aminopyrrolidin-1-yl)-2-(4-trifluoromethoxyphenyl)ethanone mono hydrochloride (0.13 g), triethylamine (95 mg), and isopropanol (0.85 mL) was heated at 130° C. in a microwave reaction apparatus for 1.5 h. The reaction mixture was diluted with chloroform, washed with 1 M aqueous sodium hydroxide, and then dried with anhydrous magnesium sulfate. The desiccant was removed by filtration, the filtrate was concentrated under reduced pressure, and then the residue was purified by silica gel column chromatography (NH silica gel, hexane/ethyl acetate=1:3–ethyl acetate) to obtain 2-((S)-1-(2-(4-trifluoromethoxyphenyl)ethanoyl)pyrrolidin-3-ylamino)quinoline-4-carboxylic acid dimethylamide (36 mg).

(2) 2-((S)-1-(2-(4-Trifluoromethoxyphenyl)ethanoyl)pyrrolidin-3-ylamino)quinoline-4-carboxylic acid dimethylamide (36 mg) was dissolved in ethyl acetate, followed by addition of a solution (0.046 mL) of 4 M HCl in ethyl acetate. The mixture was concentrated under reduced pressure, and then the resulting residue was solidified with a mixed solvent of diisopropyl ether and chloroform to obtain the title compound (21 mg).

The structures and the physical property data of this compound and similarly obtained compounds are shown in Table 3.

Example 37

Synthesis of 1-((S)-3-(4-methoxyquinazolin-2-ylamino)pyrrolidin-1-yl)-2-(4-trifluoromethoxyphenyl)ethanone (Compound 1-217)

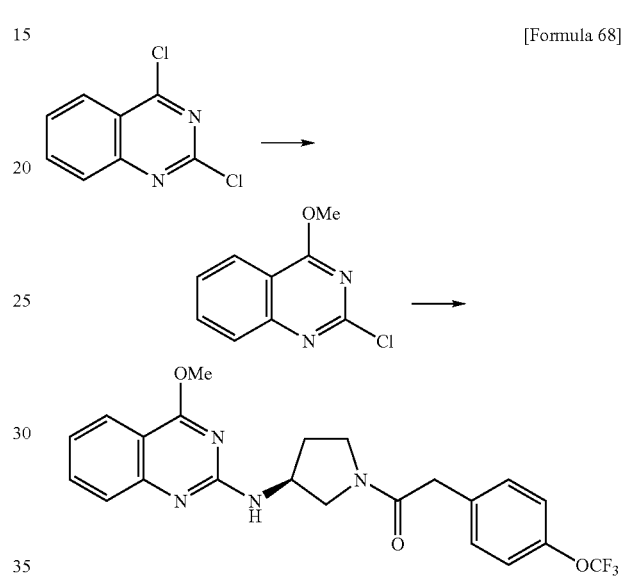

[Formula 68]

(1) Metal sodium (35 mg) was added to methanol (1.5 mL) to prepare a solution, and the solution was concentrated under reduced pressure, followed by addition of THF (1.5 mL). This suspension was added to a solution of 2,4-dichloroquinazoline (0.30 g) in THF (1.5 mL), and the mixture was stirred at room temperature for 2 h. To the reaction mixture was added saturated brine, the mixture was extracted with chloroform, and the organic layer was dried with anhydrous magnesium sulfate. The desiccant was removed by filtration, the filtrate was concentrated under reduced pressure, and then the residue was purified by silica gel column chromatography (hexane/ethyl acetate=9:1) to obtain 2-chloro-4-methoxyquinazoline (0.27 g).

(2) A mixture of 2-chloro-4-methoxyquinazoline (0.25 g), 1-((S)-3-aminopyrrolidin-1-yl)-2-(4-trifluoromethoxyphenyl)ethanone mono hydrochloride (0.42 g), triethylamine (0.33 g), and THF (3.2 mL) was heated at 100° C. in a microwave reaction apparatus for 3 h. The reaction mixture was diluted with chloroform, washed with 1 M aqueous sodium hydroxide, and then dried with anhydrous magnesium sulfate. The desiccant was removed by filtration, the filtrate was concentrated under reduced pressure, and then the residue was purified by silica gel column chromatography (chloroform-chloroform/methanol=95:5, and silica gel, hexane/ethyl acetate=1:2–ethyl acetate) to obtain the title compound (37 mg).

75

The structures and the physical property data of this compound and similarly obtained compounds are shown in Table 1.

Example 38

Synthesis of 1-(2-((S)-1-(2-biphenyl-2-ylethanoyl)pyrrolidin-3-ylamino)quinazolin-4-yl)piperidine-4-carboxylic acid (Compound 1-061) and 1-(2-((S)-1-(2-biphenyl-2-ylethanoyl)pyrrolidin-3-ylamino)quinazolin-4-yl)piperidine-4-carboxylic acid amide (Compound 1-063)

[Formula 69]

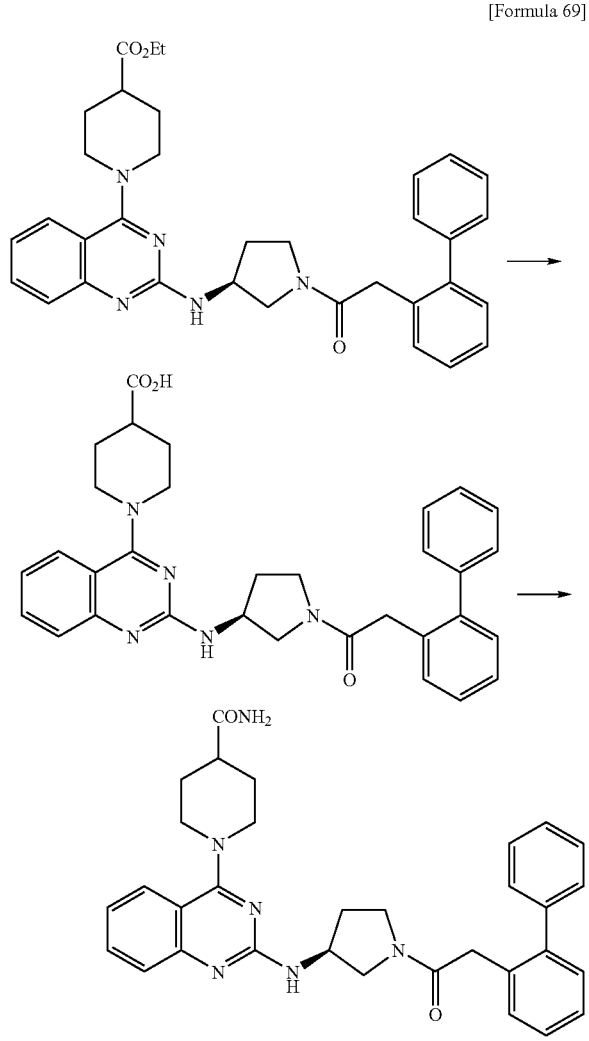

(1) Ethyl 1-(2-((S)-1-(2-biphenyl-1-ylethanoyl)pyrrolidin-3-ylamino)quinazolin-4-yl)piperidine-4-carboxylate (0.59 g) synthesized in the same manner as the method described in Example 1 was dissolved in methanol (4.5 mL), followed by addition of 2.2 M aqueous sodium hydroxide (1.3 mL), and the mixture was stirred at room temperature for 1 day. 1 M hydrochloric acid was added until the reaction solution became pH 7, the mixture was stirred at room temperature for 2 days, and then the precipitated solids were collected by filtration to obtain 1-(2-((S)-1-(2-biphenyl-2-ylethanoyl)pyrrolidin-3-ylamino)quinazolin-4-yl)piperidine-4-carboxylic acid (0.30 g).

76

(2) To a mixture of 1-(2-((S)-1-(2-biphenyl-2-ylethanoyl)pyrrolidin-3-ylamino)quinazolin-4-yl)piperidine-4-carboxylic acid (0.17 g) and DMF (5.0 mL) were added EDC.HCl (85 mg) and HOBt.H$_2$O (77 mg), followed by addition of 28% aqueous NH$_3$ (0.023 mL), and the mixture was stirred at room temperature for 17 h. The reaction solution was diluted with ethyl acetate and then washed with saturated aqueous sodium hydrogencarbonate, water, and saturated brine, and the organic layer was dried with anhydrous sodium sulfate. The desiccant was removed by filtration, the filtrate was concentrated under reduced pressure, then the residue was purified by silica gel column chromatography (NH silica gel, chloroform/methanol=10:1), and then the resulting compound was crystallized in diethyl ether to obtain 1-(2-((S)-1-(2-biphenyl-2-ylethanoyl)pyrrolidin-3-ylamino)quinazolin-4-yl)piperidine-4-carboxylic acid amide (160 mg).

The structures and the physical property data of these compounds and similarly obtained compounds are shown in Table 1.

Example 39

Synthesis of 1-((S)-3-(4-ethylquinolin-2-ylamino)pyrrolidin-1-yl)-2-(4-trifluoromethoxyphenyl)ethanone benzenesulfonate (Compound 3-029)

[Formula 70]

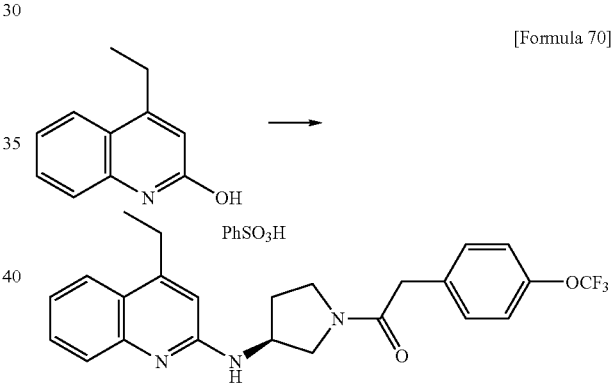

4-Ethylquinoline-1-ol (0.53 g) was dissolved in N-methylpyrrolidone (10 mL), followed by addition of sodium hydride (60% in oil, 130 mg), the mixture was stirred for 1 h, followed by addition of N-phenyl-trifluoromethane sulfonimide (1.33 g), and the mixture was stirred at room temperature for 1 h. To the reaction mixture were added sodium carbonate (0.39 g) and (S)-1-(3-aminopyrrolidin-1-yl)-2-(4-trifluoromethoxyphenyl)ethanone mono hydrochloride (1.1 g), and the mixture was stirred at 100° C. for 4 h. The reaction mixture was cooled to room temperature, followed by addition of ethyl acetate and saturated aqueous sodium hydrogencarbonate to separate the layers, and then the organic layer was washed with water and saturated brine and dried with anhydrous sodium sulfate. The desiccant was removed by filtration, the filtrate was concentrated under reduced pressure, then the residue was purified by silica gel column chromatography (NH silica gel, hexane/ethyl acetate=2:1). To the resulting residue in diethyl ether, benzenesulfonic acid monohydrate (163 mg) was added, and the precipitated crystals were collected by filtration to obtain the title compound (0.39 g).

The structures and the physical property data of this compound and similarly obtained compounds are shown in Table 3.

Example 40

Synthesis of (S)-1-(3-(4-dimethylaminothieno[3,2-d]pyrimidin-2-ylamino)pyrrolidin-1-yl)-2-(4-trifluoromethoxyphenyl)ethanethione (Compound 15-006)

[Formula 71]

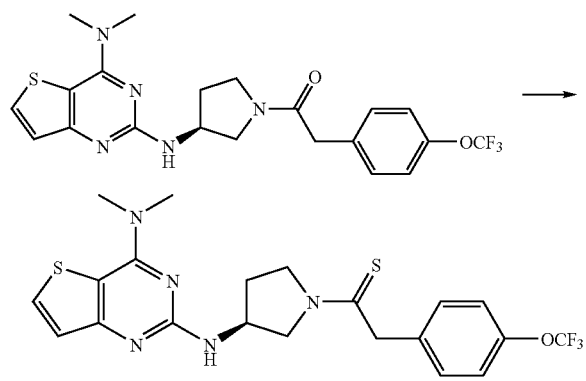

A mixture of (S)-1-(3-(4-dimethylaminothieno[3,2-d]pyrimidin-2-ylamino)pyrrolidin-1-yl)-2-(4-trifluoromethoxyphenyl)ethanone (0.10 g), Lawesson's reagent (0.087 g), and toluene (10 mL) was heated at 110° C. for 5 h with stirring. After left stand for cooling, the reaction mixture was concentrated under reduced pressure, and the residue was purified by silica gel column chromatography (silica gel, chloroform/methanol=50:1) to obtain light yellow solid (S)-1-(3-(4-dimethylaminothieno[3,2-d]pyrimidin-2-ylamino)pyrrolidin-1-yl)-2-(4-trifluoromethoxyphenyl)ethanethione (0.027 g).

The structures and the physical property data of this compound and similarly obtained compounds are shown in Table 15.

Example 41

Synthesis of (3R,4R)-(3-(4,6-dimethylquinolin-2-ylamino)-4-hydroxypyrrolidin-1-yl)-(1-(4-trifluoromethoxyphenyl)cyclopropionyl)methanone (Compound 18-006)

[Formula 72]

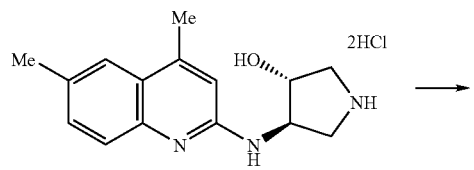

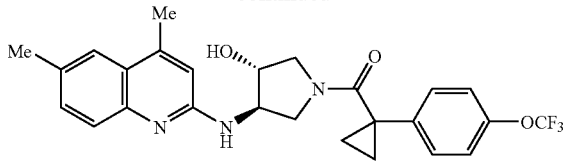

(1) To a mixture of (3R,4R)-4-(4,6-dimethylquinolin-2-ylamino)pyrrolidin-3-ol dihydrochloride (0.043 g) and DMF (1.5 mL) was added triethylamine (0.027 g). To the mixture were added 1-(4-(trifluoromethoxy)phenyl)cyclopropanecarboxylic acid (0.032 g), HOBt (0.018 g), and EDC.HCl (0.038 g), and the mixture was stirred at room temperature for 2 h. The reaction mixture was diluted with ethyl acetate and water, followed by addition of a saturated sodium hydrogencarbonate solution, and the mixture was extracted with ethyl acetate. The organic layer was dried with anhydrous magnesium sulfate, then the desiccant was removed by filtration, the filtrate was concentrated under reduced pressure, and the residue was purified by silica gel column chromatography (silica gel, chloroform/methanol=50:1, and NH silica gel, ethyl acetate). The residue was crystallized in diethyl ether to obtain white solid (3R,4R)-(3-(4,6-dimethylquinolin-2-ylamino)-4-hydroxypyrrolidin-1-yl)-(1-(4-trifluoromethoxyphenyl)cyclopropionyl)methanone (0.035 g).

The structures and the physical property data of this compound and similarly obtained compounds are shown in Tables 18, 19, and 20.

Reference Example 1

Synthesis of 2,4-dichloro-7-fluoroquinazoline (CAS174566-15-5)

[Formula 73]

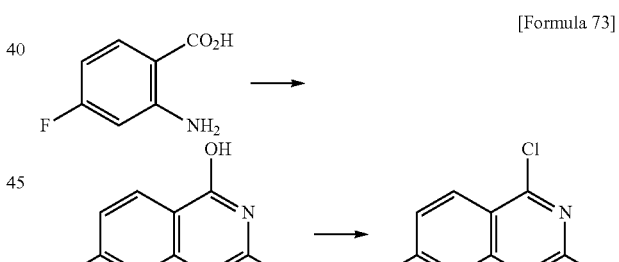

(1) A mixture of 2-amino-4-fluorobenzoic acid (25.3 g) and urea (48.9 g) was gradually added to a flask heated at 160° C. and then heated to 245° C. over 30 min. Light yellow solids were precipitated. The reaction mixture was cooled to room temperature, then methanol (250 mL) was added to the reaction mixture, the mixture was heated to reflux for 30 min, the solids were washed and cooled to room temperature, and then the precipitated solids were collected by filtration. The resulting solids were washed again with methanol (300 mL) to obtain 7-fluoroquinazoline-2,4-diol (26.3 g).

MS: ESI$^-$ (m/z) 179 (M$^-$−1)

(2) A mixture of 7-fluoroquinazoline-2,4-diol (0.96 g), phosphorus oxychloride (2.5 mL), and N,N-dimethylaniline (0.75 mL) was heated to reflux for 3.5 h. The reaction mixture was poured into ice water and extracted with chloroform, the organic layer was dried with anhydrous sodium sulfate, the desiccant was removed by filtration, the filtrate was concentrated under reduced pressure, and then the residue was purified by silica gel column chromatography (chloroform) to obtain 2,4-dichloro-7-fluoroquinazoline (0.70 g).

MS: CI⁺ (m/z) 217 (M⁺+1)

The following compounds were synthesized by the same method.

2,4-Dichloro-5-methylquinazoline (CAS78052-20-7)
2,4-Dichloro-6-methylquinazoline (CAS39576-82-4)
2,4-Dichloro-6-methoxyquinazoline (CAS105763-77-7)
2,4-Dichloro-7-trifluoromethylquinazoline (CAS864291-30-5)
2,4-Dichloro-6-fluoroquinazoline (CAS134517-57-0)
2,4-Dichloro-7-methylquinazoline (CAS25171-19-1)
2,4-Dichloro-6,7-dimethoxyquinazoline (CAS27631-29-4)

Reference Example 2

Synthesis of 2,4,6-trichloroquinazoline (CAS20028-68-6)

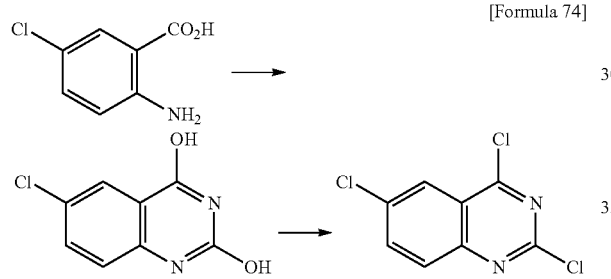

[Formula 74]

(1) To a mixture of 2-amino-5-chlorobenzoic acid (25.3 g), acetic acid (9.0 mL), and water (650 mL) was added an aqueous solution (130 mL) of potassium cyanate (15.5 g), and the mixture was stirred at room temperature for 2 days. Sodium hydroxide (59 g) was added over 30 min. Water (100 mL) was added, and then the precipitated solids were collected by filtration. The resulting solids were suspended in water (700 mL), followed by addition of 4 M hydrochloric acid (55 mL), and then the precipitated solids were collected by filtration to obtain 6-chloroquinazoline-2,4-diol (19.1 g).

MS: ESI⁻ (m/z) 195 (M⁻−1)

(2) 6-Chloroquinazoline-2,4-diol (2.5 g), phosphorus oxychloride (8.3 mL), and N,N-dimethylaniline (1.8 mL) were heated to reflux for 2.5 h. The reaction mixture was diluted with chloroform and then poured into ice water. The mixture was extracted with chloroform, then the organic layer was dried with anhydrous sodium sulfate, the desiccant was removed by filtration, and the filtrate was concentrated under reduced pressure. The residue was purified by silica gel column chromatography (ethyl acetate/hexane=1:1) to obtain the title compound (3.0 g).

MS: CI⁺ (m/z) 233 (M⁺+1)

The following compounds were synthesized by the same method.

2,4-Dichloro-6,7-difluoroquinazoline (CAS774212-69-0)
2,4-Dichloro-7-trifluoromethylquinazoline (CAS396-02-1)

Reference Example 3

Synthesis of t-butyl 4-(2-((S)-pyrrolidin-3-ylamino)quinazolin-4-yl)piperazine-1-carboxylate

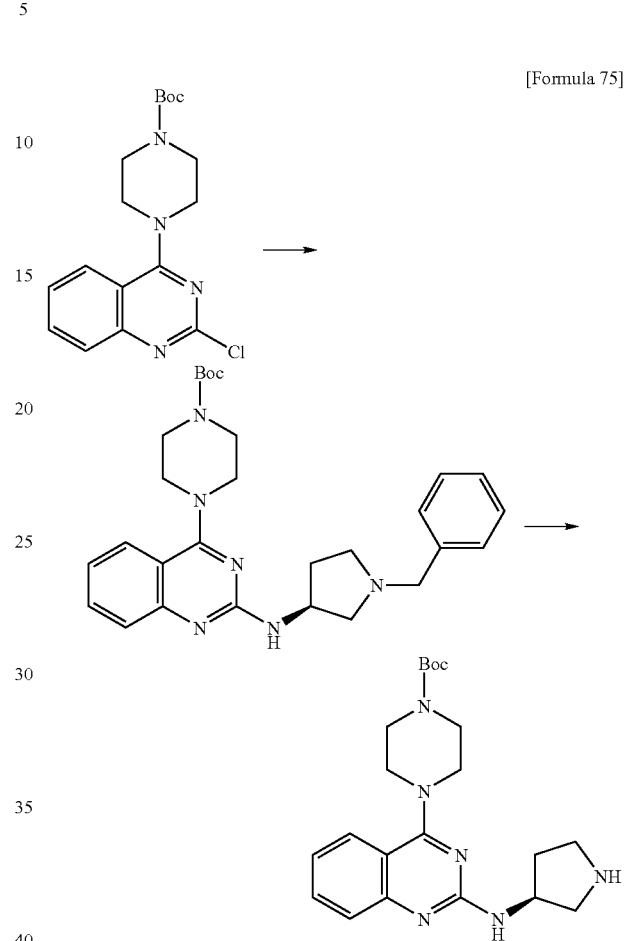

[Formula 75]

(1) A mixture of t-butyl 4-(2-chloroquinazolin-4-yl)piperazine-1-carboxylate (30 g) synthesized in the same manner as in Example 1, (S)-1-benzyl-3-aminopyrrolidine (15 g), triethylamine (8.7 g), and isopropyl alcohol (43 mL) was heated to reflux for 40 h. The reaction mixture was concentrated under reduced pressure, then water was added to the residue, and the mixture was extracted with chloroform. The organic layer was dried with anhydrous magnesium sulfate, concentrated, and then purified by silica gel column chromatography (NH silica gel, hexane/ethyl acetate=4:1) to obtain t-butyl 4-(2-((S)-1-benzylpyrrolidin-3-ylamino)quinazolin-4-yl)piperazine-1-carboxylate (26 g).

MS: ESI⁺ (m/z) 489 (M⁺+1)

(2) t-Butyl 4-(2-((S)-1-benzylpyrrolidin-3-ylamino)quinazolin-4-yl)piperazine-1-carboxylate (26 g) was dissolved in methanol (260 mL), followed by addition of 20% Pd(OH)₂/C (5.2 g), and the mixture was stirred under hydrogen atmosphere at room temperature for 16 h and at 50° C. for 8 h. 20% Pd(OH)₂/C (5.2 g) was further added, and the mixture was stirred under hydrogen atmosphere for 3 days. The catalyst was removed by filtration, then the filtrate was concentrated under reduced pressure, and the residue was purified by silica gel column chromatography (chloroform/a solution of 1 M ammonium in methanol=9:1) to obtain the title compound (6.3 g).

MS: ESI⁺ (m/z) 399 (M⁺+1)

Reference Example 4

Synthesis of 3,6-dimethyl-2,4-bistrifluoromethane-sulfonyloxypyridine

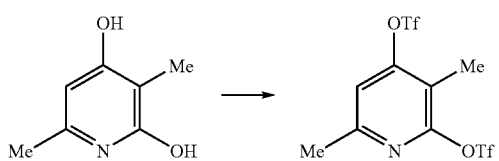

[Formula 76]

3,6-Dimethylpyridine-2,4-diol (1.0 g) was suspended in chloroform (15 mL), followed by addition of triethylamine (3.2 mL) and trifluoromethanesulfonic acid anhydride (2.8 mL) with ice cooling, and then the mixture was stirred for 1.5 h. The reaction mixture was poured into saturated aqueous sodium hydrogencarbonate, the mixture was extracted with chloroform, the organic layer was dried with anhydrous magnesium sulfate, then the desiccant was removed by filtration, the filtrate was concentrated under reduced pressure, and then the residue was purified by silica gel column chromatography (hexane/ethyl acetate=84:16) to obtain 3,6-dimethyl-2,4-bis-trifluoromethanesulfonyloxypyridine (2.6 g).

MS: CI$^+$ (m/z) 404 (M$^+$+1)

Reference Example 5

Synthesis of 2,4-dibromo-6-methylpyridine

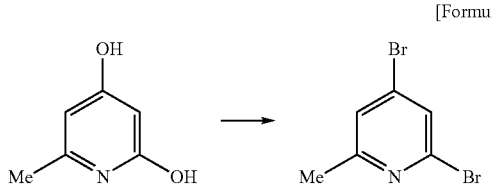

[Formula 77]

A mixture of 2,4-dihydroxy-6-methylpyridine (5.0 g) and phosphorus oxybromide (68.7 g) was stirred at 140° C. for 4.5 h. The reaction mixture was cooled to room temperature, followed by addition of chloroform, and then the mixture was poured into ice water. The layers were separated, and then aqueous layer was extracted with chloroform. The organic layer was washed with water and saturated aqueous sodium hydrogencarbonate and dried with anhydrous sodium sulfate, then the desiccant was removed by filtration, and the filtrate was concentrated under reduced pressure. The resulting solids were recrystallized with methanol and ethyl acetate to obtain 2,4-dibromo-6-methylpyridine (2.2 g).

MS: CI$^+$ (m/z) 250 (M$^+$+1)

$^1$H-NMR (200 MHz, CDCl$_3$): δ7.80-7.84 (m, 1H), 7.63-7.67 (m, 1H), 2.45 (s, 3H)

Reference Example 6

Synthesis of 2-chloro-6-methoxy-4-methylquinazoline

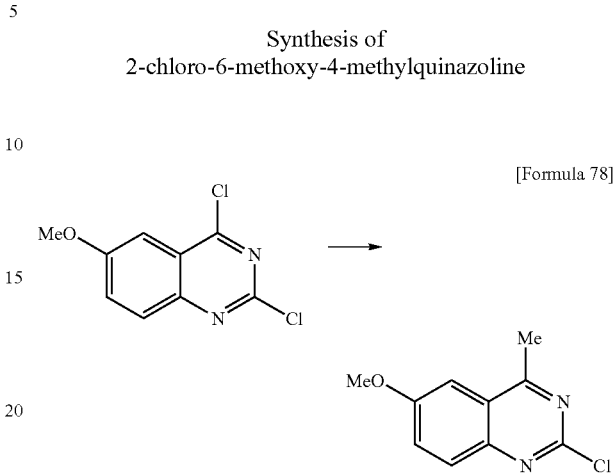

[Formula 78]

To a mixed solution of 2,4-dichloro-6-methoxyquinazoline (CAS.105763-77-7) (0.15 g), iron(III) acetyl acetonate (0.023 g), N-methyl-2-pyrrolidinone (0.4 mL), and THF (8 mL) was added a solution (0.22 mL) of 3 M methyl magnesium chloride in THF at room temperature, and the mixture was stirred for 12 h. The reaction mixture was added dropwise to a mixture of ice (30 g) and ammonium chloride (0.3 g), and then the aqueous layer was extracted with chloroform. The organic layer was concentrated under reduced pressure, and the residue was purified by silica gel column chromatography (silica gel, chloroform) and crystallized with diisopropyl ether to obtain 2-chloro-6-methoxy-4-methylquinazoline (0.08 g).

LC/MS: ESI$^+$ (m/z): 209 (M$^+$+1)

$^1$H-NMR (300 MHz, CDCl$_3$): δ7.93 (d, J=9.0 Hz, 1H), 7.36-7.42 (m, 2H), 3.97 (s, 3H), 2.69 (s, 3H)

Reference Example 7

Synthesis of 2-chloro-4,6-dimethoxyquinazoline

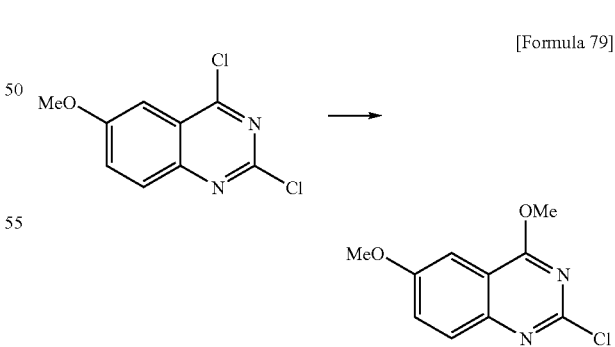

[Formula 79]

A solution of 2,4-dichloro-6-methoxyquinazoline (0.33 g) in methanol (5 mL) was added sodium methoxide (0.086 g), and the mixture was stirred at room temperature for 6 h. Water was added to the reaction mixture, and the aqueous layer was extracted with chloroform. The organic layer was concentrated under reduced pressure, and the residue was purified by silica gel column chromatography (silica gel, chloroform/methanol=50:1) to obtain 2-chloro-4,6-dimethoxyquinazoline (0.20 g).

LC/MS: ESI⁺ (m/z) 225 (M⁺+1)

Reference Example 8

Synthesis of 2-chloro-4-methyl-6-trifluoromethoxyquinoline

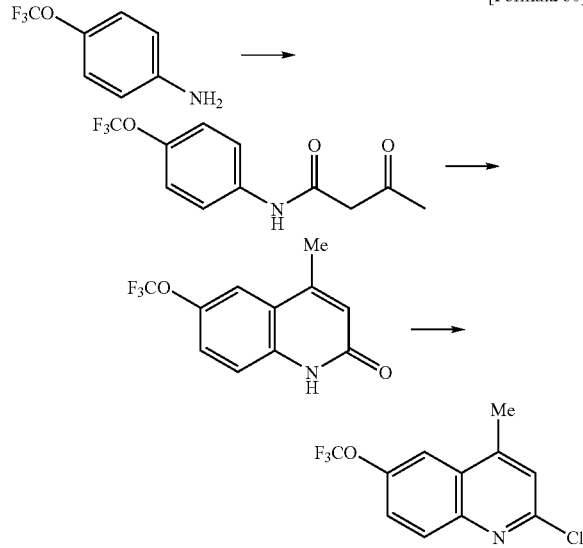

[Formula 80]

(1) 4-(Trifluoromethoxy)aniline (10 mL) was added dropwise to ethyl acetoacetate (44 mL) at 160° C., and the mixture was stirred at the same temperature for 1 h. The mixture was left stand for cooling to room temperature and crystallized with hexane to obtain 3-oxo-N-(4-(trifluoromethoxy)phenyl)butane amide (6.5 g).

(2) To concentrated sulfuric acid (32.5 mL) was added 3-oxo-N-(4-(trifluoromethoxy)phenyl)butane amide (6.5 g), and the mixture was stirred at 95° C. for 3 h. The reaction solution was added dropwise to water with ice cooling, and the precipitated crystals were collected by filtration. The resulting crystals were suspended in water, the suspension was made basic with aqueous ammonia, and the precipitated crystals were collected by filtration to obtain 4-methyl-6-(trifluoromethoxy)quinoline-2(1H)-one (1.87 g).

(3) A mixture of 4-methyl-6-(trifluoromethoxy)quinoline-2(1H)-one (1.87 g) and phosphorus oxychloride (19 mL) was stirred at 105° C. for 2.5 h. The reaction solution was added dropwise to water with ice cooling, and the precipitated crystals were collected by filtration to obtain 2-chloro-4-methyl-6-trifluoromethoxyquinoline (1.98 g).

LC/MS: ESI⁺ (m/z) 262 (M⁺+1)

$^1$H-NMR (300 MHz, CDCl₃): δ8.13 (d, J=9.1 Hz, 1H), 7.78 (s, 1H), 7.62 (d, J=9.1 Hz, 1H), 7.34 (s, 1H), 2.71 (s, 3H)

The following compounds were synthesized by the same method.

2-Chloro-6-methoxy-4-methylquinoline (CAS6340-55-2)
2,6-Dichloro-4-methylquinoline (CAS90723-71-0)
2-Chloro-4,6-dimethylquinoline (CAS3913-18-6)
2-Chloro-6-isopropyl-4-methylquinoline $^1$H-NMR (300 MHz, CDCl₃): δ8.02 (d, J=8.7 Hz, 1H), 7.74 (d, J=1.8 Hz, 1H), 7.65 (dd, J=8.7, 1.8 Hz, 1H), 7.23 (s, 1H), 3.12 (septet, J=6.9 Hz, 1H), 2.70 (s, 3H), 1.35 (d, J=6.9 Hz, 6H)

2-Chloro-6-fluoro-4-methylquinoline (CAS18529-12-9)
2-Chloro-6-ethyl-4-methylquinoline (CAS35213-56-0)
2-Chloro-6-ethoxy-4-methylquinoline (CAS857801-72-0)
2-Chloro-7-fluoro-4,6-dimethylquinoline $^1$H-NMR (300 MHz, CDCl₃): δ7.87 (d, J=7.2 Hz, 1H), 7.50 (d, J=10.2 Hz, 1H), 7.22 (s, 1H), 2.63 (s, 3H), 2.48 (s, 3H)

2-Chloro-7-fluoro-6-methoxy-4-methylquinoline
LC/MS: ESI⁺ (m/z) 226 (M⁺+1)

2-Chloro-4-ethyl-7-fluoro-6-methoxyquinoline
LC/MS: ESI⁺ (m/z) 240 (M⁺+1)

Reference Example 9

Synthesis of 2,6-dichloro-4-methoxyquinoline

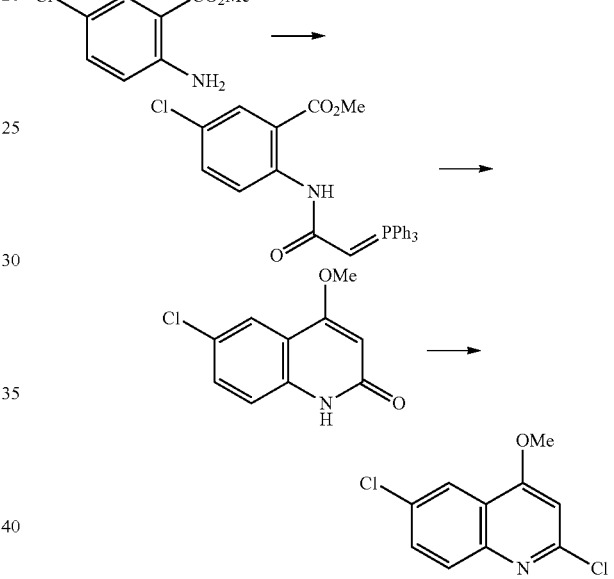

[Formula 81]

(1) To a solution of methyl 2-amino-5-chlorobenzoate (2.5 g) in DMF (25 mL) was added chloroacetyl chloride (1.4 mL) with ice cooling. The resulting white crystals were collected by filtration and washed with water. The resulting white crystals were dried to obtain methyl 5-chloro-2-(2-chloroacetamide)benzoate (5.4 g).

A mixture of methyl 5-chloro-2-(2-chloroacetamide)benzoate (3.6 g), triphenylphosphine (4.0 g), and DMF (18 mL) was stirred at 80° C. for 4 h. The resulting suspension was diluted with ethyl acetate and diisopropyl ether, and then the solids were collected by filtration and washed with a solution of ethyl acetate and diisopropyl ether. The resulting solids were suspended in water and chloroform, and the suspension was neutralized with 1 M aqueous sodium hydroxide until the phenolphthalein point. 1 M aqueous sodium hydroxide was added until the solids were completely dissolved, and the aqueous layer was extracted with chloroform. The organic layer was dried with anhydrous magnesium sulfate, and then the desiccant was removed by filtration. The filtrate was concentrated under reduced pressure to obtain methyl 5-chloro-2-(2-(triphenyl-λ⁵-phosphanyliden)-acetylamino)benzoate (3.8 g) as light yellow solids.

(2) Methyl 5-chloro-2-(2-(triphenyl-λ⁵-phosphanyliden)-acetylamino)benzoate (3.8 g) was heated at 180° C. for 1 h.

The reactant was suspended in chloroform and diisopropyl ether. Solids were collected by filtration and dried to obtain 6-chloro-4-methoxyquinoline-2(1H)-one (1.1 g).

(3) A mixture of 6-chloro-4-methoxyquinoline-2(1H)-one (1.1 g), N,N-dimethylaniline (1 mL), and phosphorus oxychloride (4 mL) was stirred at 80° C. to 90° C. for 10 h. The reaction solution was added dropwise to ice water and extracted with chloroform. The organic layer was dried with anhydrous magnesium sulfate, followed by addition of silica gel. The desiccant and silica gel were removed by filtration, and the filtrate was concentrated under reduced pressure to obtain 2,6-dichloro-4-methoxyquinoline (1.2 g) as pale yellow crystals.

LC/MS: ESI$^+$ (m/z) 228 (M$^+$+1)

$^1$H-NMR (300 MHz, CDCl$_3$): δ8.08 (d, J=2.4 Hz, 1H), 7.86 (dd, J=9.0, 2.4 Hz, 1H), 7.25 (d, J=9.0 Hz, 1H), 6.75 (s, 1H), 4.06 (s, 3H)

The following compounds were synthesized by the same method.

2-Chloro-6-fluoro-4-methoxyquinoline (CAS860296-85-1)
2-Chloro-4-methoxyquinoline (CAS4295-09-4)

Reference Example 10

Synthesis of 2-chloro-4,6-dimethoxyquinoline

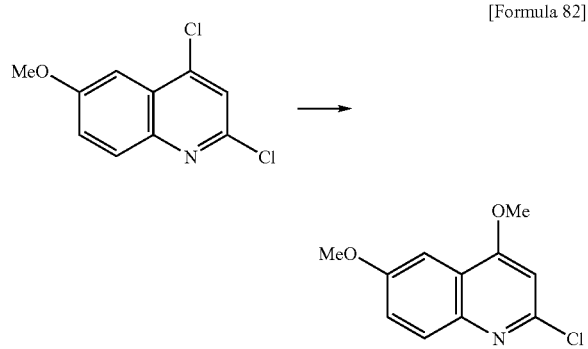

[Formula 82]

To a solution of 2,4-dichloro-6-methoxyquinoline (0.97 g) synthesized from p-anisidine and malonic acid according to the method of WO200226713 in methanol (20 mL) was added sodium methoxide (1.37 g), and the mixture was stirred at 70° C. for 3 h. The reaction solution was added dropwise to ice water, and the resulting solids were collected by filtration. The resulting solids were purified by silica gel column chromatography (hexane/ethyl acetate=5:1) to obtain 2-chloro-4,6-dimethoxyquinoline (0.61 g) as white solids.

LC/MS: ESI$^+$ (m/z) 224 (M$^+$+1)

$^1$H-NMR (300 MHz, CDCl$_3$): δ7.83 (d, J=9.0 Hz, 1H), 7.36 (d, J=2.7 Hz, 1H), 7.33 (dd, J=2.7 Hz, J=9.0 Hz, 1H), 4.04 (s, 3H), 3.91 (s, 3H)

The following compounds were synthesized by the same method.

2-Chloro-4-methoxy-6-methylquinoline (CAS123637-53-6)
2,4,6-Trichloroquinoline (CAS1677-50-5)

Reference Example 11

Synthesis of (S)-6-methoxy-4-methyl-N-(pyrrolidin-3-yl)quinolin-2-amine

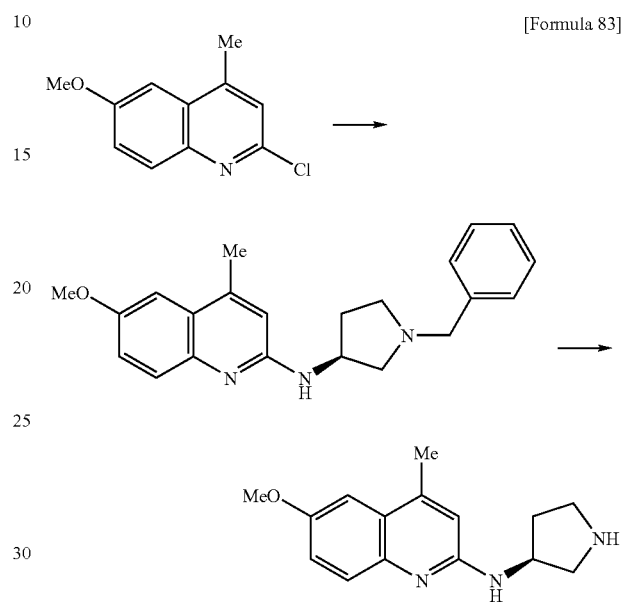

[Formula 83]

(1) To a mixture of 2-chloro-6-methoxy-4-methylquinoline (1.1 g), Pd$_2$(dba)$_3$ (0.242 g), (±)-BINAP (0.495 g), (S)-1-benzyl-3-aminopyrrolidine (1.1 g), and 1,4-dioxane (88 mL) was added sodium t-butoxide (1.65 g) under nitrogen atmosphere, and the mixture was stirred at 65° C. for 3 h. The reaction mixture was diluted with ethyl acetate and water, then the interlayer was removed by Celite filtration, and the organic layer was washed with saturated brine. The organic layer was dried with anhydrous magnesium sulfate, then the desiccant was removed by filtration, the filtrate was concentrated under reduced pressure, and the residue was purified by silica gel column chromatography (NH silica gel, hexane/ethyl acetate=10:1) to obtain (S)-N-(1-benzylpyrrolidin-3-yl)-6-methoxy-4-methylquinolin-2-amine (1.1 g).

(2) (S)-N-(1-Benzylpyrrolidin-3-yl)-6-methoxy-4-methylquinolin-2-amine (1.1 g) was dissolved in methanol (25 mL), followed by addition of 20% Pd(OH)$_2$/C (0.20 g), and the mixture was stirred at 45° C. under hydrogen atmosphere for 5 h. The catalyst was removed by Celite filtration, and then the filtrate was concentrated under reduced pressure to obtain (S)-6-methoxy-4-methyl-N-(pyrrolidin-3-yl)quinolin-2-amine (0.81 g).

LC/MS: ESI$^+$ (m/z) 258 (M$^+$+1)

$^1$H-NMR (300 MHz, CDCl$_3$): δ7.60 (d, J=9.0 Hz, 1H), 7.20 (dd, J=2.7 Hz, J=9.0 Hz, 1H), 7.08 (d, J=2.7 Hz, 1H), 6.50 (s, 1H), 4.93 (br, 1H), 4.48 (br, 1H), 3.89 (s, 3H), 3.11-3.28 (m, 3H), 2.91-3.03 (m, 2H), 2.52 (s, 3H), 2.20-2.29 (m, 1H), 1.70-1.77 (m, 1H)

Reference Example 12

Synthesis of 2-chloro-6-hydroxy-4-methylquinoline (CAS41957-91-9)

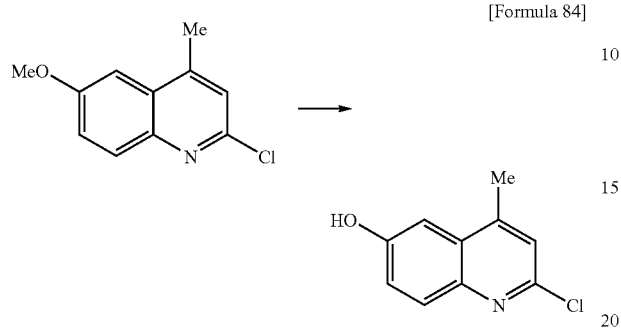

[Formula 84]

A solution of 2-chloro-6-methoxy-4-methylquinoline (0.20 g) in dichloromethane (15 mL) was cooled to −78° C., followed by addition of a solution (5.3 mL) of 1 M boron tribromide in dichloromethane, and the mixture was stirred for 12 h while slowly heating to room temperature. To the reaction mixture was added a saturated sodium hydrogencarbonate solution to make it basic, and the mixture was extracted with chloroform. The aqueous layer was reextracted with a mixture solution of ethyl acetate and n-butanol, then the organic layer was combined and concentrated under reduced pressure, and the resulting solids were washed with diethyl ether to obtain 2-chloro-6-hydroxy-4-methylquinoline (0.15 g).

LC/MS: ESI$^+$ (m/z) 194 (M$^+$+1)

ESI$^-$ (m/z) 192 (M$^-$−1)

Reference Example 13

Synthesis of 2,4-dichloro-6-methylthieno[3,2-d]pyrimidine (CAS35265-82-8)

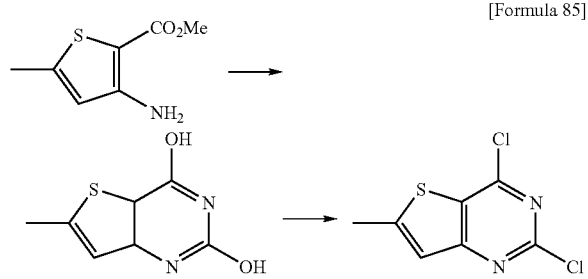

[Formula 85]

(1) A mixture of methyl 3-amino-5-methylthiophene-2-carboxylic acid (1.2 g) and urea (2.2 g) was stirred at 180° C. for 2.5 h. The mixture was left stand for cooling to room temperature, followed by 1 M aqueous sodium hydroxide (20 mL), the solids were dissolved, and the mixture was neutralized with acetic acid. The precipitated crystals were collected by filtration to obtain 6-methylthieno[3,2-d]pyrimidine-2,4-diol (0.77 g).

(2) To a mixture of 6-methylthieno[3,2-d]pyrimidine-2,4-diol (0.77 g) and phosphorus oxychloride (8 mL) was added N,N-dimethylaniline (1.6 mL) at room temperature, and the mixture was stirred at 100° C. for 2 h. The reaction solution was added dropwise to water with ice cooling, and the aqueous layer was extracted with chloroform. The organic layer was concentrated under reduced pressure, and the residue was purified by silica gel column chromatography (silica gel, chloroform) to obtain 2,4-dichloro-6-methylthieno[3,2-d]pyrimidine (0.50 g).

LC/MS: ESI$^+$ (m/z) 219 (M$^+$+1)

$^1$H-NMR (300 MHz, CDCl$_3$): δ7.20-7.21 (m, 1H), 2.73 (d, J=1.2 Hz, 3H)

Reference Example 14

Synthesis of 2,4-dichlorothieno[3,4-d]pyrimidine (CAS36948-21-7)

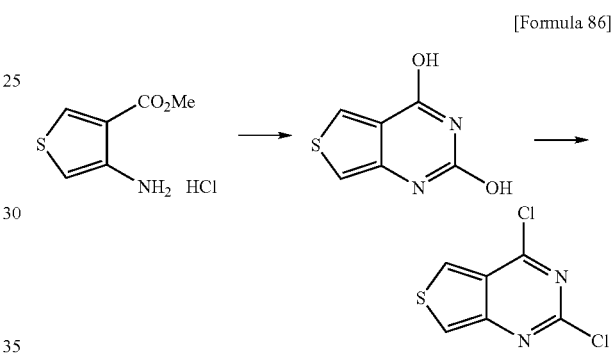

[Formula 86]

(1) A mixture of methyl 4-aminothiophene-3-carboxylic acid mono hydrochloride (1.00 g) and urea (1.8 g) was stirred at 180° C. for 1.5 h. The mixture was left stand for cooling to room temperature, followed by addition of 1 M aqueous sodium hydroxide to dissolve the solids, and the mixture was neutralized with 1 M hydrochloric acid. The precipitated crystals were collected by filtration to obtain thieno[3,4-d]pyrimidine-2,4-diol (1.0 g).

(2) To a mixture of thieno[3,4-d]pyrimidine-2,4-diol (1.00 g) and phosphorus oxychloride (10 mL) was added N,N-dimethylaniline (2.0 mL) at room temperature, and the mixture was stirred at 100° C. for 2.5 h. The reaction solution was added dropwise to water (30 g) with ice cooling, and the aqueous layer was extracted with chloroform. The organic layer was concentrated under reduced pressure, and the residue was purified by silica gel column chromatography (silica gel, chloroform) to obtain 2,4-dichlorothieno[3,4-d]pyrimidine (0.52 g).

LC/MS: ESI$^+$ (m/z) 205 (M$^+$+1)

$^1$H-NMR (300 MHz, CDCl$_3$): δ8.30 (d, J=3.6 Hz, 1H), 7.96 (d, J=3.6 Hz, 1H)

The following compounds were synthesized by the same method.

2,4-Dichloro-thieno[3,2-d]pyrimidine (CAS16234-14-3)

2,4-Dichloro-7-methylthieno[3,2-d]pyrimidine (CAS35265-83-9)

2,4-Dichloro-5-methylthieno[2,3-d]pyrimidine (CAS56844-38-3)

2,4-Dichloro-thieno[2,3-d]pyrimidine (CAS56844-38-3)

Reference Example 15

Synthesis of 2,4-dichlorothieno[3,4-b]pyridine (CAS124555-08-4)

[Formula 87]

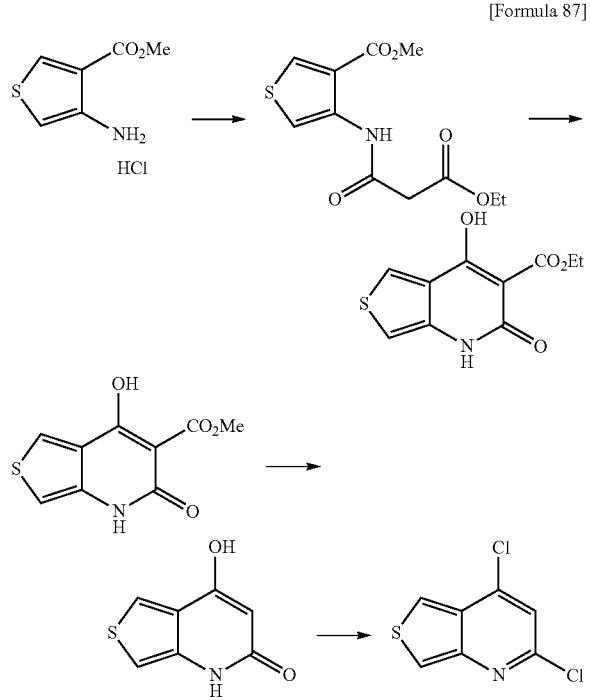

(1) Ethylmalonyl monochloride (4.6 mL) was added dropwise to a solution of methyl 4-aminothiophene-3-carboxylate mono hydrochloride (5.1 g) in DMF (50 mL), and the mixture was stirred at room temperature for 2.5 h. The reaction mixture was diluted with ethyl acetate and washed with saturated aqueous sodium hydrogencarbonate and saturated aqueous ammonium chloride. The organic layer was dried with anhydrous magnesium sulfate, followed by addition of silica gel. The desiccant and silica gel were removed by filtration, and the filtrate was concentrated under reduced pressure to obtain methyl 4-(3-ethoxy-3-oxopropanamide)thiophene-3-carboxylate (7.0 g).

(2) To a solution of methyl 4-(3-ethoxy-3-oxopropanamide)thiophene-3-carboxylate (7.0 g) in DMF (60 mL) was added sodium methoxide (5.6 g) with ice cooling, and the mixture was stirred at room temperature for 30 min. Water was added to the reaction mixture with water cooling, and the mixture was neutralized with 1 M hydrochloric acid (pH 4). The resulting white solids were collected by filtration to obtain a mixture of ethyl and methyl esters (3.1 g).

(3) To a suspension of a mixture of ethyl and methyl esters (3.1 g) in water was added potassium hydroxide (3.9 g), and the mixture was stirred at 80° C. for 5 h. Concentrated hydrochloric acid was slowly added dropwise to the reaction solution at room temperature until the reaction solution became pH 1. Subsequently, the reaction solution was stirred at 80° C. for 1 h, and then the solids were collected by filtration to obtain 4-hydroxythieno[3,4-b]pyridine-2(1H)-one (2.1 g).

(4) A mixture of 4-hydroxythieno[3,4-b]pyridine-2(1H)-one (2.1 g), N,N-dimethylaniline (2 mL), and phosphorus oxychloride (12 mL) was stirred at 95° C. for 1 h. The reaction solution was added dropwise to ice water and extracted with chloroform. The organic layer was dried with anhydrous magnesium sulfate, followed by addition of silica gel. The desiccant and silica gel were removed by filtration, and the filtrate was concentrated under reduced pressure to obtain 2,4-dichlorothieno[3,4-b]pyridine (2.3 g) as orange solids.

LC/MS: ESI$^+$ (m/z) 204 (M$^+$+1)

$^1$H-NMR (300 MHz, CDCl$_3$): δ7.95 (d, J=3.6 Hz, 1H), 7.93 (d, J=3.6 Hz, 1H), 7.10 (s, 1H)

The following compounds were synthesized by the same method.

5,7-Dichloro-thieno[3,2-b]pyridine (CAS74695-44-6)

5,7-Dichloro-2-methylthieno[3,2-b]pyridine

LC/MS: ESI$^+$ (m/z) 218 (M$^+$+1)

5,7-Dichloro-3-methylthieno[3,2-b]pyridine

LC/MS: ESI$^+$ (m/z) 218 (M$^+$+1)

$^1$H-NMR (300 MHz, CDCl$_3$): δ7.48 (q, J=0.9 Hz, 1H), 7.34 (s, 1H), 2.50 (d, J=0.9 Hz, 3H).

Reference Example 16

Synthesis of 2-chloro-4-methylthieno[3,4-b]pyridine

[Formula 88]

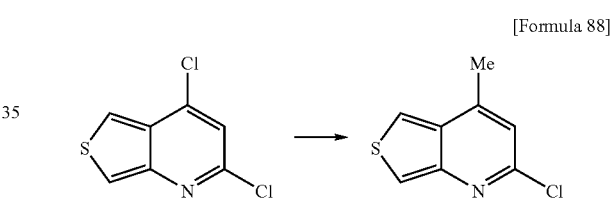

A solution (0.67 mL) of 3 M methyl magnesium chloride in THF was added dropwise to a mixture of 2,4-dichlorothieno[3,4-b]pyridine (0.37 g), iron(III) acetylacetonate (0.064 g), N-methyl-2-pyrrolidinone (1 mL), and THF (15 mL) with ice cooling, and the mixture was stirred at room temperature for 20 h. The reaction solution was diluted with water, and the mixture was extracted with chloroform. The organic layer was dried with anhydrous magnesium sulfate, then the desiccant was removed by filtration, and the filtrate was concentrated under reduced pressure. The residue was purified by silica gel column chromatography (silica gel and NH silica gel, ethyl acetate/hexane=20:1-10:1) to obtain 2-chloro-4-methylthieno[3,4-b]pyridine (0.027 g).

LC/MS: ESI$^+$ (m/z) 184 (M$^+$+1)

$^1$H-NMR (300 MHz, CDCl$_3$): δ7.89 (d, J=2.0 Hz, 1H), 7.85 (d, J=2.0 Hz, 1H), 6.99 (s, 1H), 2.62 (s, 3H)

The following compounds were synthesized by the same method.

5-Chloro-7-methylthieno[3,2-b]pyridine $^1$H-NMR (300 MHz, CDCl$_3$): δ7.76 (d, J=5.7 Hz, 1H), 7.51 (d, J=5.7 Hz, 1H), 7.13 (s, 1H), 2.59 (s. 3H)

2-Chloro-4-methylthieno[3,2-d]pyrimidine

LC/MS: ESI$^+$ (m/z) 185 (M$^+$+1)

¹H-NMR (300 MHz, CDCl₃): δ8.03 (d, J=5.4 Hz, 1H), 7.51 (d, J=5.4 Hz, 1H), 2.82 (s, 3H)

Reference Example 17

Synthesis of 2-chloro-4-ethoxythieno[3,2-d]pyrimidine (CAS16234-43-8)

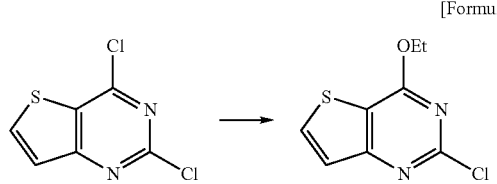

[Formula 89]

A mixture of 2,4-dichlorothieno[3,2-d]pyrimidine (0.1 g), ethanol (5 mL), water (0.5 mL) and sodium hydroxide (0.04 g) was stirred at room temperature. The precipitated solids were collected by filtration and washed with diethyl ether to obtain 2-chloro-4-ethoxythieno[3,2-d]pyrimidine (0.07 g).

LC/MS: ESI⁺ (m/z) 215 (M⁺+1)

Reference Example 18

Synthesis of 1-((S)-3-aminopyrrolidin-1-yl)-2-(4-trifluoromethoxyphenyl)ethanone mono hydrochloride

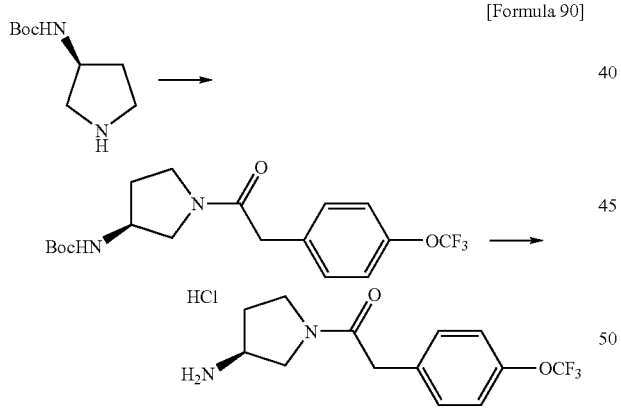

[Formula 90]

(1) To a mixed solution of t-butyl (S)pyrrolidin-3-ylcarbamate (93 g), 4-trifluoromethoxyphenylacetic acid (112 g), and THF (550 mL) were added EDC.HCl (114 g) and HOBt-1H₂O (114 g), and the mixture was stirred at room temperature for 3 days. The reaction solution was concentrated under reduced pressure, then diluted with chloroform, and washed with saturated aqueous sodium hydrogencarbonate, water, and brine. The organic layer was dried with anhydrous magnesium sulfate, then the desiccant was removed by filtration, and the filtrate was concentrated under reduced pressure. The resulting solids were washed with chloroform to obtain t-butyl ((S)-1-(2-(4-trifluoromethoxyphenyl)ethanoyl)pyrrolidin-3-yl)carbamate (144 g).

MS: ESI⁺ (m/z) 389 (M⁺+1)
¹H-NMR (600 MHz, CDCl₃): δ7.21-7.30 (m, 2H), 7.09-7.16 (m, 2H), 4.60-4.72 (m, 1H), 4.13-4.29 (m, 1H), 3.47-3.78 (m, 5H), 3.32-3.40 (m, 1H), 1.72-2.29 (m, 2H), 1.43 (s, 9H)

(2) t-Butyl ((S)-1-(2-(4-trifluoromethoxyphenyl)ethanoyl)pyrrolidin-3-yl)carbamate (144 g) was suspended in ethyl acetate (300 mL), followed by addition of a solution (278 mL) of 4 M HCl in ethyl acetate, and the mixture was stirred at room temperature for 3 days. The precipitated solids were collected by filtration to obtain the title compound (67 g). The filtrate was concentrated under reduced pressure, followed by addition of hexane and diisopropyl ether, and the precipitated solids were collected by filtration to obtain the title compound (52 g).

MS: ESI⁺ (m/z) 289 (M⁺+1)
¹H-NMR (600 MHz, CDCl₃): δ8.12-8.59 (m, 3H), 7.10-7.41 (m, 4H), 3.13-3.89 (m, 7H), 1.75-2.26 (m, 2H)

Reference Example 19

Synthesis of 1-((3R,4R)-3-amino-4-hydroxypyrrolidin-1-yl)-2-(4-trifluoromethoxyphenyl)ethanone

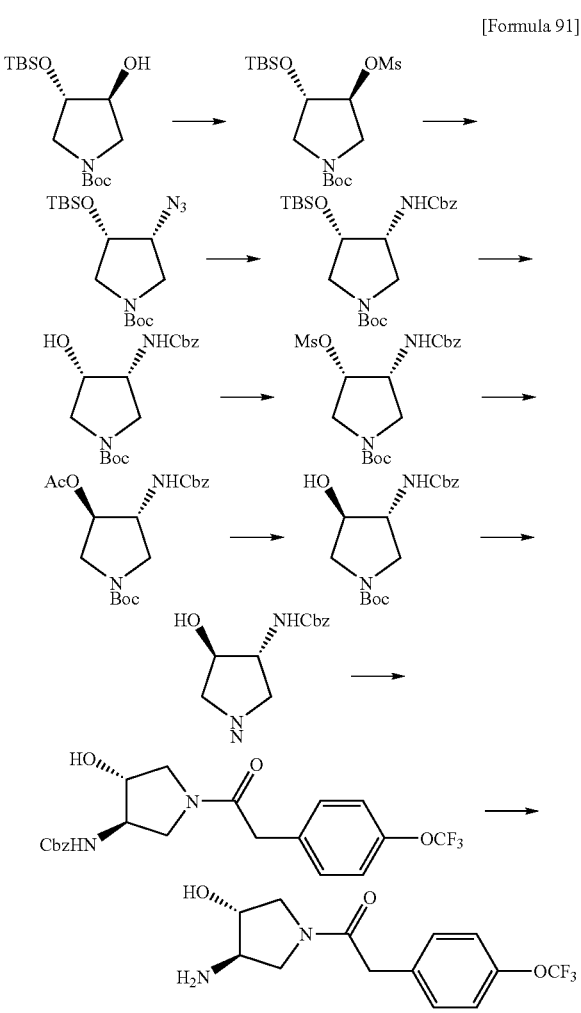

[Formula 91]

(1) t-Butyl (3S,4S)-3-(t-butyldimethylsilanyloxy)-4-hydroxypyrrolidine-1-carboxylic acid (67.6 g) obtained by the same method as described in Tetrahedron: Asymmetry 12, 1793-1799 (2001) and triethylamine (41.5 mL) were dissolved in chloroform (1.0 L) under nitrogen atmosphere and ice-cooled, then a solution of methane sulfonylchloride (19.8 mL) in chloroform (65 mL) was added dropwise, and the mixture was stirred at room temperature for 1 h. Water was added to separate the layers, then the organic layer was washed with water and dried with anhydrous sodium sulfate, and the solvent was evaporated under reduced pressure to obtain crude t-butyl (3S,4S)-3-(t-butyldimethylsilanyloxy)-4-methanesulfonyloxypyrrolidine-1-carboxylate. This compound was used in the subsequent step without purification.

MS: ESI$^+$ (m/z) 418 (M$^+$+Na)
$^1$H-NMR (600 MHz, CDCl$_3$): δ4.75-4.85 (m, 1H), 4.33-4.43 (m, 1H), 3.67-3.78 (m, 1H), 3.49-3.65 (s, 2H), 3.24-3.39 (m, 1H), 2.99-3.09 (m, 3H), 1.46 (s, 9H), 0.87 (s, 9H), 0.11 (s, 3H), 0.10 (s, 3H)

(2) The crude t-butyl (3S,4S)-3-(t-butyldimethylsilanyloxy)-4-methanesulfonyloxypyrrolidine-1-carboxylate obtained in (1) was dissolved in DMF (426 mL), followed by addition of sodium azide (34.6 g), and the mixture was heated at 120° C. for 7 h. Solids in the reaction solution were removed by filtration, the filtrate was concentrated under reduced pressure, and water and ethyl acetate were added to separate the layers. The aqueous layer was extracted with ethyl acetate, then the organic layer was washed with brine and dried with anhydrous magnesium sulfate, and then the solvent was concentrated under reduced pressure. The residue was purified by silica gel column chromatography (hexane/ethyl acetate=20:1) to obtain t-butyl (3R,4S)-3-azide-4-(t-butyldimethylsilanyloxy)pyrrolidine-1-carboxylate (47 g).

MS: ESI$^+$ (m/z) 365 (M$^+$+Na)
$^1$H-NMR (600 MHz, CDCl$_3$): δ4.28-4.48 (m, 1H), 3.66-3.85 (m, 1H), 3.18-3.60 (m, 4H), 1.45 (s, 9H), 0.91 (s, 9H), 0.13 (s, 3H), 0.11 (s, 3H)

(3) t-Butyl (3R,4S)-3-azide-4-(t-butyldimethylsilanyloxy)pyrrolidine-1-carboxylate (47 g) was dissolved in ethanol (470 mL), followed by addition of 5% Pd—C (2.4 g), and the mixture was stirred under hydrogen atmosphere for 5 h. The catalyst was removed by filtration, and then the filtrate was concentrated under reduced pressure. The residue was dissolved in THF (470 mL), followed by addition of triethylamine (23 mL) and benzyl chloroformate (21 mL), and the mixture was stirred overnight at room temperature. Water was added to separate the layers, then the aqueous layer was extracted with ethyl acetate, dried with anhydrous magnesium sulfate, and then concentrated under reduced pressure. The residue was purified by silica gel column chromatography (hexane/ethyl acetate=5:1-4:1) to obtain t-butyl (3R,4S)-3-benzyloxycarbonylamino-4-(t-butyldimethylsilanoxy)pyrrolidine-1-carboxylate (54 g).

MS: ESI$^+$ (m/z) 473 (M$^+$+Na)
$^1$H-NMR (600 MHz, CDCl$_3$): δ7.27-7.44 (m, 5H), 5.11 (s, 2H), 4.97-5.19 (m, 1H), 4.07-4.35 (m, 2H), 3.04-3.76 (m, 4H), 1.45 (s, 9H), 0.88 (s, 9H), 0.07 (s, 6H)

(4) t-Butyl (3R,4S)-3-benzyloxycarbonylamino-4-(t-butyldimethylsilanoxy)pyrrolidine-1-carboxylate (54 g) was dissolved in THF (400 mL), followed by addition of a solution (167 mL) of 1 M tetrabutyl ammonium fluoride in THF with ice cooling, and the mixture was stirred at room temperature for 3.5 h. Water was added, then the mixture was extracted with ethyl acetate, and the organic layer was dried with anhydrous magnesium sulfate and then concentrated under reduced pressure. The residue was purified by column chromatography (silica gel, hexane/ethyl acetate=1:1-1:2) to obtain t-butyl (3R,4S)-3-benzyloxycarbonylamino-4-hydroxypyrrolidine-1-carboxylate (38 g).

MS: ESI$^+$ (m/z) 359 (M$^+$+Na)
$^1$H-NMR (600 MHz, CDCl$_3$): δ7.28-7.42 (m, 5H), 5.18-5.39 (m, 1H), 5.10 (s, 2H), 4.14-4.41 (m, 2H), 3.68-3.80 (m, 1H), 3.31-3.60 (m, 2H), 3.05-3.25 (m, 1H), 1.44 (s, 9H)

(5) t-Butyl (3R,4S)-3-benzyloxycarbonylamino-4-hydroxypyrrolidine-1-carboxylate (38 g) was dissolved in chloroform (380 mL), and the mixture was ice-cooled, followed by addition of triethylamine (22 mL) and methanesulfonylchloride (11 mL). The mixture was stirred for 2 h with ice cooling, and water was added to separate the layers. The organic layer was washed with water, then dried with anhydrous magnesium sulfate, and concentrated under reduced pressure to obtain crude t-butyl (3R,4S)-3-benzyloxycarbonylamino-4-methanesulfonyloxypyrrolidine-1-carboxylate. This compound was used in the subsequent step without purification.

MS: ESI$^+$ (m/z) 437 (M$^+$+Na)
(6) The crude t-butyl (3R,4S)-3-benzyloxycarbonylamino-4-methanesulfonyloxypyrrolidine-1-carboxylate obtained in (5) was dissolved in DMF (570 mL), followed by addition of potassium acetate (39.0 g), and the mixture was stirred at 120° C. for 2.5 h. The mixture was cooled to room temperature, followed by addition of water, and the mixture was extracted with ethyl acetate. The organic layer was washed with brine, then dried with anhydrous magnesium sulfate, and concentrated under reduced pressure. The residue was purified by column chromatography (silica gel, hexane/ethyl acetate=4:1-2:1) to obtain t-butyl (3R,4R)-3-acetoxy-4-benzyloxycarbonylaminopyrrolidine-1-carboxylate (27 g).

MS: ESI$^+$ (m/z) 401 (M$^+$+Na)
$^1$H-NMR (600 MHz, CDCl$_3$): δ7.27-7.47 (m, 5H), 4.86-5.24 (m, 4H), 4.09-4.25 (m, 1H), 3.56-3.87 (m, 2H), 3.17-3.50 (m, 2H), 2.06 (s, 3H), 1.44 (s, 9H)

(7) t-Butyl (3R,4R)-3-acetoxy-4-benzyloxycarbonylaminopyrrolidine-1-carboxylate (27 g) was dissolved in methanol (350 mL), followed by addition of potassium carbonate (16 g) with ice cooling, and the mixture was stirred overnight at room temperature. Water was added, and then the mixture was extracted with ethyl acetate. The organic layer was dried with anhydrous magnesium sulfate and then concentrated under reduced pressure. The residue was purified by silica gel column chromatography (hexane/ethyl acetate=4:1-2:1) to obtain t-butyl (3R,4R)-3-benzyloxycarbonylamino-4-hydroxypyrrolidine-1-carboxylate (22 g).

MS: ESI$^+$ (m/z) 359 (M$^+$+Na)
$^1$H-NMR (600 MHz, CDCl$_3$): δ7.29-7.39 (m, 5H), 4.83-5.22 (m, 3H), 3.07-4.34 (m, 7H), 1.44 (s, 9H)

(8) t-Butyl (3R,4R)-3-benzyloxycarbonylamino-4-hydroxypyrrolidine-1-carboxylate (16 g) was dissolved in chloroform (143 mL), followed by addition of a solution (72 mL) of 4 M HCl in 1,4-dioxane, and the mixture was stirred overnight at room temperature. The solvent was evaporated under reduced pressure to obtain benzyl ((3R,4R)-4-hydroxypyrrolidin-3-yl)carbamate mono hydrochloride. This compound was used in the subsequent step without purification.

MS: ESI$^+$ (m/z) 237 (M$^+$+1)
(9) Benzyl ((3R,4R)-4-hydroxypyrrolidin-3-yl)carbamate mono hydrochloride obtained in (8) was dissolved in chloroform (143 mL), followed by addition of triethylamine (7.2 g) and 4-trifluoromethoxyphenylacetic acid (12 g), and then EDC.HCl (11 g) was added. The mixture was stirred at room temperature for 2 h, then the solvent was evaporated under reduced pressure, and the residue was purified by column chromatography (silica gel, ethyl acetate) to obtain benzyl ((3R,4R)-4-hydroxy-1-(2-(4-trifluoromethoxyphenyl)ethanoyl)pyrrolidin-3-yl)carbamate (14 g).

MS: ESI⁺ (m/z) 461 (M⁺+Na)

¹H-NMR (600 MHz, CDCl₃): δ7.28-7.39 (m, 5H), 7.24 (d, J=8.3 Hz, 2H), 7.13 (d, J=8.3 Hz, 2H), 4.98-5.28 (m, 3H), 3.58 (d, J=2.8 Hz, 2H), 3.30-4.36 (m, J=2.8 Hz, 7H)

(10) Benzyl ((3R,4R)-4-hydroxy-1-(2-(4-trifluoromethoxyphenyl)ethanoyl)pyrrolidin-3-yl)carbamate (14 g) was dissolved in methanol (140 mL), followed by addition of 5% Pd—C (2.4 g), and the mixture was stirred overnight under hydrogen atmosphere. The catalyst was removed by filtration, and then the filtrate was concentrated under reduced pressure. The precipitated solids were washed with a mixed solvent of isopropyl ether and hexane to obtain the title compound (8.6 g).

MS: ESI⁺ (m/z) 305 (M⁺+1)

¹H-NMR (600 MHz, CDCl₃): δ7.28-7.39 (m, 5H), 7.24 (d, J=8.3 Hz, 2H), 7.13 (d, J=8.3 Hz, 2H), 4.98-5.28 (m, 3H), 3.58 (d, J=2.8 Hz, 2H), 3.30-4.36 (m, J=2.8 Hz, 7H)

HPLC retention time, 8.4 min (CHIRALPAK AD-H (4.6× 250 mm, Daicel Chemical Industries, Ltd.); mobile phase, hexane/isopropanol=80:20; flow rate, 0.8 mL/min; temperature, 40° C.)

Reference 1-((3S,4S)-3-amino-4-hydroxypyrrolidin-1-yl)-2-(4-trifluoromethoxyphenyl)ethanone HPLC retention time, 7.9 min (CHIRALPAK AD-H (4.6× 250 mm, Daicel Chemical Industries, Ltd.); mobile phase, hexane/isopropanol=80:20; flow rate, 0.8 mL/min; temperature, 40° C.)

Reference Example 20

Synthesis of t-butyl (3R,4R)-3-benzylamino-4-hydroxypyrrolidine-1-carboxylate (−)-mandelate

[Formula 92]

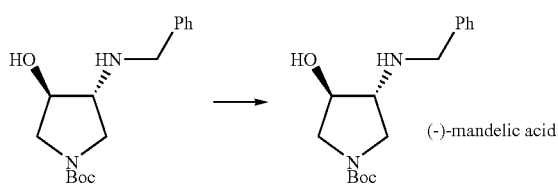

(1) t-Butyl (3RS,4RS)-3-benzylamino-4-hydroxypyrrolidine-1-carboxylate (1.0 g) in the racemic form obtained by the same method as described in Tetrahedron: Asymmetry 12, 2989-2997 (2001) was suspended in a mixed solvent of acetonitrile (10 mL) and water (0.09 mL), followed by addition of (−)-mandelic acid (572 mg), the mixture was stirred at 70° C. for 45 min and then at room temperature for 3 days. The precipitates were collected by filtration to obtain t-butyl (3RS,4RS)-3-benzylamino-4-hydroxypyrrolidine-1-carboxylate (−)-mandelate racemate (1.2 g).

MS: ESI⁺ (m/z) 293 (M⁺+1)

(2) t-Butyl (3RS,4RS)-3-benzylamino-4-hydroxypyrrolidine-1-carboxylate (−)-mandelate (1.2 g) was recrystallized 3 times with a mixed solvent of acetonitrile and water (20:1) to obtain optically active t-butyl (3R,4R)-3-benzylamino-4-hydroxypyrrolidine-1-carboxylate (−)-mandelate (240 mg).

HPLC retention time, 19.2 min (CHIRALCEL OJ (4.6× 250 mm, Daicel Chemical Industries, Ltd.); mobile phase, hexane/ethanol=95:5; flow rate, 0.8 mL/min; temperature, 40° C.)

Reference Example 21

Synthesis of 1-((3R,4R)-3-amino-4-methoxypyrrolidin-1-yl)-2-(4-trifluoromethoxyphenyl)ethanone

[Formula 93]

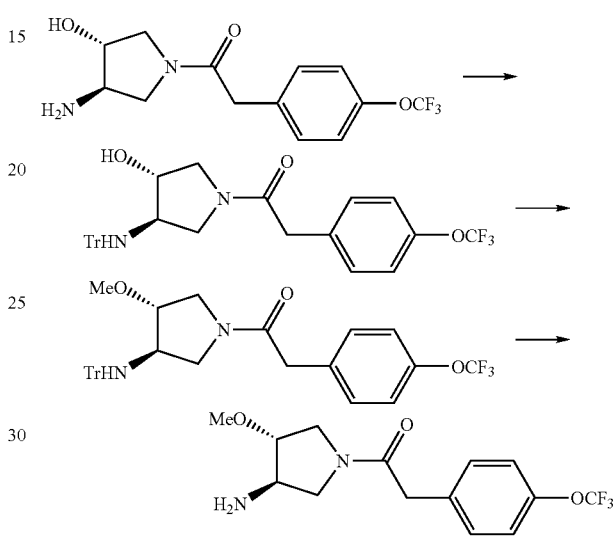

(1) 1-((3R,4R)-3-Amino-4-hydroxypyrrolidin-1-yl)-2-(4-trifluoromethoxyphenyl)ethanone (1.0 g) was dissolved in chloroform (30 mL) and THF (10 mL), followed by addition of triethylamine (0.55 mL) and triphenylmethyl chloride (1.4 g), and the mixture was stirred at room temperature for 4 days. The reaction mixture was concentrated under reduced pressure, and the residue was purified by column chromatography (silica gel, hexane/ethyl acetate=4:1-2:1) to obtain 1-((3R,4R)-3-hydroxy-4-(tritylamino)pyrrolidin-1-yl)-2-(4-trifluoromethoxyphenyl)ethanone (1.1 g).

MS: ESI⁺ (m/z) 569 (M⁺+Na)

(2) Sodium hydride (60% in oil) was washed with hexane and suspended in THF (10 mL), methyl iodide (0.19 mL), and a solution of 1-((3R,4R)-3-hydroxy-4-(tritylamino)pyrrolidin-1-yl)-2-(4-trifluoromethoxyphenyl)ethanone (1.1 g) in THF (10 mL) were added with ice cooling, and the mixture was stirred for 2 h. Water was added to the reaction mixture, and the mixture was extracted with ethyl acetate, and then the organic layer was washed with brine and then dried with anhydrous magnesium sulfate. The desiccant was removed by filtration, then the filtrate was concentrated under reduced pressure, and the residue was purified by silica gel column chromatography (hexane/ethyl acetate=4:1-2:1) to obtain 1-((3R,4R)-3-methoxy-4-(tritylamino)pyrrolidin-1-yl)-2-(4-trifluoromethoxyphenyl)ethanone (0.67 g).

MS: ESI⁺ (m/z) 583 (M⁺+Na)

(3) 1-((3R,4R)-3-Methoxy-4-(tritylamino)pyrrolidin-1-yl)-2-(4-trifluoromethoxyphenyl)ethanone (0.65 g) was dissolved in diethyl ether (5 mL), followed by addition of 5 M hydrochloric acid (5 mL), and the mixture was stirred at room temperature for 17 h. The layers were separated, and the aqueous layer was washed with diethyl ether, 1 M aqueous sodium hydroxide was added to make it basic, and the mixture was extracted with chloroform. The organic layer was dried with anhydrous magnesium sulfate, the desiccant was removed by filtration, and then the filtrate was concentrated under reduced pressure to obtain the title compound (0.35 g).

MS: ESI$^+$ (m/z) 319 (M$^+$+1)

$^1$H-NMR (600 MHz, CDCl$_3$): δ7.23-7.33 (m, 2H), 7.10-7.20 (m, 2H), 3.17-3.85 (m, 12H)

Reference Example 22

Synthesis of (2-chloro-6-ethylpyrimidin-4-yl)dimethylamine

[Formula 94]

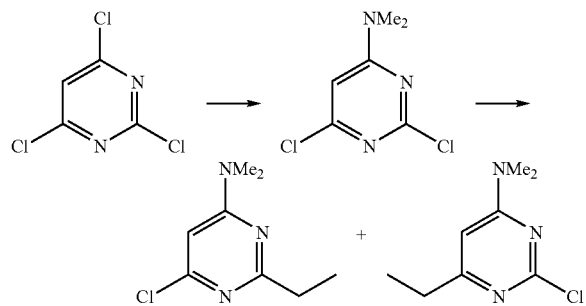

(1) A mixture of 2,4,6-trichloropyrimidine (10 g), N,N-diisopropylethylamine (8.5 g), and THF (50 mL) was ice-cooled, and a solution of 50% aqueous dimethyl amine (4.9 g) in THF (10 mL) was added dropwise. The mixture was stirred at room temperature for 1 day, then the reaction mixture was concentrated, and the residue was diluted with chloroform and then washed with saturated aqueous sodium hydrogencarbonate. The organic layer was dried with anhydrous sodium sulfate, the desiccant was removed by filtration, and then the filtrate was concentrated under reduced pressure. The residue was purified by column chromatography (silica gel, hexane/ethyl acetate=4:1-1:1) to obtain (2,6-dichloropyrimidin-4-yl)dimethylamine (9.9 g).

MS: ESI$^+$ (m/z) 192 (M$^+$+1)

(2) A mixture of zinc bromide (2.6 g) and THF (15 mL) was cooled to −60 to −70° C., a solution (3.8 mL) of 3 M ethylmagnesium bromide in diethyl ether was added dropwise, the mixture was stirred at −75° C. for 70 min and then at room temperature for 1 h, followed by addition of a solution of Pd(PPh$_3$)$_4$ (0.60 g) and (2,6-dichloropyrimidin-4-yl)dimethylamine (2.0 g) in THF (8 mL), and the mixture was heated to reflux for 17 h. The mixture was cooled to room temperature, then the reaction mixture was diluted with chloroform, washed with saturated aqueous ammonium chloride, and then extracted with chloroform. The organic layer was dried with anhydrous sodium sulfate, the desiccant was removed by filtration, then the filtrate was concentrated under reduced pressure, and the residue was purified by silica gel column chromatography (hexane/ethyl acetate=15:1) to obtain the title compound (0.18 g) and (6-chloro-2-ethylpyrimidin-4-yl)dimethylamine (0.46 g).

MS: ESI$^+$ (m/z) 186 (M$^+$+1)

Reference Example 23

Synthesis of 4-ethylquinolin-2-ol

[Formula 95]

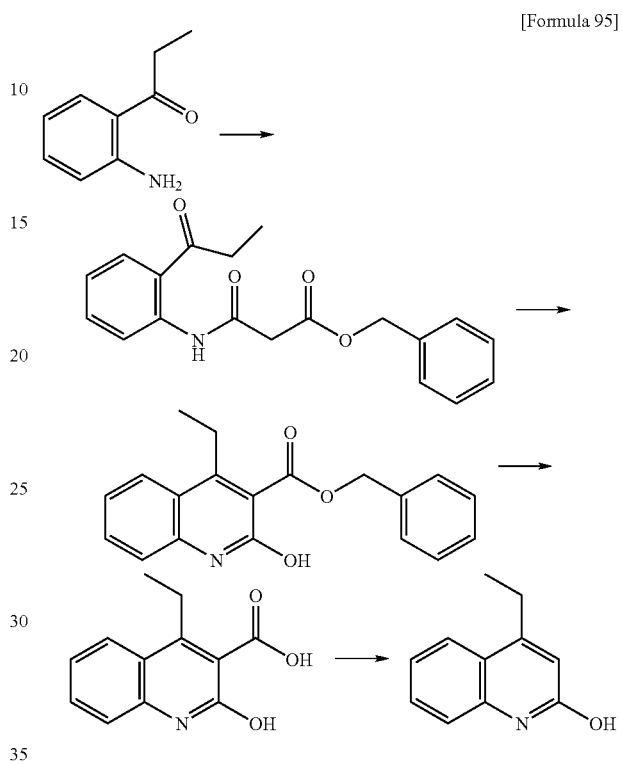

(1) To a mixture of 1-(2-aminophenyl)propan-1-one (CAS1196-28-7) (4.6 g), monobenzyl malonate (7.2 g), and THF (46 mL) were added EDC.HCl (7.1 g) and HOBt.H$_2$O (7.1 g), and the mixture was stirred at room temperature for 14 h and then heated to reflux for 8 h. The solvent was evaporated under reduced pressure, and the residue was diluted with ethyl acetate and then washed with saturated aqueous sodium hydrogencarbonate and saturated brine. The organic layer was dried with anhydrous sodium sulfate, the desiccant was removed by filtration, then the filtrate was concentrated under reduced pressure, and the residue was purified by silica gel column chromatography (hexane/ethyl acetate=9:1) to obtain benzyl N-(2-propionylphenyl)malonamate (1.8 g).

MS: ESI$^+$ (m/z) 348 (M$^+$+Na)

(2) Benzyl N-(2-propionylphenyl)malonamate (1.8 g) was dissolved in ethanol (20 mL), followed by addition of potassium t-butoxide (0.65 g), and the mixture was stirred at room temperature for 3 h. The precipitated solids were collected by filtration and washed with water to obtain benzyl 4-ethyl-2-hydroxyquinoline-3-carboxylate (1.4 g).

MS: ESI$^+$ (m/z) 308 (M$^+$+1)

(3) Benzyl 4-ethyl-2-hydroxyquinoline-3-carboxylate (1.2 g) was suspended in methanol (12 mL) and THF (6 mL), followed by addition of 5% Pd—C (120 mg), and the mixture was stirred at 40° C. for 1 day. The catalyst was removed by filtration, and then the filtrate was concentrated under reduced pressure to obtain 4-ethyl-2-hydroxyquinoline-3-carboxylic acid (0.85 g). This compound was used in the subsequent step without purification.

MS: ESI$^+$ (m/z) 218 (M$^+$+1)

(4) A mixture of 4-ethyl-2-hydroxyquinoline-3-carboxylic acid (0.84 g) and diphenyl ether (2.5 mL) was heated at 250° C. for 2 h with stirring. The mixture was cooled to room temperature and purified by silica gel column chromatography (chloroform/methanol=50:1) to obtain the title compound (0.57 g).

MS: ESI+ (m/z) 174 (M++1)

The following compounds were obtained in the same manner.

4-Isopropylquinoline-2-ol (CAS328956-40-7)

Reference Example 24

Synthesis of 2-chloroquinoline-4-carboxylic acid dimethylamide

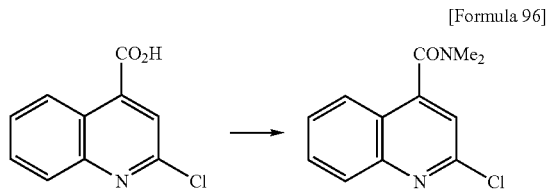

[Formula 96]

To a mixture of 2-chloroquinoline-4-carboxylic acid (5.0 g) and THF (48 mL) was added a small amount of DMF, followed by addition of thionyl chloride (1.8 mL) with ice cooling. The mixture was stirred at room temperature for 1 h and then at 60° C. for 1 h. The mixture was cooled to room temperature and then concentrated under reduced pressure, and the residue was diluted with chloroform (30 mL). The mixture was ice-cooled, followed by addition of 50% aqueous dimethyl amine (20 mL), and the mixture was stirred for 10 min. 1 M aqueous sodium hydroxide was added, the mixture was extracted with chloroform, the organic layer was dried with anhydrous magnesium sulfate, then the desiccant was removed by filtration, and the filtrate was concentrated under reduced pressure. The residue was purified by silica gel column chromatography (hexane/ethyl acetate=7:3) to obtain the title compound (4.6 g).

MS: ESI+ (m/z) 257 (M++Na)

Reference Example 25

Synthesis of (3RS,4RS)-4-(4-dimethylamino-6-methylpyrimidin-2-ylamino)pyrrolidin-3-ol dihydrochloride

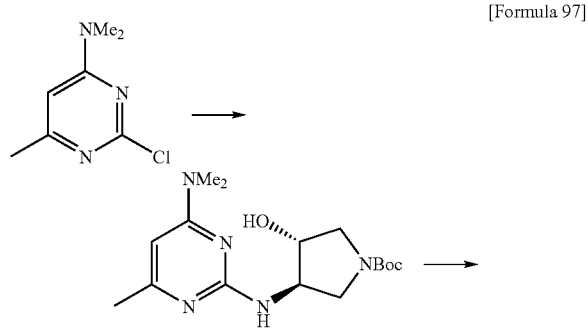

[Formula 97]

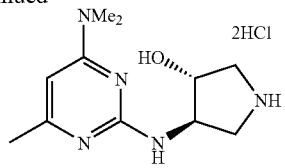

(1) 2-Chloro-4-dimethylamino-6-methylpyrimidine (3.5 g), t-butyl (3RS,4RS)-3-amino-4-hydroxypyrrolidine-1-carboxylate (4.5 g), N,N-diisopropylethylamine (5.3 mL), and n-butanol (10 mL) were stirred at 120° C. for 8 days. To the reaction mixture were added chloroform and saturated aqueous sodium hydrogencarbonate to separate the layers. The aqueous layer was extracted with chloroform, then the organic layer was dried with anhydrous sodium sulfate, the desiccant was removed by filtration, and then the filtrate was concentrated under reduced pressure. The residue was purified by silica gel column chromatography (chloroform/methanol=9:1) to obtain t-butyl (3RS,4RS)-3-(4-dimethylamino-6-methylpyrimidin-2-ylamino)-4-hydroxypyrrolidine-1-carboxylate (5.9 g).

MS: ESI+ (m/z) 338 (M++1)

(2) t-Butyl (3RS,4RS)-3-(4-dimethylamino-6-methylpyrimidin-2-ylamino)-4-hydroxypyrrolidine-1-carboxylate (1.0 g) was dissolved in ethyl acetate (10 mL), followed by addition of a solution (7.5 mL) of 4 M HCl in ethyl acetate, and the mixture was stirred at room temperature for 2 h. Diethyl ether was added to the solution, and the precipitated crystals were collected by filtration to obtain the title compound (0.89 g).

MS: ESI+ (m/z) 238 (M++1)

Reference Example 26

Synthesis of ((3RS,4RS)-4-fluoropyrrolidin-3-yl)-(4-methyl-6-morpholin-4-ylpyrimidin-2-yl)amine

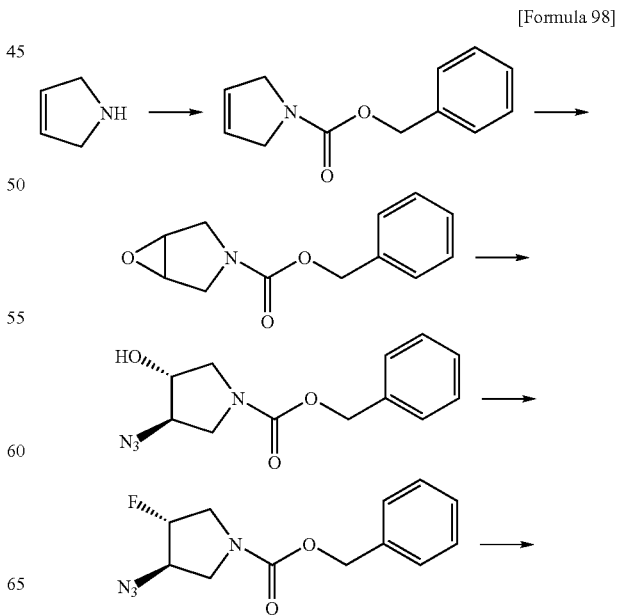

[Formula 98]

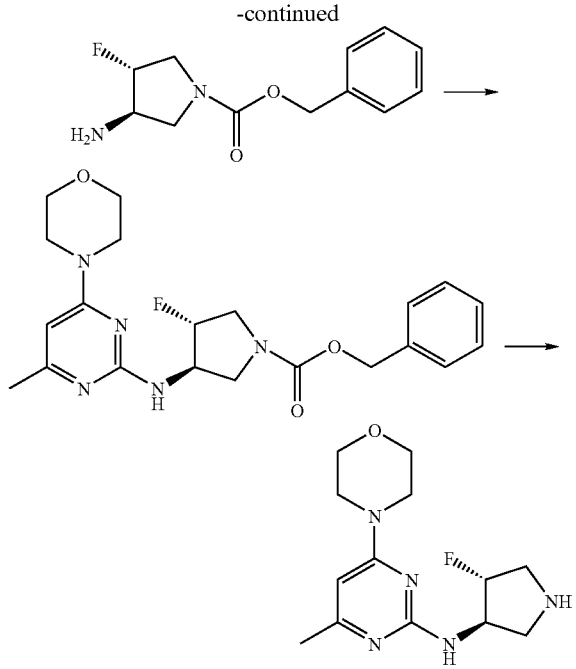

(1) A mixture of 3-pyrroline (9.1 g), N,N-diisopropylethylamine (28 mL), and chloroform (46 mL) was ice-cooled, benzyl chloroformate (26 g) was added dropwise, and then the mixture was stirred at room temperature for 15 h. The reaction solution was diluted with chloroform, washed with saturated aqueous sodium hydrogencarbonate, saturated aqueous ammonium chloride, and saturated brine, and then dried with anhydrous sodium sulfate. The desiccant was removed by filtration, then the filtrate was concentrated under reduced pressure, and the residue was purified by silica gel column chromatography (hexane/ethyl acetate=7:3) to obtain benzyl 2,5-dihydropyrrole-1-carboxylate (26 g).

MS: ESI$^+$ (m/z) 226 (M$^+$+Na)

(2) Benzyl 2,5-dihydropyrrole-1-carboxylate (25 g) was dissolved in chloroform (125 mL), and mCPBA (39 g) was slowly added with ice cooling. The mixture was stirred at room temperature for 1 day, then diluted with chloroform, and washed with saturated aqueous sodium thiosulfate and saturated aqueous sodium hydrogencarbonate. The organic layer was dried with anhydrous sodium sulfate, then the desiccant was removed by filtration, the filtrate was concentrated under reduced pressure, and the residue was purified by silica gel column chromatography (hexane/ethyl acetate=8:2-1:99) to obtain benzyl 6-oxa-3-azabicyclo[3.1.0]hexane-3-carboxylate (18 g).

MS: ESI$^+$ (m/z) 242 (M$^+$+Na)

(3) To a mixture of benzyl 6-oxa-3-azabicyclo[3.1.0]hexane-3-carboxylate (15 g), acetone (120 g), water (34 mL), and ammonium chloride (8.1 g) was added sodium azide (23 g), and the mixture was stirred at 70° C. for 8 h. Water was added to the reaction solution, and the mixture was extracted with chloroform. The organic layer was dried with anhydrous sodium sulfate, then the desiccant was removed by filtration, the filtrate was concentrated under reduced pressure, and the residue was purified by silica gel column chromatography (hexane/ethyl acetate=9:1-1:99) to obtain benzyl (3RS,4RS)-3-azide-4-hydroxypyrrolidine-1-carboxylate (13 g).

MS: ESI$^+$ (m/z) 285 (M$^+$+Na)

(4) Benzyl (3RS,4RS)-3-azide-4-hydroxypyrrolidine-1-carboxylate (5.5 g) was dissolved in methylene chloride (110 mL), the mixture was cooled to −73° C., followed by addition of DAST (Et$_2$NSF$_3$) (6.8 g), and the mixture was stirred for 1 h and then at room temperature for 14 h. The reaction mixture was poured into 10% aqueous sodium hydrogencarbonate and extracted with ethyl acetate. The organic layer was dried with anhydrous sodium sulfate, then the desiccant was removed by filtration, the filtrate was concentrated under reduced pressure, and the residue was purified by column chromatography (silica gel, hexane/ethyl acetate=8:2-1:99, and NH silica gel, hexane:ethyl acetate=4:1-ethyl acetate) to obtain benzyl (3RS,4RS)-3-azide-4-fluoropyrrolidine-1-carboxylate (3.9 g) (refer to Bioorg. Med. Chem. Lett., 8, 1953-1958, [1998]).

MS: ESI$^+$ (m/z) 287 (M$^+$+Na)

(5) A mixture of benzyl (3RS,4RS)-3-azide-4-fluoropyrrolidine-1-carboxylate (3.0 g) and THF (30 mL) was ice-cooled, followed by addition of triphenylphosphine (3.2 g), and the mixture was stirred at room temperature for 15 h. The reaction solution was concentrated under reduced pressure, the residue was purified by silica gel column chromatography (silica gel, chloroform/a solution of 8 M ammonia in methanol=10:1) to obtain benzyl (3RS,4RS)-3-amino-4-fluoropyrrolidine-1-carboxylate (5.5 g).

MS: ESI$^+$ (m/z) 239 (M$^+$+1)

(6) A mixture of 4-(2-chloro-6-methylpyrimidin-4-yl)morpholine (180 mg), benzyl (3RS,4RS)-3-amino-4-fluoropyrrolidine-1-carboxylate (240 mg), Pd(OAc)$_2$ (38 mg), 2-(di-t-butylphosphino)biphenyl (0.10 g), sodium t-butoxide (0.24 g), and toluene (2 mL) was heated to reflux under nitrogen atmosphere for 6 h. The reaction solution was extracted with chloroform and dried with anhydrous magnesium sulfate. The desiccant was removed by filtration, then the filtrate was concentrated under reduced pressure, and the residue was purified by silica gel column chromatography (NH silica gel, hexane/ethyl acetate=1:2) to obtain benzyl (3RS,4RS)-3-fluoro-4-(4-methyl-6-morpholin-4-ylpyrimidin-2-ylamino)pyrrolidine-1-carboxylate (25 mg).

MS: ESI$^+$ (m/z) 416 (M$^+$+1)

(7) Benzyl (3RS,4RS)-3-fluoro-4-(4-methyl-6-morpholin-4-ylpyrimidin-2-ylamino)pyrrolidine-1-carboxylate (20 mg) was dissolved in methanol (1 mL), followed by addition of 5% Pd—C (40 mg), and the mixture was stirred under hydrogen atmosphere for 6 h. The catalyst was removed by filtration, and then the filtrate was concentrated under reduced pressure to obtain ((3RS,4RS)-4-fluoropyrrolidin-3-yl)-(4-methyl-6-morpholin-4-ylpyrimidin-2-yl)amine (13 mg).

MS: ESI$^+$ (m/z) 282 (M$^+$+1)

Reference Example 27

Synthesis of (3R,4R)-4-(4,6-dimethylquinolin-2-ylamino)pyrrolidin-3-ol di hydrochloride

[Formula 99]

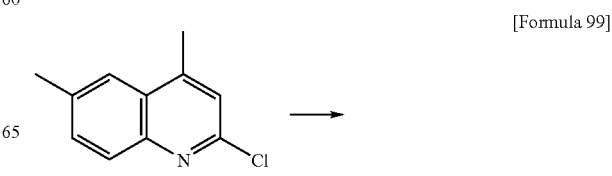

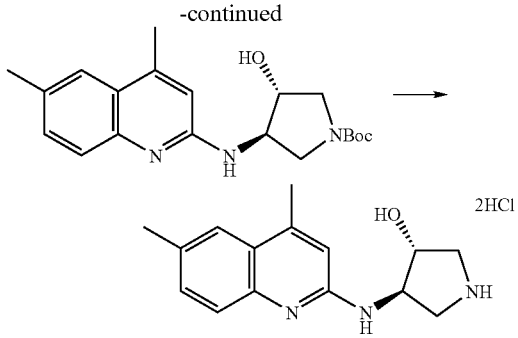

(1) To a mixture of 2-chloro-4,6-dimethylquinoline (0.40 g), Pd₂(dba)₃ (0.095 g), (±)-BINAP (0.20 g), (S)-t-butyl 3-amino-4-hydroxypyrrolidine-1-carboxylate (0.51 g), and 1,4-dioxane (8 mL) was added sodium t-butoxide (0.60 g) under nitrogen atmosphere, and the mixture was stirred at 70° C. for 1 h. The reaction mixture was diluted with ethyl acetate and water, the interlayer was removed by Celite filtration, and the organic layer was washed with saturated brine. The organic layer was dried with anhydrous magnesium sulfate, then the desiccant was removed by filtration, the filtrate was concentrated under reduced pressure, and the solids were washed with ethyl acetate and diisopropyl ether to obtain (3R,4R)-t-butyl 3-(4,6-dimethylquinolin-2-ylamino)-4-hydroxypyrrolidine-1-carboxylate (0.39 g).

(2) (3R,4R)-t-Butyl 3-(4,6-dimethylquinolin-2-ylamino)-4-hydroxypyrrolidine-1-carboxylate (0.39 g) was dissolved in 4 M HCl in 1,4-dioxane (5 mL), and the mixture was stirred at room temperature for 2 h. To the reaction suspension was added diisopropyl ether, the mixture was stirred, and then the solids were collected by filtration to obtain (3R,4R)-4-(4,6-dimethylquinolin-2-ylamino)pyrrolidin-3-ol di hydrochloride (0.32 g).

LC/MS: ESI⁺ (m/z) 258 (M⁺+1)

¹H-NMR (300 MHz, DMSO-d₆): δ13.5 (br, 1H), 10.01 (br, 1H), 9.52 (br, 1H), 9.45 (br, 1H), 8.28 (br, 1H), 7.81 (s, 1H), 7.55-7.70 (m, 1H), 7.01 (br, 1H), 6.21 (br, 1H), 4.78 (br, 1H), 4.41 (s, 1H), 3.65-3.90 (m, 1H), 3.40-3.60 (m, 1H), 3.10-3.30 (m, 1H), 2.62 (s, 3H), 2.47 (s, 3H)

The following compounds were obtained in the same manner.

(3R,4R)-4-(6-Ethyl-4-methylquinolin-2-ylamino)pyrrolidin-3-ol dihydrochloride
LC/MS: ESI⁺ (m/z) 272 (M⁺+1)

(3R,4R)-4-(6-Ethoxy-4-methylquinolin-2-ylamino)pyrrolidin-3-ol dihydrochloride
LC/MS: ESI⁺ (m/z) 288 (M⁺+1)

Reference Example 28

Synthesis of 1-(4-trifluoromethoxyphenyl)cyclopropanecarboxylic acid

[Formula 100]

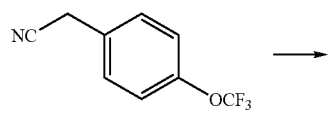

(1) 50% aqueous sodium hydroxide (250 g) was slowly added dropwise to a mixture of 1-bromo-2-chloroethane (250 mL), 4-(trifluoromethoxy)phenylacetonitrile (5.0 g), and benzyltriethylammonium chloride (4.6 g) with stirring at 50° C., and the mixture was stirred at 65° C. for 1 h. After the reaction mixture was left stand for cooling, water was added to separate the organic layer, and the organic layer was washed with 1 M hydrochloric acid and water.

The organic layer was dried with anhydrous magnesium sulfate, then the desiccant was removed by filtration, the filtrate was concentrated under reduced pressure, and the residue was purified by silica gel column chromatography (silica gel, chloroform) to obtain yellow oily 1-(4-trifluoromethoxyphenyl)cyclopropanecarbonitrile (6.2 g).

(2) A mixture of 1-(4-trifluoromethoxyphenyl)cyclopropanecarbonitrile (4.0 g), 25% aqueous sodium hydroxide (0.46 mL), 30% aqueous hydrogen peroxide (25 mL), and methanol (100 mL) was heated at 55° C. for 1 h with stirring. The reaction mixture was concentrated under reduced pressure, the precipitated crystals were collected by filtration, to obtain white solid 1-(4-(trifluoromethoxy)phenyl)cyclopropanecarbamide (4.5 g).

(3) A mixture of 1-(4-trifluoromethoxyphenyl)cyclopropanecarbamide (4.5 g), 15% aqueous sodium hydroxide (150 mL), and methanol (60 mL) was heated at 78° C. for 18 h with stirring. The reaction mixture was left stand for cooling, then the reaction solution was adjusted to pH 2 using 15% hydrochloric acid and concentrated under reduced pressure. The precipitated crystals were collected by filtration to obtain white solid 1-(4-(trifluoromethoxy)phenyl)cyclopropanecarboxylic acid (4.5 g).

LC/MS: ESI⁺ (m/z) 247 (M⁺+1)

¹H-NMR (300 MHz, DMSO-d₆): δ7.43-7.47 (m, 2H), 7.27-7.30 (m, 2H), 1.45-1.48 (m, 2H), 1.15-1.19 (m, 2H)

The following compounds were synthesized by the same method.

1-(4-(Difluoromethoxy)phenyl)cyclopropanecarboxylic acid (CAS869969-80-2)

1-(4-Fluorophenyl)cyclopropanecarboxylic acid (CAS773100-29-1)

1-(3,4-Difluorophenyl)cyclopropanecarboxylic acid (CAS186347-67-1)

1-(4-Chlorophenyl)cyclopropanecarboxylic acid (CAS72934-37-3)

Reference Example 29

Synthesis of (S)-N-(1-benzylpyrrolidin-3-yl)-6-methyl-4-trifluoromethylpyridin-2-amine

[Formula 101]

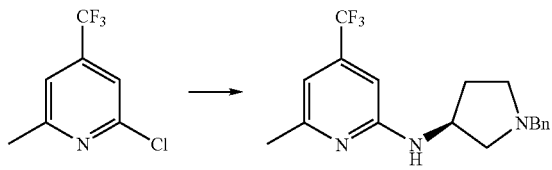

A mixture of 2-chloro-6-methyl-4-trifluoromethylpyridine (0.196 g), (S)-1-benzyl-3-aminopyrrolidine (0.529 g), diethylene glycol (4 mL), and N,N-diisopropylethylamine (0.52 mL) was heated at 140° C. for 2 h using a microwave reaction apparatus. After completion of the reaction, water and ethyl acetate were added to the reaction solution, the mixture was extracted with ethyl acetate, washed with saturated brine, and then dried with anhydrous magnesium sulfate, then the desiccant was removed by filtration, and then the crude product obtained by concentration under reduced pressure was purified by silica gel column chromatography (silica gel, hexane/ethyl acetate=5:1-2:1) to obtain (S)-N-(1-benzylpyrrolidin-3-yl)-6-methyl-4-trifluoromethylpyridin-2-amine (0.082 g).

$^1$H-NMR (300 MHz, DMSO-$d_6$): δ7.20-7.34 (m, 5H), 6.60 (s, 1H), 6.32 (s, 1H), 5.01 (d, J=8.00 Hz, 1H), 4.20-4.30 (m, 1H), 3.63 (d, J=5.8 Hz, 2H), 2.75-2.85 (m, 2H), 2.50-2.60 (m, 1H), 2.40 (s, 3H), 2.30-2.50 (m, 2H), 1.60-1.70 (m, 1H)

Reference Example 30

Synthesis of 2-chloro-6-methoxymethyl-4-methylquinoline

[Formula 102]

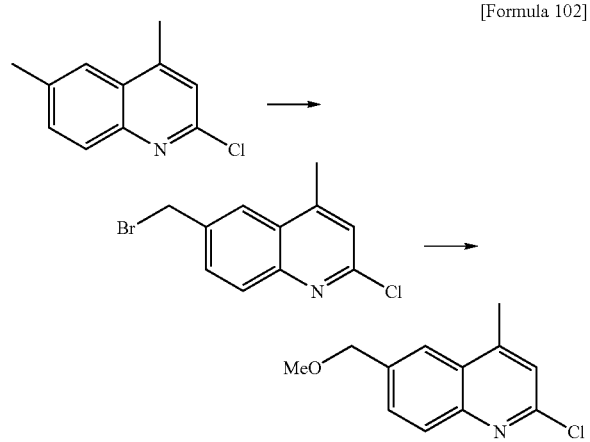

(1) To a solution of 2-chloro-4,6-dimethylquinoline (1.31 g) in chloroform (20 mL) was added N-bromosuccinimide (1.24 g) at room temperature. The reaction solution was heated at 70° C., and benzoyl peroxide (0.25 g) was divided into 5 portions and added at intervals of a few tens of min. The mixture was stirred at the same temperature for 1 h. The reaction solution was cooled to room temperature and diluted with ethyl acetate, then the organic layer was washed with a mixed solution of saturated aqueous sodium thiosulfate and saturated brine and saturated brine. The organic layer was dried with anhydrous magnesium sulfate, then the desiccant was removed by filtration, and the filtrate was concentrated under reduced pressure. The resulting residue was purified by silica gel column chromatography (ethyl acetate/hexane=10:1) to obtain 6-bromomethyl-2-chloro-4-methylquinoline (0.79 g).

LC/MS: ESI$^+$ (m/z): 270 (M$^+$+1)
$^1$H-NMR (700 MHz, CDCl$_3$): δ7.99 (d, J=8.8 Hz, 1H), 7.94 (d, J=1.6 Hz, 1H), 7.74 (dd, J=1.6 Hz, J=8.8 Hz, 1H), 7.26 (s, 1H), 4.67 (s, 2H), 2.69 (s, 3H)

(2) To a solution of 6-bromomethyl-2-chloro-4-methylquinoline (0.40 g) in methanol (8 mL) was added 1 M aqueous sodium hydroxide (4 mL) at room temperature, and the mixture was stirred at 70° C. for 30 min. After cooled to room temperature, the reaction solution was diluted with ethyl acetate. The organic layer was washed with saturated brine, the organic layer was dried with anhydrous magnesium sulfate, the desiccant was removed by filtration, and the filtrate was concentrated under reduced pressure. The resulting residue was purified by silica gel column chromatography (ethyl acetate/hexane=1:4) to obtain 2-chloro-6-methoxymethyl-4-methylquinoline (0.31 g).

LC/MS: ESI$^+$ (m/z): 222 (M$^+$+1)
$^1$H-NMR (300 MHz, CDCl$_3$): δ8.00 (d, J=9.0 Hz, 1H), 7.92 (d, J=1.5 Hz, 1H), 7.69 (dd, J=1.5 Hz, J=9.0 Hz, 1H), 7.25 (s, 1H), 4.65 (s, 2H), 3.48 (s, 3H), 2.70 (s, 3H)

Reference Example 31

Synthesis of (2-chloro-4-methylquinolin-6-yl)methanol

[Formula 103]

To a solution of 6-bromomethyl-2-chloro-4-methylquinoline (0.39 g) in dimethyl sulfide (5 mL) was added 1 M aqueous sodium hydroxide (5 mL) at room temperature, and the mixture was stirred at 70° C. for 1 h. After cooled to room temperature, the reaction solution was diluted with ethyl acetate. The organic layer was washed with saturated brine, the organic layer was dried with anhydrous magnesium sulfate, then the desiccant was removed by filtration, and the filtrate was concentrated under reduced pressure. The resulting residue was purified by silica gel column chromatography (ethyl acetate/hexane=3:1–ethyl acetate/hexane/chloroform=1:3:1–ethyl acetate) to obtain (2-chloro-4-methylquinolin-6-yl)methanol (0.14 g).

LC/MS: ESI$^+$ (m/z): 208 (M$^+$+1)

The conditions for HPLC listed in Tables 1 to 20 are shown below.

HPLC conditions: Capcell Pak UG120, 4.6 mm×150 mm (Shiseido Co., Ltd.); column temperature, 40° C.; flow rate, 1.0 mL/min; mobile phase, [A] 0.1% $H_3PO_4$/$CH_3CN$=60/40, [B] 0.1% $H_3PO_4$/$CH_3CN$=65/35, [A] 0.1% $H_3PO_4$/$CH_3CN$=70/30, [D] 0.1% $H_3PO_4$/$CH_3CN$=73/27, [E] 0.1% $H_3PO_4$/$CH_3CN$=75/25, [F] 0.1% $H_3PO_4$/$CH_3CN$=80/20, [G] 0.1% $H_3PO_4$/$CH_3CN$=85/15, [H] 0.1% $H_3PO_4$/$CH_3CN$=90/10, [I] ($H_2O$/$CH_3CN$/$H_3PO_4$/SDS [700 mL/300 mL/1 mL/2 g])/$CH_3CN$=50/50, [J] ($H_2O$/$CH_3CN$/$H_3PO_4$/SDS [700 mL/300 mL/1 mL/2 g])/$CH_3CN$=60/40, [K] ($H_2O$/$CH_3CN$/$H_3PO_4$/SDS [700 mL/300 mL/1 mL/2 g])/$CH_3CN$=65/35, [L] ($H_2O$/$CH_3CN$/$H_3PO_4$/SDS [700 mL/300 mL/1 mL/2 g])/$CH_3CN$=70/30, [M] ($H_2O$/$CH_3CN$/$H_3PO_4$/SDS [700 mL/300 mL/1 mL/2 g])/$CH_3CN$=75/25, [N] ($H_2O$/$CH_3CN$/$H_3PO_4$/SDS [700 mL/300 mL/1 mL/2 g])/$CH_3CN$=80/20, [O] 10 mM $AcONH_4$/$CH_3CN$=25/75, [P] 10 mM $AcONH_4$/$CH_3CN$=40/60, [Q] 10 mM $AcONH_4$/$CH_3CN$=45/55, [R] 10 mM $AcONH_4$/$CH_3CN$=50/50.

TABLE 1

| Compound No. | Example No. | $R^{1a}$ | $X^1$ | $X^2$ | —Ar | MS*[1] [Ionization method] | Retention time (min) [Mobile phase] |
|---|---|---|---|---|---|---|---|
| 1-001*[2] | 1 | Me-N(Me)- | H | H | 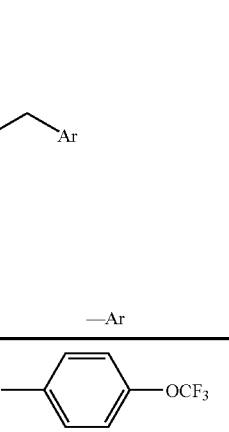 —OCF$_3$ | 460(M$^+$ + 1) [ESI(Pos.)] | 18.7 [E] |
| 1-002 | 1 | Me-N(Me)- | 5-Me | H |  —OCF$_3$ | 474(M$^+$ + 1) [ESI(Pos.)] | 9.5 [C] |
| 1-003 | 1 | Me-N(Me)- | 6-Me | H | 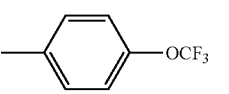 —OCF$_3$ | 474(M$^+$ + 1) [ESI(Pos.)] | 10.4 [C] |
| 1-004 | 1 | Me-N(Me)- | 7-Me | H |  —OCF$_3$ | 474(M$^+$ + 1) [ESI(Pos.)] | 9.9 [C] |
| 1-005 | 1 | Me-N(Me)- | 6-OMe | H | 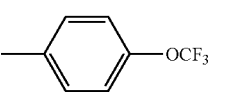 —OCF$_3$ | 490(M$^+$ + 1) [ESI(Pos.)] | 11.1 [C] |
| 1-006 | 1 | Me-N(Me)- | 6-OMe | 7-OMe |  —OCF$_3$ | 520(M$^+$ + 1) [ESI(Pos.)] | 7.9 [C] |
| 1-007*[2] | 1 | Me-N(Me)- | 6-F | H | 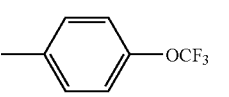 —OCF$_3$ | 478(M$^+$ + 1) [ESI(Pos.)] | 9.0 [C] |
| 1-008*[2] | 1 | Me-N(Me)- | 7-F | H |  —OCF$_3$ | 478(M$^+$ + 1) [ESI(Pos.)] | 8.5 [C] |
| 1-009*[2] | 1 | Me-N(Me)- | 6-F | 7-F | 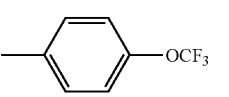 —OCF$_3$ | 496(M$^+$ + 1) [ESI(Pos.)] | 7.6 [C] |
| 1-010 | 1 | Me-N(Me)- | 6-Cl | H |  —OCF$_3$ | 494(M$^+$ + 1) [ESI(Pos.)] | 13.8 [C] |

TABLE 1-continued

[Structure: quinazoline core with X¹ at position 5, positions 6,7,8 with X², R^1a at position 4, NH-pyrrolidinyl-C(O)-CH2-Ar substituent]

| Compound No. | Example No. | R^1a | X¹ | X² | —Ar | MS*1 [Ionization method] | Retention time (min) [Mobile phase] |
|---|---|---|---|---|---|---|---|
| 1-011*2 | 1 | Me-N(Me)-CH2- (N-methyl, with NMe2) | 7-Cl | H | -C6H4-OCF3 | 494(M+ + 1) [ESI(Pos.)] | 11.4 [C] |
| 1-012 | 1 | MeO-CH2CH2-N(Me)-CH2CH2-OMe | H | H | -C6H4-OCF3 | 548(M+ + 1) [ESI(Pos.)] | 9.5 [C] |
| 1-013 | 1 | Pr-N(CH2-cyclopropyl)- (N-Me) | 6-F | H | -C6H4-OCF3 | 546(M+ + 1) [ESI(Pos.)] | 5.2 [A] |
| 1-014*2 | 1 | Pr-N(CH2-cyclopropyl)- (N-Me) | 7-F | H | -C6H4-OCF3 | 546(M+ + 1) [ESI(Pos.)] | 18.7 [A] |
| 1-015 | 1 | Pr-N(CH2-cyclopropyl)- (N-Me) | 6-Cl | H | -C6H4-OCF3 | 562(M+ + 1) [ESI(Pos.)] | 12.3 [A] |
| 1-016 | 1 | HN(Me)-CH(cyclopropyl)2 | H | H | -C6H4-OCF3 | 526(M+ + 1) [ESI(Pos.)] | 9.0 [B] |
| 1-017 | 1 | HN(Me)-CH2CH2-CN | H | H | -C6H4-OCF3 | 485(M+ + 1) [ESI(Pos.)] | 6.0 [C] |
| 1-018 | 1 | HN(Me)-CH2CH2-morpholino | 6-Me | H | -C6H4-OCF3 | 559(M+ + 1) [ESI(Pos.)] | 7.0 [F] |
| 1-019 | 1 | HN(Me)-CH2CH2-(2-pyridyl) | 6-Me | H | -C6H4-OCF3 | 551(M+ + 1) [ESI(Pos.)] | 5.0 [E] |
| 1-020 | 1 | HN(Me)-CH2-CONMe2 | H | H | -C6H4-OCF3 | 517(M+ + 1) [ESI(Pos.)] | 7.7 [E] |

TABLE 1-continued
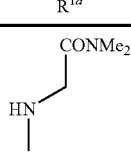
| Compound No. | Example No. | R$^{1a}$ | X$^1$ | X$^2$ | —Ar | MS*$^1$ [Ionization method] | Retention time (min) [Mobile phase] |
|---|---|---|---|---|---|---|---|
| 1-021 | 1 | 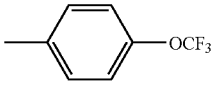 | 6-Me | H | 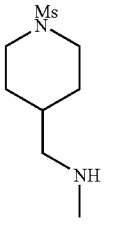 | 531(M$^+$ + 1) [ESI(Pos.)] | 14.2 [E] |
| 1-022 | 1 | 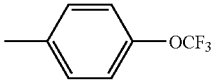 | H | H | 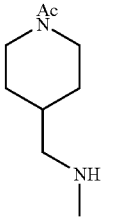 | 607(M$^+$ + 1) [ESI(Pos.)] | 8.8 [C] |
| 1-023 | 1 | 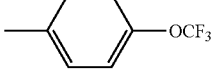 | 6-Me | H | 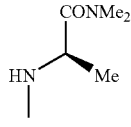 | 585(M$^+$ + 1) [ESI(Pos.)] | 22.1 [E] |
| 1-024 | 1 | 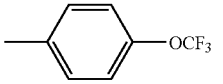 | H | H | 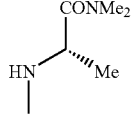 | 531(M$^+$ + 1) [ESI(Pos.)] | 5.8 [C] |
| 1-025 | 1 | 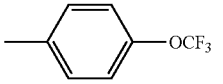 | H | H | 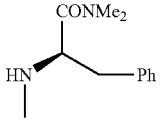 | 531(M$^+$ + 1) [ESI(Pos.)] | 6.0 [C] |
| 1-026 | 1 | 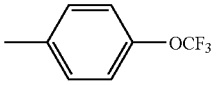 | H | H | 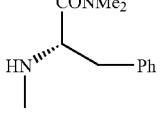 | 607(M$^+$ + 1) [ESI(Pos.)] | 4.8 [A] |
| 1-027 | 1 | 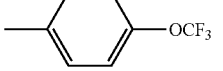 | H | H | 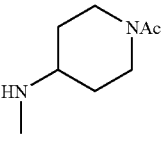 | 607(M$^+$ + 1) [ESI(Pos.)] | 5.1 [A] |
| 1-028 | 1 | 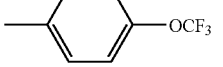 | 6-OMe | H | | 587(M$^+$ + 1) [ESI(Pos.)] | 16.1 [C] |

TABLE 1-continued

| Compound No. | Example No. | R1a | X1 | X2 | —Ar | MS*1 [Ionization method] | Retention time (min) [Mobile phase] |
|---|---|---|---|---|---|---|---|
| 1-029 | 1 | 4-(methylamino)-1-(methylsulfonyl)piperidine | H | H | 4-(trifluoromethoxy)phenyl | 593(M+ + 1) [ESI(Pos.)] | 7.0 [C] |
| 1-030 | 1 | 4-(methylamino)-1-(methylsulfonyl)piperidine | 6-Me | H | 4-(trifluoromethoxy)phenyl | 607(M+ + 1) [ESI(Pos.)] | 7.6 [B] |
| 1-031 | 1 | (3S)-1-acetyl-3-(methylamino)pyrrolidine | 6-Cl | H | 4-(trifluoromethoxy)phenyl | 577(M+ + 1) [ESI(Pos.)] | 13.5 [E] |
| 1-032 | 1 | (3S)-1-acetyl-3-(methylamino)pyrrolidine | 6-OMe | H | 4-(trifluoromethoxy)phenyl | 573(M+ + 1) [ESI(Pos.)] | 12.2 [E] |
| 1-033 | 1 | (3S)-3-(methylamino)-1-(methylsulfonyl)pyrrolidine | H | H | biphenyl-2-yl | 571(M+ + 1) [ESI(Pos.)] | 5.9 [C] |
| 1-034 | 1 | (3S)-3-(methylamino)-1-(methylsulfonyl)pyrrolidine | H | H | 4'-(trifluoromethoxy)biphenyl-2-yl | 655(M+ + 1) [ESI(Pos.)] | 7.9 [B] |
| 1-035 | 1 | (3S)-3-(methylamino)-1-(methylsulfonyl)pyrrolidine | H | H | 3,4-dichlorophenyl | 563(M+ + 1) [ESI(Pos.)] | 10.6 [E] |

TABLE 1-continued
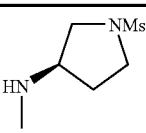
| Compound No. | Example No. | R¹ᵃ | X¹ | X² | —Ar | MS*¹ [Ionization method] | Retention time (min) [Mobile phase] |
|---|---|---|---|---|---|---|---|
| 1-036 | 1 | 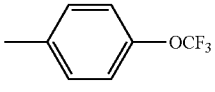 | H | H | 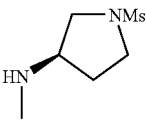 | 579(M⁺ + 1) [ESI(Pos.)] | 7.1 [C] |
| 1-037 | 1 | 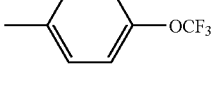 | 6-F | 7-F | 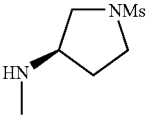 | 615(M⁺ + 1) [ESI(Pos.)] | 8.0 [C] |
| 1-038 | 1 | 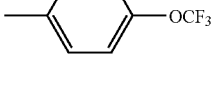 | 6-Cl | H | 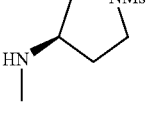 | 613(M⁺ + 1) [ESI(Pos.)] | 7.2 [C] |
| 1-039 | 1 | 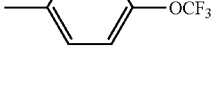 | 6-Me | H | 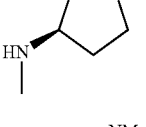 | 593(M⁺ + 1) [ESI(Pos.)] | 8.8 [C] |
| 1-040 | 1 | 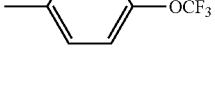 | 6-OMe | H | 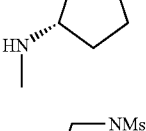 | 609(M⁺ + 1) [ESI(Pos.)] | 7.0 [C] |
| 1-041 | 1 | 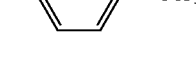 | H | H | 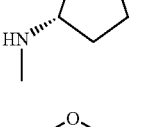 | 579(M⁺ + 1) [ESI(Pos.)] | 5.8 [C] |
| 1-042 | 1 | 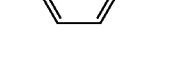 | 6-Me | H | 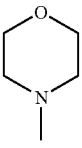 | 593(M⁺ + 1) [ESI(Pos.)] | 6.6 [B] |
| 1-043*²,⁴ | 1 | 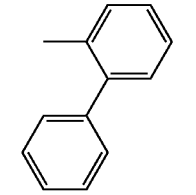 | H | H | 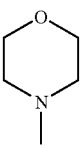 | 516(M⁺ + Na) [ESI(Pos.)] | 7.4 [R] |
| 1-044 | 1 | 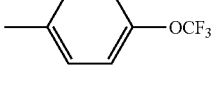 | 6-F | H |  | 520(M⁺ + 1) [ESI(Pos.)] | 5.2 [C] |

TABLE 1-continued

| Compound No. | Example No. | R1a | X1 | X2 | —Ar | MS*1 [Ionization method] | Retention time (min) [Mobile phase] |
|---|---|---|---|---|---|---|---|
| 1-045*2 | 1 | morpholine | 7-F | H | C6H4-OCF3 | 520(M+ + 1) [ESI(Pos.)] | 7.2 [C] |
| 1-046 | 1 | morpholine | 6-F | 7-F | C6H4-OCF3 | 538(M+ + 1) [ESI(Pos.)] | 8.8 [C] |
| 1-047 | 1 | morpholine | 6-Cl | H | C6H4-OCF3 | 536(M+ + 1) [ESI(Pos.)] | 7.7 [B] |
| 1-048 | 1 | morpholine | 5-Me | H | C6H4-OCF3 | 516(M+ + 1) [ESI(Pos.)] | 6.8 [C] |
| 1-049 | 1 | morpholine | 6-Me | H | C6H4-OCF3 | 516(M+ + 1) [ESI(Pos.)] | 7.3 [C] |
| 1-050 | 1 | morpholine | 7-Me | H | C6H4-OCF3 | 516(M+ + 1) [ESI(Pos.)] | 6.9 [C] |
| 1-051 | 1 | morpholine | 6-OMe | H | C6H4-OCF3 | 532(M+ + 1) [ESI(Pos.)] | 9.9 [C] |
| 1-052 | 1 | morpholine | 6-OMe | 7-OMe | C6H4-OCF3 | 562(M+ + 1) [ESI(Pos.)] | 8.1 [C] |

TABLE 1-continued

| Compound No. | Example No. | R1a | X1 | X2 | —Ar | MS*1 [Ionization method] | Retention time (min) [Mobile phase] |
|---|---|---|---|---|---|---|---|
| 1-053 | 1 | morpholine (N-linked) | 7-CF3 | H | 4-OCF3-phenyl | 570(M+ + 1) [ESI(Pos.)] | 15.3 [C] |
| 1-054 | 1 | 2,6-dimethylmorpholine (N-linked) | H | H | 2-biphenyl | 522(M+ + 1) [ESI(Pos.)] | 5.4 [B] |
| 1-055*2,4 | 1 | pyrrolidine (N-linked) | H | H | 2-biphenyl | 478(M+ + 1) [ESI(Pos.)] | 5.5 [Q] |
| 1-056*2,4 | 1 | piperidine (N-linked) | H | H | 2-biphenyl | 492(M+ + 1) [ESI(Pos.)] | 12.8 [Q] |
| 1-057*2,5 | 1 | 3,5-dimethylpiperidine (N-linked) | H | H | 2-biphenyl | 520(M+ + 1) [ESI(Pos.)] | |
| 1-058*2 | 1 | 2,6-dimethylpiperidine (N-linked) | H | H | 2-biphenyl | 520(M+ + 1) [ESI(Pos.)] | |

TABLE 1-continued

| Compound No. | Example No. | R^1a | X^1 | X^2 | —Ar | MS[*1] [Ionization method] | Retention time (min) [Mobile phase] |
|---|---|---|---|---|---|---|---|
| 1-059 | 1 | CF$_3$, 1-methylpiperidin-4-yl | H | H | 4-(OCF$_3$)phenyl-methyl | 568(M$^+$ + 1) [ESI(Pos.)] | 6.0 [A] |
| 1-060[*2] | 1 | Ph, 1-methylpiperidin-4-yl | H | H | 2-biphenyl-methyl | 568(M$^+$ + 1) [ESI(Pos.)] | |
| 1-061 | 38 | CO$_2$H, 1-methylpiperidin-4-yl | H | H | 2-biphenyl-methyl | 536(M$^+$ + 1) [ESI(Pos.)] | |
| 1-062 | 1 | CO$_2$Et, 1-methylpiperidin-4-yl | H | H | 2-biphenyl-methyl | 564(M$^+$ + 1) [ESI(Pos.)] | |
| 1-063 | 38 | CONH$_2$, 1-methylpiperidin-4-yl | H | H | 2-biphenyl-methyl | 535(M$^+$ + 1) [ESI(Pos.)] | 5.7 [L] |
| 1-064 | 11 | CONH$_2$, 1-methylpiperidin-4-yl | 7-Cl | H | 2-methyl-4'-(OCF$_3$)biphenyl | 653(M$^+$ + 1) [ESI(Pos.)] | |

TABLE 1-continued

| Compound No. | Example No. | R1a | X1 | X2 | —Ar | MS*1 [Ionization method] | Retention time (min) [Mobile phase] |
|---|---|---|---|---|---|---|---|
| 1-065 | 1 | CONMe2, 1-methylpiperidin-4-yl | H | H | 4-OCF3-phenyl | 571(M+ + 1) [ESI(Pos.)] | 6.0 [C] |
| 1-066 | 1 | CONMe2, 1-methylpiperidin-4-yl | 6-F | H | 4-OCF3-phenyl | 589(M+ + 1) [ESI(Pos.)] | 5.3 [C] |
| 1-067*2 | 1 | CONMe2, 1-methylpiperidin-4-yl | 7-F | H | 4-OCF3-phenyl | 589(M+ + 1) [ESI(Pos.)] | 7.5 [C] |
| 1-068 | 1 | CONMe2, 1-methylpiperidin-4-yl | 6-Cl | H | 4-OCF3-phenyl | 605(M+ + 1) [ESI(Pos.)] | 11.8 [C] |
| 1-069 | 1 | CONMe2, 1-methylpiperidin-4-yl | 6-Me | H | 4-OCF3-phenyl | 585(M+ + 1) [ESI(Pos.)] | 10.3 [C] |
| 1-070 | 1 | CONMe2, 1-methylpiperidin-4-yl | 6-OMe | H | 4-OCF3-phenyl | 601(M+ + 1) [ESI(Pos.)] | 8.5 [C] |

TABLE 1-continued

| Compound No. | Example No. | R¹ᵃ | X¹ | X² | —Ar | MS*¹ [Ionization method] | Retention time (min) [Mobile phase] |
|---|---|---|---|---|---|---|---|
| 1-071 | 1 | pyrrolidine-carbonyl-(1-methylpiperidin-4-yl) | 6-OMe | H | 4-OCF₃-phenyl | 627(M⁺ + 1) [ESI(Pos.)] | 13.0 [C] |
| 1-072 | 1 | morpholine-carbonyl-(1-methylpiperidin-4-yl) | 6-OMe | H | 4-OCF₃-phenyl | 643(M⁺ + 1) [ESI(Pos.)] | 7.2 [C] |
| 1-073 | 1 | (4-fluorophenyl)carbonyl-(1-methylpiperidin-4-yl) | H | H | 2-biphenyl | 614(M⁺ + 1) [ESI(Pos.)] | 12.7 [J] |
| 1-074*³,⁴ | 3 | 4-amino-(1-methylpiperidin-4-yl) | H | H | 2-biphenyl | 507(M⁺ + 1) [ESI(Pos.)] | 5.5 [F] |
| 1-075 | 1 | 4-Ms-(1-methylpiperidin-4-yl) | H | H | 4-OCF₃-phenyl | 578(M⁺ + 1) [ESI(Pos.)] | 8.1 [C] |

TABLE 1-continued

| Compound No. | Example No. | R¹ᵃ | X¹ | X² | —Ar | MS*¹ [Ionization method] | Retention time (min) [Mobile phase] |
|---|---|---|---|---|---|---|---|
| 1-076 | 1 | Ms-piperidine-N-Me | 6-Cl | H | phenyl-OCF₃ | 612(M⁺ + 1) [ESI(Pos.)] | 6.9 [C] |
| 1-077 | 1 | Ms-piperidine-N-Me | 6-Me | H | phenyl-OCF₃ | 592(M⁺ + 1) [ESI(Pos.)] | 21.0 [E] |
| 1-078 | 1 | Ms-piperidine-N-Me | 6-OMe | H | phenyl-OCF₃ | 608(M⁺ + 1) [ESI(Pos.)] | 6.2 [C] |
| 1-079*² | 1 | HO-piperidine-N-Me | H | H | biphenyl | 508(M⁺ + 1) [ESI(Pos.)] | 10.1 [E] |
| 1-080 | 1 | MeO-piperidine-N-Me | H | H | phenyl-OCF₃ | 530(M⁺ + 1) [ESI(Pos.)] | 13.3 [C] |
| 1-081*² | 1 | 4-F-phenyl-O-piperidine-N-Me | H | H | biphenyl | 602(M⁺ + 1) [ESI(Pos.)] | |

TABLE 1-continued

| Compound No. | Example No. | R[1a] | X[1] | X[2] | —Ar | MS*[1] [Ionization method] | Retention time (min) [Mobile phase] |
|---|---|---|---|---|---|---|---|
| 1-082 | 1 | MeO-CH2-(1-methylpiperidin-4-yl) | H | H | 4-OCF3-phenyl | 544(M+ + 1) [ESI(Pos.)] | 12.7 [B] |
| 1-083*[2] | 1 | CN-(1-methylpiperidin-4-yl) | H | H | 2-biphenyl | 517(M+ + 1) [ESI(Pos.)] | 5.3 [J] |
| 1-084 | 1 | CN-(1-methylpiperidin-4-yl) | H | H | 4-OCF3-phenyl | 525(M+ + 1) [ESI(Pos.)] | 6.7 [C] |
| 1-085 | 1 | MsHN-CH2-(1-methylpiperidin-4-yl) | H | H | 4-OCF3-phenyl | 607(M+ + 1) [ESI(Pos.)] | 9.3 [C] |
| 1-086*[4] | 4 | NHAc-(1-methylpiperidin-4-yl) | H | H | 2-biphenyl | 549(M+ + 1) [ESI(Pos.)] | 3.7 [J] |
| 1-087 | 1 | NHAc-(1-methylpiperidin-4-yl) | H | H | 4-OCF3-phenyl | 557(M+ + 1) [ESI(Pos.)] | 10.2 [E] |

TABLE 1-continued

| Compound No. | Example No. | R[1a] | X[1] | X[2] | —Ar | MS*[1] [Ionization method] | Retention time (min) [Mobile phase] |
|---|---|---|---|---|---|---|---|
| 1-088 | 1 | 4-(NHMs)-1-methylpiperidine | H | H | 4-(OCF₃)phenyl | 593(M⁺ + 1) [ESI(Pos.)] | 5.6 [C] |
| 1-089 | 1 | 4-((4-fluorophenyl)amino)-1-methylpiperidine | H | H | 2-biphenyl | 601(M⁺ + 1) [ESI(Pos.)] | 12.1 [J] |
| 1-090 | 1 | 4-morpholino-1-methylpiperidine | H | H | 4-(OCF₃)phenyl | 585(M⁺ + 1) [ESI(Pos.)] | 7.9 [F] |
| 1-091 | 1 | 4-morpholino-1-methylpiperidine | 6-F | H | 4-(OCF₃)phenyl | 603(M⁺ + 1) [ESI(Pos.)] | 8.3 [F] |
| 1-092 | 1 | 4-morpholino-1-methylpiperidine | 7-F | H | 4-(OCF₃)phenyl | 603(M⁺ + 1) [ESI(Pos.)] | 8.6 [F] |

TABLE 1-continued
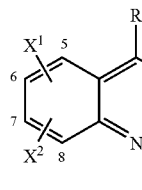
| Compound No. | Example No. | R1a | X1 | X2 | —Ar | MS*1 [Ionization method] | Retention time (min) [Mobile phase] |
|---|---|---|---|---|---|---|---|
| 1-093 | 1 | 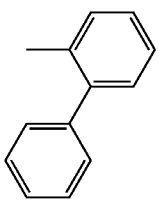 | H | H | 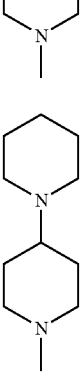 | 561(M+ + 1) [ESI(Pos.)] | 7.3 [J] |
| 1-094 | 1 | 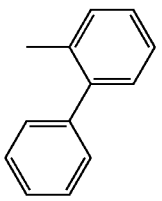 | H | H | 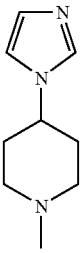 | 575(M+ + 1) [ESI(Pos.)] | 7.6 [J] |
| 1-095 | 1 | 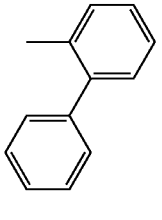 | H | H | 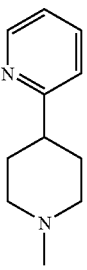 | 558(M+ + 1) [ESI(Pos.)] | 6.1 [J] |
| 1-096 | 1 | 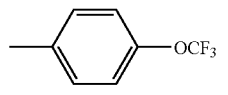 | H | H | 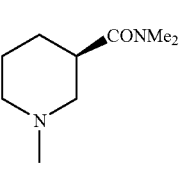 | 577(M+ + 1) [ESI(Pos.)] | 6.7 [E] |
| 1-097 | 1 | 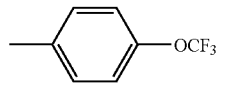 | H | H | 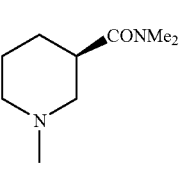 | 571(M+ + 1) [ESI(Pos.)] | 6.0 [C] |

TABLE 1-continued

| Compound No. | Example No. | R¹ᵃ | X¹ | X² | —Ar | MS*¹ [Ionization method] | Retention time (min) [Mobile phase] |
|---|---|---|---|---|---|---|---|
| 1-098 | 1 | (3-CONMe₂, N-methyl piperidine) | 6-Me | H | 4-OCF₃-phenyl | 585(M⁺ + 1) [ESI(Pos.)] | 12.9 [C] |
| 1-099 | 1 | (3-CONMe₂, N-methyl piperidine) | H | H | 4-OCF₃-phenyl | 571(M⁺ + 1) [ESI(Pos.)] | 5.8 [C] |
| 1-100 | 1 | (2-pyridyl)-N-methyl tetrahydropyridine | H | H | 4-OCF₃-phenyl | 575(M⁺ + 1) [ESI(Pos.)] | 4.3 [C] |
| 1-101 | 1 | N-methyl tetrahydroisoquinoline | 7-F | H | 2-biphenyl | 558(M⁺ + 1) [ESI(Pos.)] | 6.2 [I] |
| 1-102*³ | 3 | 4-methyl piperazine | H | H | 2-biphenyl | 493(M⁺ + 1) [ESI(Pos.)] | 3.5 [F] |
| 1-103*³ | 6 | 4-methyl piperazine | H | H | 2-(4-methylphenyl)phenyl | 507(M⁺ + 1) [ESI(Pos.)] | 7.5 [J] |

TABLE 1-continued

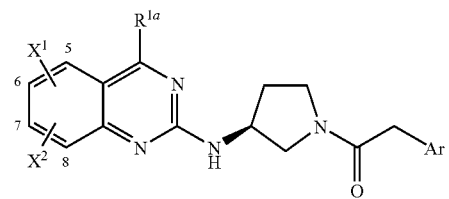

| Compound No. | Example No. | $R^{1a}$ | $X^1$ | $X^2$ | —Ar | MS*1 [Ionization method] | Retention time (min) [Mobile phase] |
|---|---|---|---|---|---|---|---|
| 1-104*3 | 6 | 4-methylpiperazin-1-yl (NH) | H | H | 4'-fluoro-2-methylbiphenyl | 511(M+ + 1) [ESI(Pos.)] | 6.3 [J] |
| 1-105*3 | 6 | 4-methylpiperazin-1-yl (NH) | H | H | 4'-methoxy-2-methylbiphenyl | 523(M+ + 1) [ESI(Pos.)] | 5.9 [J] |
| 1-106*3 | 6 | 4-methylpiperazin-1-yl (NH) | H | H | 4'-trifluoromethoxy-2-methylbiphenyl | 577(M+ + 1) [ESI(Pos.)] | 10.3 [J] |
| 1-107*3 | 6 | 4-methylpiperazin-1-yl (NH) | H | H | 3'-fluoro-2-methylbiphenyl | 511(M+ + 1) [ESI(Pos.)] | 6.3 [J] |
| 1-108*3 | 6 | 4-methylpiperazin-1-yl (NH) | H | H | 3'-nitro-2-methylbiphenyl | 538(M+ + 1) [ESI(Pos.)] | 6.1 [J] |

TABLE 1-continued

| Compound No. | Example No. | R^{1a} | X^1 | X^2 | —Ar | MS*^1 [Ionization method] | Retention time (min) [Mobile phase] |
|---|---|---|---|---|---|---|---|
| 1-109*^3 | 6 | 1-methylpiperazin-4-yl (NH) | H | H | 2'-fluoro-2-methyl-biphenyl | 511(M+ + 1) [ESI(Pos.)] | 5.7 [J] |
| 1-110*^3 | 6 | 1-methylpiperazin-4-yl (NH) | H | H | 3',4'-difluoro-2-methyl-biphenyl | 529(M+ + 1) [ESI(Pos.)] | 7.1 [J] |
| 1-111*^3 | 6 | 1-methylpiperazin-4-yl (NH) | H | H | 3'-chloro-4'-fluoro-2-methyl-biphenyl | 545(M+ + 1) [ESI(Pos.)] | 8.4 [J] |
| 1-112*^3 | 6 | 1-methylpiperazin-4-yl (NH) | H | H | 4'-trifluoromethyl-2-methyl-biphenyl | 561(M+ + 1) [ESI(Pos.)] | 9.5 [J] |
| 1-113 | 35 | 1-methylpiperazin-4-yl (NH) | H | H | 4-methylphenyl | 417(M+ + 1) [ESI(Pos.)] | 5.4 [K] |
| 1-114*^3 | 5 | 1-methylpiperazin-4-yl (NH) | H | H | 4-chloro-methylphenyl | 451(M+ + 1) [ESI(Pos.)] | 6.6 [K] |

TABLE 1-continued

| Compound No. | Example No. | R¹ᵃ | X¹ | X² | —Ar | MS*¹ [Ionization method] | Retention time (min) [Mobile phase] |
|---|---|---|---|---|---|---|---|
| 1-115 | 35 | N-methylpiperazinyl (NH) | H | H | 4-OMe-phenyl | 447(M⁺ + 1) [ESI(Pos.)] | 5.3 [K] |
| 1-116*³ | 3 | N-methylpiperazinyl (NH) | H | H | 4-OCF₃-phenyl | 501(M⁺ + 1) [ESI(Pos.)] | |
| 1-117 | 35 | N-methylpiperazinyl (NH) | H | H | 2-Br-phenyl | 495(M⁺ + 1) [ESI(Pos.)] | 6.8 [K] |
| 1-118*³ | 3 | N-methylpiperazinyl (NH) | 6-F | H | 2-biphenyl | 511(M⁺ + 1) [ESI(Pos.)] | 6.3 [J] |
| 1-119*³ | 3 | N-methylpiperazinyl (NH) | 7-F | H | 2-biphenyl | 511(M⁺ + 1) [ESI(Pos.)] | 5.2 [F] |
| 1-120*³,⁴ | 3 | N-methylpiperazinyl (NH) | 6-F | 7-F | 2-biphenyl | 529(M⁺ + 1) [ESI(Pos.)] | 4.7 [J] |

TABLE 1-continued

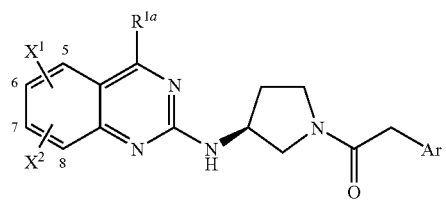

| Compound No. | Example No. | R<sup>1a</sup> | X<sup>1</sup> | X<sup>2</sup> | —Ar | MS*1 [Ionization method] | Retention time (min) [Mobile phase] |
|---|---|---|---|---|---|---|---|
| 1-121*3 | 3 | 1-methylpiperazinyl (NH linker) | 7-Cl | H | 2-biphenyl | 527(M+ + 1) [ESI(Pos.)] | 7.1 [F] |
| 1-122*3 | 3 | 1-methylpiperazinyl (NH linker) | 7-Me | H | 2-biphenyl | 507(M+ + 1) [ESI(Pos.)] | 7.1 [F] |
| 1-123*3 | 3 | 1-methylpiperazinyl (NH linker) | 7-CF$_3$ | H | 2-biphenyl | 561(M+ + 1) [ESI(Pos.)] | |
| 1-124*3 | 3 | 1-methylpiperazinyl (NH linker) | 6-OMe | 7-OMe | 2-biphenyl | 553(M+ + 1) [ESI(Pos.)] | 4.9 [F] |
| 1-125 | 1 | 4-Boc-1-methylpiperazinyl | H | H | 2-biphenyl | 593(M+ + 1) [ESI(Pos.)] | |
| 1-126*3,5 | 1 | 2-Me-4-methylpiperazinyl (NH) | H | H | 2-biphenyl | 507(M+ + 1) [ESI(Pos.)] | 4.4 10.5 [J] |

TABLE 1-continued

| Compound No. | Example No. | R¹ᵃ | X¹ | X² | —Ar | MS*¹ [Ionization method] | Retention time (min) [Mobile phase] |
|---|---|---|---|---|---|---|---|
| 1-127*³,⁵ | 1 | 2,6-dimethyl-4-methylpiperazinyl | H | H | 2-methylbiphenyl | 521(M⁺ + 1) [ESI(Pos.)] | 4.0 [F] |
| 1-128 | 1 | 4-methyl-3-oxopiperazinyl | H | H | 2-methylbiphenyl | 507(M⁺ + 1) [ESI(Pos.)] | 4.4 [L] |
| 1-129 | 6 | 4-methyl-3-oxopiperazinyl | H | H | 2-methyl-4'-(trifluoromethoxy)biphenyl | 613(M⁺ + Na) [ESI(Pos.)] | 7.4 [K] |
| 1-130 | 1 | 4-methyl-3-oxopiperazinyl | H | H | 2-bromo-6-methylphenyl | 509(M⁺ + 1) [ESI(Pos.)] | 4.4 [L] |
| 1-131 | 1 | 4-methyl-3-oxopiperazinyl | 7-F | H | 2-methylbiphenyl | 547(M⁺ + Na) [ESI(Pos.)] | 4.8 [K] |
| 1-132 | 1, 6 | 4-methyl-3-oxopiperazinyl | 7-F | H | 2-methyl-4'-(trifluoromethoxy)biphenyl | 631(M⁺ + Na) [ESI(Pos.)] | 8.4 [K] |

TABLE 1-continued
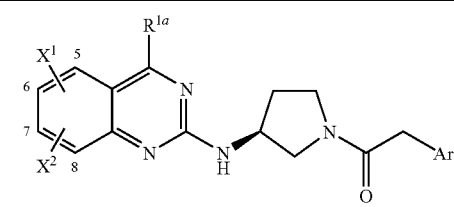
| Compound No. | Example No. | $R^{1a}$ | $X^1$ | $X^2$ | —Ar | MS*1 [Ionization method] | Retention time (min) [Mobile phase] |
|---|---|---|---|---|---|---|---|
| 1-133 | 6 | 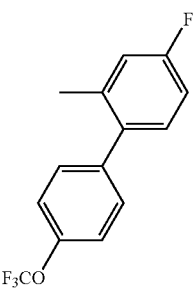 | 7-F | H | 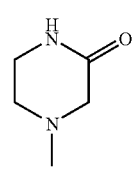 | 627(M+ + 1) [ESI(Pos.)] | |
| 1-134 | 6 | 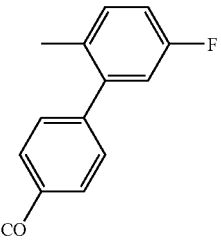 | 7-F | H | 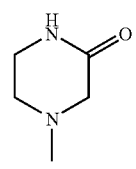 | 627(M+ + 1) [ESI(Pos.)] | |
| 1-135 | 6 | 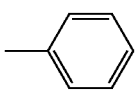 | 7-F | H | 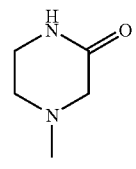 | 449(M+ + 1) [ESI(Pos.)] | 5.1 [M] |
| 1-136 | 1 | 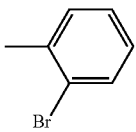 | 7-F | H | 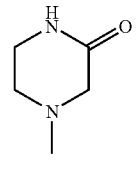 | 549(M+ + Na) [ESI(Pos.)] | 4.8 [L] |
| 1-137 | 1 | 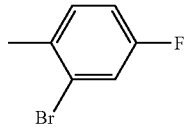 | 7-F | H | 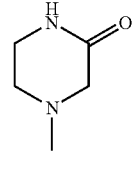 | 567(M+ + Na) [ESI(Pos.)] | 5.5 [L] |
| 1-138 | 1 | 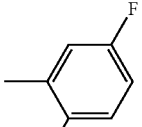 | 7-F | H | | 567(M+ + Na) [ESI(Pos.)] | 5.3 [L] |

TABLE 1-continued

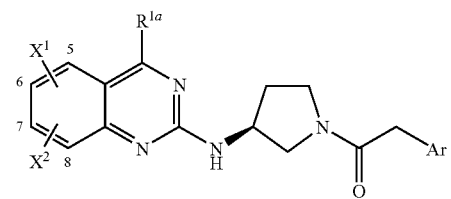

| Compound No. | Example No. | R1a | X1 | X2 | —Ar | MS*1 [Ionization method] | Retention time (min) [Mobile phase] |
|---|---|---|---|---|---|---|---|
| 1-139 | 1 | 4-methyl-piperazin-2-one | 7-F | H | 3,4-dichlorophenyl | 517(M+ + 1) [ESI(Pos.)] | 6.4 [L] |
| 1-140 | 1 | 4-methyl-piperazin-2-one | 7-F | H | 4-OCF3-phenyl | 533(M+ + 1) [ESI(Pos.)] | 6.9 [L] |
| 1-141 | 1 | 4-methyl-piperazin-2-one | 7-F | H | 4-SCF3-phenyl | 549(M+ + 1) [ESI(Pos.)] | 8.6 [L] |
| 1-142 | 1 | 4-methyl-piperazin-2-one | 7-Cl | H | 2-(4-OCF3-phenyl)phenyl | 647(M+ + Na) [ESI(Pos.)] | 6.4 [J] |
| 1-143 | 1 | 4-methyl-piperazin-2-one | 7-CF3 | H | 2-phenylphenyl | 575(M+ + 1) [ESI(Pos.)] | |
| 1-144 | 1 | 1,4-dimethyl-piperazin-2-one | 7-F | H | 2-phenylphenyl | 561(M+ + Na) [ESI(Pos.)] | 5.8 [K] |

TABLE 1-continued

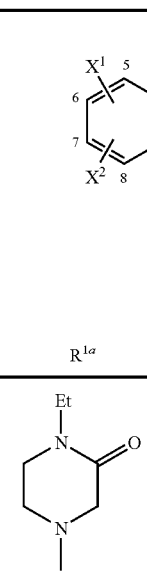

| Compound No. | Example No. | R1a | X1 | X2 | —Ar | MS*1 [Ionization method] | Retention time (min) [Mobile phase] |
|---|---|---|---|---|---|---|---|
| 1-145 | 1 | Et, N-methylpiperazinone | 7-F | H | 2-phenylphenyl | 575(M+ + Na) [ESI(Pos.)] | 6.9 [K] |
| 1-146 | 1 | iPr, N-methylpiperazinone | 7-F | H | 2-phenylphenyl | 589(M+ + Na) [ESI(Pos.)] | 8.3 [K] |
| 1-147*3,5 | 1 | 2-Ph, N-methylpiperazine | H | H | 2-phenylphenyl | 569(M+ + 1) [ESI(Pos.)] | 5.7 6.1 [J] |
| 1-148*3,4 | 1 | Me, N-methylpiperazine | H | H | 2-phenylphenyl | 529(M+ + Na) [ESI(Pos.)] | 5.5 [R] |
| 1-149*3,4 | 1 | Et, N-methylpiperazine | H | H | 2-phenylphenyl | 543(M+ + Na) [ESI(Pos.)] | 7.0 [R] |
| 1-150*3,4 | 1 | Pr, N-methylpiperazine | H | H | 2-phenylphenyl | 535(M+ + 1) [ESI(Pos.)] | 6.4 [P] |

TABLE 1-continued

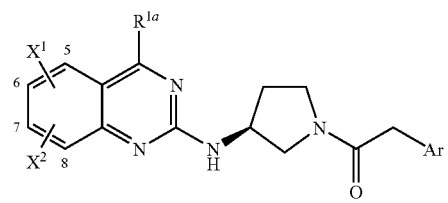

| Compound No. | Example No. | R$^{1a}$ | X$^1$ | X$^2$ | —Ar | MS*$^1$ [Ionization method] | Retention time (min) [Mobile phase] |
|---|---|---|---|---|---|---|---|
| 1-151 | 1 | tBu, N-methylpiperazinyl | H | H | 2-phenylphenyl | 549(M$^+$ + 1) [ESI(Pos.)] | 5.1 [J] |
| 1-152 | 1 | HO-ethyl-N-methylpiperazinyl | H | H | 4-OCF$_3$-phenyl | 545(M$^+$ + 1) [ESI(Pos.)] | 5.4 [F] |
| 1-153 | 1 | HO-ethyl-N-methylpiperazinyl | 6-F | H | 4-OCF$_3$-phenyl | 563(M$^+$ + 1) [ESI(Pos.)] | 5.6 [F] |
| 1-154 | 1 | HO-ethyl-N-methylpiperazinyl | 7-F | H | 4-OCF$_3$-phenyl | 563(M$^+$ + 1) [ESI(Pos.)] | 6.1 [F] |
| 1-155*$^{3,4}$ | 1 | iPr, N-methylpiperazinyl | H | H | 2-phenylphenyl | 535(M$^+$ + 1) [ESI(Pos.)] | 7.4 [J] |
| 1-156*$^4$ | 1 | iPr, N-methylpiperazinyl | H | H | 1-naphthyl | 509(M$^+$ + 1) [ESI(Pos.)] | 5.9 [J] |

TABLE 1-continued

| Compound No. | Example No. | R¹ᵃ | X¹ | X² | —Ar | MS*¹ [Ionization method] | Retention time (min) [Mobile phase] |
|---|---|---|---|---|---|---|---|
| 1-157*³,⁴ | 1 | iPr, 4-methylpiperazin-1-yl | H | H | 2-methylnaphthyl | 509(M⁺ + 1) [ESI(Pos.)] | 5.9 [J] |
| 1-158*⁴ | 1 | iPr, 4-methylpiperazin-1-yl | H | H | 4-Br-phenyl | 537(M⁺ + 1) [ESI(Pos.)] | 6.1 [J] |
| 1-159*³,⁴ | 1 | cyclopropyl, 4-methylpiperazin-1-yl | H | H | 2-biphenyl | 533(M⁺ + 1) [ESI(Pos.)] | 7.0 [P] |
| 1-160*³,⁴ | 1 | cyclopentyl, 4-methylpiperazin-1-yl | H | H | 2-biphenyl | 561(M⁺ + 1) [ESI(Pos.)] | 7.9 [P] |
| 1-161*² | 4 | Ac, 4-methylpiperazin-1-yl | H | H | 2-biphenyl | 535(M⁺ + 1) [ESI(Pos.)] | 5.2 [L] |
| 1-162 | 1 | Ac, 4-methylpiperazin-1-yl | 6-F | H | 4-OCF₃-phenyl | 561(M⁺ + 1) [ESI(Pos.)] | 14.7 [E] |

TABLE 1-continued

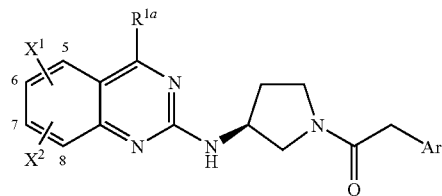

| Compound No. | Example No. | R$^{1a}$ | X$^1$ | X$^2$ | —Ar | MS*$^1$ [Ionization method] | Retention time (min) [Mobile phase] |
|---|---|---|---|---|---|---|---|
| 1-163*$^2$ | 1 | Ac-N(piperazine)-N-Me | 7-F | H | -C$_6$H$_4$-OCF$_3$ | 561(M$^+$ + 1) [ESI(Pos.)] | 4.4 [C] |
| 1-164 | 1 | Ac-N(piperazine)-N-Me | 6-Cl | H | -C$_6$H$_4$-OCF$_3$ | 577(M$^+$ + 1) [ESI(Pos.)] | 17.8 [E] |
| 1-165 | 1 | Ac-N(piperazine)-N-Me | 6-Me | H | -C$_6$H$_4$-OCF$_3$ | 557(M$^+$ + 1) [ESI(Pos.)] | 8.3 [C] |
| 1-166 | 1 | Ac-N(piperazine)-N-Me | 7-Me | H | -C$_6$H$_4$-OCF$_3$ | 557(M$^+$ + 1) [ESI(Pos.)] | 5.7 [C] |
| 1-167 | 1 | Ac-N(piperazine)-N-Me | 6-OMe | H | -C$_6$H$_4$-OCF$_3$ | 573(M$^+$ + 1) [ESI(Pos.)] | 12.5 [E] |
| 1-168 | 1 | COEt-N(piperazine)-N-Me | H | H | 2-biphenyl | 549(M$^+$ + 1) [ESI(Pos.)] | 6.0 [K] |
| 1-169 | 1 | COPr-N(piperazine)-N-Me | H | H | 2-biphenyl | 563(M$^+$ + 1) [ESI(Pos.)] | 7.4 [K] |

TABLE 1-continued
| Compound No. | Example No. | R<sup>1a</sup> | X<sup>1</sup> | X<sup>2</sup> | —Ar | MS*1 [Ionization method] | Retention time (min) [Mobile phase] |
|---|---|---|---|---|---|---|---|
| 1-170 | 1 | 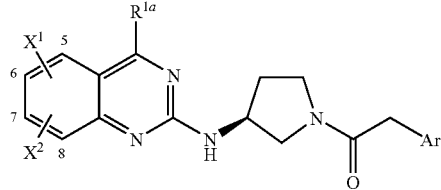 | H | H | 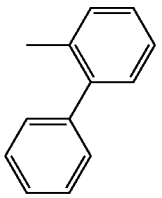 | 577(M⁺ + 1) [ESI(Pos.)] | 9.2 [K] |
| 1-171 | 1 | 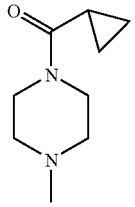 | H | H | 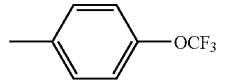 | 569(M⁺ + 1) [ESI(Pos.)] | 7.1 [C] |
| 1-172 | 1 | 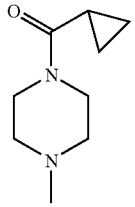 | 6-OMe | H | 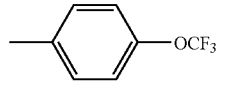 | 599(M⁺ + 1) [ESI(Pos.)] | 9.1 [C] |
| 1-173 | 1 | 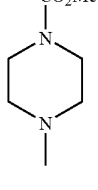 | H | H | 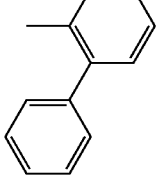 | 551(M⁺ + 1) [ESI(Pos.)] | 7.2 [K] |
| 1-174 | 1 | 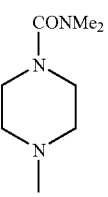 | H | H | 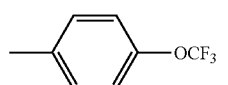 | 572(M⁺ + 1) [ESI(Pos.)] | 18.5 [E] |

TABLE 1-continued

| Compound No. | Example No. | R1a | X1 | X2 | —Ar | MS*1 [Ionization method] | Retention time (min) [Mobile phase] |
|---|---|---|---|---|---|---|---|
| 1-175 | 1 | 4-methylpiperazine-N-C(O)-morpholine | 6-OMe | H | 4-OCF3-phenyl | 644(M+ + 1) [ESI(Pos.)] | 7.1 [C] |
| 1-176 | 1 | 4-methylpiperazine-N-C(O)-(3-pyridyl) | 6-OMe | H | 4-OCF3-phenyl | 636(M+ + 1) [ESI(Pos.)] | 10.1 [E] |
| 1-177 | 1 | 4-methyl-1-Ms-piperazine | H | H | 4-OCF3-phenyl | 579(M+ + 1) [ESI(Pos.)] | 6.1 [C] |
| 1-178 | 1 | 4-methyl-1-Ms-piperazine | 6-F | H | 4-OCF3-phenyl | 597(M+ + 1) [ESI(Pos.)] | 13.5 [C] |
| 1-179 | 1 | 4-methyl-1-Ms-piperazine | 7-F | H | 4-OCF3-phenyl | 597(M+ + 1) [ESI(Pos.)] | 6.6 [C] |
| 1-180 | 1 | 4-methyl-1-Ms-piperazine | 6-Cl | H | 4-OCF3-phenyl | 613(M+ + 1) [ESI(Pos.)] | 12.0 [C] |

TABLE 1-continued

| Compound No. | Example No. | R1a | X1 | X2 | —Ar | MS*1 [Ionization method] | Retention time (min) [Mobile phase] |
|---|---|---|---|---|---|---|---|
| 1-181 | 1 | Ms-piperazine-N-Me | 6-Me | H | C6H4-OCF3 | 593(M+ + 1) [ESI(Pos.)] | 7.4 [B] |
| 1-182 | 1 | Ms-piperazine-N-Me | 6-OMe | H | C6H4-OCF3 | 609(M+ + 1) [ESI(Pos.)] | 9.4 [C] |
| 1-183 | 1 | SO2Et-piperazine-N-Me | H | H | C6H4-OCF3 | 593(M+ + 1) [ESI(Pos.)] | 9.8 [C] |
| 1-184 | 1 | SO2CF3-piperazine-N-Me | H | H | C6H4-OCF3 | 633(M+ + 1) [ESI(Pos.)] | 6.4 [A] |
| 1-185*3 | 1 | Ph-piperazine-N-Me | H | H | biphenyl | 569(M+ + 1) [ESI(Pos.)] | 9.7 [J] |
| 1-186 | 1 | 2-pyridyl-piperazine-N-Me | H | H | C6H4-OCF3 | 578(M+ + 1) [ESI(Pos.)] | 5.5 [E] |

TABLE 1-continued

| Compound No. | Example No. | R1a | X1 | X2 | —Ar | MS*1 [Ionization method] | Retention time (min) [Mobile phase] |
|---|---|---|---|---|---|---|---|
| 1-187 | 1 | 4-(pyridin-2-yl)-1-methylpiperazine | 6-F | H | 4-OCF3-phenyl | 596(M+ + 1) [ESI(Pos.)] | 5.8 [E] |
| 1-188 | 1 | 4-(pyridin-2-yl)-1-methylpiperazine | 7-F | H | 4-OCF3-phenyl | 596(M+ + 1) [ESI(Pos.)] | 5.8 [E] |
| 1-189 | 1 | 1-methylpyrrolidin-2-yl-CONMe2 | H | H | 4-OCF3-phenyl | 557(M+ + 1) [ESI(Pos.)] | 4.7 [C] |
| 1-190 | 1 | 1-methylpyrrolidin-2-yl-CONMe2 | H | H | 4-OCF3-phenyl | 557(M+ + 1) [ESI(Pos.)] | 4.2 [C] |
| 1-191 | 1 | 1-methylpyrrolidin-2-yl-CONMe2 | 6-Me | H | 4-OCF3-phenyl | 571(M+ + 1) [ESI(Pos.)] | 6.1 [B] |
| 1-192*3,5 | 3 | 3-amino-1-methylpyrrolidine | H | H | 2-biphenyl | 493(M+ + 1) [ESI(Pos.)] | |

TABLE 1-continued

| Compound No. | Example No. | R$^{1a}$ | X$^1$ | X$^2$ | —Ar | MS*$^1$ [Ionization method] | Retention time (min) [Mobile phase] |
|---|---|---|---|---|---|---|---|
| 1-193*$^{3,5}$ | 3 | NH$_2$, N-methylpyrrolidin-3-yl | H | H | 4-OCF$_3$-phenyl | 501(M$^+$ + 1) [ESI(Pos.)] | |
| 1-194*$^3$ | 3 | NH$_2$, (N-methylpyrrolidin-3-yl) | H | H | 2-biphenyl | 493(M$^+$ + 1) [ESI(Pos.)] | 3.6 [F] |
| 1-195*$^3$ | 3 | NH$_2$, (N-methylpyrrolidin-3-yl) | H | H | 2-biphenyl | 493(M$^+$ + 1) [ESI(Pos.)] | 3.9 [F] |
| 1-196 | 1 | NHAc, (N-methylpyrrolidin-3-yl) | H | H | 4-OCF$_3$-phenyl | 543(M$^+$ + 1) [ESI(Pos.)] | 9.5 [E] |
| 1-197 | 1 | NHAc, (N-methylpyrrolidin-3-yl) | H | H | 4-OCF$_3$-phenyl | 543(M$^+$ + 1) [ESI(Pos.)] | 13.0 [E] |
| 1-198 | 1 | NHMs, (N-methylpyrrolidin-3-yl) | H | H | 4-OCF$_3$-phenyl | 579(M$^+$ + 1) [ESI(Pos.)] | 13.8 [E] |
| 1-199 | 1 | NHMs, (N-methylpyrrolidin-3-yl) | H | H | 4-OCF$_3$-phenyl | 579(M$^+$ + 1) [ESI(Pos.)] | 5.1 [C] |

TABLE 1-continued
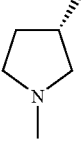
| Compound No. | Example No. | R[1a] | X[1] | X[2] | —Ar | MS[*1] [Ionization method] | Retention time (min) [Mobile phase] |
|---|---|---|---|---|---|---|---|
| 1-200 | 1 | 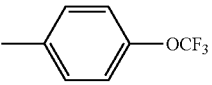 | H | H | 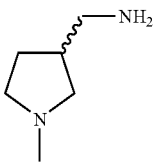 | 557($M^+$ + 1) [ESI(Pos.)] | 7.7 [C] |
| 1-201*[3,5] | 3 | 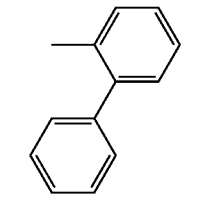 | H | H | 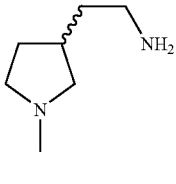 | 507($M^+$ + 1) [ESI(Pos.)] | 5.7 [F] |
| 1-202*[3,5] | 3 | 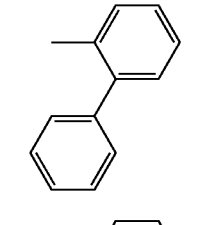 | H | H | 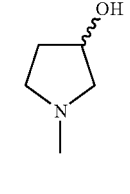 | 521($M^+$ + 1) [ESI(Pos.)] | 5.7 [F] |
| 1-203*[5] | 1 | 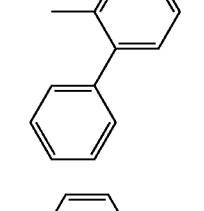 | H | H | 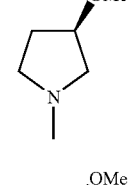 | 494($M^+$ + 1) [ESI(Pos.)] | 4.0 [J] |
| 1-204 | 1 | 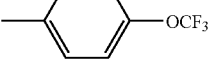 | H | H | 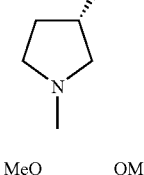 | 516($M^+$ + 1) [ESI(Pos.)] | 10.8 [C] |
| 1-205 | 1 | 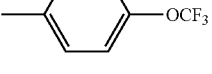 | H | H | 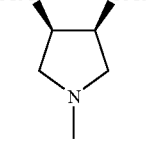 | 516($M^+$ + 1) [ESI(Pos.)] | 11.2 [C] |
| 1-206 | 1 | 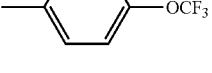 | H | H |  | 546($M^+$ + 1) [ESI(Pos.)] | 5.9 [B] |

TABLE 1-continued

| Compound No. | Example No. | R1a | X1 | X2 | —Ar | MS*1 [Ionization method] | Retention time (min) [Mobile phase] |
|---|---|---|---|---|---|---|---|
| 1-207 | 1 | (3,4-dimethoxy-1-methylpyrrolidinyl) | 6-Me | H | 4-OCF3-phenyl | 560(M+ + 1) [ESI(Pos.)] | 8.3 [B] |
| 1-208 | 1 | (3,4-dimethoxy-1-methylpyrrolidinyl) | 6-OMe | H | 4-OCF3-phenyl | 576(M+ + 1) [ESI(Pos.)] | 10.7 [C] |
| 1-209 | 1 | (1-methylimidazol-yl) | H | H | 2-biphenyl | 497(M+ + Na) [ESI(Pos.)] |  |
| 1-210*3 | 3 | (4-NH-1-methyl-1,4-diazepan-yl) | H | H | 2-biphenyl | 507(M+ + 1) [ESI(Pos.)] | 4.1 [F] |
| 1-211 | 2 | (4-Me-1-methyl-1,4-diazepan-yl) | H | H | 4-OCF3-phenyl | 529(M+ + 1) [ESI(Pos.)] | 6.6 [F] |
| 1-212*2 | 4 | (4-NAc-1-methyl-1,4-diazepan-yl) | H | H | 2-biphenyl | 549(M+ + 1) [ESI(Pos.)] | 3.9 [J] |

TABLE 1-continued

Structure: quinazoline with X¹ at position 5, position 6, position 7, X² at position 8, R¹ᵃ at position 4, and at position 2 an NH linked to a (3S)-pyrrolidinyl group whose N bears a —C(=O)—CH₂—Ar acyl group.

| Compound No. | Example No. | R¹ᵃ | X¹ | X² | —Ar | MS*¹ [Ionization method] | Retention time (min) [Mobile phase] |
|---|---|---|---|---|---|---|---|
| 1-213 | 1 | 1,4-diazepan-1-yl with NAc | H | H | 4-OCF₃-phenyl | 557(M⁺ + 1) [ESI(Pos.)] | 5.2 [C] |
| 1-214 | 1 | 1,4-diazepan-1-yl with NMs | H | H | 4-OCF₃-phenyl | 593(M⁺ + 1) [ESI(Pos.)] | 5.7 [C] |
| 1-215 | 1 | 1,4-diazepan-1-yl with SO₂CF₃ | H | H | 4-OCF₃-phenyl | 647(M⁺ + 1) [ESI(Pos.)] | 5.4 [A] |
| 1-216 | 1 | Me | 6-OMe | H | 4-OCF₃-phenyl | 461(M⁺ + 1) [ESI(Pos.)] | 5.4 [B] |
| 1-217 | 37 | OMe | H | H | 4-OCF₃-phenyl | 447(M⁺ + 1) [ESI(Pos.)] | |
| 1-218 | 1 | OMe | 6-OMe | H | 4-OCF₃-phenyl | 447(M⁺ + 1) [ESI(Pos.)] | 4.5 [B] |
| 1-219 | 9 | cyclohexyl | H | H | 4-OCF₃-phenyl | 499(M⁺ + 1) [ESI(Pos.)] | 9.9 [A] |
| 1-220*²,⁴ | 9 | phenyl | H | H | 2-phenyl-phenyl (biphenyl) | 507(M⁺ + Na) [ESI(Pos.)] | |

*¹ESI: electronspray ionization
*²Mono-HCl salt
*³Di-HCl salt
*⁴Racemic mixtuer
*⁵Diastereomer mixture TABLE 2
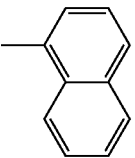
| Compound No. | Example No. | Q¹ | Q² | —Ar | MS[1] [Ionization method] |
|---|---|---|---|---|---|
| 2-001 | 7 | Single bond | —CH$_2$— | 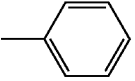 | 467 (M⁺ + 1) [ESI(Pos.)] |
| 2-002 | 7 | Single bond | —CH$_2$— | 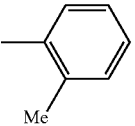 | 417 (M⁺ + 1) [ESI(Pos.)] |
| 2-003 | 8 | Single bond | —CH$_2$— | 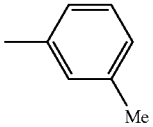 | 431 (M⁺ + 1) [ESI(Pos.)] |
| 2-004 | 8 | Single bond | —CH$_2$— |  | 431 (M⁺ + 1) [ESI(Pos.)] |
| 2-005 | 8 | Single bond | —CH$_2$— |  | 431 (M⁺ + 1) [ESI(Pos.)] |
| 2-006 | 8 | Single bond | —CH$_2$— | 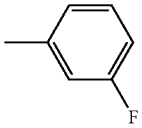 | 435 (M⁺ + 1) [ESI(Pos.)] |
| 2-007 | 8 | Single bond | —CH$_2$— |  | 435 (M⁺ + 1) [ESI(Pos.)] |
| 2-008 | 7 | Single bond | —CH$_2$— | 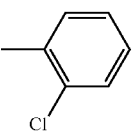 | 435 (M⁺ + 1) [ESI(Pos.)] |
| 2-009 | 8 | Single bond | —CH$_2$— |  | 451 (M⁺ + 1) [ESI(Pos.)] |

TABLE 2-continued

| Compound No. | Example No. | Q¹ | Q² | —Ar | MS*¹ [Ionization method] |
|---|---|---|---|---|---|
| 2-010 | 8 | Single bond | —CH$_2$— | 3-Cl-phenyl | 451 (M$^+$ + 1) [ESI(Pos.)] |
| 2-011 | 7 | Single bond | —CH$_2$— | 4-Cl-phenyl | 451 (M$^+$ + 1) [ESI(Pos.)] |
| 2-012 | 7 | Single bond | —CH$_2$— | 2-Br-phenyl | 495 (M$^+$ + 1) [ESI(Pos.)] |
| 2-013 | 8 | Single bond | —CH$_2$— | 3-Br-phenyl | 495 (M$^+$ + 1) [ESI(Pos.)] |
| 2-014 | 8 | Single bond | —CH$_2$— | 4-Br-phenyl | 495 (M$^+$ + 1) [ESI(Pos.)] |
| 2-015 | 8 | Single bond | —CH$_2$— | 2-I-phenyl | 543 (M$^+$ + 1) [ESI(Pos.)] |
| 2-016 | 8 | Single bond | —CH$_2$— | 3-I-phenyl | 543 (M$^+$ + 1) [ESI(Pos.)] |
| 2-017 | 8 | Single bond | —CH$_2$— | 4-I-phenyl | 543 (M$^+$ + 1) [ESI(Pos.)] |
| 2-018 | 8 | Single bond | —CH$_2$— | 2-MeO-phenyl | 447 (M$^+$ + 1) [ESI(Pos.)] |

TABLE 2-continued

| Compound No. | Example No. | Q¹ | Q² | —Ar | MS[*1] [Ionization method] |
|---|---|---|---|---|---|
| 2-019 | 7 | Single bond | —CH$_2$— | 3-OMe-phenyl | 447 (M$^+$ + 1) [ESI(Pos.)] |
| 2-020 | 7 | Single bond | —CH$_2$— | 4-OMe-phenyl | 447 (M$^+$ + 1) [ESI(Pos.)] |
| 2-021 | 8 | Single bond | —CH$_2$— | 2-OCF$_3$-phenyl | 501 (M$^+$ + 1) [ESI(Pos.)] |
| 2-022 | 8 | Single bond | —CH$_2$— | 3-OCF$_3$-phenyl | 501 (M$^+$ + 1) [ESI(Pos.)] |
| 2-023 | 8 | Single bond | —CH$_2$— | 4-OCF$_3$-phenyl | 501 (M$^+$ + 1) [ESI(Pos.)] |
| 2-024 | 8 | Single bond | —CH$_2$— | 2-OEt-phenyl | 461 (M$^+$ + 1) [ESI(Pos.)] |
| 2-025 | 8 | Single bond | —CH$_2$— | 4-OEt-phenyl | 461 (M$^+$ + 1) [ESI(Pos.)] |
| 2-026 | 8 | Single bond | —CH$_2$— | 4-OBu-phenyl | 489 (M$^+$ + 1) [ESI(Pos.)] |
| 2-027 | 8 | Single bond | —CH$_2$— | 3-OPh-phenyl | 509 (M$^+$ + 1) [ESI(Pos.)] |
| 2-028 | 8 | Single bond | —CH$_2$— | 4-OPh-phenyl | 509 (M$^+$ + 1) [ESI(Pos.)] |

TABLE 2-continued
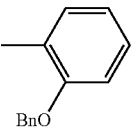
| Compound No. | Example No. | Q¹ | Q² | —Ar | MS[*1] [Ionization method] |
|---|---|---|---|---|---|
| 2-029 | 8 | Single bond | —CH$_2$— | 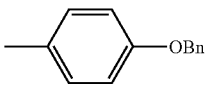 | 523 (M$^+$ + 1) [ESI(Pos.)] |
| 2-030 | 7 | Single bond | —CH$_2$— | 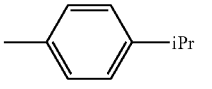 | 523 (M$^+$ + 1) [ESI(Pos.)] |
| 2-031 | 8 | Single bond | —CH$_2$— | 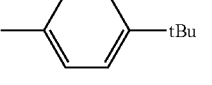 | 459 (M$^+$ + 1) [ESI(Pos.)] |
| 2-032 | 8 | Single bond | —CH$_2$— | 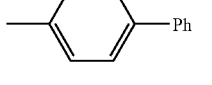 | 473 (M$^+$ + 1) [ESI(Pos.)] |
| 2-033 | 8 | Single bond | —CH$_2$— | 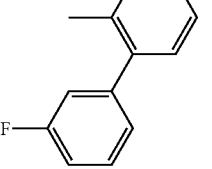 | 493 (M$^+$ + 1) [ESI(Pos.)] |
| 2-034 | 8 | Single bond | —CH$_2$— | 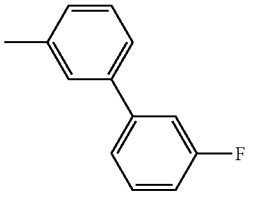 | 511 (M$^+$ + 1) [ESI(Pos.)] |
| 2-035 | 8 | Single bond | —CH$_2$— | 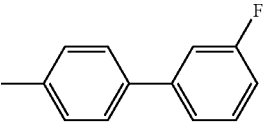 | 511 (M$^+$ + 1) [ESI(Pos.)] |
| 2-036 | 8 | Single bond | —CH$_2$— |  | 511 (M$^+$ + 1) [ESI(Pos.)] |

TABLE 2-continued
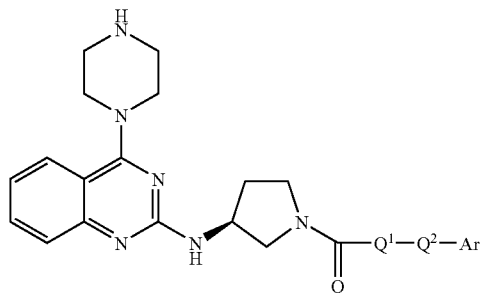
| Compound No. | Example No. | Q¹ | Q² | —Ar | MS*¹ [Ionization method] |
|---|---|---|---|---|---|
| 2-037 | 8 | Single bond | —CH₂— | 2-methyl-4'-fluorobiphenyl | 511 (M⁺ + 1) [ESI(Pos.)] |
| 2-038 | 8 | Single bond | —CH₂— | 3-methyl-4'-fluorobiphenyl | 511 (M⁺ + 1) [ESI(Pos.)] |
| 2-039 | 8 | Single bond | —CH₂— | 2-methyl-3'-chlorobiphenyl | 527 (M⁺ + 1) [ESI(Pos.)] |
| 2-040 | 8 | Single bond | —CH₂— | 3-methyl-3'-chlorobiphenyl | 527 (M⁺ + 1) [ESI(Pos.)] |
| 2-041 | 8 | Single bond | —CH₂— | 4-methyl-3'-chlorobiphenyl | 527 (M⁺ + 1) [ESI(Pos.)] |

TABLE 2-continued

| Compound No. | Example No. | Q¹ | Q² | —Ar | MS[*1] [Ionization method] |
|---|---|---|---|---|---|
| 2-042 | 8 | Single bond | —CH$_2$— | 2'-methyl-4-chlorobiphenyl | 527 (M$^+$ + 1) [ESI(Pos.)] |
| 2-043 | 8 | Single bond | —CH$_2$— | 3'-methyl-4-chlorobiphenyl | 527 (M$^+$ + 1) [ESI(Pos.)] |
| 2-044 | 8 | Single bond | —CH$_2$— | 4'-methyl-4-chlorobiphenyl | 527 (M$^+$ + 1) [ESI(Pos.)] |
| 2-045 | 8 | Single bond | —CH$_2$— | 2'-methyl-2-chlorobiphenyl | 527 (M$^+$ + 1) [ESI(Pos.)] |
| 2-046 | 8 | Single bond | —CH$_2$— | 3'-methyl-2-chlorobiphenyl | 527 (M$^+$ + 1) [ESI(Pos.)] |
| 2-047 | 8 | Single bond | —CH$_2$— | 4'-methyl-2-chlorobiphenyl | 527 (M$^+$ + 1) [ESI(Pos.)] |

TABLE 2-continued

| Compound No. | Example No. | Q¹ | Q² | —Ar | MS[*1] [Ionization method] |
|---|---|---|---|---|---|
| 2-048 | 8 | Single bond | —CH₂— | 3'-methyl-3,5-dichlorobiphenyl | 561 (M⁺ + 1) [ESI(Pos.)] |
| 2-049 | 8 | Single bond | —CH₂— | 4'-methyl-3,5-dichlorobiphenyl | 561 (M⁺ + 1) [ESI(Pos.)] |
| 2-050 | 8 | Single bond | —CH₂— | 2'-methyl-3,5-difluorobiphenyl | 529 (M⁺ + 1) [ESI(Pos.)] |
| 2-051 | 8 | Single bond | —CH₂— | 3'-methyl-3,5-difluorobiphenyl | 529 (M⁺ + 1) [CI(Pos.)] |
| 2-052 | 8 | Single bond | —CH₂— | 4'-methyl-3,5-difluorobiphenyl | 529 (M⁺ + 1) [ESI(Pos.)] |

TABLE 2-continued
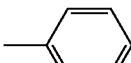
| Compound No. | Example No. | Q¹ | Q² | —Ar | MS*¹ [Ionization method] |
|---|---|---|---|---|---|
| 2-053 | 8 | Single bond | —CH₂— | 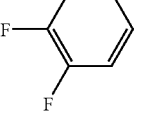 | 529 (M⁺ + 1) [ESI(Pos.)] |
| 2-054 | 8 | Single bond | —CH₂— | 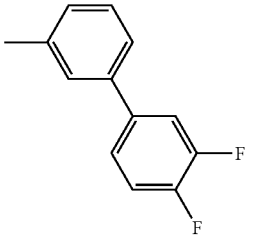 | 529 (M⁺ + 1) [ESI(Pos.)] |
| 2-055 | 8 | Single bond | —CH₂— | 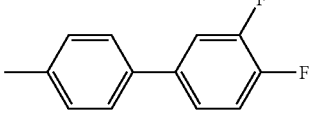 | 529 (M⁺ + 1) [ESI(Pos.)] |
| 2-056 | 8 | Single bond | —CH₂— | 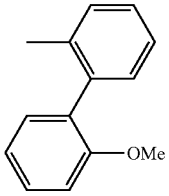 | 523 (M⁺ + 1) [ESI(Pos.)] |
| 2-057 | 8 | Single bond | —CH₂— | 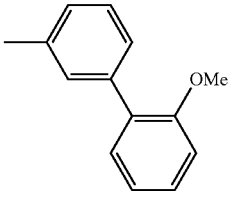 | 523 (M⁺ + 1) [ESI(Pos.)] |
| 2-058 | 8 | Single bond | —CH₂— | 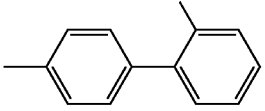 | 523 (M⁺ + 1) [ESI(Pos.)] |

TABLE 2-continued
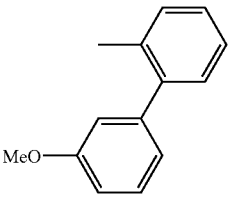
| Compound No. | Example No. | Q¹ | Q² | —Ar | MS[*1] [Ionization method] |
|---|---|---|---|---|---|
| 2-059 | 8 | Single bond | —CH$_2$— | 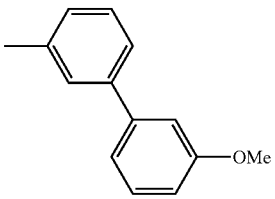 | 523 (M$^+$ + 1) [ESI(Pos.)] |
| 2-060 | 8 | Single bond | —CH$_2$— | 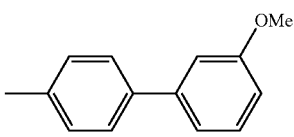 | 523 (M$^+$ + 1) [ESI(Pos.)] |
| 2-061 | 8 | Single bond | —CH$_2$— | 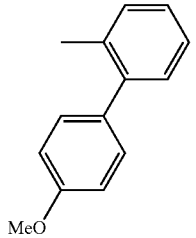 | 523 (M$^+$ + 1) [ESI(Pos.)] |
| 2-062 | 8 | Single bond | —CH$_2$— | 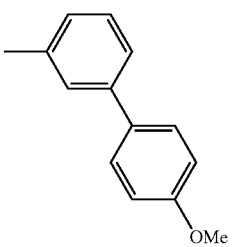 | 523 (M$^+$ + 1) [ESI(Pos.)] |
| 2-063 | 8 | Single bond | —CH$_2$— | 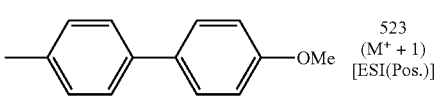 | 523 (M$^+$ + 1) [ESI(Pos.)] |
| 2-064 | 8 | Single bond | —CH$_2$— | | 523 (M$^+$ + 1) [ESI(Pos.)] |

TABLE 2-continued

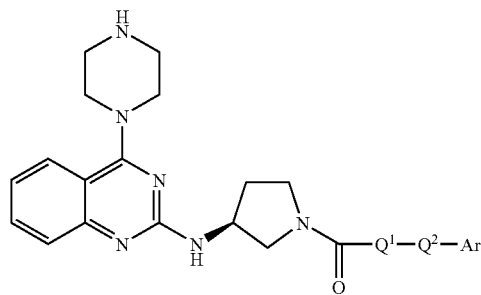

| Compound No. | Example No. | Q¹ | Q² | —Ar | MS[*1] [Ionization method] |
|---|---|---|---|---|---|
| 2-065 | 8 | Single bond | —CH$_2$— | 2-methyl-3'-ethoxybiphenyl | 537 (M$^+$ + 1) [ESI(Pos.)] |
| 2-066 | 8 | Single bond | —CH$_2$— | 3-methyl-3'-ethoxybiphenyl | 537 (M$^+$ + 1) [ESI(Pos.)] |
| 2-067 | 8 | Single bond | —CH$_2$— | 4-methyl-3'-ethoxybiphenyl | 537 (M$^+$ + 1) [ESI(Pos.)] |
| 2-068 | 8 | Single bond | —CH$_2$— | 2-methyl-(trifluoromethyl)phenyl | 485 (M$^+$ + 1) [ESI(Pos.)] |
| 2-069 | 8 | Single bond | —CH$_2$— | 3-(trifluoromethyl)phenyl | 485 (M$^+$ + 1) [ESI(Pos.)] |
| 2-070 | 8 | Single bond | —CH$_2$— | 4-(dimethylamino)phenyl | 460 (M$^+$ + 1) [ESI(Pos.)] |
| 2-071 | 8 | Single bond | —CH$_2$— | 2-(phenylamino)phenyl | 508 (M$^+$ + 1) [ESI(Pos.)] |

TABLE 2-continued
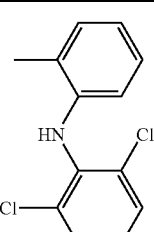
| Compound No. | Example No. | Q¹ | Q² | —Ar | MS[*1] [Ionization method] |
|---|---|---|---|---|---|
| 2-072 | 8 | Single bond | —CH$_2$— | 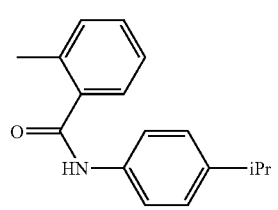 | 576 (M$^+$ + 1) [ESI(Pos.)] |
| 2-073 | 8 | Single bond | —CH$_2$— | 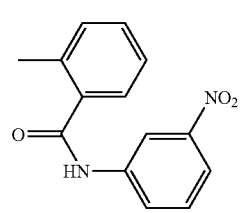 | 578 (M$^+$ + 1) [ESI(Pos.)] |
| 2-074 | 8 | Single bond | —CH$_2$— | 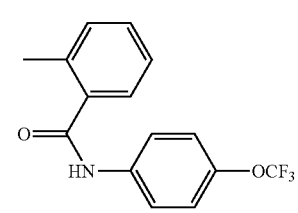 | 581 (M$^+$ + 1) [ESI(Pos.)] |
| 2-075 | 8 | Single bond | —CH$_2$— | | 620 (M$^+$ + 1) [ESI(Pos.)] |
| 2-076 | 8 | Single bond | —CH$_2$— | 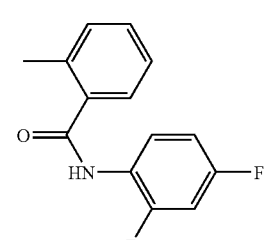 | 572 (M$^+$ + 1) [ESI(Pos.)] |

TABLE 2-continued

| Compound No. | Example No. | Q¹ | Q² | —Ar | MS[*1] [Ionization method] |
|---|---|---|---|---|---|
| 2-077 | 8 | Single bond | —CH$_2$— | 2-methyl-N-(3-chlorophenyl)benzamide group | 570 (M$^+$ + 1) [ESI(Pos.)] |
| 2-078 | 8 | Single bond | —CH$_2$— | 2-methyl-N-(2,4-dichlorophenyl)benzamide group | 604 (M$^+$ + 1) [ESI(Pos.)] |
| 2-079 | 8 | Single bond | —CH$_2$— | 2-methyl-N-(3-bromophenyl)benzamide group | 614 (M$^+$ + 1) [ESI(Pos.)] |
| 2-080 | 8 | Single bond | —CH$_2$— | 3-methyl-N-(4-methylphenyl)furan-2-carboxamide group | 540 (M$^+$ + 1) [ESI(Pos.)] |
| 2-081 | 8 | Single bond | —CH$_2$— | 2-nitrophenyl group | 462 (M$^+$ + 1) [ESI(Pos.)] |
| 2-082 | 8 | Single bond | —CH$_2$— | 3-nitrophenyl group | 462 (M$^+$ + 1) [ESI(Pos.)] |
| 2-083 | 8 | Single bond | —CH$_2$— | 4-nitrophenyl group | 462 (M$^+$ + 1) [ESI(Pos.)] |

TABLE 2-continued

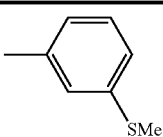

| Compound No. | Example No. | Q¹ | Q² | —Ar | MS[*1] [Ionization method] |
|---|---|---|---|---|---|
| 2-084 | 8 | Single bond | —CH$_2$— | 3-SMe-C$_6$H$_4$— | 463 (M$^+$ + 1) [ESI(Pos.)] |
| 2-085 | 8 | Single bond | —CH$_2$— | 4-SMe-C$_6$H$_4$— | 463 (M$^+$ + 1) [ESI(Pos.)] |
| 2-086 | 8 | Single bond | —CH$_2$— | 2-SCF$_3$-C$_6$H$_4$— | 517 (M$^+$ + 1) [ESI(Pos.)] |
| 2-087 | 8 | Single bond | —CH$_2$— | 4-SCF$_3$-C$_6$H$_4$— | 517 (M$^+$ + 1) [ESI(Pos.)] |
| 2-088 | 8 | Single bond | —CH$_2$— | 3-Ms-C$_6$H$_4$— | 495 (M$^+$ + 1) [ESI(Pos.)] |
| 2-089 | 8 | Single bond | —CH$_2$— | 4-Ms-C$_6$H$_4$— | 495 (M$^+$ + 1) [ESI(Pos.)] |
| 2-090 | 8 | Single bond | —CH$_2$— | 3-(pyridin-3-yl)-C$_6$H$_4$— | 494 (M$^+$ + 1) [ESI(Pos.)] |
| 2-091 | 8 | Single bond | —CH$_2$— | 4-(pyridin-3-yl)-C$_6$H$_4$— | 494 (M$^+$ + 1) [ESI(Pos.)] |
| 2-092 | 8 | Single bond | —CH$_2$— | 2,6-diF-C$_6$H$_3$— | 453 (M$^+$ + 1) [ESI(Pos.)] |

TABLE 2-continued

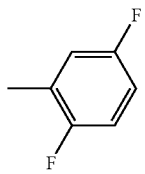

| Compound No. | Example No. | Q¹ | Q² | —Ar | MS[*1] [Ionization method] |
|---|---|---|---|---|---|
| 2-093 | 8 | Single bond | —CH$_2$— | 2,5-difluorophenyl | 453 (M$^+$ + 1) [ESI(Pos.)] |
| 2-094 | 8 | Single bond | —CH$_2$— | 3,5-difluorophenyl | 453 (M$^+$ + 1) [ESI(Pos.)] |
| 2-095 | 8 | Single bond | —CH$_2$— | 2,4-difluorophenyl | 453 (M$^+$ + 1) [ESI(Pos.)] |
| 2-096 | 8 | Single bond | —CH$_2$— | 3,4-difluorophenyl | 453 (M$^+$ + 1) [ESI(Pos.)] |
| 2-097 | 8 | Single bond | —CH$_2$— | 2,3-difluorophenyl | 453 (M$^+$ + 1) [ESI(Pos.)] |
| 2-098 | 8 | Single bond | —CH$_2$— | 2-chloro-6-fluorophenyl | 469 (M$^+$ + 1) [ESI(Pos.)] |
| 2-099 | 8 | Single bond | —CH$_2$— | 3-chloro-5-fluorophenyl | 469 (M$^+$ + 1) [ESI(Pos.)] |

TABLE 2-continued

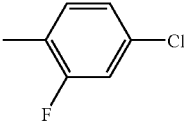

| Compound No. | Example No. | Q¹ | Q² | —Ar | MS*1 [Ionization method] |
|---|---|---|---|---|---|
| 2-100 | 8 | Single bond | —CH$_2$— | 2-F, 4-Cl phenyl | 469 (M$^+$ + 1) [ESI(Pos.)] |
| 2-101 | 8 | Single bond | —CH$_2$— | 2-Cl, 4-F phenyl | 469 (M$^+$ + 1) [ESI(Pos.)] |
| 2-102 | 8 | Single bond | —CH$_2$— | 3-Cl, 4-F phenyl | 469 (M$^+$ + 1) [ESI(Pos.)] |
| 2-103 | 8 | Single bond | —CH$_2$— | 2-F, 3-Cl phenyl | 469 (M$^+$ + 1) [ESI(Pos.)] |
| 2-104 | 8 | Single bond | —CH$_2$— | 2,3-diCl phenyl | 485 (M$^+$ + 1) [ESI(Pos.)] |
| 2-105 | 8 | Single bond | —CH$_2$— | 2,4-diCl phenyl | 485 (M$^+$ + 1) [ESI(Pos.)] |
| 2-106 | 8 | Single bond | —CH$_2$— | 3,4-diCl phenyl | 485 (M$^+$ + 1) [ESI(Pos.)] |
| 2-107 | 8 | Single bond | —CH$_2$— | 3-Br, 4-F phenyl | 513 (M$^+$ + 1) [ESI(Pos.)] |

TABLE 2-continued
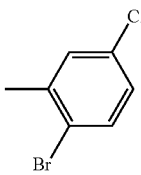
| Compound No. | Example No. | Q¹ | Q² | —Ar | MS*¹ [Ionization method] |
|---|---|---|---|---|---|
| 2-108 | 8 | Single bond | —CH$_2$— | 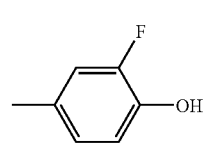 | 529 (M$^+$ + 1) [ESI(Pos.)] |
| 2-109 | 8 | Single bond | —CH$_2$— | 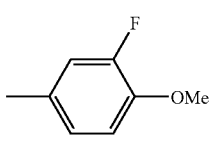 | 449 (M$^-$ − 1) [ESI(Neg.)] |
| 2-110 | 8 | Single bond | —CH$_2$— | 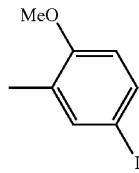 | 465 (M$^+$ + 1) [ESI(Pos.)] |
| 2-111 | 8 | Single bond | —CH$_2$— | 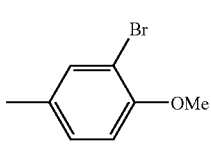 | 573 (M$^+$ + 1) [ESI(Pos.)] |
| 2-112 | 8 | Single bond | —CH$_2$— | 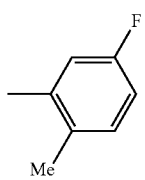 | 525 (M$^+$ + 1) [ESI(Pos.)] |
| 2-113 | 8 | Single bond | —CH$_2$— | 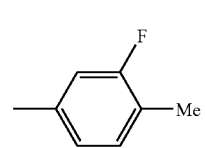 | 449 (M$^+$ + 1) [ESI(Pos.)] |
| 2-114 | 8 | Single bond | —CH$_2$— |  | 449 (M$^+$ + 1) [ESI(Pos.)] |

TABLE 2-continued

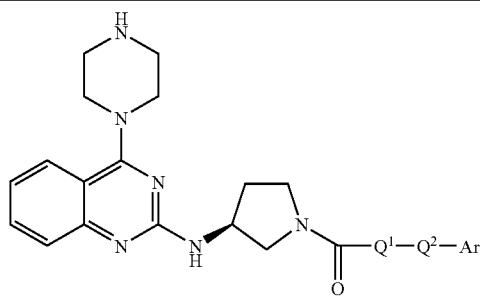

| Compound No. | Example No. | Q¹ | Q² | —Ar | MS[*1] [Ionization method] |
|---|---|---|---|---|---|
| 2-115 | 8 | Single bond | —CH$_2$— | 3-methyl-5-(trifluoromethyl)phenyl | 503 (M$^+$ + 1) [ESI(Pos.)] |
| 2-116 | 8 | Single bond | —CH$_2$— | 4-fluoro-2-(trifluoromethyl)-methylphenyl | 503 (M$^+$ + 1) [ESI(Pos.)] |
| 2-117 | 8 | Single bond | —CH$_2$— | 4-fluoro-3-(trifluoromethyl)-methylphenyl | 503 (M$^+$ + 1) [ESI(Pos.)] |
| 2-118 | 8 | Single bond | —CH$_2$— | 3-fluoro-4-(trifluoromethyl)-methylphenyl | 503 (M$^+$ + 1) [ESI(Pos.)] |
| 2-119 | 8 | Single bond | —CH$_2$— | 4-fluoro-2-(trifluoromethyl)-methylphenyl | 503 (M$^+$ + 1) [ESI(Pos.)] |
| 2-120 | 8 | Single bond | —CH$_2$— | 2-fluoro-3-(trifluoromethyl)-methylphenyl | 503 (M$^+$ + 1) [ESI(Pos.)] |
| 2-121 | 8 | Single bond | —CH$_2$— | 3-fluoro-6-(trifluoromethyl)-methylphenyl | 503 (M$^+$ + 1) [ESI(Pos.)] |
| 2-122 | 8 | Single bond | —CH$_2$— | 3-fluoro-4-(trifluoromethyl)-methylphenyl | 503 (M$^+$ + 1) [ESI(Pos.)] |

TABLE 2-continued
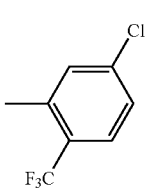
| Compound No. | Example No. | Q¹ | Q² | —Ar | MS*¹ [Ionization method] |
|---|---|---|---|---|---|
| 2-123 | 8 | Single bond | —CH₂— | 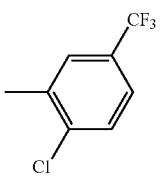 | 519 (M⁺ + 1) [ESI(Pos.)] |
| 2-124 | 8 | Single bond | —CH₂— | 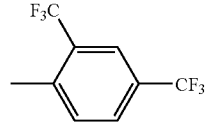 | 519 (M⁺ + 1) [ESI(Pos.)] |
| 2-125 | 8 | Single bond | —CH₂— | 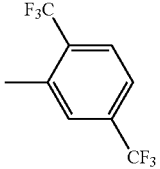 | 553 (M⁺ + 1) [ESI(Pos.)] |
| 2-126 | 8 | Single bond | —CH₂— | 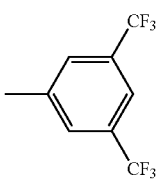 | 553 (M⁺ + 1) [ESI(Pos.)] |
| 2-127 | 8 | Single bond | —CH₂— | 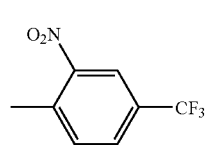 | 553 (M⁺ + 1) [ESI(Pos.)] |
| 2-128 | 8 | Single bond | —CH₂— | 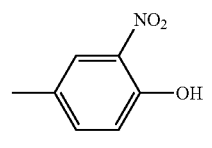 | 530 (M⁺ + 1) [ESI(Pos.)] |
| 2-129 | 8 | Single bond | —CH₂— |  | 478 (M⁺ + 1) [ESI(Pos.)] |

TABLE 2-continued
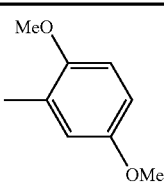
| Compound No. | Example No. | Q¹ | Q² | —Ar | MS[*1] [Ionization method] |
|---|---|---|---|---|---|
| 2-130 | 7 | Single bond | —CH$_2$— | 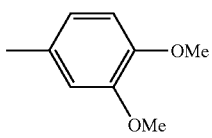 | 477 (M$^+$ + 1) [ESI(Pos.)] |
| 2-131 | 7 | Single bond | —CH$_2$— | 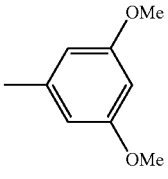 | 477 (M$^+$ + 1) [ESI(Pos.)] |
| 2-132 | 8 | Single bond | —CH$_2$— | 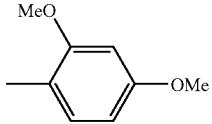 | 477 (M$^+$ + 1) [ESI(Pos.)] |
| 2-133 | 8 | Single bond | —CH$_2$— | 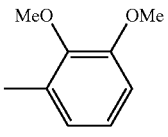 | 477 (M$^+$ + 1) [ESI(Pos.)] |
| 2-134 | 8 | Single bond | —CH$_2$— | 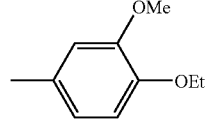 | 477 (M$^+$ + 1) [ESI(Pos.)] |
| 2-135 | 8 | Single bond | —CH$_2$— | 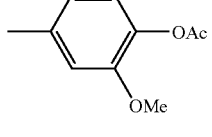 | 491 (M$^+$ + 1) [ESI(Pos.)] |
| 2-136 | 8 | Single bond | —CH$_2$— | 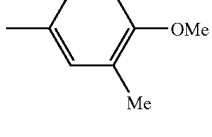 | 505 (M$^+$ + 1) [ESI(Pos.)] |
| 2-137 | 8 | Single bond | —CH$_2$— |  | 461 (M$^+$ + 1) [ESI(Pos.)] |

TABLE 2-continued

| Compound No. | Example No. | Q¹ | Q² | —Ar | MS[*1] [Ionization method] |
|---|---|---|---|---|---|
| 2-138 | 8 | Single bond | —CH$_2$— | 2,4-dimethylphenyl | 445 (M$^+$ + 1) [ESI(Pos.)] |
| 2-139 | 8 | Single bond | —CH$_2$— | 3,5-dimethylphenyl | 445 (M$^+$ + 1) [ESI(Pos.)] |
| 2-140 | 8 | Single bond | —CH$_2$— | 2,3,6-trichlorophenyl | 519 (M$^+$ + 1) [ESI(Pos.)] |
| 2-141 | 8 | Single bond | —CH$_2$— | 2-chloro-3,6-difluorophenyl | 487 (M$^+$ + 1) [ESI(Pos.)] |
| 2-142 | 8 | Single bond | —CH$_2$— | 6-chloro-2,3-difluorophenyl | 487 (M$^+$ + 1) [ESI(Pos.)] |
| 2-143 | 8 | Single bond | —CH$_2$— | 2,4-dichloro-5-fluorophenyl | 503 (M$^+$ + 1) [ESI(Pos.)] |
| 2-144 | 8 | Single bond | —CH$_2$— | 2,3,4-trifluorophenyl | 471 (M$^+$ + 1) [ESI(Pos.)] |

TABLE 2-continued

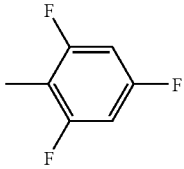

| Compound No. | Example No. | Q¹ | Q² | —Ar | MS*[1] [Ionization method] |
|---|---|---|---|---|---|
| 2-145 | 8 | Single bond | —CH$_2$— | 2,4,6-trifluorophenyl | 471 (M$^+$ + 1) [ESI(Pos.)] |
| 2-146 | 8 | Single bond | —CH$_2$— | 2,4,5-trifluorophenyl | 471 (M$^+$ + 1) [ESI(Pos.)] |
| 2-147 | 8 | Single bond | —CH$_2$— | 3,4,5-trifluorophenyl | 471 (M$^+$ + 1) [ESI(Pos.)] |
| 2-148 | 8 | Single bond | —CH$_2$— | 2,3,6-trifluorophenyl | 471 (M$^+$ + 1) [ESI(Pos.)] |
| 2-149 | 8 | Single bond | —CH$_2$— | 2,6-difluoro-3-methylphenyl | 467 (M$^+$ + 1) [ESI(Pos.)] |
| 2-150 | 8 | Single bond | —CH$_2$— | 2,3-difluoro-4-methylphenyl (with Me) | 467 (M$^+$ + 1) [ESI(Pos.)] |
| 2-151 | 8 | Single bond | —CH$_2$— | 2-chloro-5-fluoro-3-methylphenyl | 483 (M$^+$ + 1) [ESI(Pos.)] |

TABLE 2-continued
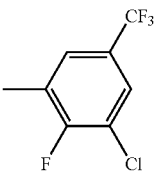
| Compound No. | Example No. | Q¹ | Q² | —Ar | MS*¹ [Ionization method] |
|---|---|---|---|---|---|
| 2-152 | 8 | Single bond | —CH₂— | 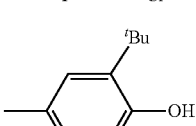 | 537 (M⁺ + 1) [ESI(Pos.)] |
| 2-153 | 8 | Single bond | —CH₂— | 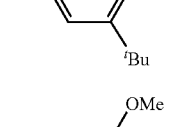 | 545 (M⁺ + 1) [ESI(Pos.)] |
| 2-154 | 8 | Single bond | —CH₂— | 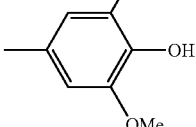 | 493 (M⁺ + 1) [ESI(Pos.)] |
| 2-155 | 8 | Single bond | —CH₂— | 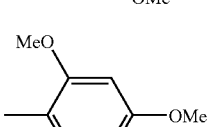 | 507 (M⁺ + 1) [ESI(Pos.)] |
| 2-156 | 8 | Single bond | —CH₂— | 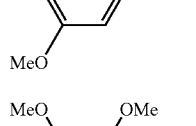 | 507 (M⁺ + 1) [ESI(Pos.)] |
| 2-157 | 8 | Single bond | —CH₂— | 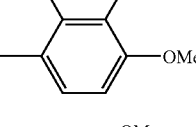 | 507 (M⁺ + 1) [ESI(Pos.)] |
| 2-158 | 8 | Single bond | —CH₂— |  | 522 (M⁺ + 1) [ESI(Pos.)] |

TABLE 2-continued
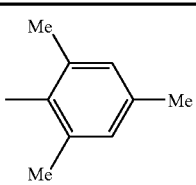
| Compound No. | Example No. | Q¹ | Q² | —Ar | MS[*1] [Ionization method] |
|---|---|---|---|---|---|
| 2-159 | 8 | Single bond | —CH$_2$— | 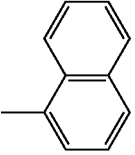 | 459 (M$^+$ + 1) [ESI(Pos.)] |
| 2-160 | 8 | Single bond | —CH$_2$— | 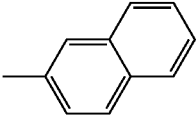 | 467 (M$^+$ + 1) [ESI(Pos.)] |
| 2-161 | 8 | Single bond | —CH$_2$— | 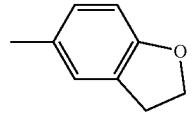 | 467 (M$^+$ + 1) [ESI(Pos.)] |
| 2-162 | 8 | Single bond | —CH$_2$— | 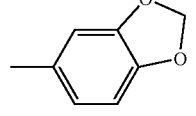 | 459 (M$^+$ + 1) [ESI(Pos.)] |
| 2-163 | 8 | Single bond | —CH$_2$— | 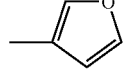 | 461 (M$^+$ + 1) [ESI(Pos.)] |
| 2-164 | 8 | Single bond | —CH$_2$— | 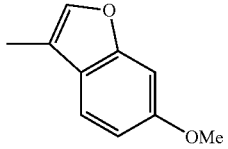 | 407 (M$^+$ + 1) [ESI(Pos.)] |
| 2-165 | 8 | Single bond | —CH$_2$— |  | 487 (M$^+$ + 1) [ESI(Pos.)] |
| 2-166 | 8 | Single bond | —CH$_2$— |  | 470 (M$^+$ + 1) [ESI(Pos.)] |

TABLE 2-continued

| Compound No. | Example No. | Q¹ | Q² | —Ar | MS*¹ [Ionization method] |
|---|---|---|---|---|---|
| 2-167 | 8 | Single bond | —CH₂— | 3-methyl-4,5,6,7-tetrafluoroindol-2-yl | 526 (M⁻ − 1) [ESI(Neg.)] |
| 2-168 | 8 | Single bond | —CH₂— | 3-methyl-5-methoxyindol-2-yl | 486 (M⁺ + 1) [ESI(Pos.)] |
| 2-169 | 8 | Single bond | —CH₂— | 3-methyl-6-benzyloxyindol-2-yl | 562 (M⁺ + 1) [ESI(Pos.)] |
| 2-170 | 8 | Single bond | —CH₂— | 1,3-dimethylindol-2-yl | 470 (M⁺ + 1) [ESI(Pos.)] |
| 2-171 | 8 | Single bond | —CH₂— | 1-(4-fluorobenzyl)-3-methylindol-2-yl | 564 (M⁺ + 1) [ESI(Pos.)] |
| 2-172 | 8 | Single bond | —CH₂— | 2,3-dimethyl-5-methoxyindol-? | 500 (M⁺ + 1) [ESI(Pos.)] |

TABLE 2-continued

| Compound No. | Example No. | Q¹ | Q² | —Ar | MS*[1] [Ionization method] |
|---|---|---|---|---|---|
| 2-173 | 8 | Single bond | —CH$_2$— | 3-methyl-6-OBn-1H-indol-2-yl | 562 (M$^+$ + 1) [ESI(Pos.)] |
| 2-174 | 8 | Single bond | —CH$_2$— | 4-methyl-1H-imidazol-5-yl | 407 (M$^+$ + 1) [ESI(Pos.)] |
| 2-175 | 7 | Single bond | —CH$_2$— | thiophen-2-yl | 423 (M$^+$ + 1) [ESI(Pos.)] |
| 2-176 | 8 | Single bond | —CH$_2$— | 2,4-dimethylthiazol-5-yl | 452 (M$^+$ + 1) [ESI(Pos.)] |
| 2-177 | 8 | Single bond | —CH$_2$— | 2-phenyl-4-methylthiazol-5-yl | 500 (M$^+$ + 1) [ESI(Pos.)] |
| 2-178 | 8 | Single bond | —CH$_2$— | 2-phenyl-4-methyl-5-methylthiazol-yl | 514 (M$^+$ + 1) [ESI(Pos.)] |
| 2-179 | 8 | Single bond | —CH$_2$— | 2-(4-chlorophenyl)-4-methylthiazol-5-yl | 534 (M$^+$ + 1) [ESI(Pos.)] |

TABLE 2-continued
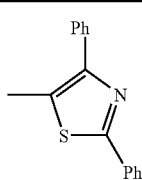
| Compound No. | Example No. | Q¹ | Q² | —Ar | MS*1 [Ionization method] |
|---|---|---|---|---|---|
| 2-180 | 8 | Single bond | —CH$_2$— | 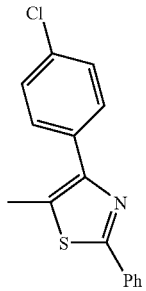 | 576 (M$^+$ + 1) [ESI(Pos.)] |
| 2-181 | 8 | Single bond | —CH$_2$— | 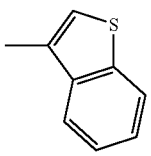 | 610 (M$^+$ + 1) [ESI(Pos.)] |
| 2-182 | 8 | Single bond | —CH$_2$— | 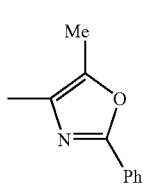 | 473 (M$^+$ + 1) [ESI(Pos.)] |
| 2-183 | 8 | Single bond | —CH$_2$— | 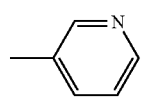 | 498 (M$^+$ + 1) [ESI(Pos.)] |
| 2-184 | 8 | Single bond | —CH$_2$— | 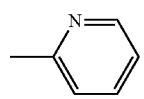 | 418 (M$^+$ + 1) [ESI(Pos.)] |
| 2-185 | 8 | Single bond | —CH$_2$— | 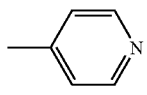 | 418 (M$^+$ + 1) [ESI(Pos.)] |
| 2-186 | 8 | Single bond | —CH$_2$— |  | 418 (M$^+$ + 1) [ESI(Pos.)] |

TABLE 2-continued
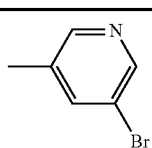
| Compound No. | Example No. | Q¹ | Q² | —Ar | MS*¹ [Ionization method] |
|---|---|---|---|---|---|
| 2-187 | 8 | Single bond | —CH₂— | 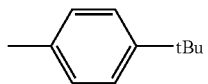 | 496 (M⁺ + 1) [ESI(Pos.)] |
| 2-188 | 7 | —CH₂— | —O— | 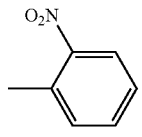 | 489 (M⁺ + 1) [ESI(Pos.)] |
| 2-189 | 7 | —CH₂— | —O— | 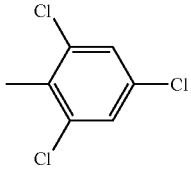 | 478 (M⁺ + 1) [ESI(Pos.)] |
| 2-190 | 8 | —CH₂— | —O— | 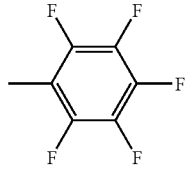 | 535 (M⁺ + 1) [ESI(Pos.)] |
| 2-191 | 7 | —CH₂— | —O— | 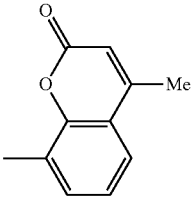 | 523 (M⁺ + 1) [ESI(Pos.)] |
| 2-192 | 7 | —CH₂— | —O— | 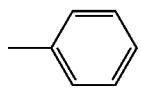 | 515 (M⁺ + 1) [ESI(Pos.)] |
| 2-193 | 7 | —CH₂— | —S— | 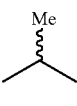 | 449 (M⁺ + 1) [ESI(Pos.)] |
| 2-194*² | 8 | Single bond | 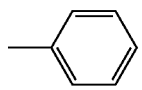 |  | 431 (M⁺ + 1) [ESI(Pos.)] |
| 2-195*² | 8 | Single bond | 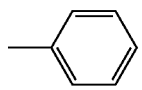 | 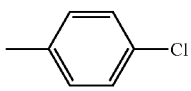 | 465 (M⁺ + 1) [ESI(Pos.)] |

TABLE 2-continued

| Compound No. | Example No. | Q¹ | Q² | —Ar | MS*¹ [Ionization method] |
|---|---|---|---|---|---|
| 2-196*² | 8 | Single bond | Me, isopropyl | 4-Me-C₆H₄ | 445 (M⁺ + 1) [ESI(Pos.)] |
| 2-197*² | 8 | Single bond | Me, isopropyl | 4-iBu-C₆H₄ | 487 (M⁺ + 1) [ESI(Pos.)] |
| 2-198*² | 8 | Single bond | Me, isopropyl | 3-F-4-Ph-C₆H₃ | 525 (M⁺ + 1) [ESI(Pos.)] |
| 2-199*² | 8 | Single bond | Me, isopropyl | 3-(COPh)-C₆H₄ | 535 (M⁺ + 1) [ESI(Pos.)] |
| 2-200*² | 8 | Single bond | Me, isopropyl | 4-NO₂-C₆H₄ | 476 (M⁺ + 1) [ESI(Pos.)] |
| 2-201*² | 8 | Single bond | Me, isopropyl | 6-OMe-naphth-2-yl | 511 (M⁺ + 1) [ESI(Pos.)] |
| 2-202*² | 8 | Single bond | Me, isopropyl | 4-(2-thienyl-CO)-C₆H₄ | 541 (M⁺ + 1) [ESI(Pos.)] |
| 2-203 | 8 | Single bond | Me, isopropyl | Ph | 431 (M⁺ + 1) [ESI(Pos.)] |
| 2-204 | 8 | Single bond | Me, isopropyl | 4-iBu-C₆H₄ | 487 (M⁺ + 1) [ESI(Pos.)] |

TABLE 2-continued

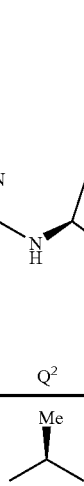

| Compound No. | Example No. | Q¹ | Q² | —Ar | MS*¹ [Ionization method] |
|---|---|---|---|---|---|
| 2-205 | 8 | Single bond | Me, isobutyl | 3-F, 4-Ph phenyl | 525 (M⁺ + 1) [ESI(Pos.)] |
| 2-206 | 8 | Single bond | Me, isobutyl | 6-OMe naphthalen-2-yl | 511 (M⁺ + 1) [ESI(Pos.)] |
| 2-207 | 8 | Single bond | Me, isobutyl | phenyl | 431 (M⁺ + 1) [ESI(Pos.)] |
| 2-208 | 8 | Single bond | Me, isobutyl | 3-F, 4-Ph phenyl | 525 (M⁺ + 1) [ESI(Pos.)] |
| 2-209 | 8 | Single bond | Me, isobutyl | 6-OMe naphthalen-2-yl | 511 (M⁺ + 1) [ESI(Pos.)] |
| 2-210*² | 7 | Single bond | Me, CH(OMe) | phenyl | 447 (M⁺ + 1) [ESI(Pos.)] |
| 2-211*² | 7 | Single bond | Et, isobutyl | phenyl | 445 (M⁺ + 1) [ESI(Pos.)] |
| 2-212 | 8 | Single bond | Et, isobutyl | phenyl | 445 (M⁺ + 1) [ESI(Pos.)] |
| 2-213 | 8 | Single bond | Et, isobutyl | phenyl | 445 (M⁺ + 1) [ESI(Pos.)] |
| 2-214*² | 7 | Single bond | Et, CH(OMe) | phenyl | 461 (M⁺ + 1) [ESI(Pos.)] |
| 2-215*² | 8 | Single bond | iPr, isobutyl | phenyl | 459 (M⁺ + 1) [ESI(Pos.)] |

TABLE 2-continued
| Compound No. | Example No. | Q¹ | Q² | —Ar | MS*¹ [Ionization method] |
|---|---|---|---|---|---|
| 2-216*² | 8 | Single bond | 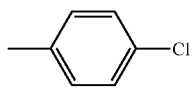 |  | 493 (M⁺ + 1) [ESI(Pos.)] |
| 2-217 | 8 | Single bond | 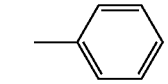 |  | 445 (M⁺ + 1) [ESI(Pos.)] |
| 2-218 | 8 | Single bond | 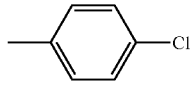 | 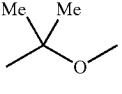 | 479 (M⁺ + 1) [ESI(Pos.)] |
| 2-219 | 7 | Single bond | 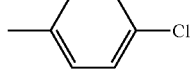 |  | 495 (M⁺ + 1) [ESI(Pos.)] |
| 2-220 | 8 | Single bond | 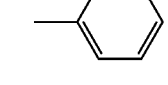 |  | 443 (M⁺ + 1) [ESI(Pos.)] |
| 2-221 | 8 | Single bond | 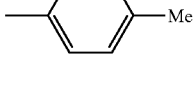 |  | 457 (M⁺ + 1) [ESI(Pos.)] |
| 2-222 | 8 | Single bond | 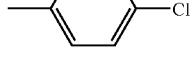 |  | 477 (M⁺ + 1) [ESI(Pos.)] |
| 2-223 | 8 | Single bond | 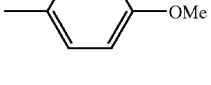 |  | 473 (M⁺ + 1) [ESI(Pos.)] |
| 2-224 | 8 | Single bond | 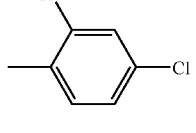 | 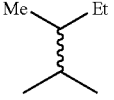 | 511 (M⁺ + 1) [ESI(Pos.)] |
| 2-225*² | 8 | Single bond | 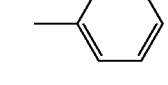 |  | 473 (M⁺ + 1) [ESI(Pos.)] |
| 2-226 | 8 | Single bond | 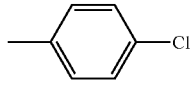 |  | 491 (M⁺ + 1) [ESI(Pos.)] |

TABLE 2-continued

| Compound No. | Example No. | Q¹ | Q² | —Ar | MS[*1] [Ionization method] |
|---|---|---|---|---|---|
| 2-227[*2] | 8 | Single bond | cyclopentyl (isopropyl substituent, wavy bond) | phenyl | 485 (M⁺ + 1) [ESI(Pos.)] |
| 2-228 | 8 | Single bond | 1,1-dimethylcyclopentyl | phenyl | 471 (M⁺ + 1) [ESI(Pos.)] |
| 2-229 | 8 | Single bond | 1,1-dimethylcyclopentyl | 4-Me-phenyl | 485 (M⁺ + 1) [ESI(Pos.)] |
| 2-230 | 8 | Single bond | 1,1-dimethylcyclopentyl | 2-F-phenyl | 489 (M⁺ + 1) [ESI(Pos.)] |
| 2-231 | 8 | Single bond | 1,1-dimethylcyclopentyl | 3-F-phenyl | 489 (M⁺ + 1) [ESI(Pos.)] |
| 2-232 | 8 | Single bond | 1,1-dimethylcyclopentyl | 4-F-phenyl | 489 (M⁺ + 1) [ESI(Pos.)] |
| 2-233 | 8 | Single bond | 1,1-dimethylcyclopentyl | 4-OMe-phenyl | 501 (M⁺ + 1) [ESI(Pos.)] |
| 2-234 | 8 | Single bond | 1,1-dimethylcyclopentyl | 2-Cl-4-F-phenyl | 523 (M⁺ + 1) [ESI(Pos.)] |
| 2-235 | 8 | Single bond | 1,1-dimethylcyclopentyl | 2,6-di-F... 2-F-3-Cl-phenyl | 523 (M⁺ + 1) [ESI(Pos.)] |

TABLE 2-continued

| Compound No. | Example No. | Q¹ | Q² | —Ar | MS[*1] [Ionization method] |
|---|---|---|---|---|---|
| 2-236[*2] | 8 | Single bond | cyclohexyl (racemic) | phenyl | 499 (M⁺ + 1) [ESI(Pos.)] |
| 2-237 | 8 | Single bond | 1-methylcyclohexyl | phenyl | 485 (M⁺ + 1) [ESI(Pos.)] |
| 2-238 | 8 | Single bond | 1-methylcyclohexyl | 4-Me-phenyl | 499 (M⁺ + 1) [ESI(Pos.)] |
| 2-239 | 8 | Single bond | 1-methylcyclohexyl | 2-F-phenyl | 503 (M⁺ + 1) [ESI(Pos.)] |
| 2-240 | 8 | Single bond | 1-methylcyclohexyl | 3-F-phenyl | 503 (M⁺ + 1) [ESI(Pos.)] |
| 2-241 | 8 | Single bond | 1-methylcyclohexyl | 4-F-phenyl | 503 (M⁺ + 1) [ESI(Pos.)] |
| 2-242 | 8 | Single bond | 1-methylcyclohexyl | 4-Cl-phenyl | 519 (M⁺ + 1) [ESI(Pos.)] |
| 2-243 | 8 | Single bond | 1-methylcyclohexyl | 4-OMe-phenyl | 515 (M⁺ + 1) [ESI(Pos.)] |

TABLE 2-continued

| Compound No. | Example No. | Q¹ | Q² | —Ar | MS[1] [Ionization method] |
|---|---|---|---|---|---|
| 2-244 | 8 | Single bond | cyclohexyl (gem-dimethyl) | 2-Cl, 4-F phenyl | 537 (M⁺ + 1) [ESI(Pos.)] |
| 2-245 | 8 | Single bond | cyclohexyl (gem-dimethyl) | 2-F, 6-Cl phenyl | 537 (M⁺ + 1) [ESI(Pos.)] |
| 2-246 | 8 | Single bond | cyclohexyl (gem-dimethyl) | 2-thienyl | 491 (M⁺ + 1) [ESI(Pos.)] |
| 2-247[2] | 7 | Single bond | phenyl (isopropyl) | phenyl | 493 (M⁺ + 1) [ESI(Pos.)] |
| 2-248[2] | 8 | Single bond | naphthyl-O-CH(CH₃)- | phenyl | 559 (M⁺ + 1) [ESI(Pos.)] |
| 2-249[2] | 8 | Single bond | SPh, isopropyl | phenyl | 525 (M⁺ + 1) [ESI(Pos.)] |
| 2-250[2] | 8 | Single bond | OH, isopropyl | phenyl | 433 (M⁺ + 1) [ESI(Pos.)] |
| 2-251[2] | 8 | Single bond | OH, isopropyl | 4-F phenyl | 451 (M⁺ + 1) [ESI(Pos.)] |
| 2-252[2] | 8 | Single bond | OH, isopropyl | 3-Cl phenyl | 467 (M⁺ + 1) [ESI(Pos.)] |

TABLE 2-continued
| Compound No. | Example No. | Q¹ | Q² | —Ar | MS[1] [Ionization method] |
|---|---|---|---|---|---|
| 2-253[2] | 8 | Single bond | 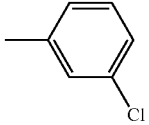 |  | 467 (M⁺ + 1) [ESI(Pos.)] |
| 2-254[2] | 8 | Single bond |  |  | 467 (M⁺ + 1) [ESI(Pos.)] |
| 2-255[2] | 8 | Single bond | 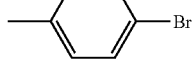 |  | 511 (M⁺ + 1) [ESI(Pos.)] |
| 2-256[2] | 8 | Single bond | 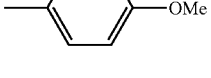 |  | 463 (M⁺ + 1) [ESI(Pos.)] |
| 2-257[2] | 8 | Single bond | 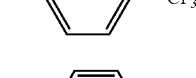 |  | 501 (M⁺ + 1) [ESI(Pos.)] |
| 2-258[2] | 8 | Single bond | 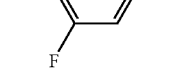 |  | 469 (M⁺ + 1) [ESI(Pos.)] |
| 2-259[2] | 8 | Single bond | 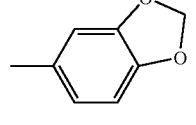 |  | 477 (M⁺ + 1) [ESI(Pos.)] |
| 2-260 | 8 | Single bond | 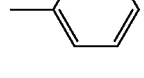 |  | 433 (M⁺ + 1) [ESI(Pos.)] |
| 2-261 | 8 | Single bond | 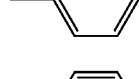 |  | 433 (M⁺ + 1) [ESI(Pos.)] |
| 2-262 | 8 | Single bond | 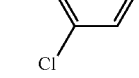 |  | 467 (M⁺ + 1) [ESI(Pos.)] |

TABLE 2-continued
| Compound No. | Example No. | Q¹ | Q² | —Ar | MS*¹ [Ionization method] |
|---|---|---|---|---|---|
| 2-263 | 8 | Single bond | 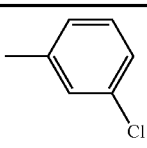 |  | 467 (M⁺ + 1) [ESI(Pos.)] |
| 2-264*² | 8 | Single bond | 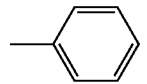 | 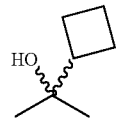 | 447 (M⁺ + 1) [ESI(Pos.)] |
| 2-265*² | 8 | Single bond | 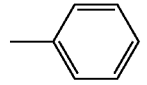 | 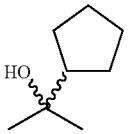 | 487 (M⁺ + 1) [ESI(Pos.)] |
| 2-266*² | 8 | Single bond | 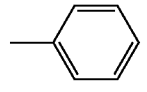 |  | 501 (M⁺ + 1) [ESI(Pos.)] |
| 2-267*² | 8 | Single bond |  |  | 471 (M⁺ + 1) [ESI(Pos.)] |
| 2-268*² | 8 | Single bond | 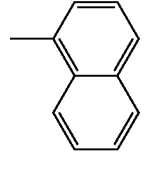 |  | 511 (M⁺ + 1) [ESI(Pos.)] |
| 2-269 | 8 | Single bond | 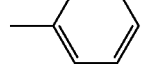 |  | 475 (M⁺ + 1) [ESI(Pos.)] |
| 2-270*² | 8 | Single bond | 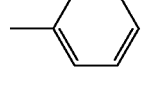 |  | 507 (M⁺ + 1) [ESI(Pos.)] |
| 2-271*² | 8 | Single bond | 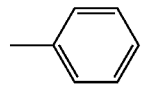 |  | 447 (M⁺ + 1) [ESI(Pos.)] |
| 2-272*² | 8 | Single bond | 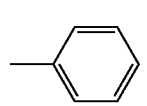 | | 474 (M⁺ + 1) [ESI(Pos.)] |

TABLE 2-continued

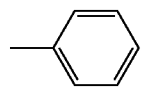

| Compound No. | Example No. | Q¹ | Q² | —Ar | MS[*1] [Ionization method] |
|---|---|---|---|---|---|
| 2-273 | 7 | —CH$_2$— | —CH$_2$— | 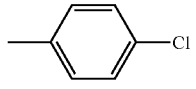 | 431 (M$^+$ + 1) [ESI(Pos.)] |
| 2-274 | 8 | —CH$_2$— | —CH$_2$— | 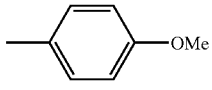 4-Cl-C$_6$H$_4$— | 465 (M$^+$ + 1) [ESI(Pos.)] |
| 2-275 | 8 | —CH$_2$— | —CH$_2$— | 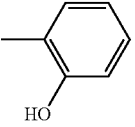 4-OMe-C$_6$H$_4$— | 461 (M$^+$ + 1) [ESI(Pos.)] |
| 2-276 | 8 | —CH$_2$— | —CH$_2$— | 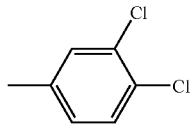 2-OH-C$_6$H$_4$— | 447 (M$^+$ + 1) [ESI(Pos.)] |
| 2-277 | 8 | —CH$_2$— | —CH$_2$— | 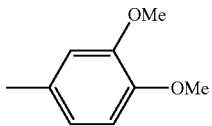 3,4-di-Cl-C$_6$H$_3$— | 499 (M$^+$ + 1) [ESI(Pos.)] |
| 2-278 | 8 | —CH$_2$— | —CH$_2$— | 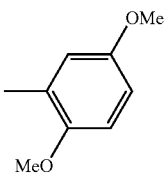 3,4-di-OMe-C$_6$H$_3$— | 491 (M$^+$ + 1) [ESI(Pos.)] |
| 2-279 | 8 | —CH$_2$— | —CH$_2$— | 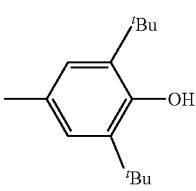 2,5-di-OMe-C$_6$H$_3$— | 491 (M$^+$ + 1) [ESI(Pos.)] |
| 2-280 | 8 | —CH$_2$— | —CH$_2$— | 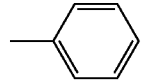 3,5-di-$^t$Bu-4-OH-C$_6$H$_2$— | 559 (M$^+$ + 1) [ESI(Pos.)] |
| 2-281 | 8 | —CH$_2$— | —CPh$_2$— | C$_6$H$_5$— | 583 (M$^+$ + 1) [ESI(Pos.)] |

TABLE 2-continued
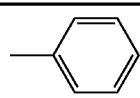
| Compound No. | Example No. | Q¹ | Q² | —Ar | MS[*1] [Ionization method] |
|---|---|---|---|---|---|
| 2-282 | 8 | —CH$_2$— | —NH— | 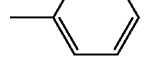 | 432 (M⁺ + 1) [ESI(Pos.)] |
| 2-283 | 7 | —CH$_2$— | —O— | 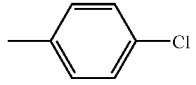 | 433 (M⁺ + 1) [ESI(Pos.)] |
| 2-284 | 7 | —CH$_2$— | —O— | 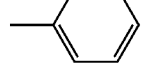 | 467 (M⁺ + 1) [ESI(Pos.)] |
| 2-285 | 7 | —CH$_2$— | —O—CH$_2$— | 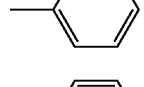 | 447 (M⁺ + 1) [ESI(Pos.)] |
| 2-286 | 8 | —CH$_2$— | —S—CH$_2$— |  | 463 (M⁺ + 1) [ESI(Pos.)] |
| 2-287 | 8 | —(CH$_2$)$_2$— | 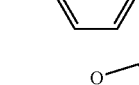 |  | 459 (M⁺ + 1) [ESI(Pos.)] |
| 2-288 | 8 | —(CH$_2$)$_2$— | 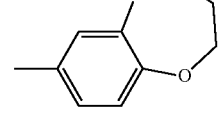 |  | 531 (M⁺ + 1) [ESI(Pos.)] |
| 2-289 | 8 | —(CH$_2$)$_2$— | 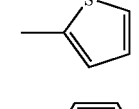 | 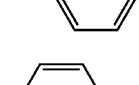 | 465 (M⁺ + 1) [ESI(Pos.)] |
| 2-290 | 8 | —(CH$_2$)$_2$— | —CH$_2$— | 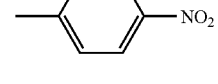 | 445 (M⁺ + 1) [ESI(Pos.)] |
| 2-291 | 8 | —(CH$_2$)$_2$— | —CH$_2$— | 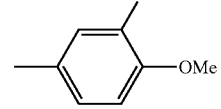 | 490 (M⁺ + 1) [ESI(Pos.)] |
| 2-292 | 8 | —(CH$_2$)$_2$— | —CH$_2$— |  | 505 (M⁺ + 1) [ESI(Pos.)] |

TABLE 2-continued
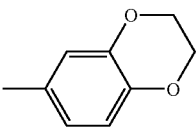
| Compound No. | Example No. | Q¹ | Q² | —Ar | MS[*1] [Ionization method] |
|---|---|---|---|---|---|
| 2-293 | 8 | —(CH$_2$)$_2$— | —CH$_2$— | 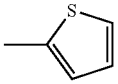 | 503 (M⁺ + 1) [ESI(Pos.)] |
| 2-294 | 8 | —(CH$_2$)$_2$— | —CH$_2$— | 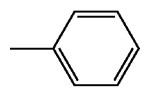 | 451 (M⁺ + 1) [ESI(Pos.)] |
| 2-295 | 7 | —(CH$_2$)$_3$— | —O— | 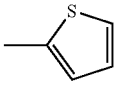 | 461 (M⁺ + 1) [ESI(Pos.)] |
| 2-296 | 8 | —(CH$_2$)$_3$— | —CH$_2$— | 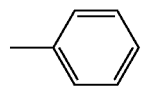 | 465 (M⁺ + 1) [ESI(Pos.)] |
| 2-297 | 8 | —(CH$_2$)$_9$— | —CH$_2$— | 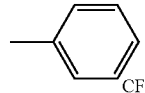 | 543 (M⁺ + 1) [ESI(Pos.)] |
| 2-298 | 7 | | —CH=CH$_2$— | 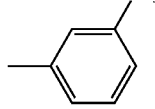 | 429 (M⁺ + 1) [ESI(Pos.)] |
| 2-299 | 7 | | —CH=CH$_2$— | 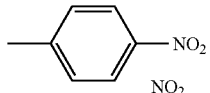 | 497 (M⁺ + 1) [ESI(Pos.)] |
| 2-300 | 7 | | —CH=CH$_2$— | 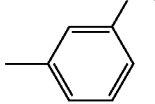 | 474 (M⁺ + 1) [ESI(Pos.)] |
| 2-301 | 8 | | —CH=CH$_2$— | 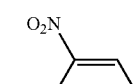 | 474 (M⁺ + 1) [ESI(Pos.)] |
| 2-302 | 8 | | —CH=CH$_2$— | 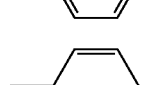 | 474 (M⁺ + 1) [ESI(Pos.)] |
| 2-303 | 7 | | —C(CH$_3$)=CH$_2$— |  | 443 (M⁺ + 1) [ESI(Pos.)] |
[*1]ESI: electronspray ionization
[*2]Diastereomer mixture

TABLE 3

| Compound No. | Example No. | R¹ᵃ | X¹ | X² | —Q²— | —Ar | MS*¹ [Ionization method] | Retention time (min) [Mobile phase] |
|---|---|---|---|---|---|---|---|---|
| 3-001*² | 1 | Me₂N–(NMe) | H | H | CH₂ | 4-OCF₃-C₆H₄– | 459(M⁺ + 1) [ESI(Pos.)] | 8.4 [C] |
| 3-002*⁵ | 1 | Me₂N–(NMe) | H | H | CH₂ | 2-biphenyl | 451(M⁺ + 1) [ESI(Pos.)] | |
| 3-003*²,⁵ | 1 | Me₂N–(NMe) | H | H | CH₂ | 2-biphenyl | 451(M⁺ + 1) [ESI(Pos.)] | 5.7 [J] |
| 3-004*⁵ | 1 | Me₂N–(NMe) | H | H | CH₂ | 1-naphthyl | 425(M⁺ + 1) [ESI(Pos.)] | |
| 3-005*⁵ | 1 | Me₂N–(NMe) | H | H | CH₂ | 2-naphthyl | 425(M⁺ + 1) [ESI(Pos.)] | |
| 3-006*⁶ | 1 | Me₂N–(NMe) | H | H | CH₂ | 4-Br-C₆H₄– | 425(M⁺ + 1) [ESI(Pos.)] | 4.6 [J] |
| 3-007*⁵ | 1 | piperidinyl | H | H | CH₂ | 2-biphenyl | 491(M⁺ + 1) [ESI(Pos.)] | 5.1 [O] |
| 3-008*⁵ | 1 | pyrrolidinyl | H | H | CH₂ | 2-biphenyl | 477(M⁺ + 1) [ESI(Pos.)] | 5.6 [R] |

TABLE 3-continued
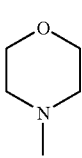
| Compound No. | Example No. | R[1a] | X[1] | X[2] | —Q[2]— | —Ar | MS[*1] [Ionization method] | Retention time (min) [Mobile phase] |
|---|---|---|---|---|---|---|---|---|
| 3-009[*5] | 1 | 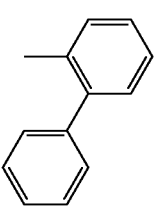 | H | H | $CH_2$ | 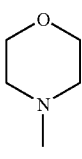 | 493($M^+$ + 1) [ESI(Pos.)] | |
| 3-010 | 1 | 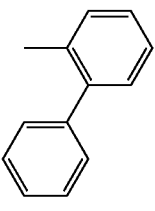 | H | H | $CH_2$ | 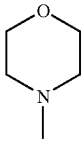 | 493($M^+$ + 1) [ESI(Pos.)] | 6.8 [C] |
| 3-011 | 19 | 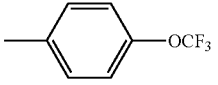 | 6-OMe | H | $CH_2$ | 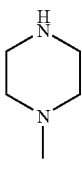 | 531($M^+$ + 1) [ESI(Pos.)] | 6.2 [C] |
| 3-012 | 34 | 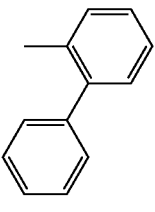 | H | H | $CH_2$ | 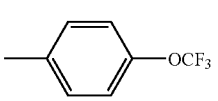 | 492($M^+$ + 1) [ESI(Pos.)] | 5.8 [J] |
| 3-013 | 20 | Cl | 6-OMe | H | $CH_2$ | 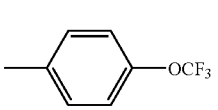 | 480($M^+$ + 1) [ESI(Pos.)] | 5.9 [B] |
| 3-014[*2] | 10 | Me | H | H | $CH_2$ | 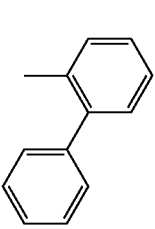 | 430($M^+$ + 1) [ESI(Pos.)] | 6.0 [C] |
| 3-015[*5] | 10 | Me | H | H | $CH_2$ | | 422($M^+$ + 1) [ESI(Pos.)] | 4.8 [J] |

TABLE 3-continued

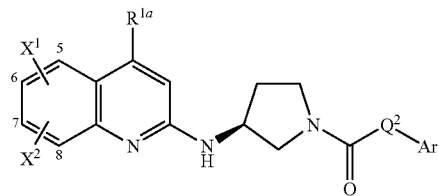

| Compound No. | Example No. | R1a | X1 | X2 | —Q2— | —Ar | MS*1 [Ionization method] | Retention time (min) [Mobile phase] |
|---|---|---|---|---|---|---|---|---|
| 3-016*5 | 10 | Me | H | H | CH2 | 1-naphthyl | 396(M+ + 1) [ESI(Pos.)] | |
| 3-017*5 | 10 | Me | H | H | CH2 | 2-naphthyl | 396(M+ + 1) [ESI(Pos.)] | |
| 3-018*5 | 10 | Me | H | H | CH2 | 4-Br-C6H4 | 424(M+ + 1) [ESI(Pos.)] | 6.3 [Q] |
| 3-019 | 20 | Me | 6-F | H | CH2 | 4-OCF3-C6H4 | 448(M+ + 1) [ESI(Pos.)] | 5.5 [C] |
| 3-020 | 20 | Me | 6-Cl | H | CH2 | 4-OCF3-C6H4 | 464(M+ + 1) [ESI(Pos.)] | 8.3 [C] |
| 3-021 | 20 | Me | 6-Me | H | CH2 | 4-OCF3-C6H4 | 444(M+ + 1) [ESI(Pos.)] | 7.4 [C] |
| 3-022 | 22 | Me | 6-OH | H | CH2 | 4-OCF3-C6H4 | 446(M+ + 1) [ESI(Pos.)] | 8.3 [E] |
| 3-023 | 20 | Me | 6-OMe | H | CH2 | 4-OCF3-C6H4 | 460(M+ + 1) [ESI(Pos.)] | 7.4 [C] |
| 3-024 | 21 | Me | 6-OMe | H | CH2 | 4-CF3-C6H4 | 444(M+ + 1) [ESI(Pos.)] | 14.7 [E] |
| 3-025 | 21 | Me | 6-OMe | H | CH2 | 3,4-diCl-C6H3 | 444(M+ + 1) [ESI(Pos.)] | 5.4 [C] |
| 3-026 | 20 | Me | 6-OCF3 | H | CH2 | 4-OCF3-C6H4 | 514(M+ + 1) [ESI(Pos.)] | 7.1 [B] |

TABLE 3-continued

| Compound No. | Example No. | R^1a | X^1 | X^2 | —Q^2— | —Ar | MS*1 [Ionization method] | Retention time (min) [Mobile phase] |
|---|---|---|---|---|---|---|---|---|
| 3-027 | 20 | Me | 6-OH | 7-iPr | CH$_2$ | —C$_6$H$_4$—OCF$_3$ | 488(M$^+$ + 1) [ESI(Pos.)] | 5.8 [B] |
| 3-028 | 20 | Me | 6-iPr | H | CH$_2$ | —C$_6$H$_4$—OCF$_3$ | 472(M$^+$ + 1) [ESI(Pos.)] | 8.1 [B] |
| 3-029*4 | 39 | Et | H | H | CH$_2$ | —C$_6$H$_4$—OCF$_3$ | 444(M$^+$ + 1) [ESI(Pos.)] | |
| 3-030*4 | 39 | iPr | H | H | CH$_2$ | —C$_6$H$_4$—OCF$_3$ | 458(M$^+$ + 1) [ESI(Pos.)] | |
| 3-031 | 24 | OMe | H | H | CH$_2$ | —C$_6$H$_4$—OCF$_3$ | 446(M$^+$ + 1) [ESI(Pos.)] | 6.4 [C] |
| 3-032 | 24 | OMe | 6-F | H | CH$_2$ | —C$_6$H$_4$—OCF$_3$ | 464(M$^+$ + 1) [ESI(Pos.)] | 6.5 [C] |
| 3-033 | 24 | OMe | 6-Cl | H | CH$_2$ | —C$_6$H$_4$—OCF$_3$ | 480(M$^+$ + 1) [ESI(Pos.)] | 10.2 [C] |
| 3-034 | 24 | OMe | 6-Me | H | CH$_2$ | —C$_6$H$_4$—OCF$_3$ | 460(M$^+$ + 1) [ESI(Pos.)] | 9.1 [C] |
| 3-035 | 24 | OMe | 6-OMe | H | CH$_2$ | —C$_6$H$_4$—OCF$_3$ | 476(M$^+$ + 1) [ESI(Pos.)] | 6.6 [C] |
| 3-036*2 | 36 | CONMe$_2$ | H | H | CH$_2$ | —C$_6$H$_4$—OCF$_3$ | 487(M$^+$ + 1) [ESI(Pos.)] | |
| 3-037 | 22 | Me | 6-OH | H | C(Me)$_2$ | —C$_6$H$_4$—Cl | 424(M$^+$ + 1) [ESI(Pos.)] | 5.9 [E] |
| 3-038 | 22 | Me | 6-OH | H | cyclopropylidene | —C$_6$H$_4$—Cl | 422(M$^+$ + 1) [ESI(Pos.)] | 5.3 [E] |
| 3-039 | 22 | Me | 6-OH | H | bicyclo[1.1.1]pentyl | —C$_6$H$_4$—Cl | 436(M$^+$ + 1) [ESI(Pos.)] | 5.3 [E] |

TABLE 3-continued

| Compound No. | Example No. | R¹ᵃ | X¹ | X² | —Q²— | —Ar | MS[*1] [Ionization method] | Retention time (min) [Mobile phase] |
|---|---|---|---|---|---|---|---|---|
| 3-040 | 26 | Me | 6-OH | H |  | 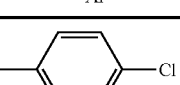 | 410(M⁺ + 1) [ESI(Pos.)] | 5.5 [E] |
| 3-041 | 21 | Me | 6-OMe | H |  |  | 438(M⁺ + 1) [ESI(Pos.)] | 6.6 [C] |
| 3-042 | 21 | Me | 6-OMe | H | 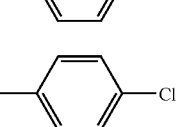 |  | 436(M⁺ + 1) [ESI(Pos.)] | 10.7 [E] |
| 3-043 | 21 | Me | 6-OMe | H |  | 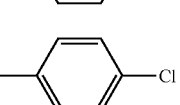 | 450(M⁺ + 1) [ESI(Pos.)] | 8.3 [C] |
| 3-044 | 25 | Me | 6-OMe | H |  |  | 424(M⁺ + 1) [ESI(Pos.)] | 5.0 [C] |
| 3-045 | 21 | OMe | 6-Me | H | 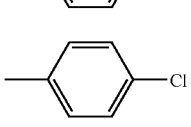 |  | 438(M⁺ + 1) [ESI(Pos.)] | 12.2 [C] |
| 3-046 | 21 | OMe | 6-Me | H |  | 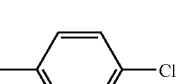 | 436(M⁺ + 1) [ESI(Pos.)] | 9.9 [C] |
| 3-047 | 21 | OMe | 6-Me | H |  |  | 450(M⁺ + 1) [ESI(Pos.)] | 6.0 [B] |
| 3-048 | 25 | OMe | 6-Me | H | 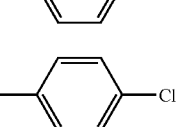 |  | 424(M⁺ + 1) [ESI(Pos.)] | 8.9 [C] |
| 3-049 | 20 | Me | 6-OEt | H | CH₂ |  | 474(M⁺ + 1) [ESI(Pos.)] | 6.6 [J] |
| 3-050 | 21 | Me | 6-OMe | H | 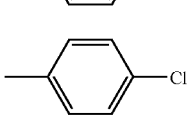 |  | 486(M⁺ + 1) [ESI(Pos.)] | 7.8 [C] |

[*1]ESI: electrospray ionization
[*2]Mono-HCl salt
[*3]Di-HCl salt
[*4]Mono-PhSO₃H salt
[*5]Racemic mixtuer TABLE 4
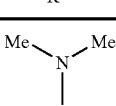
| Compound No. | Example No. | $R^{1b}$ | $X^3$ | $X^4$ | —Ar | MS[*1] [Ionization method] | Retention time (min) [Mobile phase] |
|---|---|---|---|---|---|---|---|
| 4-001[*2,6] | 1 | Me₂N— | H | H | 2-biphenyl | 402(M⁺ + 1) [ESI(Pos.)] | |
| 4-002[*2,6] | 1 | Me₂N— | H | H | 1-naphthyl | 376(M⁺ + 1) [ESI(Pos.)] | |
| 4-003[*6] | 1 | Me₂N— | H | H | 2-naphthyl | 376(M⁺ + 1) [ESI(Pos.)] | |
| 4-004[*6] | 1 | Me₂N— | H | H | 4-Br-C₆H₄ | 426(M⁺ + Na) [ESI(Pos.)] | |
| 4-005[*2] | 1 | Me₂N— | H | Me | 2-biphenyl | 416(M⁺ + 1) [ESI(Pos.)] | 7.0 [E] |
| 4-006[*2] | 11 | Me₂N— | H | Me | 4-OCF₃-C₆H₄ | 424(M⁺ + 1) [ESI(Pos.)] | 6.9 [K] |
| 4-007[*4] | 5-1 | Me₂N— | H | Me | 3-OPh-C₆H₄ | 432(M⁺ + 1) [ESI(Pos.)] | 7.1 [C] |
| 4-008[*4] | 5-1 | Me₂N— | H | Me | 3,5-(OMe)₂-C₆H₃ | 400(M⁺ + 1) [ESI(Pos.)] | 6.8 [F] |

TABLE 4-continued

| Compound No. | Example No. | R^1b | X^3 | X^4 | —Ar | MS*1 [Ionization method] | Retention time (min) [Mobile phase] |
|---|---|---|---|---|---|---|---|
| 4-009*2 | 11 | Me₂N–(Me) | H | Me | 3,4-dichlorophenyl | 408(M⁺ + 1) [ESI(Pos.)] | 6.3 [K] |
| 4-010 | 11 | Me₂N–(Me) | H | Et | 4-OCF₃-phenyl | 438(M⁺ + 1) [ESI(Pos.)] | |
| 4-011*2,6 | 1 | Me₂N–(Me) | H | Ph | 2-biphenyl | 478(M⁺ + 1) [ESI(Pos.)] | |
| 4-012 | 11 | Me₂N–(Me) | Me | H | 4-OCF₃-phenyl | 424(M⁺ + 1) [ESI(Pos.)] | |
| 4-013 | 11 | NH₂ | H | Me | 4-OCF₃-phenyl | 396(M⁺ + 1) [ESI(Pos.)] | |
| 4-014 | 11 | HN(Me)– | H | Me | 4-OCF₃-phenyl | 410(M⁺ + 1) [ESI(Pos.)] | |
| 4-015*3 | 1 | HN(Me)– | H | Me | 3,4-dichlorophenyl | 394(M⁺ + 1) [ESI(Pos.)] | 5.4 [K] |
| 4-016*4 | 1 | HN–CH₂CH₂OH | H | Me | 4-OCF₃-phenyl | 440(M⁺ + 1) [ESI(Pos.)] | 8.5 [M] |
| 4-017 | 11 | Et₂CH–NH– | H | Me | 4-OCF₃-phenyl | 466(M⁺ + 1) [ESI(Pos.)] | |
| 4-018 | 1 | HN–CH₂-(3-pyridyl) | H | Me | 4-OCF₃-phenyl | 487(M⁺ + 1) [ESI(Pos.)] | 6.3 [J] |

TABLE 4-continued
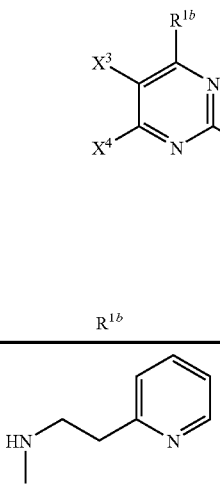
| Compound No. | Example No. | R$^{1b}$ | X$^3$ | X$^4$ | —Ar | MS*1 [Ionization method] | Retention time (min) [Mobile phase] |
|---|---|---|---|---|---|---|---|
| 4-019*4 | 1 | 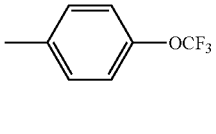 | H | Me | 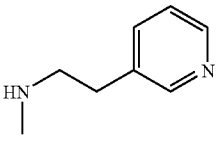 | 501(M$^+$ + 1) [ESI(Pos.)] | 11.0 [G] |
| 4-020 | 1 | 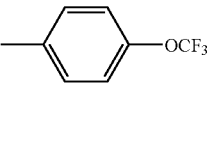 | H | Me | 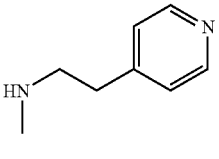 | 501(M$^+$ + 1) [ESI(Pos.)] | |
| 4-021 | 5-1 | 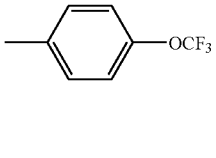 | H | Me | 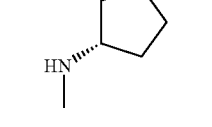 | 501(M$^+$ + 1) [ESI(Pos.)] | |
| 4-022 | 1 | 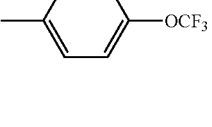 | H | Me | 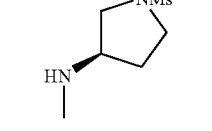 | 543(M$^+$ + 1) [ESI(Pos.)] | 7.1 [E] |
| 4-023 | 1 | 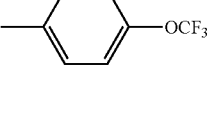 | H | Me | 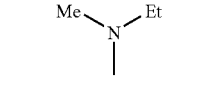 | 543(M$^+$ + 1) [ESI(Pos.)] | 6.9 [E] |
| 4-024 | 11 | 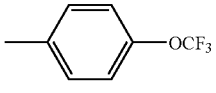 | H | Me | 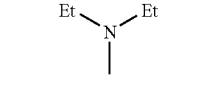 | 438(M$^+$ + 1) [ESI(Pos.)] | |
| 4-025 | 5 | 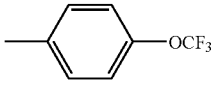 | H | Me | 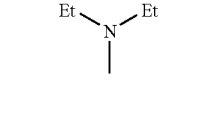 | 452(M$^+$ + 1) [ESI(Pos.)] | |
| 4-026*5 | 5 | 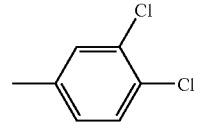 | H | Me | 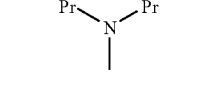 | 436(M$^+$ + 1) [ESI(Pos.)] | |
| 4-027 | 11 | 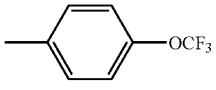 | H | Me | 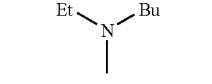 | 480(M$^+$ + 1) [ESI(Pos.)] | |
| 4-028 | 11 | 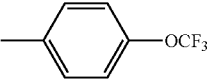 | H | Me | | 480(M$^+$ + 1) [ESI(Pos.)] | |

TABLE 4-continued

| Compound No. | Example No. | R^1b | X^3 | X^4 | —Ar | MS*1 [Ionization method] | Retention time (min) [Mobile phase] |
|---|---|---|---|---|---|---|---|
| 4-029 | 11 | Et-N(Me)-Bn | H | Me | -C6H4-OCF3 | 514(M+ + 1) [ESI(Pos.)] | |
| 4-030 | 11 | Me-N(Me)-CH2CH2Ph | H | Me | -C6H4-OCF3 | 514(M+ + 1) [ESI(Pos.)] | |
| 4-031 | 1 | Me-N(Me)-CH2-(3-pyridyl) | H | Me | -C6H4-OCF3 | 501(M+ + 1) [ESI(Pos.)] | 6.1 [F] |
| 4-032 | 1 | Me-N(Me)-C(O)-(3-pyridyl) | H | Me | -C6H4-OCF3 | 515(M+ + 1) [ESI(Pos.)] | 7.1 [C] |
| 4-033 | 11 | Et-N(Me)-CH2CH2-OMe | H | Me | -C6H4-OCF3 | 482(M+ + 1) [ESI(Pos.)] | 8.9 [K] |
| 4-034 | 11 | Et-N(Me)-CH2CH2-OPh | H | Me | -C6H4-OCF3 | 544(M+ + 1) [ESI(Pos.)] | |
| 4-035 | 11 | cPrCH2-N(Me)-Pr | H | Me | -C6H4-OCF3 | 492(M+ + 1) [ESI(Pos.)] | 5.6 [I] |
| 4-036 | 11 | cPrCH2-N(Me)-Pr | Me | Me | -C6H4-OCF3 | 506(M+ + 1) [ESI(Pos.)] | |
| 4-037 | 5 | cPrCH2-N(Me)-Pr | F | Me | -C6H4-OCF3 | 510(M+ + 1) [ESI(Pos.)] | |
| 4-038 | 11 | cPrCH2-N(Me)-Pr | H | Pr | -C6H4-OCF3 | 520(M+ + 1) [ESI(Pos.)] | |
| 4-039 | 11 | pyrrolidin-1-yl | H | Me | -C6H4-OCF3 | 450(M+ + 1) [ESI(Pos.)] | |

TABLE 4-continued

| Compound No. | Example No. | R¹ᵇ | X³ | X⁴ | —Ar | MS*¹ [Ionization method] | Retention time (min) [Mobile phase] |
|---|---|---|---|---|---|---|---|
| 4-040 | 11 | 1-methylpiperidin-4-yl | H | Me | 4-(trifluoromethoxy)phenyl | 464(M⁺ + 1) [ESI(Pos.)] | |
| 4-041 | 11 | 1-methylpiperidine-4-carboxamide | H | Me | 2-methyl-4'-(trifluoromethoxy)biphenyl | 583(M⁺ + 1) [ESI(Pos.)] | |
| 4-042*⁴ | 11 | 1-methylpiperidine-4-carboxamide | H | Me | 4-(trifluoromethoxy)phenyl | 507(M⁺ + 1) [ESI(Pos.)] | 7.8 [K] |
| 4-043*² | 1 | 1-methylpiperidine-4-CONMe₂ | H | Me | 4-(trifluoromethoxy)phenyl | 535(M⁺ + 1) [ESI(Pos.)] | 11.0 [E] |
| 4-044 | 11 | 4-morpholinyl (N-methyl) | H | Me | 4-(trifluoromethoxy)phenyl | 466(M⁺ + 1) [ESI(Pos.)] | 14.0 [M] |
| 4-045*³,⁶ | 3 | 4-methylpiperazin-1-yl | Me | H | 2-phenylphenyl | 457(M⁺ + 1) [ESI(Pos.)] | |

TABLE 4-continued
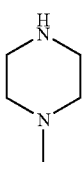
| Compound No. | Example No. | R<sup>1b</sup> | X³ | X⁴ | —Ar | MS*1 [Ionization method] | Retention time (min) [Mobile phase] |
|---|---|---|---|---|---|---|---|
| 4-046*3,6 | 3 | 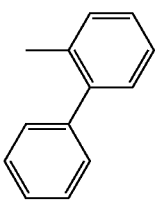 | H | Me | 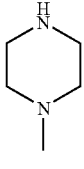 | 457(M⁺ + 1) [ESI(Pos.)] | 3.1 [F] |
| 4-047*3 | 3 | 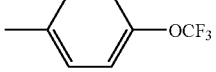 | H | Me | 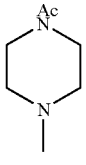 | 465(M⁺ + 1) [ESI(Pos.)] | 4.9 [J] |
| 4-048 | 1 | 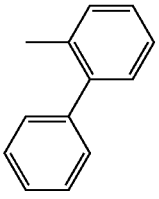 | H | Me | 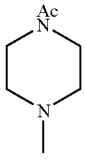 | 499(M⁺ + 1) [ESI(Pos.)] | 9.1 [M] |
| 4-049*4 | 11 | 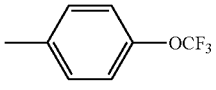 | H | Me | 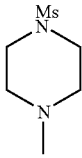 | 507(M⁺ + 1) [ESI(Pos.)] | 9.0 [K] |
| 4-050*4 | 11 | 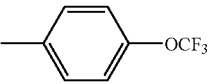 | H | Me | 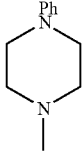 | 543(M⁺ + 1) [ESI(Pos.)] | 13.8 [K] |
| 4-051 | 1 | 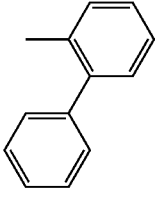 | H | Me |  | 533(M⁺ + 1) [ESI(Pos.)] | 10.1 [J] |

TABLE 4-continued
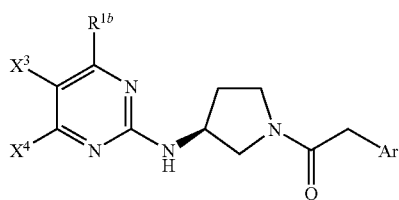
| Compound No. | Example No. | R¹ᵇ | X³ | X⁴ | —Ar | MS*¹ [Ionization method] | Retention time (min) [Mobile phase] |
|---|---|---|---|---|---|---|---|
| 4-052 | 11 | 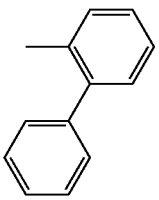 | H | Me | 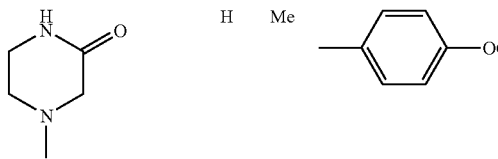 | 471(M⁺ + 1) [ESI(Pos.)] | 6.8 [M] |
| 4-053 | 11 | 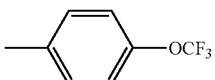 | H | Me | 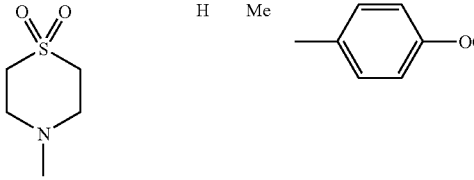 | 479(M⁺ + 1) [ESI(Pos.)] | 11.6 [N] |
| 4-054 | 1 | 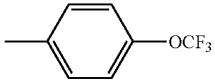 | H | Me | 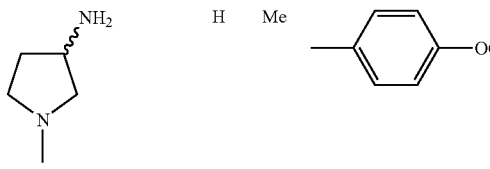 | 514(M⁺ + 1) [ESI(Pos.)] | 6.4 [E] |
| 4-055*³,⁷ | 3 | 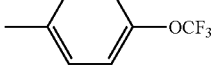 | H | Me | 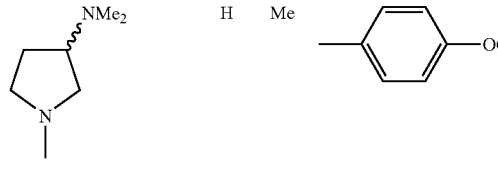 | 465(M⁺ + 1) [ESI(Pos.)] | |
| 4-056*⁴,⁷ | 1 | 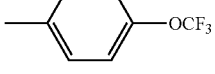 | H | Me | 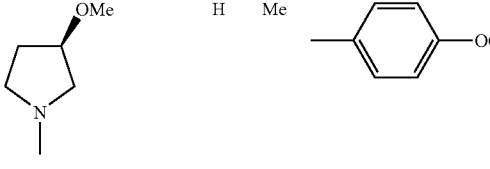 | 493(M⁺ + 1) [ESI(Pos.)] | 27.9 [H] |
| 4-057 | 1 | 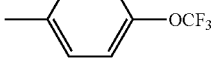 | H | Me | 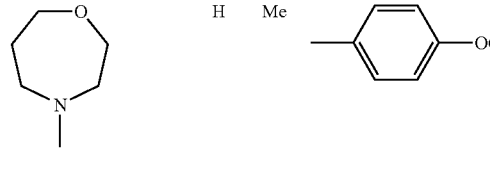 | 480(M⁻ + 1) [ESI(Pos.)] | 4.9 [C] |
| 4-058 | 2 | 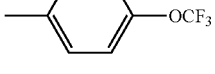 | H | Me | 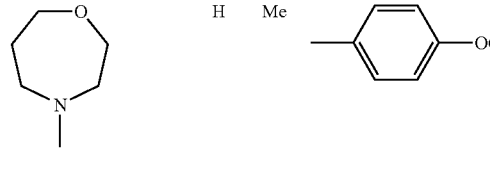 | 480(M⁻ + 1) [ESI(Pos.)] | 9.4 [E] |

TABLE 4-continued

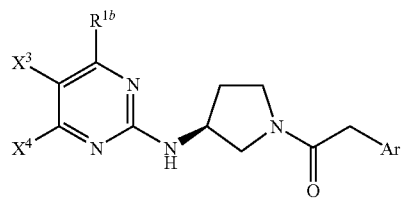

| Compound No. | Example No. | $R^{1b}$ | $X^3$  $X^4$ | —Ar | MS[*1] [Ionization method] | Retention time (min) [Mobile phase] |
|---|---|---|---|---|---|---|
| 4-059[*2,6] | 1 | Me-N(Me)- | —(CH$_2$)$_4$— | 2-biphenyl | 456(M$^-$ + 1) [ESI(Pos.)] |  |
| 4-060[*2,6] | 1 | Me-N(Me)- | —(CH$_2$)$_4$— | 1-naphthyl | 430(M$^+$ + 1) [ESI(Pos.)] |  |
| 4-061[*2,6] | 1 | Me-N(Me)- | —(CH$_2$)$_4$— | 2-naphthyl | 430(M$^+$ + 1) [ESI(Pos.)] |  |
| 4-062[*2,6] | 1 | Me-N(Me)- | —(CH$_2$)$_4$— | 4-Br-phenyl | 458(M$^+$ + 1) [ESI(Pos.)] |  |
| 4-063 | 11 | cyclopropylmethyl-N(Me)-Pr | —(CH$_2$)$_3$— | 4-OCF$_3$-phenyl | 518(M$^+$ + 1) [ESI(Pos.)] | 5.9 [I] |
| 4-064 | 11 | cyclopropylmethyl-N(Me)-Pr | —(CH$_2$)$_4$— | 4-OCF$_3$-phenyl | 532(M$^+$ + 1) [ESI(Pos.)] |  |
| 4-065[*6] | 3 | 4-methylpiperazinyl | —(CH$_2$)$_4$— | 2-biphenyl | 497(M$^+$ + 1) [ESI(Pos.)] | 16.0 [G] |

[*1]ESI: electrospray ionization
[*2]Mono-HCl salt
[*3]Di-HCl salt
[*4]Mono-maleate
[*5]Mono-benzenesulfonate
[*6]Racemic mixture
[*7]Diastereomer mixture

TABLE 5

| Compound No. | Example No. | R^(1b) | X^3 | X^4 | R^1 | —Ar | MS*1 [Ionization method] | Retention time (min) [Mobile phase] |
|---|---|---|---|---|---|---|---|---|
| 5-001 | 13 | Me\N/Me (NMe) | H | Me | H | —C6H4—OCF3 | 423(M+ + 1) [ESI(Pos.)] | 6.3 [K] |
| 5-002 | 16 | Me\N/Me (NMe) | H | Me | Me | —C6H4—OCF3 | 437(M+ + 1) [ESI(Pos.)] | 5.0 [C] |
| 5-003 | 14 | morpholino | H | Me | H | —C6H4—OCF3 | 465(M+ + 1) [ESI(Pos.)] | 7.3 [E] |
| 5-004 | 16 | morpholino | H | Me | Me | —C6H4—OCF3 | 479(M+ + 1) [ESI(Pos.)] | 11.0 [E] |
| 5-005 | 16 | thiomorpholino | H | Me | H | —C6H4—OCF3 | 481(M+ + 1) [ESI(Pos.)] | 9.4 [C] |
| 5-006 | 17 | 1,1-dioxothiomorpholino | H | Me | H | —C6H4—OCF3 | 513(M+ + 1) [ESI(Pos.)] | 6.0 [E] |
| 5-007 | 14 | pyrrolidin-1-yl | H | Me | H | —C6H4—OCF3 | 449(M+ + 1) [ESI(Pos.)] | 8.3 [C] |
| 5-008 | 16 | piperidin-1-yl | H | Me | H | —C6H4—OCF3 | 463(M+ + 1) [ESI(Pos.)] | 12.3 [C] |

TABLE 5-continued
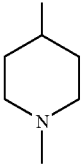
| Compound No. | Example No. | R^{1b} | X^3 | X^4 | R^1 | —Ar | MS*1 [Ionization method] | Retention time (min) [Mobile phase] |
|---|---|---|---|---|---|---|---|---|
| 5-009 | 14 | 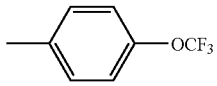 | H | Me | H | 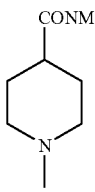 | 477(M+ + 1) [ESI(Pos.)] | 7.5 [B] |
| 5-010 | 14 | 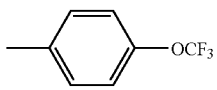 | H | Me | H | 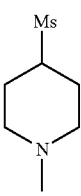 | 534(M+ + 1) [ESI(Pos.)] | 8.5 [E] |
| 5-011 | 14 | 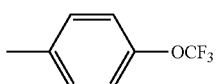 | H | Me | H | 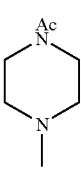 | 541(M+ + 1) [ESI(Pos.)] | 7.1 [E] |
| 5-012 | 14 | 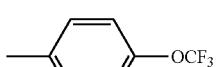 | H | Me | H | 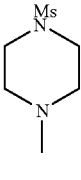 | 506(M+ + 1) [ESI(Pos.)] | 4.8 [E] |
| 5-013 | 14 | 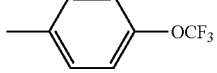 | H | Me | H | 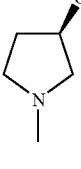 | 542(M+ + 1) [ESI(Pos.)] | 8.2 [E] |
| 5-014 | 14 | 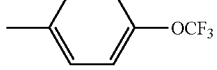 | H | Me | H |  | 479(M+ + 1) [FAB(Pos.)] | 5.0 [C] |
| 5-015*2 | 18 | Me | H | Me | H | 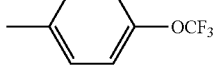 | 394(M+ + 1) [ESI(Pos.)] | |

TABLE 5-continued

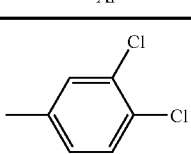

| Compound No. | Example No. | R[1b] | X[3] | X[4] | R[1] | —Ar | MS[*1] [Ionization method] | Retention time (min) [Mobile phase] |
|---|---|---|---|---|---|---|---|---|
| 5-016[*2] | 18 | Me | H | Me | H | 3,4-dichlorophenyl | 378(M[+] + 1) [ESI(Pos.)] | |
| 5-017 | 21 | CF₃ | H | Me | H | 4-OCF₃-phenyl | 448(M[+] + 1) [ESI(Pos.)] | |
| 5-018 | 15 | Cl | H | Me | H | 4-OCF₃-phenyl | 414(M[+] + 1) [ESI(Pos.)] | 6.9 [C] |
| 5-019 | 16 | N-methylmorpholine | H | Me | H | 2-biphenyl | 457(M[+] + 1) [ESI(Pos.)] | |
| 5-020 | 13 | N-methylmorpholine | H | Me | H | 2-PhO-phenyl | 473(M[+] + 1) [ESI(Pos.)] | |
| 5-021 | 13 | N-methylmorpholine | H | Me | H | 4-Me-phenyl | 395(M[+] + 1) [ESI(Pos.)] | |
| 5-022 | 13 | N-methylmorpholine | H | Me | H | 4-CF₃-phenyl | 449(M[+] + 1) [ESI(Pos.)] | |
| 5-023 | 13 | N-methylmorpholine | H | Me | H | 4-OMe-phenyl | 411(M[+] + 1) [ESI(Pos.)] | |

[*1]ESI: electronspray ionization, FAB: fast atom bombardment
[*2]Racemic mixtuer

TABLE 6

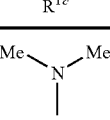

| Compound No. | Example No. | R<sup>1c</sup> | X⁵ | X⁶ | Z¹ | —Ar | MS*¹ [Ionization method] | Retention time (min) [Mobile phase] |
|---|---|---|---|---|---|---|---|---|
| 6-001*² | 27 | Me₂N–CH₂– (Me-N(Me)-CH₂–) | H | H | H | 4-OCF₃-C₆H₄– | 466(M⁺ + 1) [ESI(Pos.)] | 6.5 [C] |
| 6-002 | 27 | cyclopropyl-CH₂-N(Ph)-CH(Me)– | H | H | H | 4-OCF₃-C₆H₄– | 534(M⁺ + 1) [ESI(Pos.)] | |
| 6-003*² | 27 | morpholinomethyl | H | H | H | 4-OCF₃-C₆H₄– | 508(M⁺ + 1) [ESI(Pos.)] | 7.8 [C] |
| 6-004 | 27 | Me₂N-CH₂– | H | Me | H | 4-OCF₃-C₆H₄– | 480(M⁺ + 1) [ESI(Pos.)] | 13.0 [C] |
| 6-005 | 27 | Me–CH< | H | H | H | 4-OCF₃-C₆H₄– | 437(M⁺ + 1) [ESI(Pos.)] | 7.9 [A] |
| 6-006 | 27 | OEt–CH< | H | H | H | 4-OCF₃-C₆H₄– | 467(M⁺ + 1) [ESI(Pos.)] | 9.1 [B] |
| 6-007 | 27 | HO-CH₂CH₂-O-CH₂– | H | H | H | 4-OCF₃-C₆H₄– | 483(M⁺ + 1) [ESI(Pos.)] | 9.5 [E] |
| 6-008 | 27 | HO-CH< | H | H | H | 4-OCF₃-C₆H₄– | 439(M⁺ + 1) [ESI(Pos.)] | 7.4 [B] |
| 6-009 | 27 | 4-acetylpiperazin-1-yl-methyl | H | H | H | 4-OCF₃-C₆H₄– | 549(M⁺ + 1) [ESI(Pos.)] | |
| 6-010*² | 27 | HO-CH₂CH₂-N(H)-CH< | H | H | H | 4-OCF₃-C₆H₄– | 482(M⁺ + 1) [ESI(Pos.)] | |

TABLE 6-continued

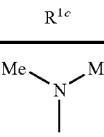

| Compound No. | Example No. | R1c | X5 | X6 | Z1 | —Ar | MS*1 [Ionization method] | Retention time (min) [Mobile phase] |
|---|---|---|---|---|---|---|---|---|
| 6-011 | 29 | Me-N(Me)-Me | Me | H | H | 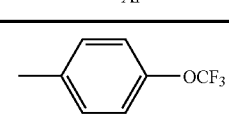 | 480(M+ + 1) [ESI(Pos.)] | 6.9 [C] |
| 6-012 | 29 | Me-N(Me)-Me | Me | H | OH | 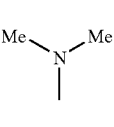 | 496(M+ + 1) [ESI(Pos.)] | 9.1 [E] |
| 6-013 | 32 | Me-N(Me)-Me | —C=C—C=C— | | H | 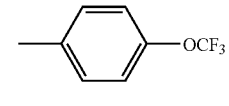 | 516(M+ + 1) [ESI(Pos.)] | |

*1ESI: electronspray ionization
*2Mono-maleate

TABLE 7

| Compound No. | Example No. | R1c | X5 | X6 | Z1 | —Ar | MS*1 [Ionization method] | Retention time (min) [Mobile phase] |
|---|---|---|---|---|---|---|---|---|
| 7-001 | 30 | Me-N(Me)-Me | Me | H | H | 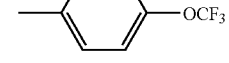 | 479(M+ + 1) [ESI(Pos.)] | 8.0 [C] |
| 7-002 | 30 | 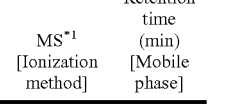 | H | H | H |  | 583(M+ + 1) [ESI(Pos.)] | 10.2 [E] |
| 7-003 | 30 | 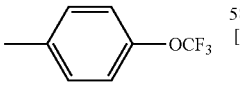 | H | H | H | 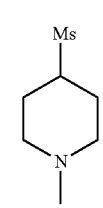 | 507(M− + 1) [ESI(Pos.)] | 5.5 [C] |

TABLE 7-continued

| Compound No. | Example No. | R$^{1c}$ | X$^5$ | X$^6$ | Z$^1$ | —Ar | MS*1 [Ionization method] | Retention time (min) [Mobile phase] |
|---|---|---|---|---|---|---|---|---|
| 7-004 | 30 | 4-Ac-piperazin-1-yl | H | H | H | 4-OCF$_3$-C$_6$H$_4$- | 548(M$^-$ + 1) [ESI(Pos.)] | 8.1 [E] |
| 7-005 | 32 | N(Me)-CH(Me)$_2$ (Me,N,Me with Me below N) | H | H | H | 4-OCF$_3$-C$_6$H$_4$- | 465(M$^-$ + 1) [ESI(Pos.)] | |
| 7-006 | 31 | NHMe | H | H | H | 4-OCF$_3$-C$_6$H$_4$- | 436(M$^+$ + 1) [ESI(Pos.)] | 5.6 [C] |
| 7-007 | 30 | 4-morpholinyl (N-Me) | H | H | OH | 4-OCF$_3$-C$_6$H$_4$- | 523(M$^+$ + 1) [ESI(Pos.)] | 10.6 [E] |
| 7-008 | 30 | 4-Ac-piperazin-1-yl | H | H | OH | 4-OCF$_3$-C$_6$H$_4$- | 564(M$^+$ + 1) [ESI(Pos.)] | 6.3 [E] |
| 7-009 | 30 | 3-(NHMe)-1-(NMs)-pyrrolidinyl | H | H | H | 4-OCF$_3$-C$_6$H$_4$- | 584(M$^+$ + 1) [ESI(Pos.)] | 11.4 [E] |
| 7-010 | 30 | N(Me)-CH(Me)$_2$ | Me | H | OH | 4-OCF$_3$-C$_6$H$_4$- | 495(M$^+$ + 1) [ESI(Pos.)] | 9.1 [C] |

*1ESI: electrospray ionization

TABLE 8

| Compound No. | Example No. | R¹ᶜ | X⁵ | X⁶ | Z¹ | —Ar | MS*¹ [Ionization method] | Retention time (min) [Mobile phase] |
|---|---|---|---|---|---|---|---|---|
| 8-001 | 27 | Me\N/Me | H | H | H | 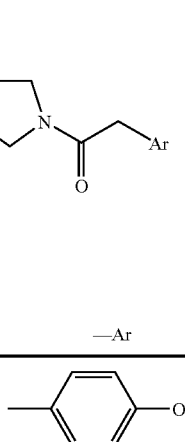 | 466(M⁺ + 1) [ESI(Pos.)] | 15.3 [E] |
| 8-002*² | 27 | HN(Me)CH₂CH₂OH | H | H | H | 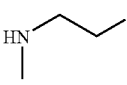 | 482(M⁺ + 1) [ESI(Pos.)] | |
| 8-003 | 28 | 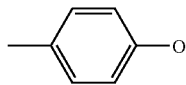 | H | H | H | 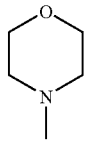 | 508(M⁺ + 1) [ESI(Pos.)] | 9.2 [E] |
| 8-004 | 28 | 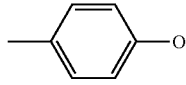 (N-Ac piperazine) | H | H | H | 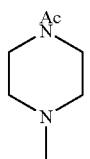 | 549(M⁺ + 1) [ESI(Pos.)] | 5.5 [E] |
| 8-005 | 28 | 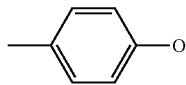 (Ms piperidine) | H | H | H | 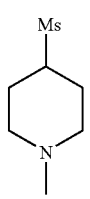 | 584(M⁺ + 1) [ESI(Pos.)] | 8.4 [E] |
| 8-006 | 28 | 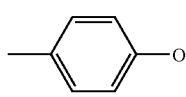 (morpholine) | H | H | OH | 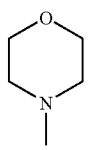 | 524(M⁺ + 1) [ESI(Pos.)] | 7.5 [E] |
| 8-007 | 28 | 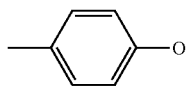 (N-Ac piperazine) | H | H | OH | 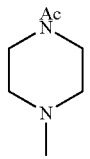 | 565(M⁺ + 1) [ESI(Pos.)] | 5.0 [E] |
| 8-008 | 28 | Me\N/Me | H | H | OH | 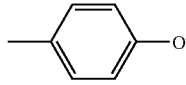 | 482(M⁺ + 1) [ESI(Pos.)] | 7.2 [E] |

*¹ESI: electrospray ionization
*²Mono-maleate

TABLE 9

| Compound No. | Example No. | R^1c | X^5 | X^6 | Z^1 | —Ar | MS*1 [Ionization method] | Retention time (min) [Mobile phase] |
|---|---|---|---|---|---|---|---|---|
| 9-001 | 32 | Me-N(Me)-Me | H | H | H | -C6H4-OCF3 | 465(M^+ + 1) [ESI(Pos.)] | |
| 9-002 | 30 | morpholinyl | H | H | H | -C6H4-OCF3 | 507(M^+ + 1) [ESI(Pos.)] | 14.2 [E] |
| 9-003 | 30 | morpholinyl | H | H | OH | -C6H4-OCF3 | 523(M^+ + 1) [ESI(Pos.)] | 9.8 [E] |
| 9-004 | 31 | Me | H | H | H | -C6H4-OCF3 | 436(M^+ + 1) [ESI(Pos.)] | 11.2 [E] |

*1 ESI: electronspray ionization

TABLE 10

| Compound No. | Example No. | R^1c | X^5 | X^6 | Z^1 | —Ar | MS*1 [Ionization method] | Retention time (min) [Mobile phase] |
|---|---|---|---|---|---|---|---|---|
| 10-001 | 27 | Me-N(Me)-Me | Me | H | H | -C6H4-OCF3 | 480(M^+ + 1) [ESI(Pos.)] | 7.3 [E] |
| 10-002 | 27 | Me-N(Me)-Me | H | H | H | -C6H4-OCF3 | 466(M^+ + 1) [ESI(Pos.)] | 15.3 [C] |

*1 ESI: electronspray ionization

TABLE 11

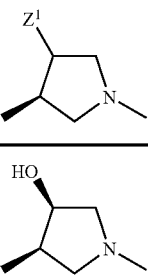

| Compound No. | Example No. | R^{1a} | X^1 | Z^1 | MS*[1] [Ionization method] | Retention time (min) [Mobile phase] |
|---|---|---|---|---|---|---|
| 11-001 | 1 | Me-N(Me)- | H | (HO, trans-3-hydroxy-4-methyl-N-methylpyrrolidine) | 476(M⁺ + 1) [ESI(Pos.)] | 4.4 [C] |
| 11-002 | 1 | Me-N(Me)- | H | (HO, trans-3-hydroxy-4-methyl-N-methylpyrrolidine) | 476(M⁺ + 1) [ESI(Pos.)] | 4.4 [C] |
| 11-003 | 1 | 1-methyl-4-(CONMe₂)piperidin-4-yl | H | (HO-pyrrolidine) | 587(M⁺ + 1) [ESI(Pos.)] | 11.8 [E] |
| 11-004 | 1 | 4-Ac-1-methylpiperazin-... | H | (HO-pyrrolidine) | 559(M⁺ + 1) [ESI(Pos.)] | 6.5 [C] |
| 11-005 | 1 | morpholin-4-yl | H | (HO-pyrrolidine) | 518(M⁺ + 1) [ESI(Pos.)] | 4.2 [C] |
| 11-006 | 1 | 1-methyl-4-(CONMe₂)piperidin-4-yl | 6-F | (HO-pyrrolidine) | 605(M⁺ + 1) [ESI(Pos.)] | 5.1 [C] |
| 11-007 | 1 | 4-Ac-1-methylpiperazin-... | 6-F | (HO-pyrrolidine) | 577(M⁺ + 1) [ESI(Pos.)] | 7.1 [E] |

TABLE 11-continued

| Compound No. | Example No. | R^{1a} | X^1 | Z^1 | MS*1 [Ionization method] | Retention time (min) [Mobile phase] |
|---|---|---|---|---|---|---|
| 11-008 | 1 | | 6-Cl | | 629(M⁺ + 1) [ESI(Pos.)] | 5.9 [C] |
| 11-009 | 1 | | 6-Cl | | 552(M⁺ + 1) [ESI(Pos.)] | 7.1 [C] |
| 11-010 | 1 | | 6-Cl | | 628(M⁺ + 1) [ESI(Pos.)] | 13.9 [E] |
| 11-011 | 1 | | 6-Cl | | 593(M⁺ + 1) [ESI(Pos.)] | 11.5 [E] |
| 11-012 | 1 | | 6-OMe | | 625(M⁺ + 1) [ESI(Pos.)] | 15.6 [E] |
| 11-013 | 1 | | 6-OMe | | 548(M⁺ + 1) [ESI(Pos.)] | 15.3 [C] |
| 11-014 | 1 | | 6-OMe | | 624(M⁺ + 1) [ESI(Pos.)] | 12.1 [E] |

TABLE 11-continued

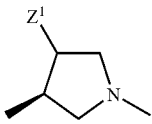

| Compound No. | Example No. | R¹ᵃ | X¹ | Z¹ | MS*¹ [Ionization method] | Retention time (min) [Mobile phase] |
|---|---|---|---|---|---|---|
| 11-015 | 1 | *N-Ac piperazinyl-N-Me* | 6-OMe | *HO-pyrrolidinyl-N-Me* | 589(M⁺ + 1) [ESI(Pos.)] | 9.1 [E] |
| 11-016 | 9 | *cyclohexyl* | H | *HO-pyrrolidinyl-N-Me* | 515(M⁺ + 1) [ESI(Pos.)] | 7.8 [A] |

*¹ESI: electrospray ionization

TABLE 12

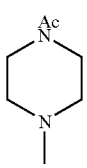

| Compound No. | Example No. | R¹ᵃ | X¹ | Z¹ | MS*¹ [Ionization method] | Retention time (min) [Mobile phase] |
|---|---|---|---|---|---|---|
| 12-001 | 19 | *morpholinyl* | 6-OMe | *HO-pyrrolidinyl-N-Me* | 547(M⁺ + 1) [ESI(Pos.)] | 5.8 [C] |
| 12-002 | 20 | Me | H | *HO-pyrrolidinyl-N-Me* | 446(M⁺ + 1) [ESI(Pos.)] | 10.5 [E] |
| 12-003 | 20 | Me | 6-Cl | *HO-pyrrolidinyl-N-Me* | 480(M⁺ + 1) [ESI(Pos.)] | 6.9 [C] |

TABLE 12-continued
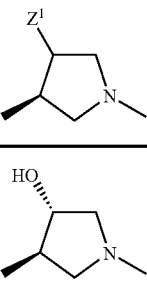
| Compound No. | Example No. | R$^{1a}$ | X$^1$ | Z$^1$ 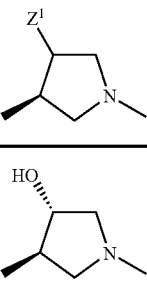 | MS*$^1$ [Ionization method] | Retention time (min) [Mobile phase] |
|---|---|---|---|---|---|---|
| 12-004 | 20 | Me | 6-Me | 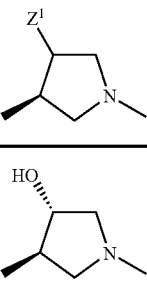 | 460(M$^+$ + 1) [ESI(Pos.)] | 6.4 [C] |
| 12-005 | 20 | Me | 6-Me | 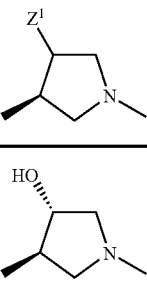 | 474(M$^+$ + 1) [ESI(Pos.)] | 5.9 [B] |
| 12-006 | 20 | Me | 6-iPr | 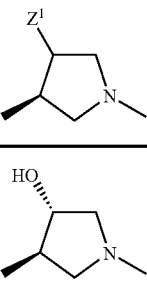 | 488(M$^+$ + 1) [ESI(Pos.)] | 6.2 [B] |
| 12-007 | 22 | Me | 6-OH | 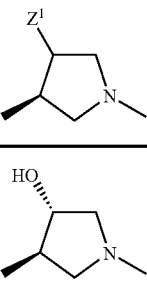 | 462(M$^+$ + 1) [ESI(Pos.)] | 8.8 [E] |
| 12-008 | 23 | Me | 6-OH | 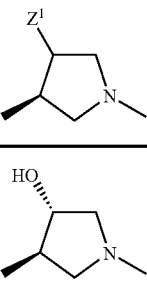 | 476(M$^+$ + 1) [ESI(Pos.)] | 5.8 [C] |
| 12-009 | 20 | Me | 6-OMe | 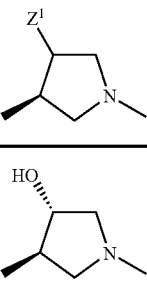 | 476(M$^+$ + 1) [ESI(Pos.)] | 13.6 [E] |
| 12-010 | 20 | Me | 6-OMe | 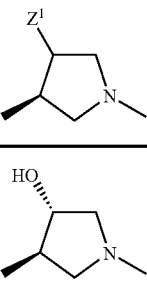 | 490(M$^+$ + 1) [ESI(Pos.)] | 6.8 [C] |
| 12-011 | 20 | Me | 6-OCF$_3$ | HO <br>  | 530(M$^+$ + 1) [ESI(Pos.)] | 6.2 [B] |

TABLE 12-continued

| Compound No. | Example No. | R<sup>1a</sup> | X<sup>1</sup> | Z<sup>1</sup> | MS*[1] [Ionization method] | Retention time (min) [Mobile phase] |
|---|---|---|---|---|---|---|
| 12-012 | 24 | OMe | H | HO-pyrrolidine-Me | 462(M⁺ + 1) [ESI(Pos.)] | 12.9 [E] |
| 12-013 | 24 | OMe | 6-F | HO-pyrrolidine-Me | 480(M⁺ + 1) [ESI(Pos.)] | 5.2 [C] |
| 12-014 | 24 | OMe | 6-Cl | HO-pyrrolidine-Me | 496(M⁺ + 1) [ESI(Pos.)] | 7.9 [C] |
| 12-015 | 24 | OMe | 6-Me | HO-pyrrolidine-Me | 476(M⁺ + 1) [ESI(Pos.)] | 6.8 [C] |
| 12-016 | 24 | OMe | 6-Me | MeO-pyrrolidine-Me | 490(M⁺ + 1) [ESI(Pos.)] | 6.8 [B] |
| 12-017 | 24 | OMe | 6-OMe | HO-pyrrolidine-Me | 492(M⁺ + 1) [ESI(Pos.)] | 16.5 [E] |
| 12-018 | 24 | OMe | 6-OMe | MeO-pyrrolidine-Me | 506(M⁺ + 1) [ESI(Pos.)] | 5.3 [B] |

*[1]ESI: electronspray ionization

TABLE 13
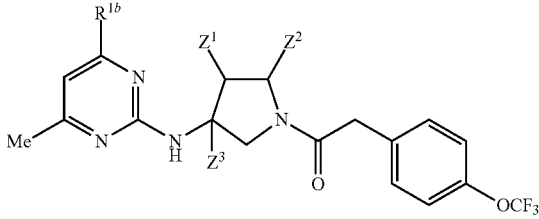
| Compound No. | Example No. | R[1b] | 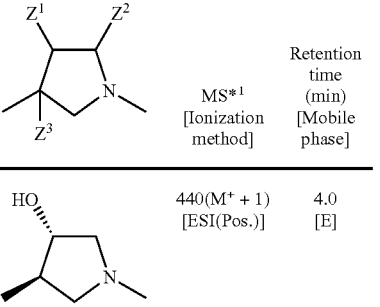 Z[3] | MS[*1] [Ionization method] | Retention time (min) [Mobile phase] |
|---|---|---|---|---|---|
| 13-001[*2,3] | 5 |  | 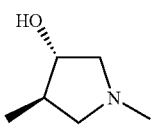 | 440(M[+] + 1) [ESI(Pos.)] | 4.0 [E] |
| 13-002 | 1 | 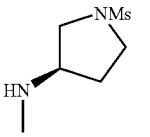 | 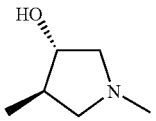 | 559(M[+] + 1) [ESI(Pos.)] | 4.8 [E] |
| 13-003 | 1 | 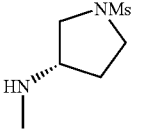 | 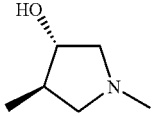 | 559(M[+] + 1) [ESI(Pos.)] | 5.1 [E] |
| 13-004 | 2 | 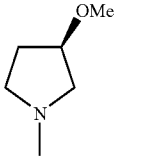 | 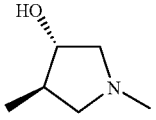 | 496(M[+] + 1) [ESI(Pos.)] | 8.0 [E] |
| 13-005 | 2 | 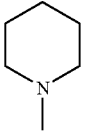 | 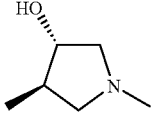 | 480(M[+] + 1) [ESI(Pos.)] | 5.4 [C] |
| 13-006 | 2 | 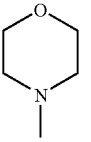 | 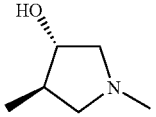 | 482(M[+] + 1) [ESI(Pos.)] | 5.2 [E] |

TABLE 13-continued
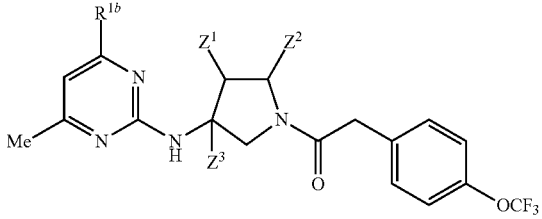
| Compound No. | Example No. | R$^{1b}$ | Z$^1$ Z$^2$ Z$^3$ | MS*$^1$ [Ionization method] | Retention time (min) [Mobile phase] |
|---|---|---|---|---|---|
| 13-007 | 1 | 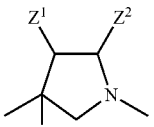 | 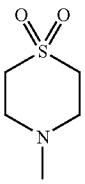 | 530(M$^+$ + 1) [ESI(Pos.)] | 4.5 [E] |
| 13-008 | 2 | 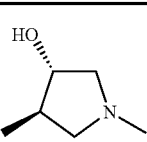 | 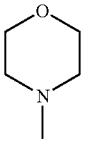 | 496(M$^+$ + 1) [ESI(Pos.)] | 11.0 [E] |
| 13-009 | 12 | 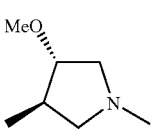 | 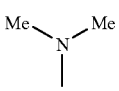 | 482(M$^+$ + 1) [ESI(Pos.)] | |
| 13-010*$^2$ | 12 | 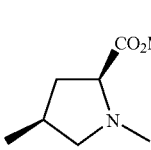 | 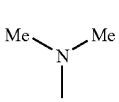 | 495(M$^+$ + 1) [ESI(Pos.)] | |
| 13-011*$^3$ | 5 | 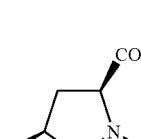 | 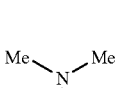 | 438(M$^+$ + 1) [ESI(Pos.)] | |
| 13-012*$^3$ | 5 | 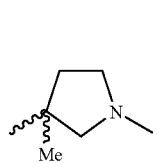 | 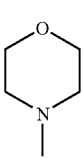 | 484(M$^+$ + 1) [ESI(Pos.)] | 5.2 [J] |
*$^1$ESI: electronspray ionization
*$^2$Mono-HCl salt
*$^3$Racemic mixtue TABLE 14
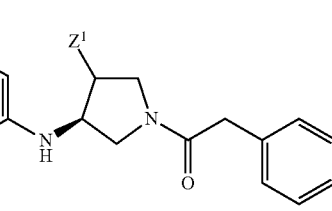
| Compound No. | Example No. | R$^{1b}$ | 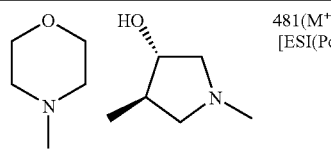 Z$^1$ | MS*$^1$ [Ionization method] | Retention time (min) [Mobile phase] |
|---|---|---|---|---|---|
| 14-001 | 15 | 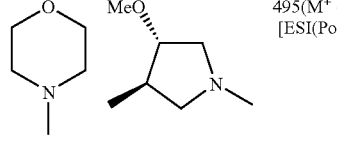 | 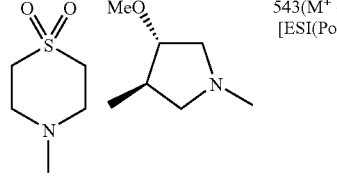 HO | 481(M$^+$ + 1) [ESI(Pos.)] | 6.0 [E] |
| 14-002 | 16 | 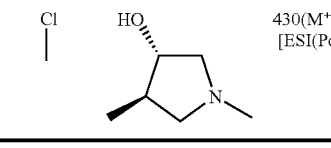 | 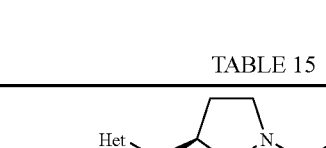 MeO | 495(M$^+$ + 1) [ESI(Pos.)] | 6.0 [C] |
| 14-003 | 16 |  | 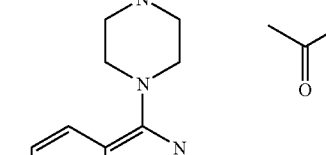 MeO | 543(M$^+$ + 1) [ESI(Pos.)] | 4.7 [C] |
| 14-004 | 15 | Cl | 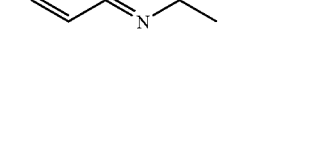 HO | 430(M$^+$ + 1) [ESI(Pos.)] | 5.3 [C] |
*$^1$ESI: electronspray ionization
TABLE 15
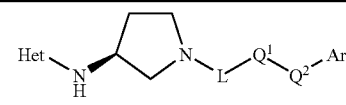
| Compound No. | Example No. | Het— | —L—Q$^1$—Q$^2$—Ar | MS*$^1$ [Ionization method] | Retention time (min) [Mobile phase] |
|---|---|---|---|---|---|
| 15-001*$^{2,3}$ | 5 | 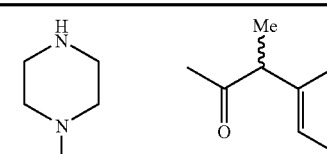 | 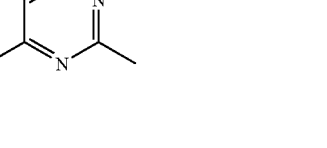 | 465(M$^+$ + 1) [ESI(Pos.)] | 7.2 8.2 [K] |

TABLE 15-continued

| Compound No. | Example No. | Het— | —L—Q¹—Q²—Ar | MS*¹ [Ionization method] | Retention time (min) [Mobile phase] |
|---|---|---|---|---|---|
| 15-002*² | 5 | (piperazine-quinazoline, 2-Me) | C(Me)(Me)-C(=O)-C6H4-Cl | 479(M⁺ + 1) [ESI(Pos.)] | 7.2 [K] |
| 15-003 | 5 | (piperazinone-7-F-quinazoline, 2-Me) | cyclopropyl-C(=O)-C6H4-Cl | 509(M⁺ + 1) [ESI(Pos.)] | |
| 15-004 | 16 | (thiomorpholine-1,1-dioxide-2,6-dimethylpyridine) | cyclopropyl-C(=O)-C6H4-Cl | 489(M⁺ + 1) [ESI(Pos.)] | 8.0 [F] |
| 15-005*²,⁴ | 1 | (N-iPr-piperazine-quinazoline, 2-Me) | CH2CH2-C(=O)-biphenyl | 549(M⁺ + 1) [ESI(Pos.)] | 8.2 [Q] |
| 15-006 | 40 | (NMe2-thienopyrimidine, 2-Me) | CH2-C(=S)-C6H4-OCF3 | 482(M⁺ + 1) [ESI(Pos.)] | |

*¹ESI: electronspray ionization
*²Di-HCl salt
*³Diastereomer mixture
*⁴Racemic mixture

TABLE 16*¹

| Compound No. | Example No. | Het— | —Ar | MS*² [Ionization method] | Retention time (min) [Mobile phase] |
|---|---|---|---|---|---|
| 16-001*³,⁴ | 3 | | | 515(M⁺ + Na) [ESI(Pos.)] | 5.5 [F] |
| 16-023*³,⁴ | 3 | | | 495(M⁺ + 1) [ESI(Pos.)] | 5.1 [G] |
| 16-003*³,⁴ | 3 | | | 529(M⁺ + 1) [ESI(Pos.)] | 5.6 [F] |
| 16-004*³,⁴ | 3 | | | 457(M⁺ + 1) [ESI(Pos.)] | |

TABLE 16*1-continued
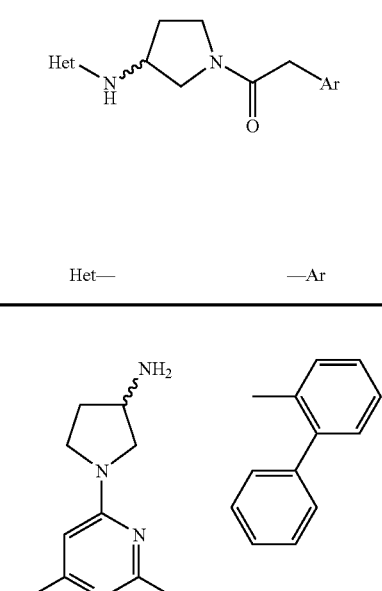
| Compound No. | Example No. | Het— | —Ar | MS*2 [Ionization method] | Retention time (min) [Mobile phase] |
|---|---|---|---|---|---|
| 16-005*3,4 | 3 | 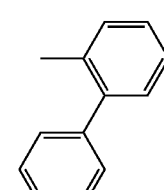 | 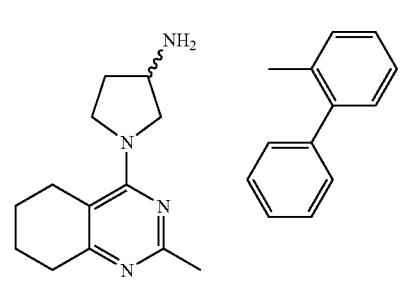 | 457(M+ + 1) [ESI(Pos.)] | 3.4 [F] |
| 16-006*4 | 3 | 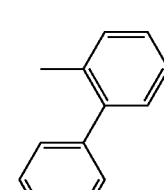 | 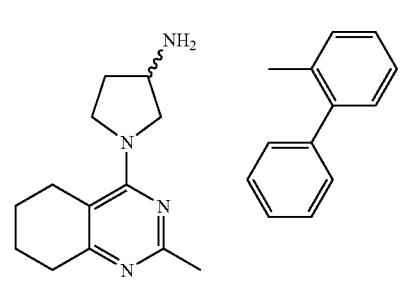 | 497(M+ + 1) [ESI(Pos.)] | 4.7 [F] |
| 16-007*4 | 33 | 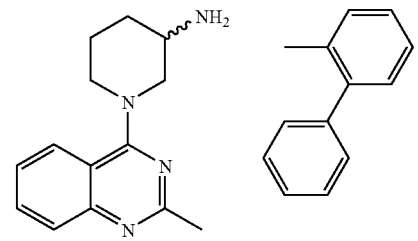 | 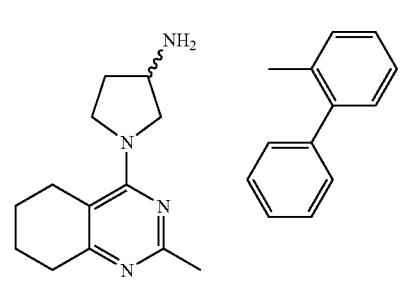 | 507(M+ + 1) [ESI(Pos.)] | 5.6 [F] |
| 16-008*3,4 | 1 | 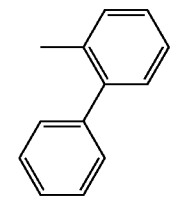 | 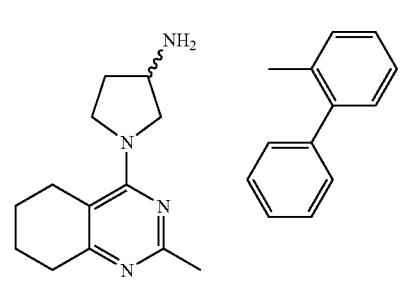 | 521(M+ + 1) [ESI(Pos.)] | 4.1 [R] |
*1Diastereomer mixture
*2ESI: electronspray ionization
*3Di-HCl salt
*4Racemic mixture

TABLE 17

| Compound No. | Example No. | R¹ᵃ | X¹ | X² | —Ar | MS*¹ [Ionization method] |
|---|---|---|---|---|---|---|
| 17-001*²,³ | 3 | 3-amino-1-methylpyrrolidinyl | H | H | 2-biphenyl | 493(M⁺ + 1) [ESI(Pos.)] |
| 17-002*²,³ | 1 | 2,6-dimethyl-4-methylpiperazinyl | H | H | 2-biphenyl | 521(M⁺ + 1) [ESI(Pos.)] |

*¹ESI: electrospray ionization
*²Di-HCl salt
*³Diastereomer mixture

TABLE 18

| Compound No. | Example No. | R¹ᵃ | X¹ | Z¹ | Q² | Ar | MS*¹ [Ionization method] | Retention time (min) [Mobile phase] |
|---|---|---|---|---|---|---|---|---|
| 18-001 | 41 | Me | Me | (3-hydroxy-4-methyl-1-methylpyrrolidinyl) | $CH_2$ | 4-$SO_2Me$-phenyl | 454(M⁺ + 1) [ESI(Pos.)] | 6.1 [M] |
| 18-002 | 41 | Me | Me | (3-hydroxy-4-methyl-1-methylpyrrolidinyl) | $CH_2$ | 4-$SCF_3$-phenyl | 476(M⁺ + 1) [ESI(Pos.)] | 6.3 [J] |

TABLE 18-continued

| Compound No. | Example No. | R$^{1a}$ | X$^1$ | Z$^1$ (pyrrolidine) | Q$^2$ | Ar | MS*$^1$ [Ionization method] | Retention time (min) [Mobile phase] |
|---|---|---|---|---|---|---|---|---|
| 18-003 | 41 | Me | Me | HO,,/pyrrolidine-N-Me | CH$_2$ | benzo[1,3]dioxol-5-yl | 420(M$^+$ + 1) [ESI(Pos.)] | 4.1 [K] |
| 18-004 | 41 | Me | Et | HO,,/pyrrolidine-N-Me | CH$_2$ | 4-OCF$_3$-phenyl | 474(M$^+$ + 1) [ESI(Pos.)] | 6.5 [J] |
| 18-005 | 41 | Me | OEt | HO,,/pyrrolidine-N-Me | CH$_2$ | 4-OCF$_3$-phenyl | 490(M$^+$ + 1) [ESI(Pos.)] | 5.8 [J] |
| 18-006 | 41 | Me | Me | HO,,/pyrrolidine-N-Me | cyclopropylidene | 4-OCF$_3$-phenyl | 486(M$^+$ + 1) [ESI(Pos.)] | 8.1 [B] |
| 18-007 | 41 | Me | Me | HO,,/pyrrolidine-N-Me | cyclopropylidene | 4-Cl-phenyl | 436(M$^+$ + 1) [ESI(Pos.)] | 6.6 [K] |
| 18-008 | 41 | Me | Me | HO,,/pyrrolidine-N-Me | CH$_2$ | pyridin-3-yl | 377(M$^+$ + 1) [ESI(Pos.)] | 5.7 [K] |
| 18-009 | 41 | Me | Me | HO,,/pyrrolidine-N-Me | CH$_2$ | naphthalen-2-yl | 426(M$^+$ + 1) [ESI(Pos.)] | 5.9 [K] |

*$^1$ESI: electrospray ionization

TABLE 19

| Compound No. | Example No. | R^{1a} | X^1 | Z^1 | —Q^2— | —Ar | MS*^1 [Ionization method] | Retention time (min) [Mobile phase] |
|---|---|---|---|---|---|---|---|---|
| 19-001 | 41 | Me | Me | 3-HO, 4-Me pyrrolidine | 1,1-cyclopropyl | 3,4-difluorophenyl | 438(M^+ + 1) [ESI(Pos.)] | 6.2 [J] |
| 19-002 | 41 | Me | Me | 3-HO, 4-Me pyrrolidine | 1,1-cyclopropyl | 4-fluorophenyl | 420(M^+ + 1) [ESI(Pos.)] | 5.7 [J] |
| 19-003 | 41 | Me | Me | 3-HO, 4-Me pyrrolidine | 1,1-cyclopropyl | 4-OCHF_2 phenyl | 468(M^+ + 1) [ESI(Pos.)] | 6.3 [J] |
| 19-004 | 41 | Me | Me | 3-HO, 4-Me pyrrolidine | 1,1-cyclopropyl | 3,4-dichlorophenyl | 472(M^+ + 1) [ESI(Pos.)] | 8.1 [J] |
| 19-005 | 41 | Et | Me | 3-HO, 4-Me pyrrolidine | 1,1-cyclopropyl | 4-chlorophenyl | 450(M^+ + 1) [ESI(Pos.)] | 8.1 [J] |
| 19-006 | 41 | Et | Me | 3-HO, 4-Me pyrrolidine | 1,1-cyclopropyl | 3,4-dichlorophenyl | 458(M^+ + 1) [ESI(Pos.)] | 8.9 [J] |
| 19-007 | 21 | 2-methoxyethoxy-OH | Me | 3-Me pyrrolidine | 1,1-cyclopropyl-CH_2 | 4-fluorophenyl | 450(M^+ + 1) [ESI(Pos.)] | 5.2 [J] |
| 19-008 | 21 | 2-methoxyethoxy-OH | Me | 3-Me pyrrolidine | 1,1-cyclopropyl-CH_2 | 3,4-difluorophenyl | 468(M^+ + 1) [ESI(Pos.)] | 5.5 [J] |
| 19-009 | 21 | 2-methoxyethoxy-OH | Me | 3-Me pyrrolidine | 1,1-cyclopropyl-CH_2 | 3,4-dichlorophenyl | 501(M^+ + 1) [ESI(Pos.)] | 6.9 [J] |

TABLE 19-continued

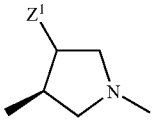

| Compound No. | Example No. | R$^{1a}$ | X$^1$ | —Q$^2$— | —Ar | MS*$^1$ [Ionization method] | Retention time (min) [Mobile phase] |
|---|---|---|---|---|---|---|---|
| 19-010 | 21 | (CH$_2$CH$_2$OCH$_3$)O- with OH | Me | CH$_2$ | -C$_6$H$_4$-OCF$_3$ | 490(M$^+$ + 1) [ESI(Pos.)] | 6.9 [J] |
| 19-011 | 21 | (CH$_2$CH$_2$OCH$_3$)O- with OH | Me | cyclopropyl-CH$_2$ | -C$_6$H$_4$-OCHF$_2$ | 498(M$^+$ + 1) [ESI(Pos.)] | 5.7 [J] |
| 19-012 | 21 | Me | OMe-ethyl | CH$_2$ | -C$_6$H$_4$-OCF$_3$ | 490(M$^+$ + 1) [ESI(Pos.)] | 6.9 [J] |
| 19-013 | 41 | Me | OMe-ethyl (HO on pyrrolidine) | cyclopropyl | -C$_6$H$_4$-F | 450(M$^+$ + 1) [ESI(Pos.)] | 5.3 [J] |
| 19-014 | 41 | Me | OH-ethyl (HO on pyrrolidine) | cyclopropyl | -C$_6$H$_4$-F | 436(M$^+$ + 1) [ESI(Pos.)] | 4.0 [J] |

*$^1$ESI: electrospray ionization

TABLE 20

| Compound No. | Example No. | R$^{1a}$ | X$^1$ | X$^2$ | —Q$^2$— | —Ar | MS*$^1$ [Ionization method] | Retention time (min) [Mobile phase] |
|---|---|---|---|---|---|---|---|---|
| 20-001 | 41 | Me | Me | F | cyclopropyl | -C$_6$H$_4$-Cl | 454(M$^+$ + 1) [ESI(Pos.)] | 7.2 [J] |

TABLE 20-continued

| Compound No. | Example No. | R^1a | X^1 | X^2 | Z^1 | —Q^2— | —Ar | MS*^1 [Ionization method] | Retention time (min) [Mobile phase] |
|---|---|---|---|---|---|---|---|---|---|
| 20-002 | 41 | Me | Me | F | HO-pyrrolidine-Me | CH_2 | 3,4-dichlorophenyl | 462(M^+ + 1) [ESI(Pos.)] | 8.0 [J] |
| 20-003 | 41 | Me | OMe | F | HO-pyrrolidine-Me | cyclopropylidene | 4-chlorophenyl | 470(M^+ + 1) [ESI(Pos.)] | 6.2 [J] |
| 20-004 | 41 | Me | OMe | F | HO-pyrrolidine-Me | CH_2 | 3,4-dichlorophenyl | 478(M^+ + 1) [ESI(Pos.)] | 6.9 [J] |
| 20-005 | 41 | Me | OMe | F | HO-pyrrolidine-Me | CH_2 | 4-OCF_3-phenyl | 494(M^+ + 1) [ESI(Pos.)] | 7.6 [J] |
| 20-006 | 41 | Me | OMe | F | HO-pyrrolidine-Me | CH_2 | 4-fluorophenyl | 428(M^+ + 1) [ESI(Pos.)] | 5.2 [J] |
| 20-007 | 41 | Me | OMe | F | HO-pyrrolidine-Me | CH_2 | 3,4-difluorophenyl | 446(M^+ + 1) [ESI(Pos.)] | 5.7 [J] |
| 20-008 | 41 | Me | OMe | F | HO-pyrrolidine-Me | CH_2 | 3-fluorophenyl | 428(M^+ + 1) [ESI(Pos.)] | 5.3 [J] |
| 20-009 | 41 | Me | OMe | F | HO-pyrrolidine-Me | CH_2 | 2,4-difluorophenyl | 446(M^+ + 1) [ESI(Pos.)] | 5.6 [J] |
| 20-010 | 41 | Me | OMe | F | HO-pyrrolidine-Me | cyclopropylidene | 4-fluorophenyl | 454(M^+ + 1) [ESI(Pos.)] | 5.6 [J] |

TABLE 20-continued

| Compound No. | Example No. | R$^{1a}$ | X$^1$ | X$^2$ | Z$^1$-pyrrolidine | —Q$^2$— | —Ar | MS*$^1$ [Ionization method] | Retention time (min) [Mobile phase] |
|---|---|---|---|---|---|---|---|---|---|
| 20-011 | 41 | Me | OMe | F | HO- | cyclopropyl | 3,4-difluorophenyl | 472(M$^+$ + 1) [ESI(Pos.)] | 6.0 [J] |
| 20-012 | 41 | Me | OMe | F | HO- | cyclopropyl | 4-OCHF$_2$-phenyl | 502(M$^+$ + 1) [ESI(Pos.)] | 6.2 [J] |
| 20-013 | 41 | Me | OMe | F | MeO- | CH$_2$ | 4-F-phenyl | 442(M$^+$ + 1) [ESI(Pos.)] | 6.3 [J] |
| 20-014 | 41 | Me | OMe | F | MeO- | CH$_2$ | 4-OCF$_3$-phenyl | 508(M$^+$ + 1) [ESI(Pos.)] | 9.5 [J] |
| 20-015 | 41 | Et | OMe | F | HO- | CH$_2$ | 4-F-phenyl | 442(M$^+$ + 1) [ESI(Pos.)] | 5.9 [J] |
| 20-016 | 41 | Et | OMe | F | HO- | CH$_2$ | 4-OCF$_3$-phenyl | 508(M$^+$ + 1) [ESI(Pos.)] | 8.9 [J] |
| 20-017 | 22 | Me | OH | F | HO- | cyclopropyl | 4-Cl-phenyl | 456(M$^+$ + 1) [ESI(Pos.)] | 4.9 [J] |
| 20-018 | 22 | Me | OH | F | HO- | CH$_2$ | 3,4-diCl-phenyl | 466(M$^+$ + 1) [ESI(Pos.)] | 5.4 [J] |

*$^1$ESI: electronspray ionization

Test Example

MC$_4$ Receptor Binding Experiment

The MC$_4$ receptor binding experiment was performed according to the method described in Pharmacology & Toxicology, 79, 161-165, 1996. The human MC$_4$ receptor expressing-cell membrane obtained by expressing the human MC$_4$ receptor in a HEK-293 cell was purchased from Biolinks K.K. The cell membrane was homogenized with 50 mM tris hydrochloride buffer (pH 7.4) containing 2 mM ethylenediaminetetraacetic acid, 10 mM calcium chloride, and 100 μM phenylmethylsulfonyl fluoride. The homogenate was centrifuged at 48,000×g at 4° C. for 20 min. The sediment obtained by centrifugation was rehomogenized with the same buffer, and the homogenate was centrifuged at 48,000×g at 4° C. for 20 min. This procedure was repeated twice. The sediment was suspended in 50 mM tris hydrochloride buffer (pH 7.4) containing 2 mM ethylenediaminetetraacetic acid, 10 mM calcium chloride, 100 μM phenylmethylsulfonyl fluoride, and 0.1% bovine serum albumin at a protein concentration of 100 μg/ml, and the suspension was used as a crude membrane preparation for the binding experiment. The crude membrane preparation (0.25 ml, 25 μg protein) was reacted with [$^{125}$I] Nle$^4$-D-Phe$^7$-α-MSH (final concentration, 0.2 nM) at 25° C. for 120 min. After completion of the reaction, the reaction solution was filtered by suction, using a cell harvester for the receptor binding experiment, onto a GF/C glass fiber filter paper immersed in 50 mM tris hydrochloride buffer (pH 7.4) containing 0.5% bovine serum for 2 h. Radioactivity on the filter paper was measured using a γ counter. The quantity of binding in the presence of 1 μM Nle$^4$-D-Phe$^7$-α-MSH was obtained as nonspecific binding, and specific binding was obtained by deducting the nonspecific binding from the total quantity, binding in the absence of 1 μM Nle$^4$-D-Phe$^7$-α-MSH. The test drug was dissolved in 100% DMSO solution and added to the membrane preparation at the same time as [$^{125}$I]Nle$^4$-D-Phe$^7$-α-MSH. The IC$_{50}$ value was obtained from the inhibition curve in the range of $10^{-10}$ to $10^{-5}$ M. The binding test results of representative compounds are shown in Table 21 as examples.

TABLE 21

| Compound No. | IC$_{50}$ (nM) |
| --- | --- |
| 1-003 | 18 |
| 1-005 | 2.8 |
| 1-019 | 10 |
| 1-032 | 0.4 |
| 1-040 | 0.4 |
| 1-045 | 21 |
| 1-058 | 180 |
| 1-073 | 39 |
| 1-078 | 1.5 |
| 1-092 | 37 |
| 1-095 | 22 |
| 1-101 | 68 |
| 1-110 | 5.1 |
| 1-111 | 3.8 |
| 1-116 | 6.7 |
| 1-128 | 7.3 |
| 1-133 | 4.4 |
| 1-174 | 21 |
| 1-176 | 1.0 |
| 1-206 | 2.3 |
| 3-001 | 28 |
| 3-011 | 6.8 |
| 3-019 | 78 |
| 3-022 | 9.5 |
| 3-023 | 2.4 |
| 3-034 | 16 |
| 3-038 | 20 |
| 3-041 | 46 |
| 4-016 | 60 |
| 4-022 | 30 |
| 4-035 | 52 |
| 4-042 | 30 |
| 4-043 | 66 |
| 4-044 | 56 |
| 4-054 | 39 |
| 4-055 | 2.3 |
| 4-058 | 28 |
| 5-003 | 26 |
| 5-006 | 9.3 |
| 5-011 | 30 |
| 5-014 | 32 |
| 6-001 | 71 |
| 6-010 | 66 |
| 7-001 | 74 |
| 7-002 | 94 |
| 7-009 | 23 |
| 7-010 | 52 |
| 8-001 | 35 |
| 8-002 | 24 |
| 8-004 | 11 |
| 8-005 | 12 |
| 8-006 | 10 |
| 8-007 | 10 |
| 9-001 | 49 |
| 11-008 | 1.3 |
| 11-009 | 6.1 |
| 11-012 | 0.3 |
| 11-014 | 1.4 |
| 11-015 | 1.0 |
| 12-001 | 2.9 |
| 12-004 | 13 |
| 12-007 | 14 |
| 12-008 | 12 |
| 12-010 | 3.0 |
| 12-017 | 3.3 |
| 12-018 | 3.4 |
| 13-001 | 99 |
| 13-002 | 25 |
| 13-004 | 46 |
| 13-005 | 21 |
| 13-008 | 36 |
| 14-001 | 16 |
| 14-002 | 19 |
| 14-003 | 7.4 |
| 15-001 | 16 |
| 15-003 | 26 |

Formulation Example 1

A granule containing the following components is produced.

| Components | |
| --- | --- |
| Compound represented by formula (1) | 10 mg |
| Lactose | 700 mg |
| Corn starch | 274 mg |
| HPC-L | 16 mg |
| | 1000 mg |

Compound represented by formula (1) and lactose are passed through a 60-mesh sieve. Corn starch is passed through a 120-mesh sieve. These components are mixed using a V-type blender. To the mixture powder added a low-viscosity aqueous hydroxypropyl cellulose (HPC-L) solution, and the mixture is kneaded, granulated (granulation by extrusion: pore size, 0.5 to 1 mm), and then dried. The resulting dry granule is passed through a vibration sieve (12/60 mesh) to obtain a granule.

Formulation Example 2

A powder for filling a capsule containing the following components is produced.

| Components | |
|---|---|
| Compound represented by formula (1) | 10 mg |
| Lactose | 79 mg |
| Corn starch | 10 mg |
| Magnesium stearate | 1 mg |
| | 100 mg |

A compound represented by formula (1) and lactose are passed through a 60-mesh sieve. Corn starch is passed through a 120-mesh sieve. These components and magnesium stearate are mixed using a V-type blender. 100 mg of 10× powder is filled in a No. 5 hard gelatin capsule.

Formulation Example 3

A granule for filling a capsule containing the following components is produced.

| Components | |
|---|---|
| Compound represented by formula (1) | 15 mg |
| Lactose | 90 mg |
| Corn starch | 42 mg |
| HPC-L | 3 mg |
| | 150 mg |

Compound represented by formula (1) and lactose are passed through a 60-mesh sieve. Corn starch is passed through 120-mesh sieve. These components are mixed using a V-type blender. To the mixture powder is added a low-viscosity aqueous hydroxypropyl cellulose (HPC-L) solution, and the mixture is kneaded, granulated, and then dried. The resulting dry granule is passed through a shaking sieve (12/60 mesh) to be sized, and 150 mg of the sieved granule is filled in a No. 4 hard gelatin capsule.

Formulation Example 4

A tablet containing the following components is produced.

| Components | |
|---|---|
| Compound represented by formula (1) | 10 mg |
| Lactose | 90 mg |
| Microcrystalline cellulose | 30 mg |
| Magnesium stearate | 5 mg |
| CMC-Na | 15 mg |
| | 150 mg |

Compound represented by formula (1), lactose, microcrystalline cellulose, and CMC-Na (carboxymethylcellulose sodium salt) are passed through a 60-mesh sieve and mixed. Magnesium stearate is added to the mixture powder to obtain a mixture powder for formulation. This mixture powder is directly tableted to obtain a 150-mg tablet.

Formulation Example 5

A formulation for intravenous infusion is produced as follows.

| | |
|---|---|
| Compound represented by formula (1) | 100 mg |
| Saturated fatty acid glyceride | 1000 ml |

A solution of the above-mentioned components is intravenously infused to a patient usually at a rate of 1 ml per min.

INDUSTRIAL APPLICABILITY

The compound of the present invention has an antagonistic action on the $MC_4$ receptor and can be used as therapeutic agents for $MC_4$-related diseases, specifically, as prophylactic or therapeutic agents for mood disorders such as depression, anxiety, anorexia, cachexia, pain, drug dependence, and the like.

The invention claimed is:

1. An aminopyrrolidine compound, a tautomer, a stereoisomer, a prodrug, or a pharmaceutically acceptable salt of the compound, or a solvate thereof represented by the formula [I]:

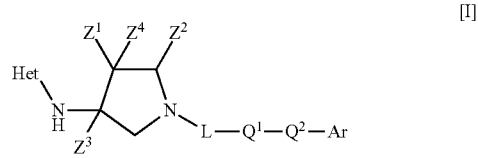

wherein Het represents an aromatic heterocyclic group represented by the following formula [II]:

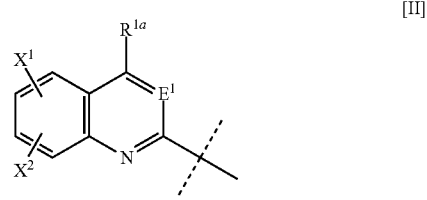

wherein $E^1$ represents a nitrogen atom or a group represented by formula $CR^1$, wherein $R^1$ represents a hydrogen atom or a $C_{1-6}$alkyl group;

$R^{1a}$ represents a group selected from the group consisting of a hydroxy group, a $C_{1-6}$alkyl group, a $C_{3-8}$cycloalkyl group, a $C_{1-6}$alkoxy group, a hydroxy$C_{2-6}$alkoxy group, a $C_{3-8}$cycloalkoxy group, a halogen atom, a trifluoromethyl group, a $C_{1-9}$heteroaryl group, a di($C_{1-6}$alkyl)aminocarbonyl group, and a group represented by —$NR^2R^3$, wherein $R^2$ and $R^3$ may be the same or different and represent a hydrogen atom, a $C_{1-6}$alkyl group which is unsubstituted or substituted with one or two substituents selected from the group consisting of a hydroxy group, a carboxy group, a carbamoyl group, a cyano group, a $C_{1-6}$alkoxy group, a $C_{3-8}$cycloalkyl group, a morpholino group, a phenyl group, a $C_{1-9}$heteroaryl group, a phenoxy group, a di($C_{1-6}$alkyl)aminocarbonyl group, a $C_{1-6}$alkoxycarbonyl group, a 1-($C_{1-6}$alkylsulfonyl)piperidin-4-yl group, and a 1-($C_{1-6}$acyl)piperidin-4-yl group, a $C_{3-8}$cycloalkyl group, a pyrrolidin-3-yl group, a piperidin-3-yl group, or a piperidin-4-yl group, wherein the pyrrolidin-3-yl group, the piperidin-3-yl group, and the piperidin-4-yl group are unsubstituted or substituted with a $C_{1-6}$alkyl group, a $C_{1-6}$alkylsulfonyl group, or a $C_{1-6}$acyl group, or $R^2$ and $R^3$, together with an adjacent nitrogen atom, form a cyclic amino group represented by the formula [V]:

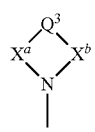
[V]

wherein $Q^3$ represents —O—, —$NR^4$—, —$CHR^5$—, —$NR^6CO$—, —$CHR^7CHR^8$—, —$CR^9$=$CR^{10}$—, —S—, —SO—, —$SO_2$—, or a single bond, $X^a$ and $X^b$ may be the same or different and represent a straight $C_{1-3}$alkylene group, wherein the alkylene group is unsubstituted or substituted with one to three substituents selected from the group consisting of a $C_{1-6}$alkyl group, a cyano group, a carboxy group, a carbamoyl group, a ($C_{1-6}$alkyl)aminocarbonyl group, a di($C_{1-6}$alkyl)aminocarbonyl group, a morpholinocarbonyl group, a pyrrolidin-1-ylcarbonyl group, a piperidin-1-ylcarbonyl group, a trifluoromethyl group, an amino$C_{1-6}$alkyl group, a di($C_{1-6}$alkyl)amino$C_{1-6}$alkyl group, a $C_{1-6}$alkoxycarbonyl group, a $C_{1-6}$alkoxy$C_{1-6}$alkyl group, a $C_{1-6}$alkylsulfonyl group, a $C_{1-6}$alkylsulfonylamino$C_{1-6}$alkyl group, a phenyl group, a phenylcarbonyl group, wherein the phenyl group and the phenylcarbonyl group are unsubstituted or substituted with one to three substituents selected from the substituent group A defined below, and a $C_{1-9}$heteroarylcarbonyl group), $R^4$ represents a hydrogen atom, a $C_{1-6}$alkyl group, a $C_{3-8}$cycloalkyl group, a phenyl group, a $C_{1-9}$heteroaryl group, a $C_{1-6}$acyl group, a $C_{3-8}$cycloalkylcarbonyl group, a $C_{1-6}$alkoxycarbonyl group, a morpholinocarbonyl group, a $C_{1-6}$alkylsulfonyl group, a trifluoromethylsulfonyl group, a hydroxy$C_{1-6}$alkyl group, a carbamoyl group, a ($C_{1-6}$alkyl)aminocarbonyl group, a di($C_{1-6}$alkyl)aminocarbonyl group, a $C_{1-9}$heteroarylcarbonyl group, a pyrrolidylcarbonyl group, or a $C_{1-6}$alkoxy$C_{2-6}$alkyl group, $R^5$ represents a hydrogen atom, a hydroxy group, a $C_{1-6}$alkoxy group, an amino group, a ($C_{1-6}$alkyl)amino group, a di($C_{1-6}$alkyl)amino group, a $C_{1-6}$acylamino group, a $C_{1-6}$alkylsulfonylamino group, a pyrrolidin-1-yl group, a piperidin-1-yl group, a morpholino group, a $C_{1-9}$heteroaryl group, a phenylamino group, or a phenoxy group, wherein the phenylamino group and the phenoxy group are unsubstituted or substituted with one to three substituents selected from the substituent group A defined below, $R^6$ represents a hydrogen atom or a $C_{1-6}$alkyl group, $R^7$ and $R^8$ may be the same or different and represent a group selected from the group consisting of a hydrogen atom, a $C_{1-6}$alkyl group, and a $C_{1-6}$alkoxy group, $R^9$ represents a phenyl group or a $C_{1-9}$heteroaryl group, wherein the phenyl group and the $C_{1-9}$heteroaryl group are unsubstituted or substituted with one to three substituents selected from the substituent group A defined below, $R^{10}$ represents a hydrogen atom, or $R^{10}$ forms a benzene ring together with $R^9$ and the carbon atoms to which they bond;

$X^1$ and $X^2$ may be the same or different and represent a group selected from the group consisting of a hydrogen atom, a $C_{1-6}$alkyl group, a $C_{1-6}$alkoxy group, a halogen atom, a phenyl group, a trifluoromethyl group, a hydroxy group, a $C_{3-8}$cycloalkyl group, a $C_{3-8}$cycloalkoxy group, a ($C_{1-6}$alkyl)amino group, a di($C_{1-6}$alkyl)amino group, a hydroxy$C_{1-6}$alkyl group, a $C_{1-6}$alkoxy$C_{1-6}$alkyl group, and a methoxy group substituted with one to three fluorine atoms;

L represents a group represented by —CO—;

Ar represents a phenyl group, a naphthyl group, or a $C_{1-9}$heteroaryl group, wherein the phenyl group, the naphthyl group, and the $C_{1-9}$heteroaryl group are unsubstituted or substituted with one to five substituents selected from the substituent group B defined below or one substituent selected from the substituent group C defined below;

$Z^1$, $Z^2$, $Z^3$, and $Z^4$ may be the same or different and represent a group selected from the group consisting of a hydrogen atom, a hydroxy group, a $C_{1-6}$alkyl group, a $C_{1-6}$alkoxy group, a halogen atom, a $C_{1-6}$alkoxycarbonyl group, and a di($C_{1-6}$alkyl)aminocarbonyl group, or $Z^4$ forms $C_{3-8}$cycloalkane together with $Z^1$;

$Q^1$ represents a single bond or —$(CH_2)_n$—, wherein n is an integer of 1 to 10;

$Q^2$ represents —$(CR^{11}R^{12})$—, —CO—, —$NR^{13}$—, —O—, —S—, —$CR^{14}$=$CR^{15}$—, —$OCH_2$—, —$SCH_2$—, or —$(CR^{16}R^{17})O$—, $R^{11}$ and $R^{12}$ may be the same or different and represent a group selected from the group consisting of a hydrogen atom, a $C_{1-6}$alkyl group, a $C_{3-8}$cycloalkyl group, a hydroxy group, a hydroxy$C_{1-6}$alkyl group, a $C_{1-6}$acyloxy group, a $C_{1-6}$alkoxy group, a $C_{1-6}$acylamino group, a phenyl group, a benzyl group, a phenyloxy group, a naphthyloxy group, and a phenylthio group, or $R^{11}$ and $R^{12}$ form $C_{3-8}$cycloalkane together, $R^{13}$ represents a hydrogen atom or a $C_{1-6}$alkyl group, $R^{14}$ and $R^{15}$ may be the same or different and represent a hydrogen atom or a $C_{1-6}$alkyl group, $R^{16}$ and $R^{17}$ may be the same or different and represent a hydrogen atom or a $C_{1-6}$alkyl group, the substituent group A includes a halogen atom, a $C_{1-6}$alkyl group, a $C_{1-6}$alkoxy group, a $C_{1-6}$alkylthio group, a trifluoromethyl group, a $C_{1-6}$alkylsulfonyl group, a methoxy group substituted with one to three fluorine atoms, a methylthio group substituted with one to three fluorine atoms, a methylsulfonyl group substituted with one to three fluorine atoms, and a nitro group, the substituent group B includes a halogen atom, a $C_{1-6}$alkyl group, a hydroxy group, a $C_{1-6}$alkoxy group, a $C_{1-6}$alkylthio group, a $C_{1-6}$alkylsulfonyl group, a trifluoromethyl group, a methoxy group substituted with one to three fluorine atoms, a methylthio group substituted with one to three fluorine atoms, a methylsulfonyl group substituted with one to three fluorine atoms, a nitro group, a phenoxy group, a benzyloxy group, a ($C_{1-6}$acyl)oxy group, an amino group, a carboxy group, a $C_{3-8}$cycloalkyl group, a $C_{3-8}$cycloalkoxy group, a ($C_{1-6}$alkyl)amino group, a di($C_{1-6}$alkyl)amino group, a hydroxy $C_{1-6}$alkyl group, a $C_{1-6}$alkoxycarbonyl group, a carbamoyl group, a sulfamoyl group, a cyano group, a methylenedioxyphenyl group, a $C_{1-9}$heteroaryl group, a phenyl group, a phenylamino group, a phenylaminocarbonyl group, a phenylcarbonyl group, a $C_{1-9}$heteroarylcarbonyl group, and a phenyl$C_{1-6}$alkyl group, wherein the phenyl group, the phenylamino group, the phenylaminocarbonyl group, the phenylcarbonyl group, the $C_{1-9}$heteroarylcarbonyl group, and the phenyl$C_{1-6}$alkyl group are unsubstituted or substituted with one to three substituents selected from the substituent group A, and the substituent group C includes a methylenedioxy group, an ethylenedioxy group, a trimethylenedioxy group, and an ethyleneoxy group.

2. The aminopyrrolidine compound, a tautomer, a stereoisomer, a prodrug, or a pharmaceutically acceptable salt of the compound, or a solvate thereof according to claim 1, wherein Het represents an aromatic heterocyclic group represented by the following formula [VI]:

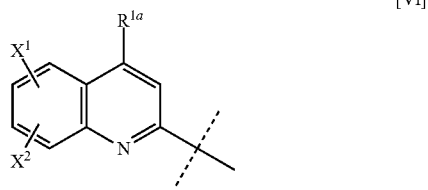

[VI]

wherein $R^{1a}$, $X^1$, and $X^2$ have the same meanings as defined in claim 1, L represents —CO—, and Ar and $Q^2$ have the same meanings as defined in claim 1, provided that when $R^{1a}$ is a hydroxy group, a $C_{1-6}$alkyl group, a $C_{1-6}$alkoxy group, a halogen atom, a trifluoromethyl group, or a group represented by —NR$^2$R$^3$, wherein $R^2$ and $R^3$ may be the same or different and represent a hydrogen atom or a $C_{1-6}$alkyl group, (i) Ar represents a phenyl group, a naphthyl group, or a $C_{1-9}$heteroaryl group, wherein the phenyl group, the naphthyl group, and the $C_{1-9}$heteroaryl group are substituted with one substituent selected from the group consisting of a hydroxy group, a $C_{1-6}$alkylthio group, a $C_{1-6}$alkylsulfonyl group, a methoxy group substituted with one to three fluorine atoms, a methylthio group substituted with one to three fluorine atoms, a methylsulfonyl group substituted with one to three fluorine atoms, a nitro group, a phenoxy group, a benzyloxy group, an amino group, a carboxy group, a $C_{3-8}$cycloalkoxy group, a ($C_{1-6}$alkyl)amino group, a di($C_{1-6}$alkyl)amino group, a hydroxy$C_{1-6}$alkyl group, a $C_{1-6}$alkoxycarbonyl group, a carbamoyl group, a sulfamoyl group, a cyano group, a phenyl group wherein the phenyl group is unsubstituted or substituted with one to three substituents selected from the substituent group A, wherein the substituent group A has the same meaning as defined in claim 1, a methylenedioxy phenyl group, and a pyridyl group, or are further substituted with one or two substituents selected from the group consisting of a halogen atom, a trifluoromethyl group, a $C_{1-6}$alkyl group, and a $C_{1-6}$alkoxy group, and/or (ii) $Q^2$ represents —(CR$^{11}$R$^{12}$)—, wherein R$^{11}$ and R$^{12}$ form a $C_{3-8}$cycloalkane together.

3. The aminopyrrolidine compound, a tautomer, a stereoisomer, a prodrug, or a pharmaceutically acceptable salt of the compound, or a solvate thereof according to claim 1 or 2, wherein Het represents an aromatic heterocyclic group represented by the following formula [VI]:

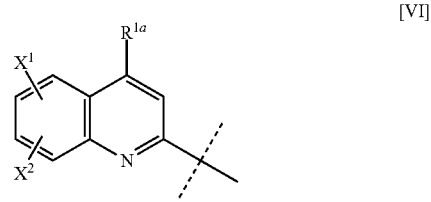

[VI]

wherein $R^{1a}$ represents a $C_{1-6}$alkyl group, a $C_{1-6}$alkoxy group, or a group represented by the formula —NR$^2$R$^3$, wherein $R^2$ and $R^3$ may be the same or different and represent a hydrogen atom or a $C_{1-6}$alkyl group, and $X^1$ and $X^2$ have the same meanings as defined in claim 1, L represents —CO—, and Ar represents a phenyl group, wherein the phenyl group is substituted with one substituent selected from the group consisting of a hydroxy group, a $C_{1-6}$alkylthio group, a $C_{1-6}$alkylsulfonyl group, a methoxy group substituted with one to three fluorine atoms, a methylthio group substituted with one to three fluorine atoms, a methylsulfonyl group substituted with one to three fluorine atoms, a nitro group, a phenoxy group, a benzyloxy group, an amino group, a carboxy group, a $C_{3-8}$cycloalkoxy group, a ($C_{1-6}$alkyl)amino group, a di($C_{1-6}$alkyl)amino group, a hydroxy$C_{1-6}$alkyl group, a $C_{1-6}$alkoxycarbonyl group, a carbamoyl group, a sulfamoyl group, a cyano group, a phenyl group, wherein the phenyl group is unsubstituted or substituted with one to three substituents selected from the substituent group A wherein the substituent group A has the same meaning as defined in claim 1, a methylenedioxyphenyl group, and a pyridyl group, or is further substituted with one or two substituents selected from the group consisting of a halogen atom, a trifluoromethyl group, a $C_{1-6}$alkyl group, and a $C_{1-6}$alkoxy group.

4. The aminopyrrolidine compound, a tautomer, a stereoisomer, a prodrug, or a pharmaceutically acceptable salt of the compound, or a solvate thereof according to claim 1 or 2, wherein Het represents an aromatic heterocyclic group represented by the following formula [VI]:

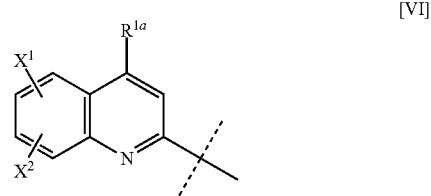

[VI]

wherein $R^{1a}$ represents a $C_{1-6}$alkyl group, a $C_{1-6}$alkoxy group, or a group represented by formula —NR$^2$R$^3$, wherein $R^2$ and $R^3$ may be the same or different and represent a hydrogen atom or a $C_{1-6}$alkyl group, and $X^1$ and $X^2$ have the same meanings as defined in claim 1, L represents —CO—, $Q^1$ represents a single bond, and $Q^2$ represents —(CR$^{11}$R$^{12}$)— (wherein, R$^{11}$ and R$^{12}$ form $C_{3-8}$cycloalkane together).

5. The aminopyrrolidine compound, a tautomer, a stereoisomer, a prodrug, or a pharmaceutically acceptable salt of the compound, or a solvate thereof according to claim 2, wherein $R^{1a}$ represents a $C_{1-6}$alkyl group or a $C_{1-6}$alkoxy group.

6. The aminopyrrolidine compound, a tautomer, a stereoisomer, a prodrug, or a pharmaceutically acceptable salt of the compound, or a solvate thereof according to claim 1 or 2, wherein Het represents an aromatic heterocyclic group represented by the following formula [VI]:

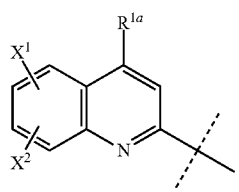

[VI]

wherein $R^{1a}$ represents a group represented by the formula $-NR^2R^3$, wherein $R^2$ and $R^3$, together with the nitrogen atom to which they bond, represents a cyclic amino group represented by the formula [V]:

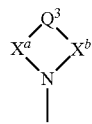

[V]

wherein $X^a$, $X^b$, and $Q^3$ have the same meanings as defined in claim 1, and $X^1$ and $X^2$ have the same meanings as defined in claim 1, and
L represents —CO—.

7. The aminopyrrolidine compound, a tautomer, a stereoisomer, a prodrug, or a pharmaceutically acceptable salt of the compound, or a solvate thereof according to claim 2, wherein $Z^1$ represent a hydrogen atom, a hydroxy group, a halogen atom, or a $C_{1-6}$alkoxy group, and $Z^2$, $Z^3$, and $Z^4$ represent a hydrogen atom.

8. The aminopyrrolidine compound, a tautomer, a stereoisomer, a prodrug, or a pharmaceutically acceptable salt of the compound, or a solvate thereof according to claim 2, wherein $Q^1$ represents a single bond, and $Q^2$ represents $-(CR^{11}R^{12})-$, wherein $R^{11}$ and $R^{12}$ both represent a hydrogen atom, or one of them is a methyl group and the other is a hydrogen atom, or $R^{11}$ and $R^{12}$ form cyclopropane together.

9. The aminopyrrolidine compound, a tautomer, a stereoisomer, a prodrug, or a pharmaceutically acceptable salt of the compound, or a solvate thereof according to claim 1, wherein Het represents an aromatic heterocyclic group represented by the following formula [VI]:

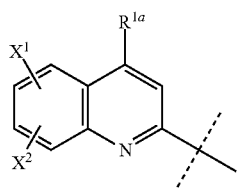

[VI]

wherein $R^{1a}$ has the same meaning as defined in claim 1, $X^1$ represents a hydroxy group, a $C_{1-6}$alkyl group, or a $C_{1-6}$alkoxy group, and $X^2$ represents a halogen atom, and L represents —CO—.

10. The aminopyrrolidine compound, a tautomer, a stereoisomer, a prodrug, or a pharmaceutically acceptable salt of the compound, or a solvate thereof according to claim 2, wherein $X^1$ represents a hydrogen atom, a hydroxy group, a $C_{1-6}$alkyl group, or a $C_{1-6}$alkoxy group, and $X^2$ represents a hydrogen atom or a halogen atom.

11. The aminopyrrolidine compound, a tautomer, a stereoisomer, a prodrug, or a pharmaceutically acceptable salt of the compound, or a solvate thereof according to claim 1, wherein Het represents an aromatic heterocyclic group represented by the following formula [VII]:

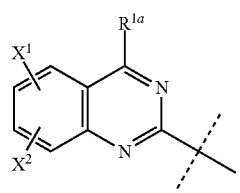

[VII]

wherein $R^{1a}$, $X^1$ and $X^2$ have the same meanings as defined in claim 1,
L represents —CO—, and
Ar, $Z^1$, and $Q^2$ have the same meanings as defined in claim 1, provided that when $R^{1a}$ is a hydroxy group, a $C_{1-6}$alkyl group, a $C_{1-6}$alkoxy group, a halogen atom, a trifluoromethyl group, or a group represented by $-NR^2R^3$, wherein $R^2$ and $R^3$ may be the same or different and represent a hydrogen atom or a $C_{1-6}$alkyl group, or $R^2$ and $R^3$ form a morpholino group, a 4-acetylpiperazino group, or a 4-phenylpiperazino group together, (i) Ar represents a phenyl group, a naphthyl group, or a $C_{1-9}$heteroaryl group, wherein the phenyl group, the naphthyl group, and the $C_{1-9}$heteroaryl group are substituted with one substituent selected from the group consisting of a hydroxy group, a $C_{1-6}$alkylthio group, a $C_{1-6}$alkylsulfonyl group, a methoxy group substituted with one to three fluorine atoms, a methylthio group substituted with one to three fluorine atoms, a methylsulfonyl group substituted with one to three fluorine atoms, a nitro group, a phenoxy group, a benzyloxy group, an amino group, a carboxy group, a $C_{3-8}$cycloalkoxy group, a ($C_{1-6}$alkyl)amino group, a di($C_{1-6}$alkyl)amino group, a hydroxy$C_{1-6}$alkyl group, a $C_{1-6}$alkoxycarbonyl group, a carbamoyl group, a sulfamoyl group, a cyano group, a phenyl group, wherein the phenyl group is unsubstituted or substituted with one to three substituents selected from the substituent group A wherein the substituent group A has the same meaning as defined in claim 1, a methylenedioxyphenyl group, and a pyridyl group, or are further substituted with one or two substituents selected from the group consisting of a halogen atom, a trifluoromethyl group, a $C_{1-6}$alkyl group, and a $C_{1-6}$alkoxy group, and $X^1$ represents a group selected from the group consisting of a $C_{1-6}$alkyl group, a $C_{1-6}$alkoxy group, a halogen atom, a phenyl group, a trifluoromethyl group, a hydroxy group, a $C_{3-8}$cycloalkyl group, a $C_{3-8}$cycloalkoxy group, a ($C_{1-6}$alkyl)amino group, a di($C_{1-6}$alkyl)amino group, a hydroxy$C_{1-6}$alkyl group, and a methoxy group substituted with one to three fluorine atoms, (ii) $Q^2$ represents
—$(CR^{11}R^{12})$—, wherein $R^{11}$ and $R^{12}$ form $C_{3-8}$cycloalkane together, and $X^1$ represents a group selected from the group consisting of a $C_{1-6}$alkyl group, a $C_{1-6}$alkoxy group, a halogen atom, a phenyl group, a trifluoromethyl group, a hydroxy group, a $C_{3-8}$cycloalkyl group, a $C_{3-8}$cycloalkoxy group, a ($C_{1-6}$alkyl)amino group, a di($C_{1-6}$alkyl)amino group, a hydroxy$C_{1-6}$alkyl group, and a methoxy group substituted with one to three fluorine atoms, (iii) Ar represents a phenyl group, a naphthyl group, or a $C_{1-9}$heteroaryl group, wherein the phenyl group, the naphthyl group, and the $C_{1-9}$heteroaryl group are substituted with one substituent selected from the group consisting of a hydroxy group, a $C_{1-6}$alkylthio group, a $C_{1-6}$alkylsulfonyl group, a methoxy group substituted with one to three fluorine atoms, a methylthio group substituted with one to three fluorine atoms, a methylsulfonyl group substituted with one to three fluorine atoms, a nitro group, a phenoxy group, a benzyloxy group, an amino group, a carboxy group, a $C_{3-8}$cycloalkoxy group, a ($C_{1-6}$alkyl)amino group, a di($C_{1-6}$alkyl)amino group, a hydroxy$C_{1-6}$alkyl group, a $C_{1-6}$alkoxycarbonyl group, a carbamoyl group, a sulfamoyl group, a cyano group, a phenyl group, wherein the phenyl group is unsubstituted or substituted with one to three substituents selected from the substituent group A wherein the substituent group A has the same meaning as defined in claim 1, a methylenedioxyphenyl group, and a pyridyl group, or are further substituted with one or two substituents selected from the group consisting of a halogen atom, a trifluoromethyl group, a $C_{1-6}$alkyl group, and a $C_{1-6}$alkoxy group, and $Z^1$ represents a group selected from the group consisting of a hydroxy group, a $C_{1-6}$alkoxy group, and a halogen atom, or (iv) $Q^2$ represents a group represented by —$(CR^{11}R^{12})$—, wherein $R^{11}$ and $R^{12}$ form $C_{3-8}$cycloalkane together, and $Z^1$ represents a group selected from the group consisting of a hydroxy group, a $C_{1-6}$alkoxy group, and a halogen atom.

12. The aminopyrrolidine compound, a tautomer, a stereoisomer, a prodrug, or a pharmaceutically acceptable salt of the compound, or a solvate thereof according to claim 1 or 11, wherein Het represents an aromatic heterocyclic group represented by the following formula [VII]:

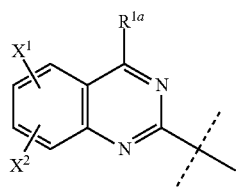

wherein $R^{1a}$ represents a $C_{1-6}$alkyl group, a $C_{1-6}$alkoxy group, or a group represented by formula —$NR^2R^3$, wherein $R^2$ and $R^3$ may be the same or different and represent a hydrogen atom or a $C_{1-6}$alkyl group, or $R^2$ and $R^3$ form a morpholino group, a 4-acetylpiperazino group, or a 4-phenylpiperazino group together, $X^1$ represents a group selected from the group consisting of a $C_{1-6}$alkyl group, a $C_{1-6}$alkoxy group, a halogen atom, a phenyl group, a trifluoromethyl group, a hydroxy group, a $C_{3-8}$cycloalkyl group, a $C_{3-8}$cycloalkoxy group, a ($C_{1-6}$alkyl)amino group, a di($C_{1-6}$alkyl)amino group, a hydroxy$C_{1-6}$alkyl group, and a methoxy group substituted with one to three fluorine atoms, and $X^2$ has the same meanings as defined in claim 1, L represents —CO—, and Ar represents a phenyl group, a naphthyl group, or a $C_{1-9}$heteroaryl group, wherein the phenyl group, the naphthyl group, and the $C_{1-9}$heteroaryl group are substituted with one substituent selected from the group consisting of a hydroxy group, a $C_{1-6}$alkylthio group, a $C_{1-6}$alkylsulfonyl group, a methoxy group substituted with one to three fluorine atoms, a methylthio group substituted with one to three fluorine atoms, a methylsulfonyl group substituted with one to three fluorine atoms, a nitro group, a phenoxy group, a benzyloxy group, an amino group, a carboxy group, a $C_{3-8}$cycloalkoxy group, a ($C_{1-6}$alkyl)amino group, a di($C_{1-6}$alkyl)amino group, a hydroxy$C_{1-6}$alkyl group, a $C_{1-6}$alkoxycarbonyl group, a carbamoyl group, a sulfamoyl group, a cyano group, a phenyl group, wherein the phenyl group is unsubstituted or substituted with one to three substituents selected from the substituent group A wherein the substituent group A has the same meaning as defined in claim 1, a methylenedioxyphenyl group, and a pyridyl group, or are further substituted with one or two substituents selected from the group consisting of a halogen atom, a trifluoromethyl group, a $C_{1-6}$alkyl group, and a $C_{1-6}$alkoxy group.

13. The aminopyrrolidine compound, a tautomer, a stereoisomer, a prodrug, or a pharmaceutically acceptable salt of the compound, or a solvate thereof according to claim 1 or 11, wherein Het represents an aromatic heterocyclic group represented by the following formula [VII]:

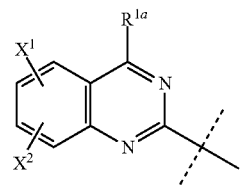

wherein $R^{1a}$ represents a $C_{1-6}$alkyl group, a $C_{1-6}$alkoxy group, or a group represented by —$NR^2R^3$, wherein $R^2$ and $R^3$ may be the same or different and represent a hydrogen atom or a $C_{1-6}$alkyl group, or $R^2$ and $R^3$ form a morpholino group, a 4-acetylpiperazino group, or a 4-phenylpiperazino group together, and $X^1$ and $X^2$ have the same meanings as defined in claim 1, $Z^1$ represents a group selected from the group consisting of a hydrogen atom, a hydroxy group, a $C_{1-6}$alkoxy group, and a halogen atom, L represents —CO—, and Ar represents a phenyl group, a naphthyl group, or a $C_{1-9}$heteroaryl group, wherein the phenyl group, the naphthyl group, and the $C_{1-9}$heteroaryl group are substituted with one substituent selected from the group consisting of a hydroxy group, a $C_{1-6}$alkylthio group, a $C_{1-6}$alkylsulfonyl group, a methoxy group substituted with one to three fluorine atoms, a methylthio group substituted with one to three fluorine atoms, a methylsulfonyl group substituted with one to three fluorine atoms, a nitro group, a phenoxy group, a benzyloxy group, an amino group, a carboxy group, a $C_{3-8}$cycloalkoxy group, a ($C_{1-6}$alkyl)amino group, a di($C_{1-6}$alkyl)amino group, a hydroxy$C_{1-6}$alkyl group, a $C_{1-6}$alkoxycarbonyl group, a carbamoyl group, a sulfamoyl group, a cyano group, a phenyl group, wherein the phenyl group is unsubstituted or substituted with one to three substituents selected from the substituent group A wherein the substituent group A has the same meaning as defined in claim 1, a methylenedioxyphenyl group, and a pyridyl group, or are further substituted with one or two substituents selected from the group consisting of a halogen atom, a trifluoromethyl group, a $C_{1-6}$alkyl group, and a $C_{1-6}$alkoxy group.

14. The aminopyrrolidine compound, a tautomer, a stereoisomer, a prodrug, or a pharmaceutically acceptable salt of the compound, or a solvate thereof according to claim 1 or 11, wherein Het represents an aromatic heterocyclic group represented by the following formula [VII]:

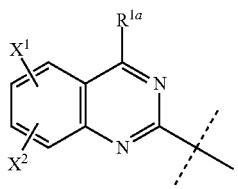

[VII]

wherein $R^{1a}$ represents a $C_{1-6}$alkyl group, a $C_{1-6}$alkoxy group, or a group represented by formula —$NR^2R^3$, wherein $R^2$ and $R^3$ may be the same or different and represent a hydrogen atom or a $C_{1-6}$alkyl group, or $R^2$ and $R^3$ form a morpholino group, a 4-acetylpiperazino group, or a 4-phenylpiperazino group together, and $X^1$ represents a group selected from the group consisting of a $C_{1-6}$alkyl group, a $C_{1-6}$alkoxy group, a halogen atom, a phenyl group, a trifluoromethyl group, a hydroxy group, a $C_{3-8}$cycloalkyl group, a $C_{3-8}$cycloalkoxy group, a ($C_{1-6}$alkyl)amino group, a di($C_{1-6}$alkyl)amino group, a hydroxy$C_{1-6}$alkyl group, and a methoxy group substituted with one to three fluorine atoms, L represents —CO—, and $Q^2$ represents —($CR^{11}R^{12}$)—, wherein $R^{11}$ and $R^{12}$ form $C_{3-8}$cycloalkane together.

15. The aminopyrrolidine compound, a tautomer, a stereoisomer, a prodrug, or a pharmaceutically acceptable salt of the compound, or a solvate thereof according to claim 1 or 11, wherein Het represents an aromatic heterocyclic group represented by the following formula [VII]:

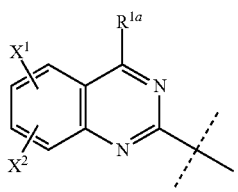

[VII]

wherein $R^{1a}$ represents a $C_{1-6}$alkyl group, a $C_{1-6}$alkoxy group, or a group represented by the formula —$NR^2R^3$, wherein $R^2$ and $R^3$ may be the same or different and represent a hydrogen atom or a $C_{1-6}$alkyl group, or $R^2$ and $R^3$ form a morpholino group, a 4-acetylpiperazino group, or a 4-phenylpiperazino group together, and $X^1$ and $X^2$ have the same meanings as defined in claim 1, $Z^1$ represents a group selected from the group consisting of a hydrogen atom, a hydroxy group, a $C_{1-6}$alkoxy group, and a halogen atom, L represents —CO—, and $Q^2$ represents —($CR^{11}R^{12}$), wherein $R^{11}$ and $R^{12}$ form a $C_{3-8}$cycloalkane together.

16. The aminopyrrolidine compound, a tautomer, a stereoisomer, a prodrug, or a pharmaceutically acceptable salt of the compound, or a solvate thereof according to claim 1 or 11, wherein Het represents an aromatic heterocyclic group represented by the following formula [VII]:

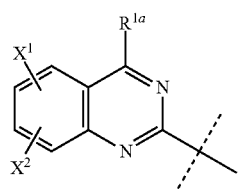

[VII]

wherein $R^{1a}$ represents a group represented by formula —$NR^2R^3$, wherein $R^2$ represents a pyrrolidin-3-yl group, a piperidin-3-yl group, or a piperidin-4-yl group, wherein the pyrrolidin-3-yl group, the piperidin-3-yl group, and the piperidin-4-yl group are unsubstituted or substituted with a $C_{1-6}$alkyl group, a $C_{1-6}$alkylsulfonyl group, or a $C_{1-6}$acyl group, and $X^1$ and $X^2$ have the same meanings as defined in claim 1, and L represents —CO—.

17. The aminopyrrolidine compound, a tautomer, a stereoisomer, a prodrug, or a pharmaceutically acceptable salt of the compound, or a solvate thereof according to claim 1 or 11, wherein Het represents an aromatic heterocyclic group represented by the following formula [VII]:

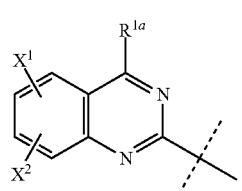

[VII]

wherein $R^{1a}$ represents a group represented by formula —$NR^2R^3$, wherein $R^2$ and $R^3$, together with the nitrogen atom to which they bond, represent a cyclic amino group represented by the formula [V]:

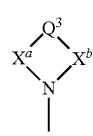

[V]

wherein $X^a$, $X^b$, and $Q^3$ have the same meanings as defined in claim 1, and $X^1$ and $X^2$ have the same meanings as defined in claim 1, $Z^1$ has the same meaning as defined in claim 1, provided that when the cyclic amino group represented by the formula (V) represents a morpholino group, a 4-acetylpiperazino group, or a 4-phenylpiperazino group, (i) $X^1$ represents a group selected from the group consisting of a $C_{1-6}$alkyl group, a $C_{1-6}$alkoxy group, a halogen atom, a phenyl group, a trifluoromethyl group, a hydroxy group, a $C_{3-8}$cycloalkyl group, a $C_{3-8}$cycloalkoxy group, a $(C_{1-6}$alkyl)amino group, a di$(C_{1-6}$alkyl)amino group, a hydroxy$C_{1-6}$alkyl group, and a methoxy group substituted with one to three fluorine atoms, and/or (ii) $Z^1$ represents a group selected from the group consisting of a hydrogen atom, a hydroxy group, a $C_{1-6}$alkoxy group, or a halogen atom, and L represents —CO—.

18. The aminopyrrolidine compound, a tautomer, a stereoisomer, a prodrug, or a pharmaceutically acceptable salt of the compound, or a solvate thereof according to claim 11, wherein $Z^1$ represents a hydrogen atom, a hydroxy group, a halogen atom, or a $C_{1-6}$alkoxy group, and $Z^2$, $Z^3$, and $Z^4$ represent a hydrogen atom.

19. The aminopyrrolidine compound, a tautomer, a stereoisomer, a prodrug, or a pharmaceutically acceptable salt of the compound, or a solvate thereof according to claim 11, wherein $Q^1$ represents a single bond, and $Q^2$ represents —$(CR^{11}R^{12})$—, wherein $R^{11}$ and $R^{12}$ both represent a hydrogen atom or one of them is a methyl group and the other is a hydrogen atom, or $R^{11}$ and $R^{12}$ form cyclopropane together.

20. The aminopyrrolidine compound, a tautomer, a stereoisomer, a prodrug, or a pharmaceutically acceptable salt of the compound, or a solvate thereof according to claim 14, wherein $Q^1$ represents a single bond.

21. The aminopyrrolidine compound, a tautomer, a stereoisomer, a prodrug, or a pharmaceutically acceptable salt of the compound, or a solvate thereof according to claim 11, wherein $X^1$ represents a hydrogen atom, a hydroxy group, a $C_{1-6}$alkyl group, a $C_{1-6}$alkoxy group, or a halogen atom, and $X^2$ represents a hydrogen atom or a halogen atom.

22. A pharmaceutical composition, containing the aminopyrrolidine compound, a tautomer, a stereoisomer, a prodrug, or a pharmaceutically acceptable salt of the compound, or a solvate thereof according to claim 1 or 2 as an active ingredient.

23. A therapeutic agent for depression, anxiety, anorexia, cachexia, pain, and drug dependence, containing the aminopyrrolidine compound, a tautomer, a stereoisomer, a prodrug, or a pharmaceutically acceptable salt of the compound, or a solvate thereof according to claim 1 or 2 as an active ingredient.

* * * * *